US011180792B2

(12) United States Patent
O'Connell et al.

(10) Patent No.: US 11,180,792 B2
(45) Date of Patent: Nov. 23, 2021

(54) METHODS AND COMPOSITIONS FOR LABELING A SINGLE-STRANDED TARGET NUCLEIC ACID

(71) Applicant: The Regents of the University of California, Oakland, CA (US)

(72) Inventors: Mitchell R. O'Connell, Berkeley, CA (US); Jennifer A. Doudna, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/540,227

(22) PCT Filed: Jan. 27, 2016

(86) PCT No.: PCT/US2016/015178
§ 371 (c)(1),
(2) Date: Jun. 27, 2017

(87) PCT Pub. No.: WO2016/123243
PCT Pub. Date: Aug. 4, 2016

(65) Prior Publication Data
US 2018/0002736 A1 Jan. 4, 2018

Related U.S. Application Data

(60) Provisional application No. 62/108,967, filed on Jan. 28, 2015.

(51) Int. Cl.
*C12Q 1/6806* (2018.01)
*C12N 9/22* (2006.01)
*C12Q 1/6818* (2018.01)
*C12Q 1/70* (2006.01)

(52) U.S. Cl.
CPC ............ *C12Q 1/6806* (2013.01); *C12N 9/22* (2013.01); *C12Q 1/6818* (2013.01); *C12Q 1/701* (2013.01)

(58) Field of Classification Search
CPC .................................................. C12N 2310/20
See application file for complete search history.

(56) References Cited

U.S. PATENT DOCUMENTS

| 5,846,726 | A | 12/1998 | Nadeau et al. |
| 8,597,886 | B2 * | 12/2013 | Smith .................... C12Q 1/683 435/6.11 |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 2014/0068797 | A1 | 3/2014 | Doudna et al. |
| 2014/0170753 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Zhang et al. |
| 2014/0189896 | A1 | 7/2014 | Zhang et al. |
| 2014/0179006 | A1 | 8/2014 | Zhang |
| 2014/0227787 | A1 | 8/2014 | Zhang |
| 2014/0234972 | A1 | 8/2014 | Zhang |
| 2014/0242664 | A1 | 8/2014 | Zhang et al. |
| 2014/0242699 | A1 | 8/2014 | Zhang |
| 2014/0242700 | A1 | 8/2014 | Zhang et al. |
| 2014/0242702 | A1 | 8/2014 | Chen et al. |
| 2014/0248702 | A1 | 9/2014 | Cong et al. |
| 2014/0256046 | A1 | 9/2014 | Zhang et al. |
| 2014/0273037 | A1 | 9/2014 | Wu |
| 2014/0273226 | A1 | 9/2014 | Wu |

(Continued)

FOREIGN PATENT DOCUMENTS

WO    WO 2013/176772    11/2013

OTHER PUBLICATIONS

Jinek et al. (2012) A Programmable Dual-RNA-Guided DNA Endonuclease in Adaptive Bacterial Immunity. Science, 337:816-821 (Year: 2012).*
Zhao et al. (2013) Restriction endonuclease-mediated real-time digestion-PCR for somatic mutation detection. International Journal of Cancer, 132:2858-2866 (Year: 2013).*
Nakayama et al. (2008) Junction Probes—Sequence Specific Detection of Nucleic Acids via Template Enhanced Hybridization Processes. Journal of American Chemical Society, 130:12560-12561 (Year: 2008).*
Aneja et al. (2008) Triple-FRET Technique for Energy Transfer Between Conjugated Polymer and TAMRA Dye with Possible Applications in Medical Diagnostics. Journal of Biological Physics, 34:487-493 (Year: 2008).*

(Continued)

*Primary Examiner* — Neil P Hammell
(74) *Attorney, Agent, or Firm* — Bozicevic Field & Francis, LLP; Paula A. Borden

(57) ABSTRACT

The present disclosure provides compositions and methods for labeling a single stranded target nucleic acid. Subject compositions include a Cas9 protein, a Cas9 guide RNA, and a quenched PAMmer. A subject quenched PAMmer is a single stranded oligonucleotide having (i) a protospacer adjacent motif (PAM) sequence; (ii) a detectable label; (iii) a quencher moiety that quenches the detectable label; and (iv) at least one of: a specificity segment positioned 5' of the PAM sequence, and an orientation segment positioned 3' of the PAM sequence. In the subject methods, the Cas9 protein cleaves the quenched PAMmer at a cleavage site positioned between the detectable label and the quencher moiety to produce: (a) a first cleavage product that is hybridized with the target nucleic acid and comprises the detectable label; and (b) a second cleavage product that is not hybridized with the target nucleic acid and comprises the quencher moiety.

27 Claims, 63 Drawing Sheets
Specification includes a Sequence Listing.

(56) References Cited

U.S. PATENT DOCUMENTS

| | | | |
|---|---|---|---|
| 2014/0273230 A1 | 9/2014 | Chen et al. | |
| 2014/0273231 A1 | 9/2014 | Cong et al. | |
| 2014/0273232 A1 | 9/2014 | Zhang et al. | |
| 2014/0273233 A1 | 9/2014 | Chen et al. | |
| 2014/0273234 A1 | 9/2014 | Zhang et al. | |
| 2014/0273235 A1 | 9/2014 | Voytas et al. | |
| 2014/0287938 A1 | 9/2014 | Zhang et al. | |
| 2014/0295556 A1 | 10/2014 | Winchester et al. | |
| 2014/0295557 A1 | 10/2014 | Winchester et al. | |
| 2014/0298547 A1 | 10/2014 | Sastry-Dent et al. | |
| 2014/0304853 A1 | 10/2014 | Ainley et al. | |
| 2014/0309487 A1 | 10/2014 | Lee et al. | |
| 2014/0310828 A1 | 10/2014 | Lee et al. | |
| 2014/0310830 A1 | 10/2014 | Zhang et al. | |
| 2014/0315985 A1 | 10/2014 | May et al. | |
| 2014/0335063 A1 | 11/2014 | Cannon et al. | |
| 2014/0335620 A1 | 11/2014 | Zhang et al. | |
| 2014/0342456 A1 | 11/2014 | Mali et al. | |
| 2014/0342457 A1 | 11/2014 | Mali et al. | |
| 2014/0342458 A1 | 11/2014 | Mali et al. | |
| 2014/0349400 A1 | 11/2014 | Jakimo et al. | |
| 2014/0349405 A1 | 11/2014 | Sontheimer et al. | |
| 2014/0356867 A1 | 12/2014 | Peter et al. | |
| 2014/0356956 A1 | 12/2014 | Church et al. | |
| 2014/0356958 A1 | 12/2014 | Mali et al. | |
| 2014/0356959 A1 | 12/2014 | Church et al. | |
| 2014/0357523 A1 | 12/2014 | Zeiner et al. | |
| 2014/0357530 A1 | 12/2014 | Zhang et al. | |
| 2014/0364333 A1 | 12/2014 | Wu et al. | |
| 2014/0377868 A1 | 12/2014 | Joung et al. | |
| 2015/0211058 A1* | 7/2015 | Carstens | C12Q 1/6844 435/5 |
| 2016/0024524 A1* | 1/2016 | Joung | C12N 9/22 435/462 |

OTHER PUBLICATIONS

Gasiunas et al. (2012) Cas9-crRNA ribonucleoprotein complex mediates specific DNA cleavage for adaptive immunity in bacteria. PNAS, E2579-E2586 (Year: 2012).*

O'Connell et al. (2014) Programmable RNA recognition and cleavage by CRISPR/Cas9. Nature, 516:263-266 and Extended Data (Year: 2014).*

Bratu et al. (2003) Visualizing the distribution and transport of mRNAs in living cells. PNAS 100(23): 13308-13313 (Year: 2003).*

Zheleznaya et al. (2006) Significant enhancement of fluorescence on hybridization of a molecular beacon to a target DNA in the presence of a site-specific DNA nickase. Analytical Biochemistry, 348:123-126 (Year: 2006).*

Auer, et al.; "Highly efficient CRISPR/Cas9-meidated knock-in in zebrafish by homology-independent DNA repair"; Genome Research; 13 pages (Oct. 31, 2013).

Bao, et al.; "Fluorescent Probes for Live-Cell RNA Detection"; Annu. Rev. Biomed. Eng.; vol. 11, pp. 25-47 (2009).

Chen, et al.; "Efficient genome editing in Caenorhabditis elegans by CRISPR-targeted homologous recombination"; Nucleic Acids Research; vol. 41, No. 20, 6 pages (Nov. 2013).

Cheng, et al.; "Multiplexed activation of endogenous genes by CRISPR-on, an RNA-guided transcriptional activator system"; Cell Research; vol. 23, No. 10, pp. 1163-1171 (Oct. 2013).

Cho, et al.; "Heritable gene knockout in Caenorhabditis elegans by direct injection of Cas9-sgRNA ribonucleoproteins";Genetics; vol. 195, No. 3, pp. 1177-1180 (Nov. 2013).

Chylinski, et al.; "The tracrRNA and Cas9 families of type II CRISPR-Cas immunity systems"; RNA Biology; vol. 10, No. 5, pp. 726-737 (May 2013).

Dicarlo, et al.; "Genome engineering in *Saccharomyces cerevisiae* using CRISPR-Cas systems"; Nucleic Acids Research; vol. 41, No. 7, pp. 4336-4343 (Apr. 2013).

Dickinson, et al.; "Engineering the Caenorhabditis elegans genome using Cas9-triggered homologous recombination"; Nature Methods; vol. 10, No. 10, pp. 1028-1034 (Oct. 2013).

Ebina, et al.; "Harnessing the CRISPR/Cas-9 system to disrupt latent HIV-1 provirus"; Science Reports; vol. 3, pp. 2510-2517 (Aug. 2013).

Fujii, et al.; "Efficient generation of large-scale genome-modified mice using gRNA and CAS9 endonuclease"; Nucleic Acids Res; vol. 41, No. 20, (Nov. 1, 2013).

Hou, et al.; "Efficient genome engineering in human pluripotent stem cells using Cas9 from Nesseria meningitdis"; Proceedings of the National Academy Sciences U S A; vol. 110, No. 39, pp. 15644-15649 (Sep. 24, 2013).

Hu, et al.; "Heritable gene-targeting with gRNA/Cas9 in rats"; Cell Research; vol. 23, No. 11, pp. 1322-1325 (Nov. 2013).

Jiang, et al.; "Demonstration of CRISPR/Cas9/sgRNA-mediated targeted gene modification in *Arabindopsis*, tobacco, sorghum and rice"; Nucleic Acids Research; vol. 41, No. 20, (Nov. 1, 2013).

Jinek, et al.; "A programmable dual-RNA-guided DNA endonuclease in adaptive bacterial immunity"; Science; vol. 337, No. 6096, pp. 816-821 (Aug. 17, 2012).

Jinek, et al.; "RNA-programmed genome editing in human cells"; Science; vol. 337, No. 6096, pp. 816-821 (Aug. 17, 2012).

Larson, et al.; "CRISPR interference (CRISPRi) for sequence-specific control of gene expression"; Nature Protocols; vol. 8, No. 11, pp. 2180-2196 (Nov. 2013).

Ma, et al.; "A guide RNA sequence design platform for the CRISPR/Cas9 system for model organism genomes"; Biomed Research International; vol. 2013, No. 270805, 4 pages (2013).

Mali, et al.; "Cas9 as a versatile tool for engineering biology"; Nature methods; vol. 10, No. 10, 957-963 (Oct. 2013).

Nakayama, et al.; "Simple and efficient CRISPR/Cas9-meditated targeted mutagenesis in Xenopus tropicalis"; Genesis; vol. 51, No. 12, pp. 835-843 (Dec. 2013).

O'CONNELL, et al.; "Programmable RNA recognition and cleavage by CRISPR/Cas9"; Nature; vol. 516. No. 7530, pp. 263-266 (Dec. 11, 2014).

Pattanayak, et al.; "Highthroughput profiling of off-target DNA cleavage reveals RNA-programmed Cas-9 nuclease specificity"; Nature Biotechnology; vol. 31, No. 9, pp. 839-843 (Sep. 2013).

Qi, et al.; Repurposing CRISPR as an RNA-guided platform for sequence-spefific control of gene expression; Cell; vol. 152, No. 5, pp. 1173-1183 (Feb. 28, 2013).

Ran, et al.; "Genome engineering using the CRISPR-Cas9 system"; Nature Protocols; vol. 8, No. 11, pp. 2281-2308 (Nov. 2013).

Ran, et al.; "Double nicking by RNA-guided CRISPR Cas9 for enhanced genome editing specificity"; Cell; vol. 154, No. 6, pp. 1380-1389 (Sep. 12, 2013).

Upadhyay, et al.; "RNA-Guided Genome Editing for Target Gene Mutations in Wheat"; G3 (Bethesda); vol. 3, No. 12, pp. 2233-2238 (Dec. 2013).

Walsh, et al.; "A variant CRISPR-Cas9 system adds versatility to genome engineering"; PNAS; vol. 110, No. 39, pp. 15514-15515 (Sep. 24, 2013).

Wang, et al.; "One-step generation of mice carrying mutations in multiple genes by CRISPR/Cas-medicated genome engineering"; Cell; vol. 153, No. 4, pp. 910-918 (May 9, 2013).

Xie, et al.: "RNA-guided genome editing in plants using a CRISPR-Cas system"; Molecular Plant; vol. 6, No. 6, pp. 1975-1983 (Oct. 9, 2013).

Yang, et al.; "One-setp generation of mice carrying reporter and conditional alleles by CRISPR/Cas mediated genome engineering"; Cell; vol. 154, No. 6, pp. 1370-1379 (Sep. 12, 2013).

Doudna, et al.; "The new frontier of genome engineering with CRISPR-Cas9"; Science; vol. 346, No. 6213 (Nov. 28, 2014).

Juskowiak; "Nucleic acid-based fluorescent probes and their analytical potential"; Anal Bioanal Chem; vol. 399, pp. 3157-3176 (2011).

Sternberg; "Mechanism and engineering of CRISPR-associated endonucleases"; Dissertation; 195 pages (2014).

* cited by examiner

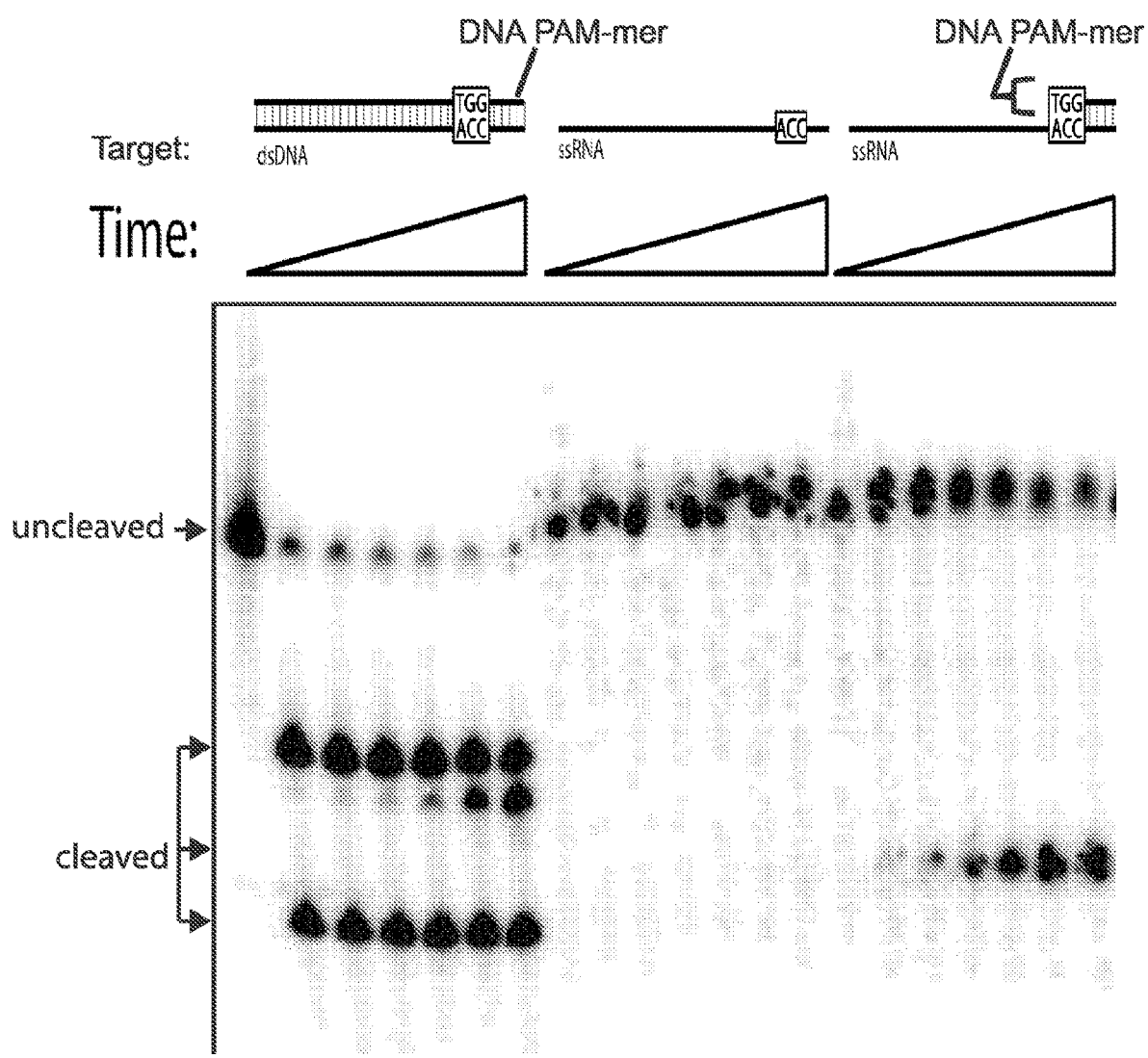

FIG. 8G
(1) Quenched PAMmer
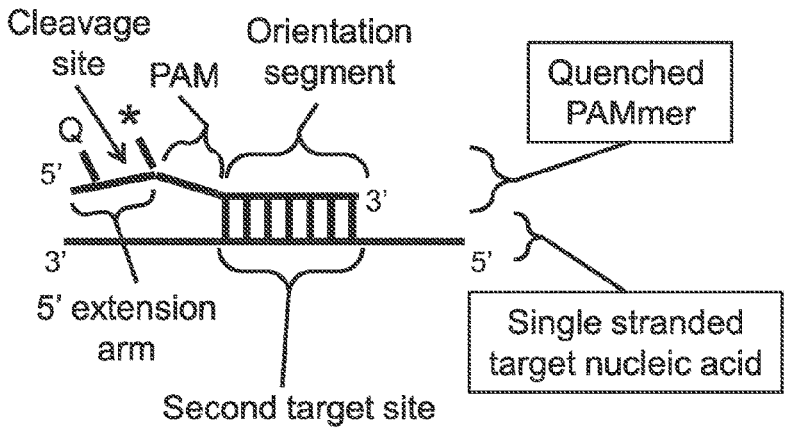
(2) Cleavage of quenched PAMmer by Cas9 protein
(if nickase, target nucleic acid not cleaved)
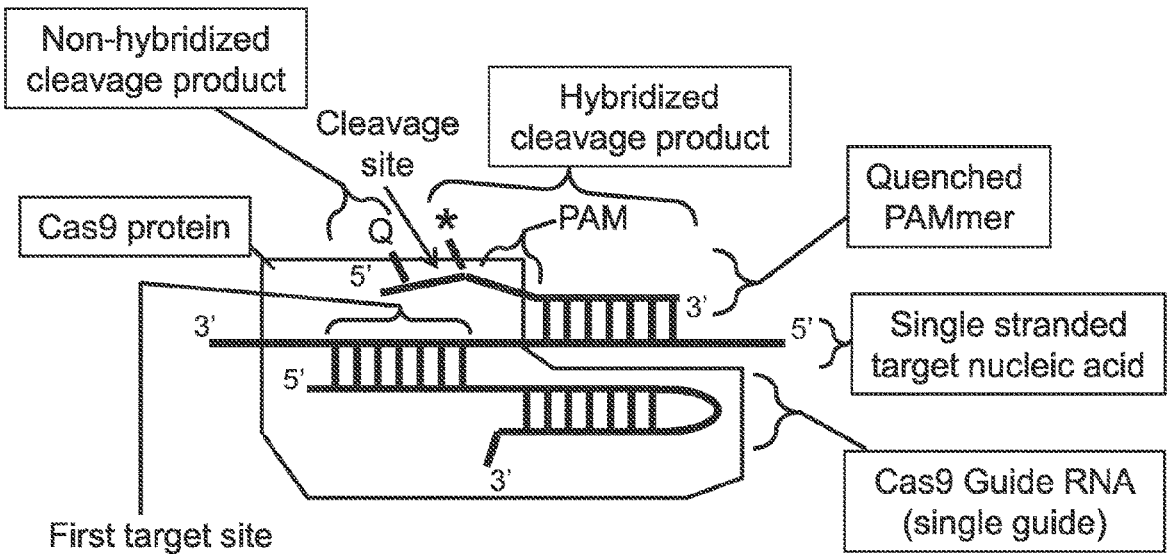
(3) Labeled target nucleic acid
(Hybridized cleavage product plus target nucleic acid)
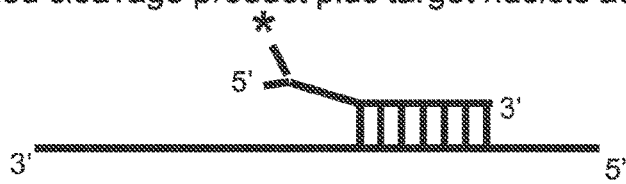

FIG. 8H
(1) Quenched PAMmer
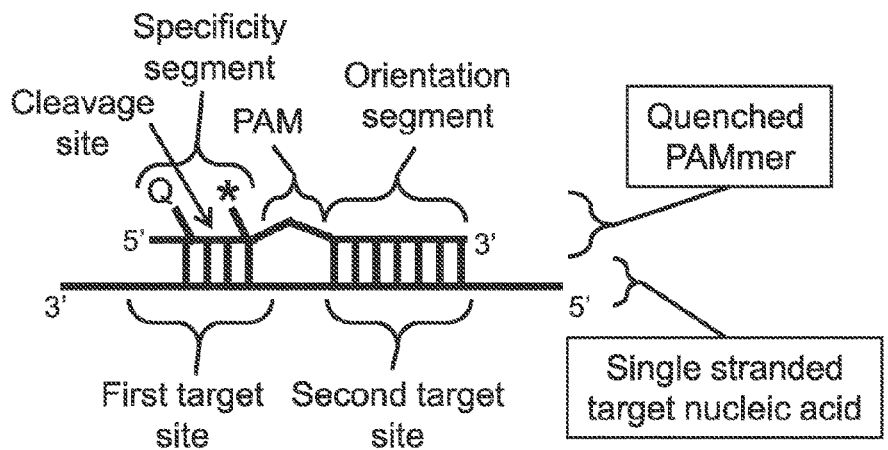
(2) Cleavage of quenched PAMmer by Cas9 protein
(if nickase, target nucleic acid not cleaved)
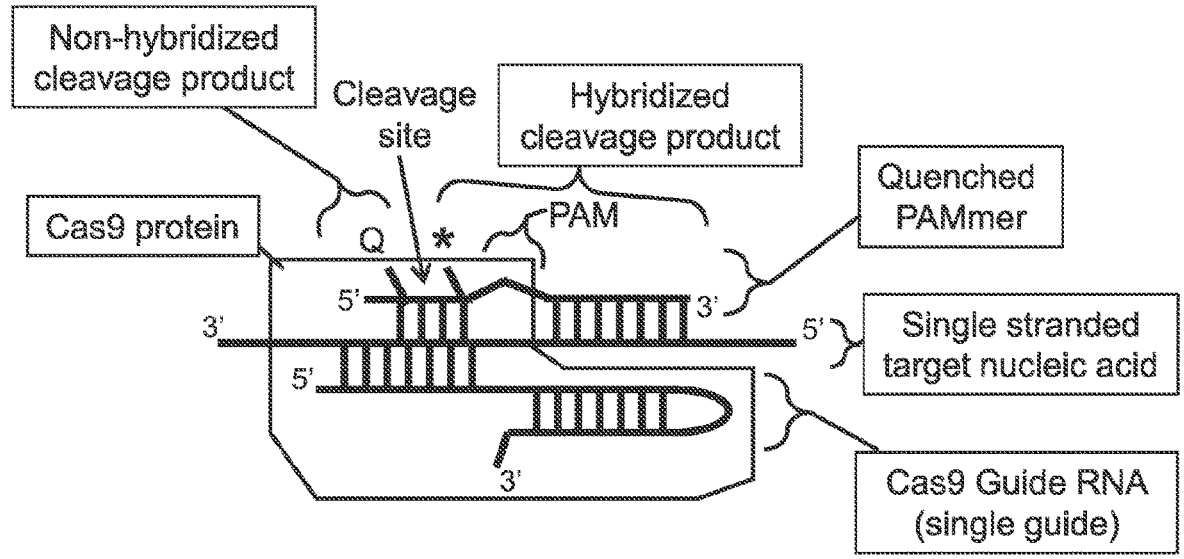
(3) Labeled target nucleic acid
(Hybridized cleavage product plus target nucleic acid)
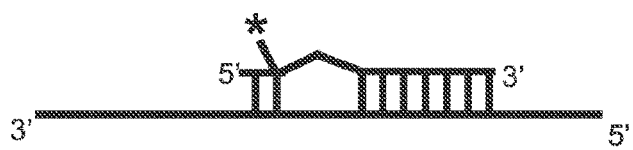

FIG. 8I
(1) Quenched PAMmer
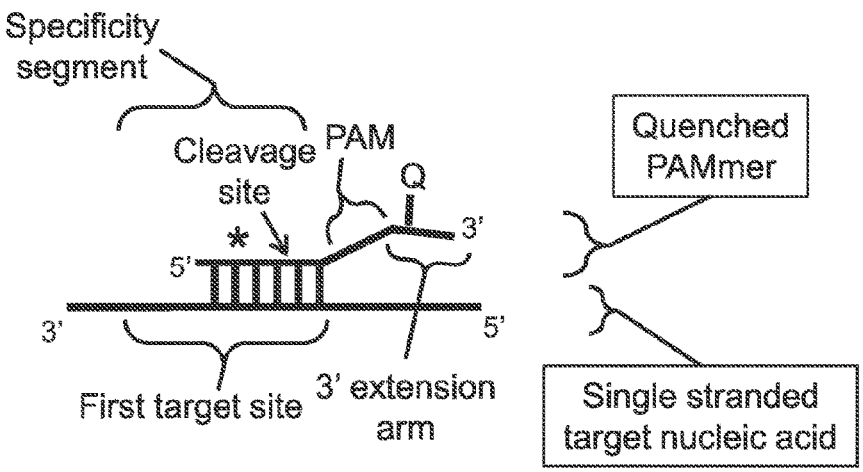
(2) Cleavage of quenched PAMmer by Cas9 protein
(if nickase, target nucleic acid not cleaved)
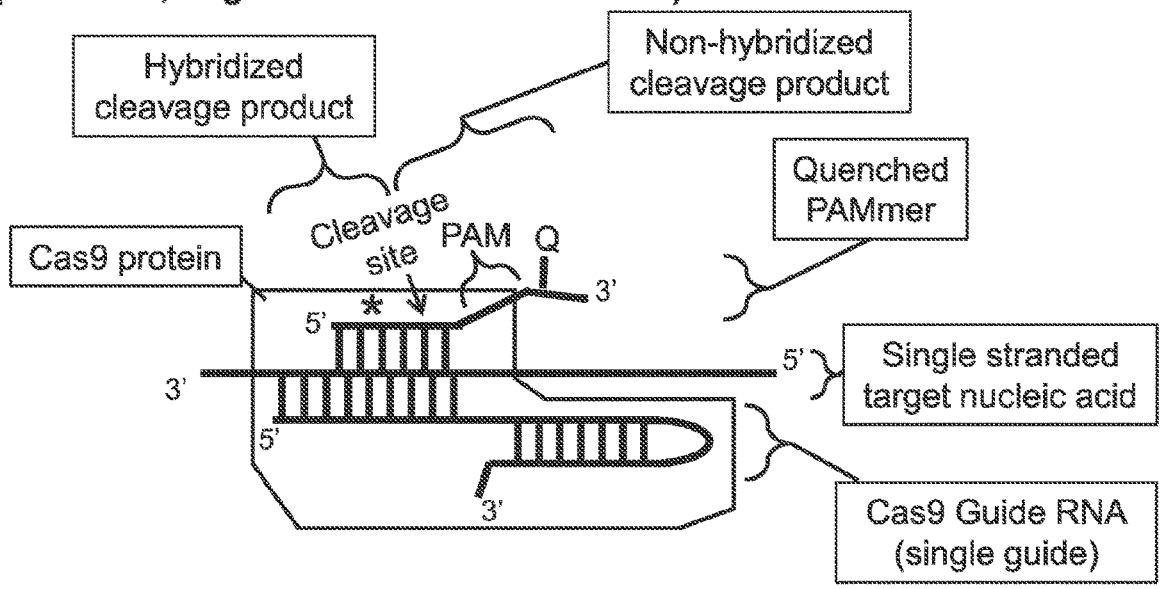
(3) Labeled target nucleic acid
(Hybridized cleavage product plus target nucleic acid)
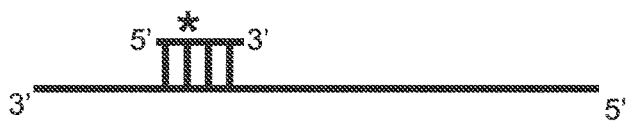

FIG. 9A

Cas9/Csn1 Streptococcus pyogenes motifs

1 MDKKYSIGLDIGTNSVGWAVITDDYKVPSKKLKGLNTDRHGIKKNLIGALL
FDSGETAEATRLKRTARRRYTRRKNRICYLQEIFSNEMAKVDDSFFHRLEE
SFLVEEDKKHERHPIFGNIVDEVAYHEKYPTIYHLRKKLADSTDKVDLRLIYL
ALAHMIKFRGHFLIEGDLNPDNSDVDKLFIQLVQTYNQLFEENPINASRVDA
KAILSARLSKSRRLENLIAQLPGEKKNGLFGNLIALSLGLTPNFKSNFDLAED
AKLQLSKDTYDDDLDNLLAQIGDQYADLFLAAKNLSDATLLSDILRVNSEITK
APLSASMIKRYDEHHQDLTLLKALVRQQLPEKYKEIFFDQSKNGYAGYIDGG
ASQEEFYKFIKPILEKMDGTEELLAKLNREDLLRKQRTFDNGSIPYQIHLGEL
HAILRRQEDFYPFLKDNREKIEKILTFRIPYYVGPLARGNSRFAWMTRKSEE
TITPWNFEEVVDKGASAQSFIERMTNFDKNLPNEKVLPKHSLLYEYFTVYN
ELTKVKYVTEGMRKPAFLSGEQKKAIVDLLFKTNRKVTVKQLKEDYFKKIEC
FDSVEISGVEDRFNASLGTYHDLLKIIKDKDFLDNEENEDILEDIVLTLTLFED
REMIEERLKTYAHLFDDKVMKQLKRRRYTGWGRLSRKLINGIRDKQSGKTI
LDFLKSDGFANRNFMQLIHDDSLTFKEDIQKAQVSGQGDSLHEHIANLAGS
2 PAIKKGILQTVKVVDELVKVMGRHKPENIVIEMARENQTTQKGQKNSRERM
KRIEEGIKELGSDILKEYPVENTQLQNEKLYLYYLQNGRDMYVDQELDINRL
3 SDYDVDHIVPQSFLKDDSIDNKVLTRSDKNRGKSDNVPSEEVVKKMKNYW
RQLLNAKLITQRKFDNLTKAERGGLSELDKVGFIKRQLVETRQITKHVAQILD
4 SRMNTKYDENDKLIREVRVITLKSKLVSDFRKDFQFYKVREINNYHHAHDAY
LNAVVGTALIKKYPKLESEFVYGDYKVYDVRKMIAKSEQEIGKATAKYFFYS
NIMNFFKTEITLANGEIRKRPLIETNGETGEIVWDKGRDFATVRKVLSMPQV
NIVKKTEVQTGGFSKESILPKRNSDKLIARKKDWDPKKYGGFDSPTVAYSVL
VVAKVEKGKSKKLKSVKELLGITIMERSSFEKDPIDFLEAKGYKEVRKDLIIKL
PKYSLFELENGRKRMLASAGELQKGNELALPSKYVNFLYLASHYEKLKGSP
EDNEQKQLFVEQHKHYLDEIIEQISEFSKRVILADANLDKVLSAYNKHRDKPI
REQAENIIHLFTLTNLGAPAAFKYFDTTIDRKRYTSTKEVLDATLIHQSITGLY
ETRIDLSQLGGD

FIG. 9B

Cas9/Csn1 Streptococcus pyogenes

Domains

1 MDKKYS<u>IGLDIGTNSVGWAVITDDYKVPSKKLKGLGNTDRHGIKKNLIGAL
LFDSGETAEATRLKRTARRRYTRRKNRICYLQEIFSNEMAKVDDSFFHRLE
ESFLVEEDKKHERHPIFGNIVDEVAYHEKYPTIYHLRKKLADSTDKVDLRLI
YLALAHMIKFRG</u>HFLIEGDLNPDNSDVDKLFIQLVQTYNQLFEENPINASRV
DAKAILSARLSKSRRLENLIAQLPGEKKNGLFGNLIALSLGLTPNFKSNFDLA
EDAKLQLSKDTYDDDLDNLLAQIGDQYADLFLAAKNLSDATLLSDILRVNSEI
TKAPLSASMIKRYDEHHQDLTLLKALVRQQLPEKYKEIFFDQSKNGYAGYID
GGASQEEFYKFIKPILEKMDGTEELLAKLNREDLLRKQRTFDNGSIPYQIHL
GELHAILRRQEDFYPFLKDNREKIEKILTFRIPYYVGPLARGNSRFAWMTRK
SEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKI
ECFDSVEISGVEDRFNASLGTYHDLLKIIKDKDFLDNEENEDILEDIVLTLTLF
EDREMIEERLKTYAHLFDDKVMKQLKRRRYTGWGRLSRKLINGIRDKQSG
KTILDFLKSDGFANRNFMQLIHDDSLTFKEDIQKAQVSGQGDSLHEHIANLA

2 GS<u>PAIKKGILQTVKVVDELVKVMGRHKPENIVIEMARENQTTQKGQKNSR
ERMKRIEEGIKELGSDILKEYPVENTQLQNEKLYLYYLQNGRDMYVDQEL
DINRLSDYDVDHIVPQSFLKDDSIDNKVLTRSDKNRGKSDNVPSEEVVKK
MKNYWRQLLNAKLITQRKFDNLTKAERGGLSELDKVGFIKRQLVETRQIT
KHVAQILDSRMNTKYDENDKLIREVRVITLKSKLVSDFRKDFQFYKVREIN
NYHHAHDAYLNAVVGTALIKKYPK</u>LESEFVYGDYKVYDVRKMIAKSEQEIG
KATAKYFFYSNIMNFFKTEITLANGEIRKRPLIETNGETGEIVWDKGRDFATV
RKVLSMPQVNIVKKTEVQTGGFSKESILPKRNSDKLIARKKDWDPKKYGGF
DSPTVAYSVLVVAKVEKGKSKKLKSVKELLGITIMERSSFEKDPIDFLEAKGY
KEVRKDLIIKLPKYSLFELENGRKRMLASAGELQKGNELALPSKYVNFLYLA
SHYEKLKGSPEDNEQKQLFVEQHKHYLDEIIEQISEFSKRVILADANLDKVL
SAYNKHRDKPIREQAENIIHLFTLTNLGAPAAFKYFDTTIDRKRYTSTKEVLD
ATLIHQSITGLYETRIDLSQLGGD

FIG. 10

|                    | Motif 1              | Motif 2       | Motif 4       |
|--------------------|----------------------|---------------|---------------|
|                    | *                    |               |               |
| S. pyogenes        | ...IGLDIGTNSVGWAVI... | ...IVIEMARE... | ...HHAHDAYL... |
| L. pneumophila     | ...IGIDLGGKFTGVCLS... | ...MMQRLAYE... | ...SHAIDATL... |
| G. proteobacterium | ...IAIDLGAKFTGVALY... | ...IIEHIARK... | ...SHVVDAVC... |
| L. innocua         | ...IGLDIGTNSVGWAVL... | ...IVVEMARE... | ...HHAHDAYL... |
| L. gasseri         | ...VGLDVGTNSCGWVAM... | ...IAIEFTRD... | ...HHAIDAYL... |
| E. rectale         | ...LALDIGIASVGWAIL... | ...IVIEMPRD... | ...HHAVDAML... |
| S. lugdunensis     | ...LGLDIGITSVGYGLI... | ...IIIELARE... | ...HHAEDALI... |
| M. synoviae        | ...IGFDLGVASVGWSIV... | ...VVIEMARE... | ...HHAVDASI... |
| M. mobile          | ...LGLDLGIASVGWCLT... | ...IVVEVTRS... | ...HHAEDAYF... |
| W. succinogenes    | ...LGVDLGISSLGWAIV... | ...VHFELARE... | ...HHAVDAII... |
| F. columnare       | ...LGLDLGTNSIGWAIR... | ...IHIEMARE... | ...HHTIDAIT... |
| F. succinogenes    | ...LGLDLGTNSIGWAVV... | ...IHLELGRD... | ...HHAMDAIV... |
| B. fragilis        | ...LGLDLGTNSIGWALV... | ...IRVELARE... | ...HHAMDALT... |
| A. cellulolyticus  | ...LGVDVGERSIGLAAV... | ...IVVELARG... | ...HHAVDAVV... |
| B. dentium         | ...IGIDVGLMSVGLAAI... | ...VQIEHVRE... | ...HHAVDAAV... |

|                    | Motif 3 |
|--------------------|---------|
|                    | *       |
| S. pyogenes        | ...DVDHIVPQSFLKD------DSIDNKVLTRSDKN... |
| L. pneumophila     | ...EIDHIYPRSLSKRHFGVIFNSEVNLIYCSSQGN... |
| G. proteobacterium | ...EIDHIIPRSLTGRTKKTVFNSEANLIYCSSKGN... |
| L. innocua         | ...DIDHIVPQSFITD------NSIDNLVLTSSAGN... |
| L. gasseri         | ...DIDHILPQSFIKD------DSLENRVLVKKAVN... |
| E. rectale         | ...EIDHIIPRSISFD------DARSNKVLVYRSEN... |
| S. lugdunensis     | ...EVDHIIPRSVSFD------NSYHNKVLVKQSEN... |
| M. synoviae        | ...EIDHVIPYSKSAD------DSWFNKLLVKKSTN... |
| M. mobile          | ...DIDHIVPRSISFD------DSFSNLVIVNKLDN... |
| W. succinogenes    | ...EIDHILPRSRSAD------DSFANKVLCLARAN... |
| F. columnare       | ...DIEHTIPRSISQD------NSQMNKTLCSLKFN... |
| F. succinogenes    | ...EIEHVIPQSLYFD------DSFSNKVICEAEVN... |
| B. fragilis        | ...DIEHIIPQARLFD------DSFSNKTLEARSVN... |
| A. cellulolyticus  | ...ELDHIVPRTDGG------SNRHENLAITCGACN... |
| B. dentium         | ...EMDHIVPRKGVGS-----TNTRVNLAAACAACN... |

```
                     1                                      36
L. innocua      (1)  GUUUUAGAGCUAUGUUAUUUUGAAUGCUAACAAAAC
S. pyogenes     (1)  GUUUUAGAGCUAUGCUGUUUUGAAUGGUCCCAAAAC
S. mutans       (1)  GUUUUAGAGCUGUGUUGUUUCGAAUGGUUCCAAAAC
S. thermophilus1 (1) GUUUUAGAGCUGUGUUGUUUCGAAUGGUUCCAAAAC
```

FIG. 12B

```
                       1                                       37
C. jejuni         (1)  AUUUUACC-AUAAAGAAAUUUAAAAAGGGACUAAAAC
S. pyogenes       (1)  GUUUUAGA-GCUAUGCUGUUUUGAAUGGUCCCAAAAC
F. novicida       (1)  GUUUCAGUUGCUGAAUUAUUUGGUAAACUACUGUUAG
M. mobile         (1)  GUUUUGGU-GUAGUAUCAUUCUUAUGUAUUCUUAAAC
N. meningitidis   (1)  GUUGUAGC-UCCCUUUCUCAUUCGCAGUGCUACAAU
P. multocida      (1)  GUUGUAGU-UCCCUCUCUCAUUCGCAGUGCUACAAU
S. thermophilus2  (1)  GUUUUUGU-ACUCUCAAGAUUUAAGUAACUGUACAAC
```

FIG. 13

| STRAIN | NUMBER OF CRISPRs | CAS54 CRISPR identifier | CRISPR REPEAT:tracrRNA BASEPAIRING |
|---|---|---|---|
| Streptococcus pyogenes SF370 | 2 | NC_002737_1 | 5' GUUUUAG--AGCUAUGCUGUUUGAAUGGUCCAAAAC 3'<br>‖‖‖‖·  ‖‖‖‖‖‖‖‖‖‖‖‖‖‖‖‖‖ ‖‖‖‖ ‖<br>3' AAAUUGAACGAUACGACAAAACUUACCAAGGUUGUU 5' |
| Streptococcus mutans UA159 | 1 | NC_004350_1 | GUUUUAG--AGCUGUGUUGUUUCGAAUGGUUCCAAAAC<br>‖‖‖‖·  ‖‖‖‖‖‖‖‖‖‖‖‖‖‖·‖‖‖‖‖ ‖‖<br>AAAUUGAACGACACAACAAAGCUUACUAAGGUUGUG |
| Streptococcus thermophilus LMD-9 | 3 | NC_008532_5 | GUUUUAG--AGCUGUGUUGUUUCGAAUGGUUCCAAAAC<br>‖‖‖‖·  ‖‖‖‖‖‖‖‖‖‖‖‖‖‖‖‖‖‖ ‖‖‖‖<br>AAAUUGAGCGACACAACAAAGCUUACCAAAGUUUGG |
| | | NC_008532_2 | GUUUUUGUACUCU-CAAGAUUAAGUAACUGUACAAC<br>‖‖‖ ‖·  ‖‖‖ ‖‖‖‖‖‖‖‖‖‖‖‖‖‖‖ ‖‖<br>AAACAUCGAAGACGUUCUAAAUUCAUUGACACAUUC |
| Listeria innocua Clip11262 | 1 | NC_003212_2 | GUUUUAG--AGCUAUGUUAUUUGAAUGCUAACAAAAC<br>‖‖‖‖·  ‖‖‖‖‖‖‖‖‖‖‖‖‖‖·‖‖‖‖‖‖‖ ‖<br>AAAUUGAACGAUACAAUAAAACUUAUGAUUGUUAUA |
| Treponema denticola ATCC35405 | 1 | NC_002967_1 | GUUUGAG--AGUUGUGUAAUUUAAGAUGGAUCUAAAC<br>‖‖‖‖·  ‖‖‖‖‖‖‖‖‖‖‖‖‖‖‖‖‖‖‖‖ ‖‖‖<br>AACUUGAGCAACACAUUAAAUUCUACCUAGAAUUUA |
| Neisseria meningitidis Z2491 | 2 | NC_003116_10 | GUUGUAGCUCCCUUUCUCAUUUCGCAGUGCUACAAU<br>·‖‖‖‖‖‖ ‖  ‖‖‖‖‖‖‖‖‖‖‖‖‖‖ ‖‖‖‖‖<br>UAACAUCGUUGCCAAGAGUAAAGCGUCACGCUGUUA |
| Streptococcus gordonii str. Challis substr. CH1 | 1 | NC_009785_2 | GUUUUUGUACUCU-CAAGAUUUAAGUAACUGUACAAC<br>‖‖‖ ‖·  ‖‖‖‖ ‖‖‖‖‖‖‖‖‖‖‖‖‖‖‖ ‖‖<br>AAACAUCGAAGACGUUCUAAAUUCAUUGACACAUUC |
| Bifidobacterium bifidum S17 | 1 | NC_014616_1 | GUUUCA-AUGCCUGUCAGAUCAAUGACUUUGACCAC<br>·   ‖‖‖‖‖‖‖‖‖‖‖ ‖‖‖‖‖‖‖‖·‖‖‖‖ ‖‖<br>AGUUAAAUACGGACAGUCCAGUUACUGGAACUAGUA |
| Lactobacillus salivarius UCC118 | 1 | NC_007929_1 | GUUUCAGAAGUAUGUUAAAUCAAUAAGGUUAAGACC<br>‖·    ‖‖ ‖‖‖‖‖‖‖‖‖‖‖‖ ‖‖‖‖·‖‖·‖‖‖<br>AAGUUGAGUCUUACAAUUUAGUUACUCCAGUUUUGG |
| Francisella tularensis subsp. novicida U112 | 2 | NC_006601_1ᵃ | CUAACAGUAGUUUACCAAAUAAUUCAGCAACUGAAAC<br>‖‖‖·  ·· ‖‖‖‖‖‖‖‖‖‖‖‖‖ ‖·‖‖‖‖‖‖‖‖‖‖<br>UUGUGUUCAUGCAUGGUUUAUUAGAUUGUUGACUUUG<br><br>CUAACAGUAGUUUACCAAAUAAUUCA-GCAACUGAAAC<br>‖   ‖  ‖·‖ ‖‖‖‖‖‖‖‖‖‖‖‖ ‖ ‖‖  ‖‖‖ ‖‖<br>UUUAAUAUUUACAUGGUUUAUUAAUUACG-ACACAUUA |
| Legionella pneumophila str. Paris | 1 | NC_006368_1 | CCAAUAAUCCCUCAUCUAAAAAUCCA-ACCACUGAAAC<br>‖‖‖ ‖   ‖‖‖‖‖‖‖‖‖ ‖‖ ‖ ‖‖‖ ‖‖‖‖‖‖<br>AUUUAAUCUUUAGUAGAUUAAAGCUAUGG-GACUUUA |

FIG. 14

*Streptococcus pyogenes*

Base-pairing *in vivo* (crRNA /tracrRNA)

```
                              crRNA (targeter)
                                    ↓
               5'- variable 20nt -GUUUUAG--AGCUAUGCUGUUUUG-3'
                                 •|||||•  ||||||||||||
  AGCCACGGUGAAAAAGUUCAACUAUUGCCUGAUCGGAAUAAAAUUGAACGAUACGACAAA-5'
  G |||||||                                ↑
    UCGGUGCUUUUUU-3'                tracrRNA (activator)
```

Example of a single guide nucleic acid

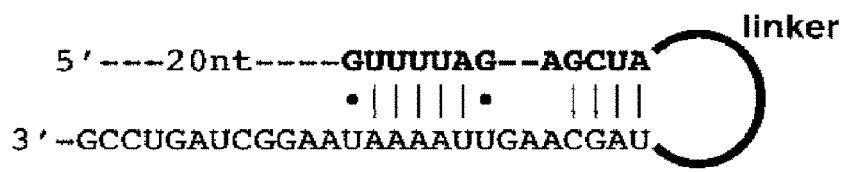

*Listeria innocua*

Base-pairing *in vivo* (crRNA /tracrRNA)

```
                              crRNA (targeter)
                                    ↓
               5'- variable 20nt-GUUUUAG--AGCUAUGUUAUUUUG-3'
                                •|||||•  ||||||||||||
  UGCCGCGAUGAAUUAAUUUUCAACUAUUGCCUGUUUCGGAAUAAAAUUGAACGAUACAAUAAA-5'
  U |||||||                              ↑
    UCGGCGCUUUUUU-3'              tracrRNA (activator)
```

Example of a single guide nucleic acid

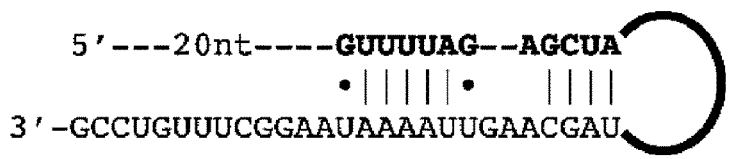

FIG. 15A

| Fusion Partner (for RNA targets) | Exemplary Function |
|---|---|
| Splicing factors (e.g., RS domains) | Allow Cas9 to affect splicing choices |
| Translation factors (e.g., initiation, elongation, release, etc.) (e.g., eIF4G) | Allow sequence specific recruitment of the ribosome to particular messages independent of the presence of a 5' cap structure |
| RNA methylases | Methylation of RNA targets |
| RNA deaminases (e..g, ADAR (adenosine deaminase acting on RNA)) | Deamination of RNA targets (e.g,. A to I and/or C to U editing of RNA targets |
| helicases | Unwind secondary structure (duplexes) |
| RNA-binding proteins | |

FIG. 15B

| Protein name | Function |
|---|---|
| Transcriptional Activators | |
| GAL4 | Transcription activation |
| VP16 | Transcription activation |
| VP64 | Transcription activation |
| p65 subdomain (NFkB) | Transcription activation |
| Transcriptional repressors | |
| KRAB | Transcription repression |
| Mad mSIN3 interaction domain (SID) | Transcription repression |
| the ERF repressor domain (ERD) | Transcription repression |
| Histone lysine methyltransferases (KMT) | |
| KMT1 family: SUV39H1, SUV39H2, G9A, ESET/SETDB1, and homologs (Clr4, Su(var)3-9) | Heterochromatin formation/transcription represson |
| KMT2 family: hSET1A, hSET1B, MLL1 to 5, ASH1, and homologs (Trx, Trr, Ash1) | Transcription activation |
| KMT3 family: SYMD2, NSD1 | Transcription activation |
| KMT4: DOT1L and homologs | Transcription activation |
| KMT5 family: Pr-SET7/8, SUV4-20H1, and homologs (PR-set7, Suv4-20, Set9) | DNA damage response, transcription repression |
| KMT6: EZH2 | Polycomb silencing |
| KMT8: RIZ1 | Transcription repression |
| Histone lysine demethylates (KDM) | |
| KDM1: LSD1/BHC110 and homologs (SpLsd1/Swm1/Saf110, Su(var)3-3) | Transcription activation and repression, heterochromatin formation |
| KDM3 family: JHDM2a/b | Androgen receptor gene activation, spermatogenesis |
| KDM4 family: JMJD2A/JHDM3A, JMJD2B, JMJD2C/GASC1, JMJD2D, and homologs (Rph1) | Transcription elongation, transcription repression, heterochromatin formation, genome integrity |
| KDM5 family: JARID1A/RBP2, JARID1B/PLU-1, JARID1C/SMCX, JARID1D/SMCY, and homologs (Lid, Jhn2, Jmj2) | Transcription repression |
| KDM6 family: UTX, JMJD3 | Transcription activation |

FIG. 15C

| Protein name | Function |
|---|---|
| Histone lysine acetyltransferases (KAT) | |
| KAT2 family: hGCN5, PCAF, and homologs (dGCN5/PCAF, Gcn5) | Transcription activation, DNA repair |
| KAT3 family: CBP, p300, and homologs (dCBP/NEJ) | Transcription activation, DNA repair |
| KAT4: TAF1 and homologs (dTAF1) | Transcription activation |
| KAT5: TIP60/PLIP, and homologs | Transcription activation, DNA repair |
| KAT6: MOZ/MYST3, MORF/MYST4, and homologs (Mst2, Sas3, CG1894) | Transcription activation and elongation, DNA replication |
| KAT7: HBO1/MYST2, and homologs (CHM, Mst2) | Transcription, DNA replication |
| KAT8: HMOF/MYST1, and homologs (dMOF, CG1894, Sas2, Mst2) | Chromatin boundaries, dosage compensation, DNA repair |
| KAT13 family: SRC1, ACTR, P160, CLOCK, and homologs | Transcription activation |
| Histone lysine deacetylases | |
| Class I: HDAC1, HDAC2, HDAC3, HDAC8, and its homologs (Rpd3, Hos1, Cir6) | Transcription repression, heterochromatin formation |
| Class IIa: HDAC4, HDAC5, HDAC7, HDAC9, and its homologs (Hda1, Cir3 etc.) | Transcription repression, heterochromatin formation |
| Class III: SIRT1, SIRT2, and its homologs (Sir2, Hst1, Hst2, Hst3, Hst4) | Transcription repression, heterochromatin formation |
| Class IV: HDAC11 | Transcription repression |
| DNA methylases (adenosine or cytosine modification) | |
| Dam (E. coli) | Restriction system |
| Dcm (E. coli) | Restriction system |
| M. SssI (Spiroplasma sp) | Restriction system |
| DNMT1 | Transcription repression, imprinting, heterochromatin formation |
| DNMT3a/DNMT3b, MET1, DRM3 (plants), and homologs | Transcription repression, imprinting, heterochromatin formation |
| Chromomethylases e.g. ZMET2, CMT1, CMT2 (plants) | Transcription repression, imprinting, heterochromatin formation |
| DNA demethylases | |
| AID/Apobec deaminase family: AID | Transcription activation, genome integrity |
| TET dioxygenase family: TET1 | Transcription activation, genome integrity |
| DEMETER glycosylase family: DME, DML1, DML2, ROS1 | Transcription activation, genome integrity |

FIG. 15D

| Protein name | Function |
|---|---|
| Boundary elements | |
| CTCF | Chromatin insulation, heterochromatin spreading suppression |
| Periphery recruitment elements | |
| Lamin A | Transcription repression |
| Lamin B | Transcription repression |
| Protein docking elements | |
| FKBP/FRB (S. pombe) | rapamycin dependent recruitment |
| Pil1/Aby1 (E. coli) | ABA dependent recruitment |

FIG. 18D
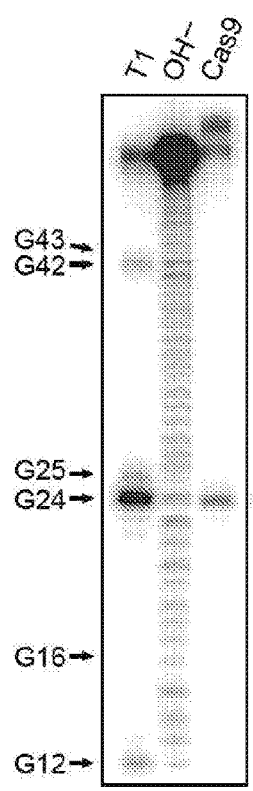
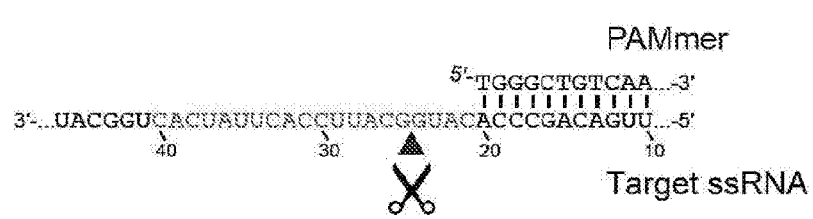
FIG. 18E
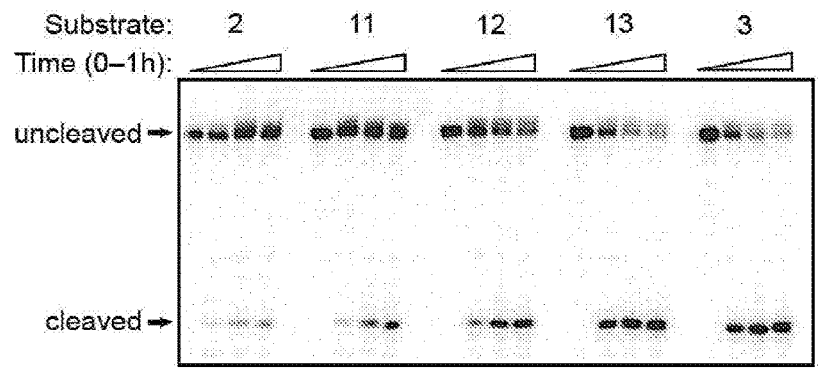

transcription

Substrates:

1. PAM dsDNA 2. non-PAM dsDNA 3. ssRNA + PAMmer 4. ssRNA + PAMmer, mismatched 5. ssRNA + PAMmer, mismatched & 5'-extended FIG. 21E
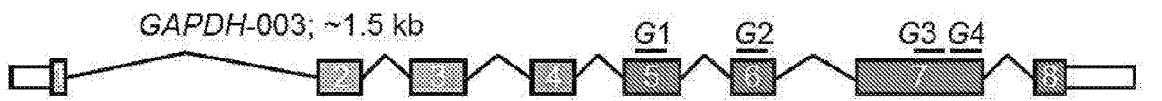
FIG. 21F
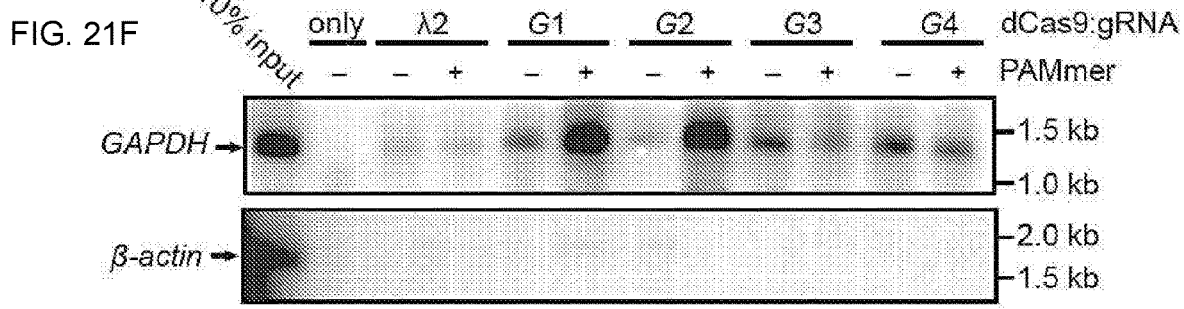
FIG. 21G
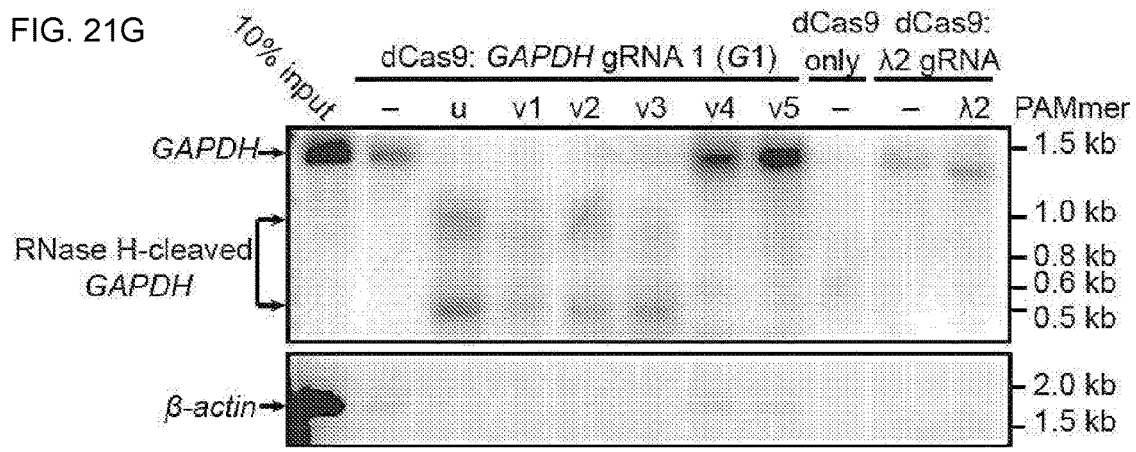
FIG. 21H
```
        5' extension PAM    3' anchor
u:   ATGACCCTAGGGGCTCCCCCCTGCAAA
v1:  AUGACCCTAGGGGCTCCCCCCUGCAAA
v2:  ATGACCCUAGGGGCTCCCCCCTGCAAA
v3:  ATGACCCUAGGGGCUCCCCCCTGCAAA
v4:  ATGACCCTAGGGGCTCCCCCCUGCAAA
v5:  ATGACCCTAGGGGCUCCCCCCTGCAAA
```

FIG. 26A
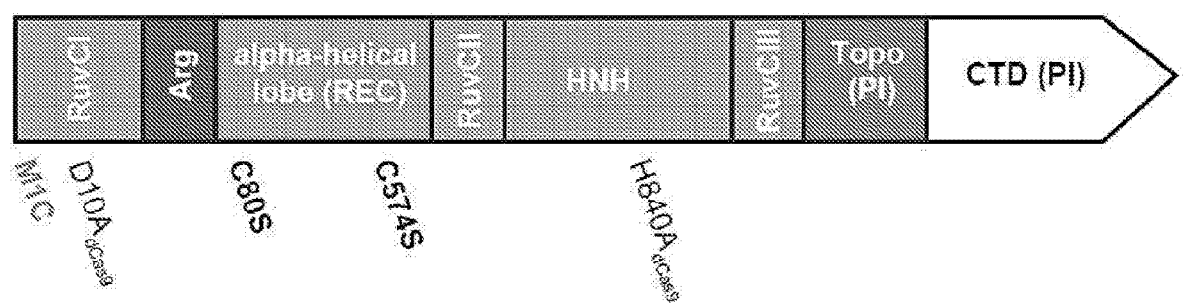
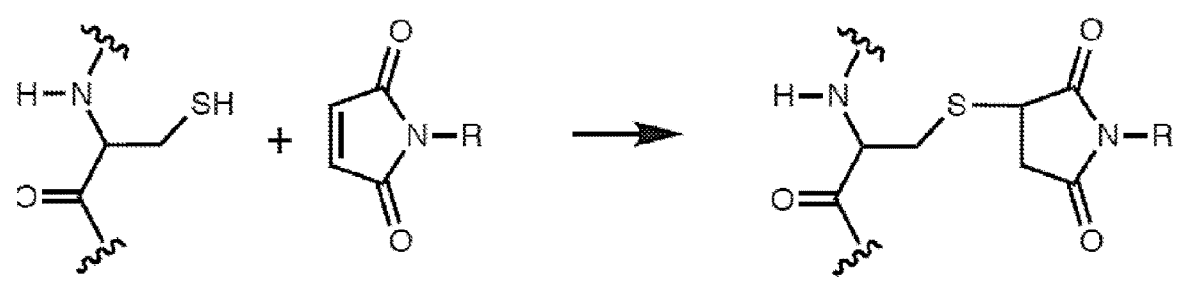
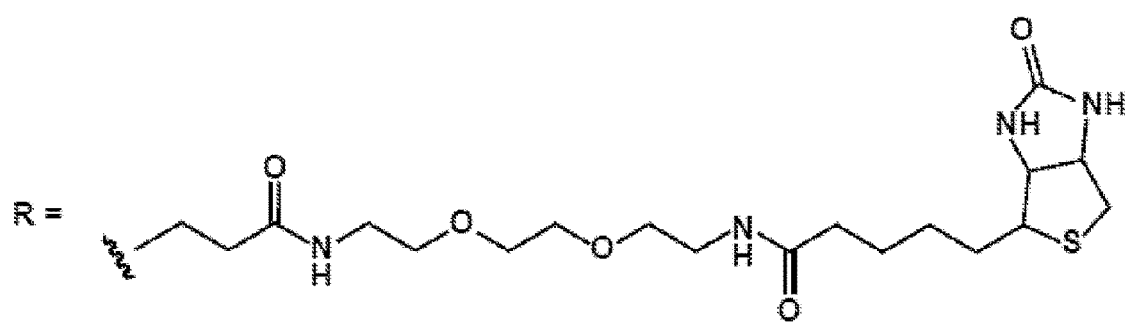

METHODS AND COMPOSITIONS FOR LABELING A SINGLE-STRANDED TARGET NUCLEIC ACID

CROSS-REFERENCE

This application is a national stage filing under 35 U.S.C. § 371 of PCT/US2016/015178, filed Jan. 27, 2016, which claims the benefit of U.S. Provisional Patent Application No. 62/108,967, filed Jan. 28, 2015, which applications are incorporated herein by reference in their entirety.

GOVERNMENT RIGHTS

This invention was made with Government support under GM102706 awarded by the National Institutes of Health. The Government has certain rights in the invention.

INCORPORATION BY REFERENCE OF SEQUENCE LISTING PROVIDED AS A TEXT FILE

A Sequence Listing is provided herewith as a text file, "BERK-276_SEQ LISTING_20190708_ST25.txt" created on Jul. 8, 2019 and having a size of 7,840 KB. The contents of the text file are incorporated by reference herein in their entirety.

INTRODUCTION

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. In Type II CRISPR-Cas systems, Cas9 functions as an RNA-guided endonuclease that uses a dual-guide RNA consisting of crRNA and trans-activating crRNA (tracrRNA) for target recognition and cleavage by a mechanism involving two nuclease active sites that together generate double-stranded DNA breaks (DSBs).

RNA-programmed Cas9 has proven to be a versatile tool for genome engineering in multiple cell types and organisms. Guided by a dual-RNA complex or a chimeric single-guide RNA, Cas9 can generate site-specific DSBs within double-stranded DNA (dsDNA) target nucleic acids, which are repaired either by non-homologous end joining (NHEJ) or homologous recombination (HR), and variants of Cas9 (nickases) can generate single-stranded DNA breaks (SSBs). Thus, the Cas9 system provides a facile means of modifying genomic information. Catalytically inactive Cas9 alone or fused to transcriptional activator or repressor domains can be used to alter transcription levels at sites within double-stranded DNA (dsDNA) target nucleic acids by binding to the target site without cleavage.

There is a need in the art for methods of labeling single stranded nucleic acids (e.g., single stranded DNA, mRNA, rRNA, tRNA, microRNA, etc.) with minimal off-target effects and with minimal background signals.

SUMMARY

The present disclosure provides compositions and methods for labeling a single stranded target nucleic acid. Subject methods include contacting a single stranded target nucleic acid with a Cas9 protein, a Cas9 guide RNA, and a quenched PAMmer. A subject quenched PAMmer is a single stranded oligonucleotide having (i) a protospacer adjacent motif (PAM) sequence; (ii) a detectable label; (iii) a quencher moiety that quenches the detectable label; and (iv) at least one of: a specificity segment positioned 5' of the PAM sequence, and an orientation segment positioned 3' of the PAM sequence. In the subject methods, the Cas9 protein cleaves the quenched PAMmer at a cleavage site positioned between the detectable label and the quencher moiety to produce: (a) a first cleavage product that is hybridized with the target nucleic acid and comprises the detectable label; and (b) a second cleavage product that is not hybridized with the target nucleic acid and comprises the quencher moiety. In some cases, the quenched PAMmer comprises an orientation segment and a specificity segment.

The subject methods lead to cleavage of the quenched PAMmer such that one cleavage product (the first cleavage product) hybridizes to the target nucleic acid (e.g., remains hybridized to the target nucleic acid) and comprises the label (e.g., retains the detectable label) while a second cleavage product comprising the quencher moiety is not hybridized with the target nucleic acid and thus moves out of proximity of the detectable label (e.g., via diffusion), thus rendering the label detectable.

In some cases, the detectable label is positioned 3' of the cleavage site, the quencher moiety is positioned 5' of the cleavage site, and the quenched PAMmer comprises an orientation segment. In some cases, the detectable label is positioned 5' of the cleavage site, the quencher moiety is positioned 3' of the cleavage site, and the quenched PAMmer comprises a specificity segment. In some cases, the detectable label and the quencher moiety are both positioned 5' of the PAM sequence. In some cases, the detectable label is positioned 3' of the PAM sequence and the quencher moiety is positioned 5' of the PAM sequence. In some cases, the detectable label is positioned 5' of the PAM sequence and the quencher moiety is positioned 3' of the PAM sequence. In some cases, the quenched PAMmer comprises a 5' extension arm, positioned 5' of the PAM sequence, wherein the 5' extension arm comprises: (a) a nucleotide sequence that does not hybridize with the target nucleic acid, and (b) the quencher moiety. In some cases, the quenched PAMmer comprises a 3' extension arm, positioned 3' of the PAM sequence, wherein the 3' extension arm comprises: (a) a nucleotide sequence that does not hybridize with the target nucleic acid, and (b) the quencher moiety.

In some cases, the PAM sequence does not hybridize with the target nucleic acid when the quenched PAMmer is hybridized with the target nucleic acid. In some cases, the target nucleic acid does not comprise a sequence that is: (i) complementary to the PAM sequence, and (ii) 5' of and adjacent to the first target site; whereby the PAM sequence does not hybridize with the target nucleic acid when the quenched PAMmer is hybridized with the target nucleic acid.

In some cases, the detectable label is a fluorescent label (e.g., a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, and a Biotium fluorescent dye (e.g., CF 640R, e.g., iCF640RN)).

In some cases, the quencher moiety can quench a fluorescent label (i.e., can quench a signal from a fluorescent label) (e.g., all fluorescent labels; fluorescent labels having emission spectra within a particular range; etc.). In some cases, the quencher moiety is a dark quencher. In some cases, the quencher moiety is selected from: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ (e.g., 5IAbRQ, iIB-QB), Iowa Black FQ (e.g., 5IAbkFQ), ZEN, IRDye QC-1, a QSY dye (e.g., QSY 7, QSY 9, QSY 21), AbsoluteQuencher, Eclipse, and a metal cluster.

In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). The subject methods can be performed outside of a cell in vitro, inside of a cell (e.g., in a living cell) in vitro or ex vivo, and/or inside of a cell (e.g., in a living cell) in vivo. Also provided are kits and libraries for performing the disclosed methods.

Features

Features of the present disclosure include a method of labeling a single stranded target nucleic acid, the method comprising contacting a single stranded target nucleic acid having a first target site comprising a first sequence of nucleotides and a second target site comprising a second sequence of nucleotides, wherein the second target site is positioned on the target nucleic acid 5' of the first target site, with: (a) a quenched PAMmer, wherein the quenched PAMmer is a single stranded oligonucleotide comprising: (a.i) a protospacer adjacent motif (PAM) sequence, (a.ii) a detectable label, (a.iii) a quencher moiety that quenches the detectable label, and (a.iv) at least one of: a specificity segment, positioned 5' of the PAM sequence, that hybridizes with nucleotides of the first target site, and an orientation segment, positioned 3' of the PAM sequence, that hybridizes with nucleotides of the second target site; (b) a Cas9 protein; and (c) a Cas9 guide RNA that forms a complex with the Cas9 protein and hybridizes with the first target site, whereby the Cas9 protein cleaves the quenched PAMmer at a cleavage site positioned between the detectable label and the quencher moiety to produce: (i) a first cleavage product that is hybridized with the target nucleic acid and comprises the detectable label; and (ii) a second cleavage product that is not hybridized with the target nucleic acid and comprises the quencher moiety.

In some cases, the detectable label is positioned 3' of the cleavage site, the quencher moiety is positioned 5' of the cleavage site, and the quenched PAMmer comprises an orientation segment. In some cases, the detectable label is positioned 5' of the cleavage site, the quencher moiety is positioned 3' of the cleavage site, and the quenched PAMmer comprises a specificity segment. In some cases, the detectable label and the quencher moiety are both positioned 5' of the PAM sequence. In some cases, the detectable label is positioned 3' of the PAM sequence and the quencher moiety is positioned 5' of the PAM sequence. In some cases, the detectable label is positioned 5' of the PAM sequence and the quencher moiety is positioned 3' of the PAM sequence. In some cases, the quenched PAMmer comprises an orientation segment and a specificity segment. In some cases, the quenched PAMmer comprises a 5' extension arm, positioned 5' of the PAM sequence, wherein the 5' extension arm comprises: (a) a nucleotide sequence that does not hybridize with the target nucleic acid, and (b) the quencher moiety. In some cases, the quenched PAMmer comprises a 3' extension arm, positioned 3' of the PAM sequence, wherein the 3' extension arm comprises: (a) a nucleotide sequence that does not hybridize with the target nucleic acid, and (b) the quencher moiety. In some cases, the PAM sequence is GG. In some cases, the PAM sequence is 5'-NGG-3', wherein N can be any nucleotide. In some cases, the PAM sequence does not hybridize with the target nucleic acid when the quenched PAMmer is hybridized with the target nucleic acid. In some cases, the target nucleic acid does not comprise a sequence that is: (i) complementary to the PAM sequence, and (ii) 5' of and adjacent to the first target site; whereby the PAM sequence does not hybridize with the target nucleic acid when the quenched PAMmer is hybridized with the target nucleic acid.

In some cases, 10 or fewer nucleotides are present in the target nucleic acid between the first and second target sites. In some cases, 2 or 3 nucleotides are present in the target nucleic acid between the first and second target sites. In some cases, the detectable label is a fluorescent label. In some cases, the fluorescent label is selected from: an Alexa Fluor® dye, an ATTO dye, a DyLight dye, a cyanine dye, a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, and a Biotium fluorescent dye (e.g., CF 640R, e.g., iCF640RN). In some cases, the quencher moiety is a dark quencher. In some cases, the quencher moiety is selected from: a dark quencher, a Black Hole Quencher® (BHQ®), a Qxl quencher, an ATTO quencher, dimethylaminoazobenzenesulfonic acid (Dabsyl), Iowa Black RQ (e.g., 5IAbRQ, iIB-QB), Iowa Black FQ (e.g., 5IAbkFQ), ZEN, IRDye QC-1, a QSY dye, AbsoluteQuencher, Eclipse, and a metal cluster. In some cases, the PAMmer comprises two or more detectable labels. In some cases, the PAMmer comprises two or more quencher moieties.

In some cases, the single stranded target nucleic acid is a single stranded RNA (ssRNA). In some cases, the target ssRNA is selected from: mRNA, rRNA, tRNA, non-coding RNA (ncRNA), long non-coding RNA (lncRNA), and microRNA (miRNA). In some cases, the target ssRNA is mRNA and the method results in a detectably labeled mRNA. In some cases, the single stranded target nucleic acid is single stranded DNA (ssDNA). In some cases, the single stranded target nucleic acid is from a virus.

In some cases, the contacting is outside of a cell in vitro. In some cases, the contacting is in a target cell in vitro or ex vivo. In some cases, the contacting is in a target cell in vivo. In some cases, the target cell is a living cell.

In some cases, the Cas9 guide RNA is a DNA/RNA hybrid nucleic acid comprising deoxyribonucleotides that hybridize with the target nucleic acid. In some cases, the Cas9 guide RNA is a Cas9 dual guide RNA. In some cases, the Cas9 guide RNA is a Cas9 single guide RNA. In some cases, the Cas9 protein is a variant Cas9 protein that cleaves the quenched PAMmer but does not cleave the target nucleic acid. In some cases, the variant Cas9 protein has a mutation in the HNH domain relative to a wild type Cas9 protein. In some cases, the Cas9 protein cleaves the quenched PAMmer and modifies the target nucleic acid. In some cases, the Cas9 protein cleaves the quenched PAMmer and cleaves the target nucleic acid.

Features of the present disclosure include a method of detecting a single stranded target nucleic acid in a sample, wherein the target nucleic acid comprises a first target site comprising a first sequence of nucleotides and a second target site comprising a second sequence of nucleotides, wherein the second target site is positioned on the target nucleic acid 5' of the first target site, the method comprising: (I) contacting the sample with: (a) a quenched PAMmer, wherein the quenched PAMmer is a single stranded oligonucleotide comprising: (a.i) a protospacer adjacent motif (PAM) sequence, (a.ii) a detectable label, (a.iii) a quencher moiety that quenches the detectable label, and (a.iv) at least one of: a specificity segment, positioned 5' of the PAM sequence, that hybridizes with nucleotides of the first target site, and an orientation segment, positioned 3' of the PAM sequence, that hybridizes with nucleotides of the second target site; (b) a Cas9 protein; and (c) a Cas9 guide RNA that forms a complex with the Cas9 protein and hybridizes with the first target site, whereby the Cas9 protein cleaves the quenched PAMmer at a cleavage site positioned between the detectable label and the quencher moiety to produce: (i) a first cleavage product that is hybridized with the target nucleic acid and comprises the detectable label; and (ii) a second cleavage product that is not hybridized with the target nucleic acid and comprises the quencher moiety; and (II) measuring a signal from the detectable label.

In some cases, the detecting is quantitative. In some cases, the detecting is qualitative. In some cases, the sample comprises single stranded nucleic acids that are not in a cell. In some cases, the sample comprises a cell and the target nucleic acid is in the cell.

Features of the present disclosure include a composition comprising: (i) a quenched PAMmer, wherein the quenched PAMmer is a single stranded oligonucleotide comprising: (a) a protospacer adjacent motif (PAM) sequence, (b) a detectable label, (c) a quencher moiety that quenches the detectable label, and (d) at least one of: a specificity segment, positioned 5' of the PAM sequence, that hybridizes with nucleotides of a first target site of a target nucleic acid, and an orientation segment, positioned 3' of the PAM sequence, that hybridizes with nucleotides of a second target site of the target nucleic acid; and (ii) a Cas9 guide RNA comprising a nucleotide sequence that hybridizes with the first target site of the target nucleic acid.

Features of the present disclosure include a kit comprising: (i) a quenched PAMmer, wherein the quenched PAMmer is a single stranded oligonucleotide comprising: (a) a protospacer adjacent motif (PAM) sequence, (b) a detectable label, (c) a quencher moiety that quenches the detectable label, and (d) at least one of: a specificity segment, positioned 5' of the PAM sequence, that hybridizes with nucleotides of a first target site of a target nucleic acid, and an orientation segment, positioned 3' of the PAM sequence, that hybridizes with nucleotides of a second target site of the target nucleic acid; and (ii) a Cas9 guide RNA comprising a nucleotide sequence that hybridizes with the first target site of the target nucleic acid; wherein (i) and (ii) are present in the same or separate containers.

Features of the present disclosure include a library comprising: two or more labeling nucleic acid pairs, wherein each labeling nucleic acid pair comprises: (i) a quenched PAMmer, wherein the quenched PAMmer is a single stranded oligonucleotide comprising: (a) a protospacer adjacent motif (PAM) sequence, (b) a detectable label, (c) a quencher moiety that quenches the detectable label, and (d) at least one of: a specificity segment, positioned 5' of the PAM sequence, that hybridizes with nucleotides of a first target site of a target nucleic acid, and an orientation segment, positioned 3' of the PAM sequence, that hybridizes with nucleotides of a second target site of the target nucleic acid; and (ii) a Cas9 guide RNA comprising a nucleotide sequence that hybridizes with the first target site of the target nucleic acid.

BRIEF DESCRIPTION OF THE DRAWINGS

FIGS. 4A-4B presents assays for activation of Cas9 cleavage by a DNA oligonucleotide complementary to a single stranded target nucleic acid (e.g., ssRNA), but lacking the PAM; and assays for activation of Cas9 cleavage where a PAMmer includes a specificity segment.

FIGS. 8A-8I provide a schematic drawing of example embodiments of subject compositions and methods. Note that the vertical lines representing hybridization are not to scale and do not necessarily represent the actual number of bases hybridized (base pairs) for any particular segment/region. (FIGS. 8A-8B) Each embodiment depicted includes a PAMmer, which is hybridized to a single stranded target nucleic acid; and a Cas9 guide RNA, which is hybridized to the target nucleic acid and is associated with a Cas9 protein. (FIGS. 8C-8D) Each embodiment depicted includes a PAMmer having a specificity segment and an orientation segment. The PAM sequence is complementary to the target nucleic acid in FIG. 8C, and is not complementary to the target nucleic acid in 8D. (FIG. 8E) Two possible embodiments of a PAMmer having a specificity segment and not having an orientation segment. (FIG. 8F) Two possible embodiments of a PAMmer having an orientation segment and not having a specificity segment. (FIGS. 8G-8I) Three example embodiments of a subject quenched PAMmer. Note that in panels G and H, the detectable label can be located at any convenient position 3' of the cleavage site, and the quencher moiety can be located at any convenient position 5' of the cleavage site, as long at the quencher moiety quenches the signal from the detectable label prior to cleavage. Note that in panel I, the detectable label can be located at any convenient position 5' of the cleavage site, and the quencher moiety can be located at any convenient position 3' of the cleavage site, as long at the quencher moiety quenches the signal from the detectable label prior to cleavage.

FIGS. 9A-9B depict the amino acid sequence of a Cas9 protein from *Streptococcus pyogenes* (SEQ ID NO:8). Cas9 has domains homologous to both HNH and RuvC endonucleases. (FIG. 9A) Motifs 1-4 are overlined. (FIG. 9B) Domains 1 and 2 are overlined.

FIG. 10 depicts a multiple sequence alignment of motifs 1-4 of Cas9 proteins from various diverse species. (*Streptococcus pyogenes* (motifs 1-4: SEQ ID NOs:260-263), *Legionella pneumophila* (motifs 1, 2, 4 and 3: SEQ ID NOs:1644-1647), *Gamma proteobacterium* (motifs 1, 2, 4 and 3: SEQ ID NOs:1648-1651), *Listeria innocua* (motifs 1, 2, 4 and 3: SEQ ID NOs:1652-1655), *Lactobacillus gasseri* (motifs 1, 2, 4 and 3: SEQ ID NOs:1656-1659), *Eubacterium rectale* (motifs 1-4: SEQ ID NOs:1660-1663), *Staphylococcus lugdunensis* (motifs 1, 2, 4 and 3: SEQ ID NOs: 1664-1667), *Mycoplasma synoviae* (motifs 1, 2, 4 and 3: SEQ ID NOs:1668-1671), *Mycoplasma mobile* (motifs 1, 2, 4 and 3: SEQ ID NOs:1672-1675), *Wolinella succinogenes* (motifs 1, 2, 4 and 3: SEQ ID NOs:1676-1679), *Flavobacterium columnare* (motifs 1, 2, 4 and 3: SEQ ID NOs:1680-1683), *Fibrobacter succinogenes* (motifs 1, 2, 4 and 3: SEQ ID NOs:1684-1687), *Bacteroides fragilis* (motifs 1, 2, 4 and 3: SEQ ID NOs:1688-1691), *Acidothermus cellulolyticus* (motifs 1, 2, 4 and 3: SEQ ID NOs:1692-1695), and *Bifidobacterium dentium* (motifs 1, 2, 4 and 3: SEQ ID NOs: 1696-1699).

Figures 11A, 11B:
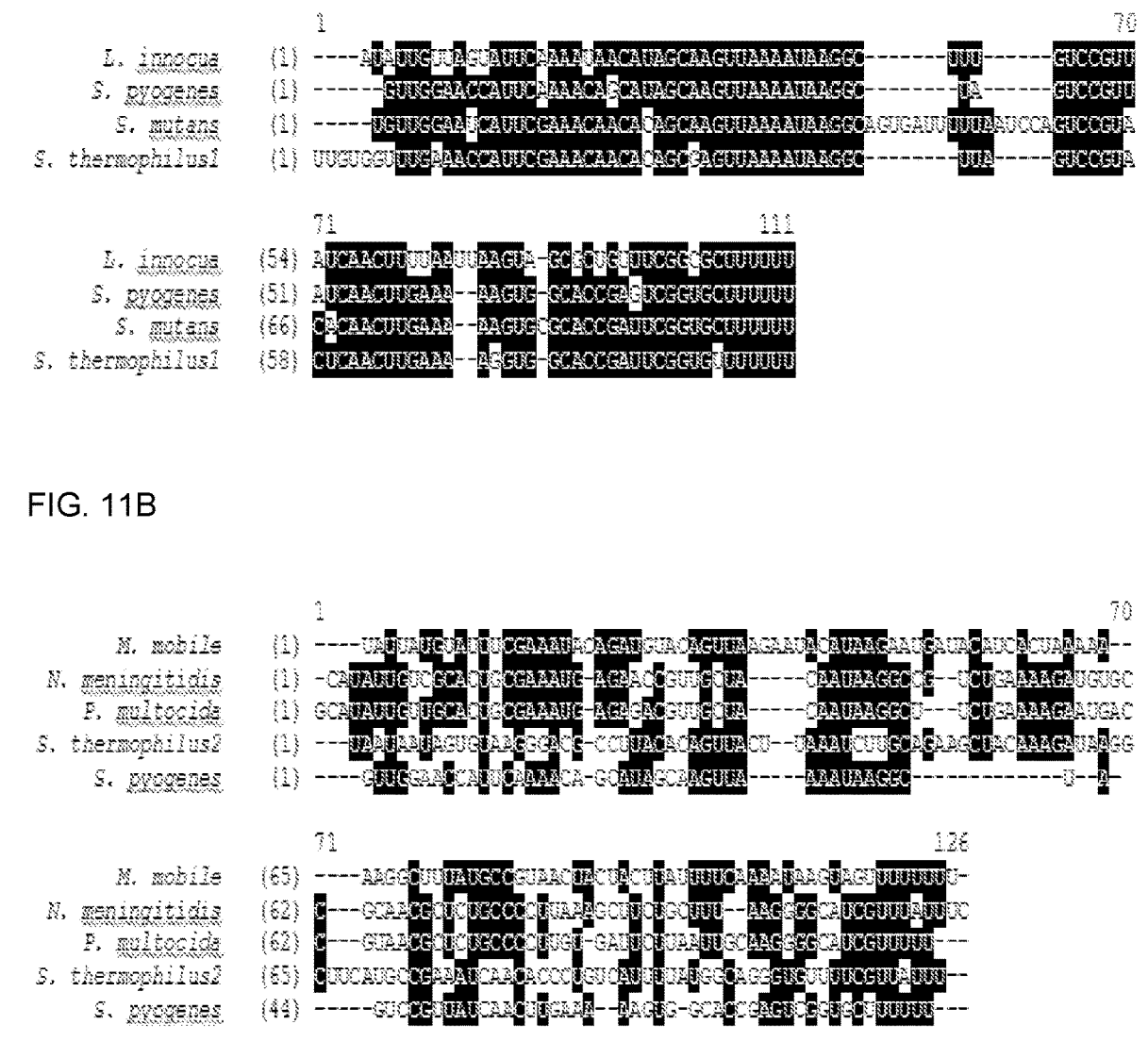

FIGS. 11A-11B provide alignments of naturally occurring tracrRNA ("activator") sequences from various species (*L. innocua* (SEQ ID NO:268); *S. pyogenes* (SEQ ID NO:267); *S. mutans* (SEQ ID NO:269); *S. thermophilus*1 (SEQ ID NO:270); *M. mobile* (SEQ ID NO:274); *N. meningitides* (SEQ ID NO:272); *P. multocida* (SEQ ID NO:273); *S. thermophilus*2 (SEQ ID NO:271); and *S. pyogenes* (SEQ ID NO:267). (FIG. 11A) multiple sequence alignment of selected tracrRNA orthologues (AlignX, VectorNTI package, Invitrogen) associated with CRISPR/Cas loci of similar architecture and highly similar Cas9 sequences. Black boxes represent shared nucleotides (FIG. 11B) multiple sequence alignment of selected tracrRNA orthologues (AlignX, VectorNTI package, Invitrogen) associated with CRISPR/Cas loci of different architecture and non-closely related Cas9 sequences. Note the sequence similarity of *N. meningitidis* and *P. multocida* tracrRNA orthologues. Black boxes represent shared nucleotides. For more exemplary activator sequences, see SEQ ID NOs:431-562.

FIGS. 12A-12B provide alignments of naturally occurring duplex-forming segments of crRNA ("targeter") sequences from various species (*L. innocua* (SEQ ID NO:577); *S. pyogenes* (SEQ ID NO:569); *S. mutans* (SEQ ID NO:574); *S. thermophilus*1 (SEQ ID NO:575); *C. jejuni* (SEQ ID NO:597); *S. pyogenes* (SEQ ID NO:569); *F. novicida* (SEQ ID NO:572); *M. mobile* (SEQ ID NO:571); *N. meningitides* (SEQ ID NO:579); *P. multocida* (SEQ ID NO:570); and *S. thermophilus*2 (SEQ ID NO:576). (A) multiple sequence alignments of exemplary duplex-forming segment of targeter sequences (AlignX, VectorNTI package, Invitrogen) associated with the loci of similar architecture and highly similar Cas9 sequences. (FIG. 12B) multiple sequence alignments of exemplary duplex-forming segment of targeter sequences (AlignX, VectorNTI package, Invitrogen) associated with the loci of different architecture and diverse Cas9 sequences. Black boxes represent shared nucleotides. For more exemplary duplex-forming segments targeter sequences, see SEQ ID NOs:563-679.

FIG. 13 provides a schematic of hybridization for naturally occurring duplex-forming segments of the crRNA ("targeter") with the duplex-forming segment of the corresponding tracrRNA orthologue ("activator"). Upper sequence, targeter; lower sequence, duplex-forming segment of the corresponding activator. The CRISPR loci belong to the Type II (Nmeni/CASS4) CRISPR/Cas system. Nomenclature is according to the CRISPR database (CRISPR DB). SEQ ID numbers are listed top to bottom: *S. pyogenes* (SEQ ID NOs:569 and 442); *S. mutans* (SEQ ID NOs:574 and 443); *S. thermophilus*1 (SEQ ID NOs:575 and 444); *S. thermophilus*2 (SEQ ID NOs:576 and 445); *L. innocua* (SEQ ID NOs:577 and 446); *T. denticola* (SEQ ID NOs:578 and 448); *N. meningitides* (SEQ ID NOs:579 and 449); *S. gordonii* (SEQ ID NOs:580 and 451); *B. bifidum* (SEQ ID NOs:581 and 452); *L. salivarius* (SEQ ID NOs:582 and 453); *F. tularensis* (SEQ ID NOs:583, 454, 584, and 455); and *L. pneumophila* (SEQ ID NOs:585 and 456). Note that some species contain more than one Type II CRISPR locus. For more exemplary activator sequences, see SEQ ID NOs:431-562. For more exemplary duplex-forming segments of targeter sequences, see SEQ ID NOs:563-679.

FIG. 14 depicts example tracrRNA (activator) and crRNA (targeter) sequences from two species. A degree of interchangeability exists; for example, the *S. pyogenes* Cas9 protein is functional with tracrRNA and crRNA derived from *L. innocua*. "I" denotes a canonical Watson-Crick base pair while "•" denotes a G-U wobble base pair. "Variable 20 nt" or "20 nt" represents the targeting segment that is complementary to a target nucleic acid (this region can be up to about 100 nt in length). Also shown is one possible design of a Cas9 single guide RNA that incorporates features of the targeter and the activator. Cas9 protein sequences from a wide variety of species are set forth as SEQ ID NOs:1-256 and 795-1346. *Streptococcus pyogenes* (top to bottom, SEQ ID NOs: 563, 478, 680); *Listeria innocua* (top to bottom, SEQ ID NOs: 564, 479, 681). The sequences provided are non-limiting examples and are meant to illustrate how single and Cas9 dual guide RNAs can be designed based on targeter and activator sequences from a wide variety of species. Various examples of suitable sequences from a wide variety of species are set forth as follows (Cas9 protein: SEQ ID NOs:1-259; tracrRNAs: SEQ ID NOs:431-562, or the complements thereof; crRNAs: SEQ ID NOs:563-679, or the complements thereof; and exemplary Cas9 single guide RNAs designed from targeter and activator sequences: SEQ ID NOs:680-682).

FIGS. 15A-15D list examples of suitable fusion partners (or fragments thereof) for a Cas9 protein (e.g., wild type Cas9, variant Cas9). Suitable fusion partners include, but are not limited to, those listed.

(FIG. 16C) Top to bottom (SEQ ID NOs:1364-1375). (FIG. 16D) Top to bottom (SEQ ID NOs:1376-1391).

FIGS. 18A-18E depict RNA-guided Cas9 cleavage of ssRNA targets in the presence of a short PAM presenting DNA oligonucleotide (PAMmer). "PAMmer" (SEQ ID NO: 1471); "Target ssRNA" (SEQ ID NO: 1472).

FIGS. 21A-21H depict RNA-guided Cas9 targeting of non-PAM sites on ssRNA; and isolation of GAPDH mRNA from HeLa cells in a tagless manner. (H) (Top to bottom, SEQ ID NOs: 1473-1478).

FIGS. 26A-26E provide data related to site-specific biotin labeling of Cas9.

FIG. 30B Top to Bottom: SEQ ID NOs:1641-1642. FIG. 30C: SEQ ID NO:1619.

DEFINITIONS

Figure 1:
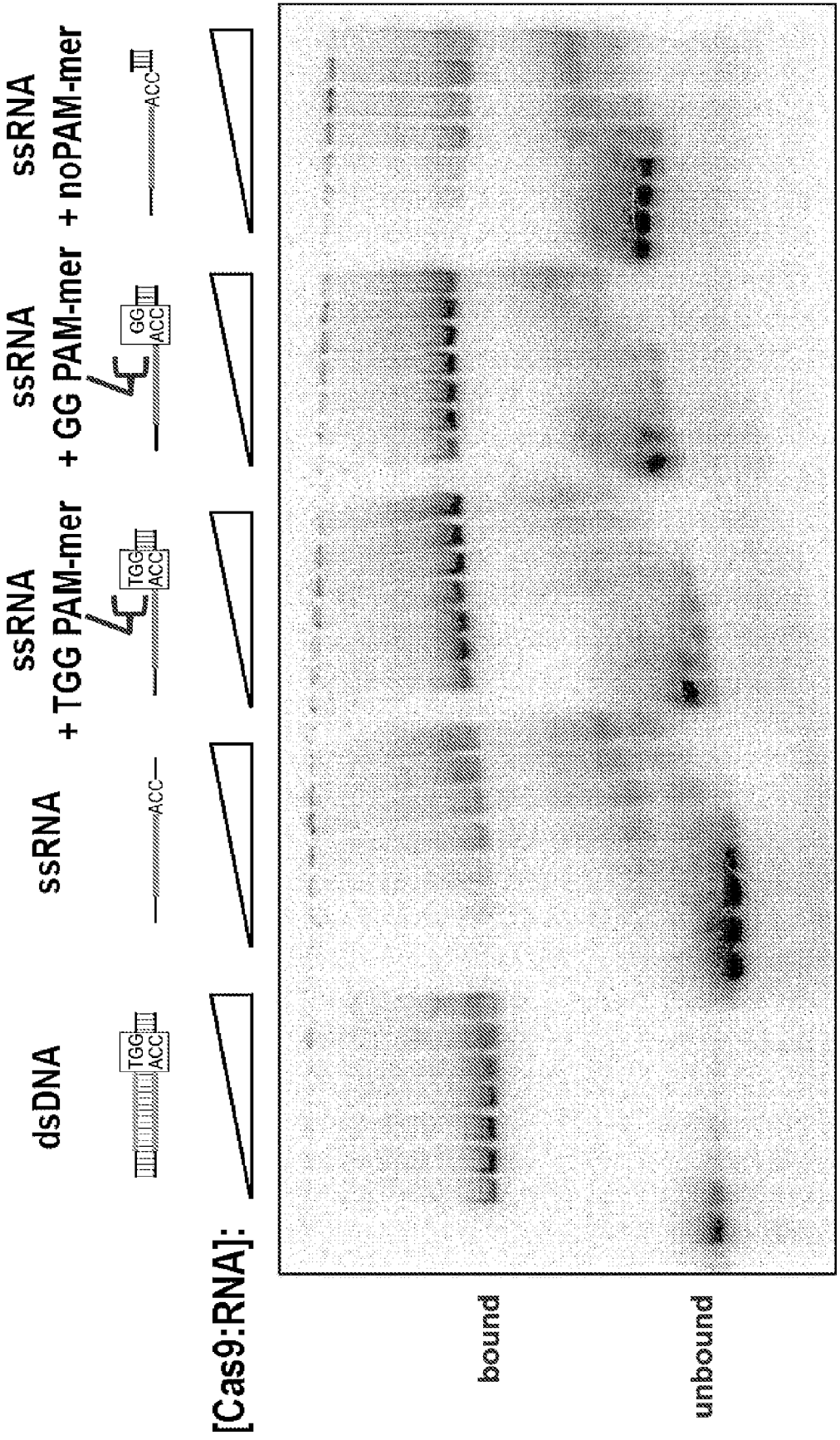
FIG. 1 presents binding assays for Cas9 binding to single stranded target nucleic acid molecules (e.g., single stranded RNA (ssRNA)) in the presence of a protospacer adjacent motif (PAM)-containing oligonucleotide ("PAMmer").

The terms "polynucleotide" and "nucleic acid," used interchangeably herein, refer to a polymeric form of nucleotides of any length, either ribonucleotides or deoxyribonucleotides. Thus, the terms "polynucleotide" and "nucleic acid" encompass single-stranded DNA; double-stranded DNA; multi-stranded DNA; single-stranded RNA; double-stranded RNA; multi-stranded RNA; genomic DNA; cDNA; DNA-RNA hybrids; and a polymer comprising purine and pyrimidine bases or other natural, chemically or biochemically modified, non-natural, or derivatized nucleotide bases.

The term "oligonucleotide" refers to a polynucleotide of between 3 and 100 nucleotides of single- or double-stranded nucleic acid (e.g., DNA, RNA, or a modified nucleic acid). However, for the purposes of this disclosure, there is no upper limit to the length of an oligonucleotide. Oligonucleotides are also known as "oligomers" or "oligos" and can be isolated from genes, transcribed (in vitro and/or in vivo), or chemically synthesized. The terms "polynucleotide" and "nucleic acid" should be understood to include, as applicable to the embodiments being described, single-stranded (such as sense or antisense) and double-stranded polynucleotides.

A "stem-loop structure" refers to a nucleic acid having a secondary structure that includes a region of nucleotides which are known or predicted to form a double strand (step portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. As is known in the art, a stem-loop structure does not require exact base-pairing. Thus, the stem may include one or more base mismatches. Alternatively, the base-pairing may be exact, i.e. not include any mismatches.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a ssRNA target nucleic acid base pairs with a DNA PAMmer, when a DNA target nucleic acid base pairs with a Cas9 guide RNA, etc.): guanine (G) can also base pair with uracil (U). For example, G/U base-pairing is partially responsible for the degeneracy (i.e., redundancy) of the genetic code in the context of tRNA anti-codon base-pairing with codons in mRNA. Thus, in the context of this disclosure, a guanine (G) (e.g., of a protein-binding segment (dsRNA duplex) of a Cas9 guide RNA molecule; of a target nucleic acid base pairing with a Cas9 guide RNA and/or a PAMmer, etc.) is considered complementary to both a uracil (U) and to an adenine (A). For example, when a G/U base-pair can be made at a given nucleotide position of a protein-binding segment (e.g., dsRNA duplex) of a Cas9 guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). The temperature and wash solution salt concentration may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Exemplary methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a Cas9 guide RNA complex and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_d$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_d$.

By "binding domain" it is meant a protein domain that is able to bind non-covalently to another molecule. A binding domain can bind to, for example, a DNA molecule (a DNA-binding domain), an RNA molecule (an RNA-binding domain) and/or a protein molecule (a protein-binding domain). In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g. tRNA, rRNA, microRNA (miRNA), a "non-coding" RNA (ncRNA), a Cas9 guide RNA, etc.).

A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., Cas9 guide RNA) or a coding sequence (e.g., Cas9 protein) and/or regulate translation of an encoded polypeptide.

As used herein, a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is wild type (and naturally occurring).

The term "chimeric" as used herein as applied to a nucleic acid or polypeptide refers to two components that are defined by structures derived from different sources. For example, where "chimeric" is used in the context of a chimeric polypeptide (e.g., a chimeric Cas9 protein), the chimeric polypeptide includes amino acid sequences that are derived from different polypeptides. A chimeric polypeptide may comprise either modified or naturally-occurring polypeptide sequences (e.g., a first amino acid sequence from a modified or unmodified Cas9 protein; and a second amino acid sequence other than the Cas9 protein). Similarly, "chimeric" in the context of a polynucleotide encoding a chimeric polypeptide includes nucleotide sequences derived from different coding regions (e.g., a first nucleotide sequence encoding a modified or unmodified Cas9 protein; and a second nucleotide sequence encoding a polypeptide other than a Cas9 protein).

The term "chimeric polypeptide" refers to a polypeptide which is made by the combination (i.e., "fusion") of two otherwise separated segments of amino sequence, usually through human intervention. A polypeptide that comprises a chimeric amino acid sequence is a chimeric polypeptide. Some chimeric polypeptides can be referred to as "fusion variants."

"Heterologous," as used herein, means a nucleotide or polypeptide sequence that is not found in the native nucleic acid or protein, respectively. For example, in a chimeric Cas9 protein, the RNA-binding domain of a naturally-occurring bacterial Cas9 protein (or a variant thereof) may be fused to a heterologous polypeptide sequence (i.e. a polypeptide sequence from a protein other than Cas9 or a polypeptide sequence from another organism). The heterologous polypeptide sequence may exhibit an activity (e.g., enzymatic activity) that will also be exhibited by the chimeric Cas9 protein (e.g., methyltransferase activity, acetyltransferase activity, kinase activity, ubiquitinating activity, etc.). A heterologous nucleic acid sequence may be linked to a naturally-occurring nucleic acid sequence (or a variant thereof) (e.g., by genetic engineering) to generate a chimeric nucleotide sequence encoding a chimeric polypeptide. As another example, in a fusion variant Cas9 protein, a variant Cas9 protein may be fused to a heterologous polypeptide (i.e. a polypeptide other than Cas9), which exhibits an activity that will also be exhibited by the fusion variant Cas9 protein. A heterologous nucleic acid sequence may be linked to a variant Cas9 protein (e.g., by genetic engineering) to generate a nucleotide sequence encoding a fusion variant polypeptide.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., Cas9 guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

A "target nucleic acid" as used herein is a polynucleotide (e.g., RNA, DNA) that includes a "target site" or "target sequence." The terms "target site" or "target sequence" are used interchangeably herein to refer to a nucleic acid sequence present in a target nucleic acid to which a targeting segment of a Cas9 guide RNA will bind (see FIG. 8A-8I), provided sufficient conditions for binding exist; and/or to which a region (segment) of a PAMmer (e.g., a specificity segment and/or an orientation segment) will bind. For example, the target site (or target sequence) 5'-GAGCAUAUC-3' within a target nucleic acid is targeted by (or is bound by, or hybridizes with, or is complementary to) the sequence 5'-GAUAUGCUC-3'. Suitable hybridization conditions include physiological conditions normally present in a cell. For a double stranded target nucleic acid, the strand of the target nucleic acid that is complementary to and hybridizes with the Cas9 guide RNA is referred to as the "complementary strand"; while the strand of the target nucleic acid that is complementary to the "complementary strand" (and is therefore not complementary to the Cas9 guide RNA) is referred to as the "noncomplementary strand" or "non-complementary strand". In cases where the target nucleic acid is a single stranded target nucleic acid (e.g., single stranded DNA (ssDNA), single stranded RNA (ssRNA)), the Cas9 guide RNA is complementary to and hybridizes with single stranded target nucleic acid.

By "Cas9 protein" (as would be recognized by one of ordinary skill in the art) it is meant a protein that binds a Cas9 guide RNA and is targeted to a specific sequence (a target site) in a target nucleic acid (e.g., Cas9 proteins are characteristic of naturally existing type II CRISPR systems). A Cas9 protein is targeted at a target site by the Cas9 guide RNA to which it is bound. The Cas9 guide RNA comprises a sequence that is complementary to a target sequence within the target nucleic acid, thus targeting the bound Cas9 protein to a specific location within the target nucleic acid (the target sequence) (e.g., stabilizing the interaction of Cas9 with the target nucleic acid). In some cases, the Cas9 protein is a naturally-occurring protein (e.g, naturally occurs in bacterial and/or archaeal cells). In other cases, the Cas9 protein is not a naturally-occurring protein (e.g., the Cas9 protein can be a variant Cas9 protein, a chimeric protein as discussed below, and the like). Examples of suitable Cas9 proteins include, but are not limited to, those set forth in SEQ ID NOs: 1-259, and 795-1346. Naturally occurring Cas9 proteins bind a Cas9 guide RNA, are thereby directed to a specific sequence within a target nucleic acid (a target site), and cleave the target nucleic acid (e.g., cleave dsDNA to generate a double strand break, cleave ssDNA, cleave ssRNA, etc.). A chimeric Cas9 protein (a Cas9 fusion protein) is a fusion protein that is fused to a heterologous protein. The fusion partner can provide an activity, e.g., enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases a portion of the Cas9 protein (e.g., the RuvC domain and/or the HNH domain) exhibits reduced nuclease activity relative to the corresponding portion of a wild type Cas9 protein. In some cases, the Cas9 protein is enzymatically inactive. In some cases, the Cas9 protein is enzymatically inactive, but retains binding to a target nucleic acid when complexed with a Cas9 guide RNA.

By "cleavage" it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. In certain embodiments, a complex comprising a Cas9 guide RNA and a Cas9 protein is used for targeted cleavage of a single stranded target nucleic acid (e.g., ssRNA, ssDNA).

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.).

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide (e.g., RuvCI, RuvCII, and RuvCIII of a Cas9 protein).

A nucleic acid molecule that binds to the Cas9 protein and targets the protein to a specific location within the target nucleic acid is referred to herein as a "Cas9 guide RNA". A Cas9 guide RNA comprises two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/ section of a complex such that a segment may comprise regions of more than one molecule. For example, in some cases the Cas9 guide RNA is one nucleic acid molecule (e.g., one RNA molecule) and the protein-binding segment therefore comprises a region of that one molecule. In other cases, the protein-binding segment (described below) of a Cas9 guide RNA includes regions of two separate molecules that are hybridized along a region of complementarity (forming a dsRNA duplex). The definition of "segment," unless otherwise specifically defined in a particular context, is not limited to a specific number of total base pairs, is not limited to any particular number of base pairs from a given nucleic acid molecule, is not limited to a particular number of separate molecules within a complex, and may include regions of nucleic acid molecules that are of any total length and may or may not include regions with complementarity to other molecules.

In some embodiments, a subject nucleic acid (e.g., a Cas9 guide RNA, a nucleic acid comprising a nucleotide sequence encoding a Cas9 guide RNA; a nucleic acid encoding a Cas9 protein; a PAMmer, etc.) comprises a modification or sequence (e.g., an additional segment at the 5' and/or 3' end) that provides for an additional desirable feature (e.g., modified or regulated stability; subcellular targeting; tracking, e.g., a fluorescent label; a binding site for a protein or protein complex; etc.). Non-limiting examples include: a 5' cap (e.g., a 7-methylguanylate cap (m7G)); a 3' polyadenylated tail (i.e., a 3' poly(A) tail); a ribozyme sequence (e.g. to allow for self-cleavage and release of a mature molecule in a regulated fashion); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the nucleic acid to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA and/or RNA, including transcriptional activators, transcriptional repressors, DNA methyltransferases, DNA demethylases, histone acetyltransferases, histone deacetylases, and the like); and combinations thereof.

A Cas9 guide RNA and a Cas9 protein form a complex (i.e., bind via non-covalent interactions). The guide RNA provides target specificity to the complex by comprising a nucleotide sequence that is complementary to a sequence of a target nucleic acid. The Cas9 protein of the complex provides the site-specific activity. In other words, the Cas9 protein is guided to a target nucleic acid sequence (e.g. a target sequence in a chromosomal nucleic acid; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; etc.) by virtue of its association with the protein-binding segment of the Cas9 guide RNA.

In some embodiments, a Cas9 guide RNA comprises two separate nucleic acid molecules: an "activator" and a "targeter" (see below) and is referred to herein as a "Cas9 dual guide RNA", a "double-molecule guide RNA", a "dual guide RNA", a "two-molecule guide RNA", or simply "dgRNA." In some embodiments, the Cas9 guide RNA has an activator and a targeter (as are present in a dual guide RNA), where the activator and targeter are covalently linked to one another (e.g., via intervening nucleotides) and is referred to herein as a "Cas9 single guide RNA", a "single-molecule guide RNA," or a "one-molecule guide RNA." The term "Cas9 guide RNA" is inclusive, referring to both Cas9 dual guide RNAs (dgRNAs) and to Cas9 single guide RNAs (sgRNAs). In some cases, a Cas9 guide RNA is a DNA/RNA hybrid molecule.

A "host cell" or "target cell" as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism.

Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This quiescent state may be temporary, i.e. reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

In some instances, a component (e.g., a nucleic acid component (e.g., a Cas9 guide RNA, a PAMmer, a quenched PAMmer, etc.); a protein component (e.g., a Cas9 protein, a variant Cas9 protein); and the like) includes a detectable label. The terms "label", "detectable label", or "label moiety" as used herein refer to any moiety that provides for signal detection and may vary widely depending on the particular nature of the assay to detect the label. Label moieties (e.g., quantum dots, tethered fluorescent proteins, etc.) of interest include both directly detectable labels (direct labels; e.g., a fluorescent label) and indirectly detectable labels (indirect labels; e.g., a binding pair member).

A fluorescent label can be any fluorescent label (e.g., a fluorescent dye (e.g., fluorescein, Texas red, rhodamine, ALEXAFLUOR® labels, and the like), a fluorescent protein (e.g., GFP, EGFP, YFP, RFP, CFP, YFP, cherry, tomato, tangerine, and any fluorescent derivative thereof), etc.). Suitable detectable (directly or indirectly) label moieties, for use in a composition or method of the present disclosure, include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^3$H, $^{125}$I, $^{35}$S, $^{14}$C, or $^{32}$P); an enzyme (an indirect label)(e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, aspirate, and the like. A "biological sample" includes a sample comprising target cells and/or normal control cells, or is suspected of comprising such cells. The definition includes biological fluids derived therefrom (e.g., cancerous cell, infected cell, etc.), e.g., a sample comprising polynucleotides and/or polypeptides that is obtained from such cells (e.g., a cell lysate or other cell extract comprising polynucleotides and/or polypeptides). A biological sample comprising an inflicted cell (e.g., cancer cell, an infected cell, etc.) from a patient can also include non-inflicted cells.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions and methods for labeling a single stranded target nucleic acid. In some cases, a composition of the present disclosure includes a Cas9 protein, a Cas9 guide RNA, and a quenched PAMmer. A subject quenched PAMmer is a single stranded oligonucleotide having (i) a protospacer adjacent motif (PAM) sequence; (ii) a detectable label; (iii) a quencher moiety that quenches the detectable label; and (iv) at least one of: a specificity segment positioned 5' of the PAM sequence, and an orientation segment positioned 3' of the PAM sequence. In the subject methods, the Cas9 protein cleaves the quenched PAMmer at a cleavage site positioned between the detectable label and the quencher moiety to produce: (a) a first cleavage product that is hybridized with the target nucleic acid and comprises the detectable label; and (b) a second cleavage product that is not hybridized with the target nucleic acid and comprises the quencher moiety. In some cases, the quenched PAMmer comprises an orientation segment and a specificity segment.

The subject methods lead to cleavage of the quenched PAMmer such that one cleavage product (the first cleavage product) hybridizes to the target nucleic acid (e.g., remains hybridized to the target nucleic acid) and comprises the label (e.g., retains the detectable label) while a second cleavage product comprising the quencher moiety is not hybridized with the target nucleic acid and thus moves out of proximity of the detectable label (e.g., via diffusion), thus rendering the label detectable.

Throughout the description below, when referring to the components (e.g., a PAMmer, e.g., a quenched PAMmer; a Cas9 guide RNA; a Cas9 protein; etc.) of subject compositions and methods, terms describing the components can also refer to nucleic acids encoding the components because components of the disclosure can be provided as nucleic acids encoding the component. For example, when a composition or method includes a Cas9 protein, it is understood that the Cas9 can be provided as the actual polypeptide or as a nucleic acid (DNA or RNA) encoding the same. Likewise, when a composition or method includes a Cas9 guide RNA, it is understood that the Cas9 guide RNA can be provided as RNA or as a nucleic acid (DNA) encoding the same. For example, in some cases a Cas9 guide RNA is a modified nucleic acid, in some cases a Cas9 guide RNA is a DNA/RNA hybrid molecule, and in some cases a Cas9 guide RNA is RNA, in which case the guide RNA can be provided as RNA or as a DNA (e.g., plasmid) encoding the Cas9 guide RNA.

Compositions and Components

The present disclosure provides compositions for labeling a single stranded target nucleic acid. A subject composition includes a quenched PAMmer and at least one of: (i) a Cas9 guide RNA (e.g., a dual-guide RNA, a single-guide RNA, an RNA/DNA hybrid guide RNA, etc.), and (ii) a Cas9 protein. FIG. 8A-8I presents schematic depictions of example embodiments of the present disclosure.

Quenched PAMmer

The present disclosure provides a quenched PAMmer. A subject "quenched PAMmer" is a PAMmer (described in more detail below) that has a detectable label and a quencher moiety that quenches the signal from the detectable label. Thus, a "quenched PAMmer" is a single stranded oligonucleotide (e.g., DNA, RNA, a modified nucleic acid (described below), etc.) that hybridizes to a single stranded target nucleic acid (thus converting the single stranded target nucleic acid into a double stranded target nucleic acid at a desired position), and provides a protospacer adjacent motif (PAM) sequence. Thus, when describing the features of a PAMmer throughout, the same description holds true for a quenched PAMmer, with the exception that a quenched PAMmer includes a detectable label and a quencher moiety. Thus, the term PAMmer encompasses the term "quenched PAMmer."

A PAMmer includes a PAM sequence and at least one of: an orientation segment (which is positioned 3' of the PAM sequence), and a specificity segment (which is positioned 5' of the PAM sequence). A specificity segment includes a nucleotide sequence that is complementary to a first target nucleotide sequence in a target nucleic acid (i.e., the sequence that is targeted by the specificity segment), where the first target nucleotide sequence overlaps (in some cases 100%) with the sequence targeted by the targeting segment of the Cas9 guide RNA. In other words, the specificity segment is complementary with (and hybridizes to) the target site of the target nucleic acid (see FIGS. 8A-8D).

An orientation segment has a nucleotide sequence that is complementary to a second target nucleotide sequence in a target nucleic acid (i.e., the sequence that is targeted by the orientation segment) (e.g., see FIG. 8A-8I). In some cases, a subject PAMmer includes a PAM sequence and an orientation segment, but does not include a specificity segment. In some cases, a subject PAMmer includes a PAM sequence and a specificity segment, but does not include an orientation segment.

In some cases, a PAMmer having a specificity segment is referred to herein as a "5' extended PAMmer." The term "5' extended PAMmer" refers to a situation in which a PAMmer includes nucleotides 5' of the PAM sequence. The term "5' extended PAMmer" encompasses a PAMmer having a specificity segment, but also encompasses a PAMmer that has nucleotides 5' of the PAM sequence that do not constitute a specificity segment. A stretch of one or more nucleotides 5' of the PAM sequence that do not constitute a specificity segment is herein referred to as a "5' extension arm". Thus, in some cases, the nucleotides that are 5' of the PAM sequence constitute a specificity segment (i.e., the nucleotides hybridize to the target nucleic acid)(see below for a more detailed discussion regarding a specificity segment), and in some cases, the nucleotide(s) that are 5' of the PAM sequence constitute a 5' extension arm (i.e., do not constitute a specificity segment, do not hybridize with the target nucleic acid). In some cases, a PAMmer (e.g., a quenched PAMmer) has a 5' extension (and the quenched PAMmer is therefore a 5' extended PAMmer), having both a 5' extension arm and a specificity segment (e.g, a 5' extension arm can be positioned 5' of a specificity segment)(e.g., see FIG. 8G). In some cases, a subject PAMmer (e.g., a quenched PAMmer) has a 3' extension arm (one or more nucleotides that are 3' of the PAM sequence that do not hybridize with the target nucleic acid)(e.g., see FIG. 8I). Like a 5' extension arm, a subject PAMmer (e.g., quenched PAMmer) can have both an orientation segment and a 3' extension arm (e.g., where the 3' extension arm is 3' of the orientation segment).

In some cases, a subject PAMmer includes a PAM sequence, an orientation segment, and a specificity segment. The number of nucleotides (nt) present in the PAMmer between a specificity segment and an orientation segment can depend on a number of factors that include, but are not limited to: the length of the PAM sequence (which is present between the specificity segment and the orientation segment); the number of nucleotides present between the target site and the orientation site of the target nucleic acid; the presence or absence of additional sequences (e.g., aptamers, protein binding sequences, linker nucleotides, stability sequences, etc.) between the specificity segment and the orientation segment; etc. In some embodiments, the number of nucleotides (nt) present in the PAMmer between a specificity segment and an orientation segment is in a range of from 2 nt to 100 nt (e.g., 2 nt to 90 nt, 2 nt to 80 nt, 2 nt to 70 nt, 2 nt to 60 nt, 2 nt to 50 nt, 2 nt to 40 nt, 2 nt to 30 nt, 2 nt to 25 nt, 2 nt to 20 nt, 2 nt to 15 nt, or 2 nt to 10 nt). In some embodiments, the number of nucleotides (nt) present in the PAMmer between the specificity segment and the orientation segment is 100 nt or less (e.g., 90 nt or less, 80 nt or less, 70 nt or less, 60 nt or less, 50 nt or less, 40 nt or less, 30 nt or less, 25 nt or less, 25 nt or less, 20 nt or less, 15 nt or less, or 10 nt or less).

In some embodiments, the PAM sequence is immediately adjacent to the orientation segment, immediately adjacent to the specificity segment, and/or immediately adjacent to both the orientation segment and the specificity segment. In some embodiments, the number of nucleotides (nt) present in the PAMmer between the PAM sequence and the specificity segment of the PAMmer is in a range of from 0 nt to 10 nt (e.g., 0 nt to 9 nt, 0 nt to 8 nt, 0 nt to 7 nt, 0 nt to 6 nt, 0 nt to 5 nt, 0 nt to 4 nt, 0 nt to 3 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 9 nt, 2 nt to 8 nt, 2 nt to 7 nt, 2 nt to 6 nt, 2 nt to 5 nt, 2 nt to 4 nt, 2 nt to 3 nt). In some embodiments, 10 or less nt (e.g., 9 or less nt, 8 or less nt, 7 or less nt, 6 or less nt, 5 or less nt, 4 or less nt, 3 or less nt, 2 or less nt, 1 or less nt, or no nt) are present in the PAMmer between the PAM sequence and the specificity segment. In some embodiments, the number of nucleotides (nt) present in the PAMmer between the PAM sequence and the orientation segment of the PAMmer is in a range of from 0 nt to 10 nt (e.g., 0 nt to 9 nt, 0 nt to 8 nt, 0 nt to 7 nt, 0 nt to 6 nt, 0 nt to 5 nt, 0 nt to 4 nt, 0 nt to 3 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 9 nt, 2 nt to 8 nt, 2 nt to 7 nt, 2 nt to 6 nt, 2 nt to 5 nt, 2 nt to 4 nt, or 2 nt to 3 nt). In some embodiments, 10 or less nt (e.g., 9 or less nt, 8 or less nt, 7 or less nt, 6 or less nt, 5 or less nt, 4 or less nt, 3 or less nt, 2 or less nt, 1 or less nt, or no nt) are present in the PAMmer between the PAM sequence and the orientation segment.

In some embodiments, a PAMmer has a length (e.g., the PAM sequence and the orientation segment have a combined length) in a range of from 2 nt to 100 nt (e.g., 2 nt to 70 nt, 2 nt to 50 nt, 2 nt to 45 nt, 2 nt to 40 nt, 2 nt to 35 nt, 2 nt to 30 nt, 2 nt to 25 nt, 2 nt to 20 nt, 2 nt to 10 nt, 2 nt to 5 nt, 3 nt to 70 nt, 3 nt to 50 nt, 3 nt to 45 nt, 3 nt to 40 nt, 3 nt to 35 nt, 3 nt to 30 nt, 3 nt to 25 nt, 3 nt to 20 nt, 3 nt to 10 nt, 3 nt to 5 nt, 5 nt to 70 nt, 5 nt to 50 nt, 5 nt to 45 nt, 5 nt to 40 nt, 5 nt to 35 nt, 5 nt to 30 nt, 5 nt to 25 nt, 5 nt to 20 nt, 10 nt to 70 nt, 10 nt to 50 nt, 10 nt to 45 nt, 10 nt to 40 nt, 10 nt to 35 nt, 10 nt to 30 nt, 10 nt to 25 nt, 10 nt to 20 nt, 10 nt to 15 nt, 15 nt to 70 nt, 15 nt to 50 nt, 15 nt to 45 nt, 15 nt to 40 nt, 15 nt to 35 nt, 15 nt to 30 nt, 15 nt to 25 nt, or 15 nt to 20 nt).

In some cases, a PAMmer is a DNA molecule. In some cases, a PAMmer is an RNA molecule. In some cases, a PAMmer is a hybrid DNA/RNA molecule (e.g., in some cases, at least the PAM sequence of the PAMmer is DNA). In some cases the PAMmer has one or more modified nucleic acids (described in more detail below with respect to nucleic acid modifications). In some embodiments, a subject PAMmer has one or more nucleotides that are 2'-O-Methyl modified nucleotides. In some embodiments, a subject PAMmer has one or more 2' Fluoro modified nucleotides. In some embodiments, a subject PAMmer has one or more LNA bases. In some embodiments, a subject PAMmer has one or more nucleotides that are linked by a phosphorothioate bond (i.e., the subject nucleic acid has one or more phosphorothioate linkages). In some embodiments, a subject PAMmer has a 5' cap (e.g., a 7-methylguanylate cap (m7G)). In some embodiments, a subject PAMmer has a combination of modified nucleotides. For example, a subject PAMmer can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage). See FIG. 17A-17B for working examples that utilize PAMmers having one or more modified nucleotides.

As mentioned above, a quenched PAMmer includes a detectable label and a quencher moiety, where the quencher moiety quenches the detectable label (i.e., the quencher moiety quenches the signal of a detectable label such that the signal from the detectable label is reduced (quenched) when the label is in proximity to the quencher moiety).

Figure 29A:
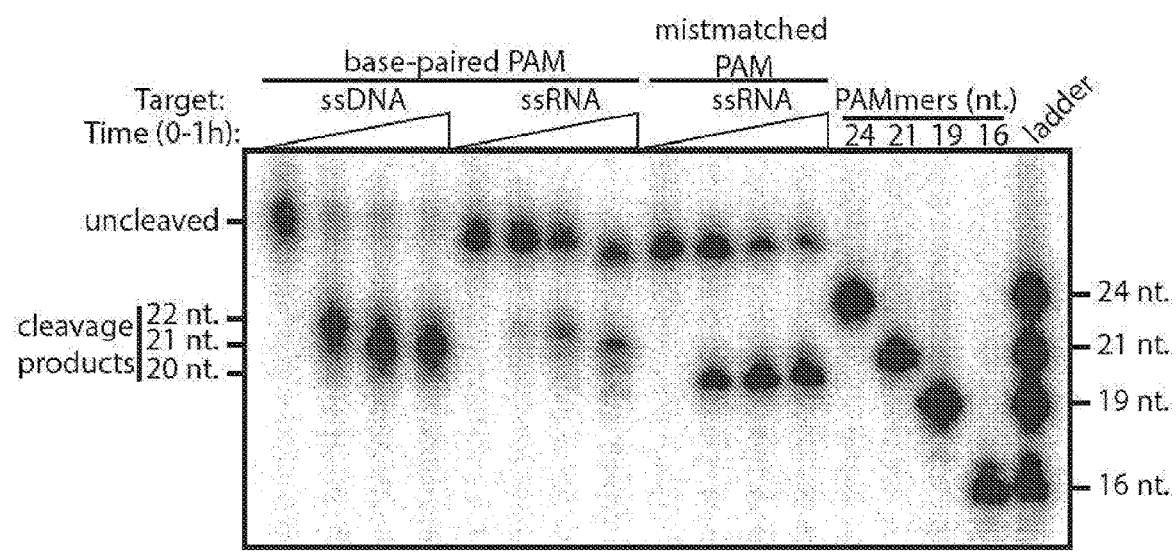
FIGS. 29A-29B provide data relating to Cas9 cleaving PAMmers having a 5' extension arm. Top to bottom: SEQ ID NOs:1638-1640.
Figure 29B:
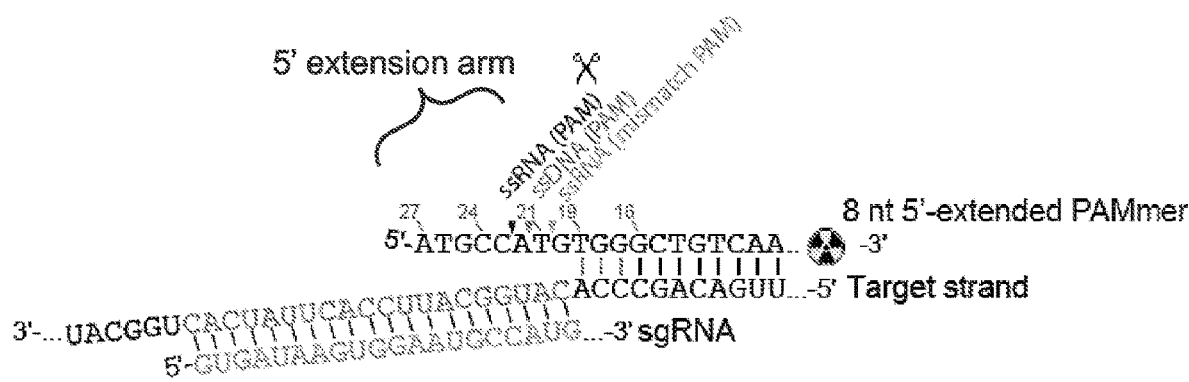

The detectable label and the quencher moiety are positioned on either side of the Cas9 cleavage site (the site at which the Cas9 protein cleaves the PAMmer, e.g., the RuvC cleavage site) such that after cleavage, the detectable label and the quencher moiety will be attached to (e.g., conjugated to) separate resulting cleavage fragments (see, e.g., FIG. 29A-29B for Cas9 cleavage site of a PAMmer). The detectable label and the quencher moiety each can be located (positioned) at any convenient location (position) of the quenched PAMmer (For non-limiting illustrative examples, see FIG. 8G, FIG. 8H, FIG. 8I, and FIG. 30A-30E) as long as the Cas9 protein cleaves between the detectable label and the quencher moiety (or as long as the one fragment resulting from Cas9 cleavage includes a detectable label that is not quenched because there is no functional quencher moiety on that same fragment), and as long as the quencher moiety quenches the signal from the detectable label prior to cleavage.

A quencher moiety can quench a signal from the detectable label (prior to cleavage of the quenched PAMmer) to various degrees. In some cases, a quencher moiety quenches the signal from the detectable label when the signal detected in the presence of the quencher moiety (prior to cleavage of the quenched PAMmer) is 95% or less of the signal detected in the absence of the quencher moiety (after cleavage of the quenched PAMmer). For example, in some cases, the signal detected in the presence of the quencher moiety (prior to cleavage of the quenched PAMmer) can be 90% or less, 80% or less, 70% or less, 60% or less, 50% or less, 40% or less, 30% or less, 20% or less, 15% or less, 10% or less, or 5% or less of the signal detected in the absence of the quencher moiety (after cleavage of the quenched PAMmer). In some cases, no signal (e.g., above background) is detected in the presence of the quencher moiety (prior to cleavage of the quenched PAMmer).

In some cases, the signal detected in the absence of the quencher moiety (after cleavage of the quenched PAMmer) is at least 1.2 fold greater (e.g., at least 1.3 fold, at least 1.5 fold, at least 1.7 fold, at least 2 fold, at least 2.5 fold, at least 3 fold, at least 3.5 fold, at least 4 fold, at least 5 fold, at least 7 fold, at least 10 fold, at least 20 fold, or at least 50 fold greater) than the signal detected in the presence of the quencher moiety (prior to cleavage of the quenched PAMmer).

For example, the detectable label can be positioned at the 5' end of the quenched PAMmer, the 3' end of the quenched PAMmer, within a 5' extension arm, within a specificity segment, within a PAM sequence, within an orientation segment, within a 3' extension arm, or at the boundary of any of the above regions (e.g., at the boundary of a 5'extension arm and a specificity segment, at the boundary of a 3'extension arm and an orientation segment, at the boundary of a specificity segment and a PAM sequence, at the boundary of an orientation segment and a PAM sequence, etc.). For example, the quencher moiety can be positioned at the 5' end of the quenched PAMmer, the 3' end of the quenched PAMmer, within a 5' extension arm, within a specificity segment, within a PAM sequence, within an orientation segment, within a 3' extension arm, or at the boundary of any of the above regions (e.g., at the boundary of a 5'extension arm and a specificity segment, at the boundary of a 3'extension arm and an orientation segment, at the boundary of a specificity segment and a PAM sequence, at the boundary of an orientation segment and a PAM sequence, etc.).

In some cases, the detectable label is positioned 5' of the cleavage site and the quencher moiety is positioned 3' of the cleavage site. In other cases, the detectable label is positioned 3' of the cleavage site and the quencher moiety is positioned 5' of the cleavage site. In some cases, the detectable label is positioned 3' of the cleavage site, the quencher moiety is positioned 5' of the cleavage site, and the quenched PAMmer comprises an orientation segment. In some cases, the detectable label is positioned 5' of the cleavage site, the quencher moiety is positioned 3' of the cleavage site, and the quenched PAMmer comprises a specificity segment. In some cases, the detectable label and the quencher moiety are both positioned 5' of the PAM sequence. In some cases, the detectable label is positioned 3' of the PAM sequence and the quencher moiety is positioned 5' of the PAM sequence. In some cases, the detectable label is positioned 5' of the PAM sequence and the quencher moiety is positioned 3' of the PAM sequence. In some cases, the quenched PAMmer comprises a 5' extension arm, positioned 5' of the PAM sequence, wherein the 5' extension arm comprises: (a) a nucleotide sequence that does not hybridize with the target nucleic acid, and (b) the quencher moiety. In some cases, the quenched PAMmer comprises a 3' extension arm, positioned 3' of the PAM sequence, wherein the 3' extension arm comprises: (a) a nucleotide sequence that does not hybridize with the target nucleic acid, and (b) the quencher moiety.

In some cases, a quenched PAMmer includes, in order from 5' to 3', a quencher moiety, a detectable label, and a PAM sequence. In some cases, a quenched PAMmer includes, in order from 5' to 3', a quencher moiety, a PAM sequence, and a detectable label. In some cases, a quenched PAMmer includes, in order from 5' to 3', a detectable label, a quencher moiety, and a PAM sequence. In some cases, a quenched PAMmer includes, in order from 5' to 3', a detectable label, a PAM sequence, and a quencher moiety.

A detectable label and/or a quencher moiety can be attached to a quenched PAMmer or to a PAMmer (to produce a quenched PAMmer) in any convenient way. For example, a detectable label and/or a quencher moiety can be conjugated to a nucleotide (a particular nucleotide position) of a quenched PAMmer (or of a PAMmer to produce a quenched PAMmer). As another example, a detectable label and/or a quencher moiety can be integrated (e.g., at a particular nucleotide position) into a quenched PAMmer (or into a PAMmer to produce a quenched PAMmer) (e.g., see FIGS. 30A-30C).

A detectable label and/or a quencher moiety can be attached to a quenched PAMmer or to a PAMmer (to produce a quenched PAMmer) using any convenient method. For example, a detectable label and/or a quencher moiety can be attached using an amino dT nucleotide and an NHS-ester containing dye (e.g., an NHS-ester containing detectable label or an NHS-ester containing quencher moiety). As another example, a detectable label and/or a quencher moiety can be integrated into a quenched PAMmer or into a PAMmer (to produce a quenched PAMmer) in such a way that the detectable label and/or quencher moiety takes the place of a nucleotide (an "internal" detectable label and/or an "internal" quencher moiety) (e.g., see FIG. 30A-30C).

In some cases, there are 50 or less nucleotides (e.g., 40 or less, 35 or less, 30 or less, 25 or less, 20 or less, 15 or less, 12 or less, 10 or less, 9 or less, 8 or less, 7 or less, 6 or less, 5 or less, 4 or less, 3 or less, 2 or less, or no nucleotides) between the detectable label (e.g., the nucleotide to which the detectable label is conjugated) and the quencher moiety (e.g., the nucleotide to which the quencher moiety is conjugated).

In some cases, the number of nucleotides between the detectable label (e.g., the nucleotide to which the detectable label is conjugated) and the quencher moiety (e.g., the nucleotide to which the quencher moiety is conjugated) is in a range of from 1 to 50 nucleotides (nt) (e.g., from 1 to 45 nt, from 1 to 40 nt, from 1 to 35 nt, from 1 to 30 nt, from 1 to 25 nt, from 1 to 20 nt, from 1 to 15 nt, from 1 to 10 nt, from 1 to 8 nt, from 1 to 6 nt, from 1 to 4 nt, from 2 to 50 nt, from 2 to 45 nt, from 2 to 40 nt, from 2 to 35 nt, from 2 to 30 nt, from 2 to 25 nt, from 2 to 20 nt, from 2 to 15 nt, from 2 to 10 nt, from 2 to 8 nt, from 2 to 6 nt, from 2 to 4 nt, from 3 to 50 nt, from 3 to 45 nt, from 3 to 40 nt, from 3 to 35 nt, from 3 to 30 nt, from 3 to 25 nt, from 3 to 20 nt, from 3 to 15 nt, from 3 to 10 nt, from 3 to 8 nt, from 3 to 6 nt, from 3 to 4 nt, from 4 to 50 nt, from 4 to 45 nt, from 4 to 40 nt, from 4 to 35 nt, from 4 to 30 nt, from 4 to 25 nt, from 4 to 20 nt, from 4 to 15 nt, from 4 to 10 nt, from 4 to 8 nt, from 4 to 6 nt, from 5 to 50 nt, from 5 to 45 nt, from 5 to 40 nt, from 5 to 35 nt, from 5 to 30 nt, from 5 to 25 nt, from 5 to 20 nt, from 5 to 15 nt, from 5 to 10 nt, from 5 to 8 nt, from 5 to 6 nt, from 6 to 50 nt, from 6 to 45 nt, from 6 to 40 nt, from 6 to 35 nt, from 6 to 30 nt, from 6 to 25 nt, from 6 to 20 nt, from 6 to 15 nt, from 6 to 10 nt, or from 6 to 8 nt).

In some cases, the number of nucleotides between the detectable label (e.g., the nucleotide to which the detectable label is conjugated) and the quencher moiety (e.g., the nucleotide to which the quencher moiety is conjugated) is in a range of from 2 to 10 nucleotides (nt) (e.g., from 2 to 8 nt, from 2 to 6 nt, from 2 to 5 nt, from 3 to 10 nt, from 3 to 8 nt, from 3 to 6 nt, from 3 to 5 nt, from 4 to 10 nt, from 4 to 8 nt, from 4 to 6 nt, from 5 to 10 nt, from 5 to 8 nt, or from 5 to 6 nt).

In some cases, the number of nucleotides between the detectable label (e.g., the nucleotide to which the detectable label is conjugated) and the quencher moiety (e.g., the nucleotide to which the quencher moiety is conjugated) is in a range of from 3 to 6 nucleotides (nt) (e.g., from 3 to 5 nt). In some cases, there are 4 nucleotides between the detectable label (e.g., the nucleotide to which the detectable label is conjugated) and the quencher moiety (e.g., the nucleotide to which the quencher moiety is conjugated).

In some cases, there are no nucleotides between the detectable label and the quencher moiety, e.g., in such cases the detectable label and the quencher moiety will still be positioned such that cleavage by a Cas9 protein separates the two. As such, in some cases, the number of nucleotides between the detectable label (e.g., the nucleotide to which the detectable label is conjugated) and the quencher moiety (e.g., the nucleotide to which the quencher moiety is conjugated) is in a range of from 0 to 50 nucleotides (nt) (e.g., from 0 to 45 nt, from 0 to 40 nt, from 0 to 35 nt, from 0 to 30 nt, from 0 to 25 nt, from 0 to 20 nt, from 0 to 15 nt, from 0 to 10 nt, from 0 to 8 nt, from 0 to 6 nt, from 0 to 4 nt, from 1 to 45 nt, from 1 to 40 nt, from 1 to 35 nt, from 1 to 30 nt, from 1 to 25 nt, from 1 to 20 nt, from 1 to 15 nt, from 1 to 10 nt, from 1 to 8 nt, from 1 to 6 nt, from 1 to 4 nt, from 2 to 50 nt, from 2 to 45 nt, from 2 to 40 nt, from 2 to 35 nt, from 2 to 30 nt, from 2 to 25 nt, from 2 to 20 nt, from 2 to 15 nt, from 2 to 10 nt, from 2 to 8 nt, from 2 to 6 nt, from 2 to 4 nt, from 3 to 50 nt, from 3 to 45 nt, from 3 to 40 nt, from 3 to 35 nt, from 3 to 30 nt, from 3 to 25 nt, from 3 to 20 nt, from 3 to 15 nt, from 3 to 10 nt, from 3 to 8 nt, from 3 to 6 nt, from 3 to 4 nt, from 4 to 50 nt, from 4 to 45 nt, from 4 to 40 nt, from 4 to 35 nt, from 4 to 30 nt, from 4 to 25 nt, from 4 to 20 nt, from 4 to 15 nt, from 4 to 10 nt, from 4 to 8 nt, from 4 to 6 nt, from 5 to 50 nt, from 5 to 45 nt, from 5 to 40 nt, from 5 to 35 nt, from 5 to 30 nt, from 5 to 25 nt, from 5 to 20 nt, from 5 to 15 nt, from 5 to 10 nt, from 5 to 8 nt, from 5 to 6 nt, from 6 to 50 nt, from 6 to 45 nt, from 6 to 40 nt, from 6 to 35 nt, from 6 to 30 nt, from 6 to 25 nt, from 6 to 20 nt, from 6 to 15 nt, from 6 to 10 nt, or from 6 to 8 nt).

In some cases, the detectable label is a fluorescent label. In some such cases, the quencher moiety quenches the signal (the light signal) from the fluorescent label (e.g., by absorbing energy in the emission spectra of the label). Thus, when the quencher moiety is not in proximity with the detectable label, the emission (the signal) from the fluorescent label is detectable because the signal is not absorbed by the quencher moiety. Any convenient donor acceptor pair (detectable label/quencher moiety pair) can be used and many suitable pairs are known in the art.

In some cases the quencher moiety absorbs energy from the detectable label and then emits a signal (e.g., light at a different wavelength). Thus, in some cases, the quencher moiety is itself a detectable label (e.g., a detectable label can be 6-carboxyfluorescein while the quencher moiety can be 6-carboxy-tetramethylrhodamine). In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a Biotium fluorescent dye (e.g., CF 640R, e.g., iCF640RN), quantum dots, and a tethered fluorescent protein.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, and a Biotium fluorescent dye (e.g., CF 640R, e.g., iCF640RN).

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a Biotium fluorescent dye (e.g., CF 640R, e.g., iCF640RN), a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties include, but are not limited to: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ (e.g., 5IAbRQ, iIB-QB), Iowa Black FQ (e.g., 5IAbkFQ), ZEN, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety is selected from: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ (e.g., 5IAbRQ, iIB-QB), Iowa Black FQ (e.g., 5IAbkFQ), ZEN, IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et. al., Annu Rev Biomed Eng. 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585 and 20030003486; and international patent applications: WO200142505 and WO200186001, all of which are hereby incorporated by reference in their entirety.

In some embodiments, a quenched PAMmer includes two or more (e.g., 3 or more, 4 or more, 5 or more, etc.) detectable labels and/or two or more (e.g., 3 or more, 4 or more, 5 or more, etc.) quencher moieties, e.g., in some cases to increase signal to noise. For example the two or more (e.g., 3 or more, 4 or more, 5 or more, etc.) detectable labels can be the same label or can be labels that elicit an additive signal. As another example, the two or more (e.g., 3 or more, 4 or more, 5 or more, etc.) quencher moieties can be the same moiety or can be different moieties that quench the same or overlapping signals, e.g., to provide increased quenching prior to cleavage.

In some embodiments, a quenched PAMmer includes two or more (e.g., 3 or more, 4 or more, 5 or more, etc.) detectable labels and/or two or more (e.g., 3 or more, 4 or more, 5 or more, etc.) quencher moieties, e.g., in some cases to label multiple different entities. As an illustrative example, the fragment of the quenched PAMmer that hybridizes with the target single stranded nucleic acid after cleavage (the hybridizing fragment, the first cleavage product) can have a first detectable label and a first quencher moiety, while the fragment of the quenched PAMmer that does not hybridize with the target single stranded nucleic acid after cleavage (the non-hybridizing fragment, the second cleavage product) can have a second detectable label (distinguishable from the first detectable label) and a second quencher moiety, where the first quencher moiety quenches the signal of the second detectable label (but does not quench the signal of the first detectable label); and the second quencher moiety quenches the signal of the first detectable label (but does not quench the signal of the second detectable label). In such a case, after cleavage, the target single stranded nucleic acid will be detectable by virtue of being hybridized to the hybridizing fragment (the first cleavage product) of the cleaved quenched PAMmer, while the non-hybridizing fragment (the second cleavage product) of the cleaved quenched PAMmer would also be detectable, but the signal of the first and second cleavage products would be distinguishable.

As another illustrative example, the fragment of the quenched PAMmer that hybridizes with the target single stranded nucleic acid after cleavage (the hybridizing fragment, the first cleavage product) can have a first detectable label, while the fragment of the quenched PAMmer that does not hybridize with the target single stranded nucleic acid after cleavage (the non-hybridizing fragment, the second cleavage product) can have a second detectable label (distinguishable from the first detectable label) and a quencher moiety that quenches the signal of the first detectable label (but does not quench the signal of the second detectable label). Thus, the uncleaved quenched PAMmer would be detectable via the second detectable label, as would the non-hybridizing fragment (the second cleavage product), because no quencher would be present to quench the second detectable label. However, the first detectable label would only be detectable after cleavage (i.e., removal of the quencher moiety). Thus, in such a scenario, one signal (from the second detectable label) would represent pre-cleaved quenched PAMmer plus the non-hybridizing fragment (the second cleavage product) of the quenched PAMmer, while another signal (from the first detectable label) would represent the hybridizing fragment (the first cleavage product) of the quenched PAMmer and would be detectable only after cleavage of the quenched PAMmer. In a similar scenario, the second detectable label could be positioned so that it will be part of the hybridizing fragment and therefore signal from the second label would represent uncleaved PAMmer plus hybridized cleavage product. In other words, the second detectable label would be constitutively 'on' and not quenched (and would represent uncleaved PAMmer plus cleaved hybridizing product) while the first detectable label would only be detectable after cleavage (and would represent the hybridizing cleavage product).

As yet another illustrative example, the above examples could be combined and three distinguishable detectable labels/quencher moieties used such that one could distinguishably (and even simultaneously) detect pre-cleavage quenched PAMmers, post-cleavage non-hybridizing fragments (the second cleavage product), and post-cleavage hybridizing fragments (the first cleavage product).

PAM Sequence

A wild type Cas9 protein normally has nuclease activity that cleaves a target nucleic acid (e.g., a double stranded DNA (dsDNA)) at a target site defined by the region of complementarity between the targeting segment of the Cas9 guide RNA and the target nucleic acid. In some cases, site-specific cleavage of the target nucleic acid occurs at locations determined by both (i) base-pairing complementarity between the Cas9 guide RNA and the target nucleic acid; and (ii) a short motif referred to as the protospacer adjacent motif (PAM) in the target nucleic acid. When a Cas9 polypeptide binds to (in some cases cleaves) a dsDNA target nucleic acid, the PAM sequence that is recognized (bound) by the Cas9 protein is present on the non-complementary strand (the strand that does not hybridize with the targeting segment of the Cas9 guide RNA) of the target DNA. Thus, when a Cas9 protein binds to (in some cases cleaves) a single stranded target nucleic acid, no PAM sequence is present because there is no non-complementary strand (see FIG. 8A-8I). A subject PAMmer provides a PAM sequence, which is positioned near the target site (the sequence targeted by the targeting segment of the Cas9 guide RNA) by the orientation segment and/or the specificity segment of the PAMmer.

In some embodiments, the PAM sequence of the PAMmer is complementary to (i.e., hybridizes with) the target nucleic acid (FIG. 1, FIG. 4A, FIG. 8A-8I). In some embodiments, the PAM sequence of the PAMmer is not complementary to (i.e., does not hybridize with) the target nucleic acid (FIG. 2B, FIG. 6, FIG. 8A-8I). In some embodiments, a PAM sequence of a PAMmer has a length in a range of from 1 nt to 15 nt (e.g., 1 nt to 14 nt, 1 nt to 13 nt, 1 nt to 12 nt, 1 nt to 11 nt, 1 nt to 10 nt, 1 nt to 9 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 15 nt, 2 nt to 14 nt, 2 nt to 13 nt, 2 nt to 12 nt, 2 nt to 11 nt, 2 nt to 10 nt, 2 nt to 9 nt, 2 nt to 8 nt, 2 nt to 7 nt, 2 nt to 6 nt, 2 nt to 5 nt, 2 nt to 4 nt, 2 nt to 3 nt, 2 nt, or 3 nt).

In some embodiments (e.g., when the Cas9 protein from *S. pyogenes* or a closely related Cas9 is used; see for example, Chylinski et al., RNA Biol. 2013 May; 10(5):726-37; and Jinek et al., Science. 2012 Aug. 17; 337(6096):816-21; both of which are hereby incorporated by reference in their entirety), the PAM sequence of the PAMmer can be GG (5'-GG-3'), or can be 5'-NGG-3', where N is any nucleotide. In some embodiments (e.g., when a Cas9 protein from *Neisseria meningitidis* or a closely related Cas9 is used), the PAM sequence of the PAMmer can be 5'-NNNNGANN-3', 5'-NNNNGTTN-3', 5'-NNNNGNNT-3', 5'-NNNNGTNN-3', 5'-NNNNGNTN-3', or 5'-NNNNGATT-3', where N is any nucleotide. In some embodiments (e.g., when a Cas9 protein from *Streptococcus thermophilus* #1 or a closely related Cas9 is used), the PAM sequence of the PAMmer can be 5'-NNAGAA-3', 5'-NNAGGA-3', 5'-NNGGAA-3', 5'-NNANAA-3', or 5'-NNGGGA-3' where N is any nucleotide. In some embodiments (e.g., when a Cas9 protein from *Treponema denticola* (TD) or a closely related Cas9 is used), the PAM sequence of the PAMmer can be 5'-NAAAAN-3', 5'-NAAAAC-3', 5'-NAAANC-3', 5'-NANAAC-3', or 5'-NNAAAC-3', where N is any nucleotide. As would be known by one of ordinary skill in the art, additional PAM sequences for other Cas9 proteins can readily be determined using bioinformatic analysis (e.g. analysis of genomic sequencing data). See Esvelt et al., Nat Methods. 2013 November; 10(11):1116-21, for additional information.

Specificity Segment

A specificity segment can be present or absent in a subject PAMmer (the PAMmer has a specificity segment, an orientation segment, or both a specificity segment and an orientation segment), and when present, the specificity segment is positioned 5' of the PAM sequence. As noted above, in some cases, a PAMmer having a specificity segment is referred to herein as a "5'-extended PAMmer." The specificity segment hybridizes to (i.e., targets) a sequence of a target nucleic that overlaps with the target site such that the PAM sequence is positioned near the target site (the sequence of the target nucleic acid that is targeted by the Cas9 guide RNA). Thus, the PAMmer provides a PAM sequence at any desired location within a target nucleic acid (e.g., by designing the specificity segment of the PAMmer to hybridize to any desired nucleotide sequence of the target nucleic acid).

A specificity segment can have a length of from 3 nucleotides (nt) to 100 nt (e.g., from 3 nt to 80 nt, from 3 nt to 50 nt, from 3 nt to 40 nt, from 5 nt to 40 nt, from 5 nt to 35 nt, from 5 nt to 30 nt, from 5 nt to 25 nt, from 10 nt to 40 nt, from 10 nt to 35 nt, from 10 nt to 30 nt, from 10 nt to 25 nt, from 10 nt to 20 nt, from 12 nt to 40 nt, from 12 nt to 35 nt, from 12 nt to 30 nt, from 12 nt to 25 nt, from 12 nt to 20 nt, from 15 nt to 40 nt, from 15 nt to 35 nt, from 15 nt to 30 nt, from 15 nt to 25 nt, from 15 nt to 20 nt, from 17 nt to 40 nt, from 17 nt to 35 nt, from 17 nt to 30 nt, from 17 nt to 25 nt, from 17 nt to 20 nt, from 18 nt to 40 nt, from 18 nt to 35 nt, from 18 nt to 30 nt, from 18 nt to 25 nt, from 18 nt to 20 nt, from 20 nt to 40 nt, from 20 nt to 35 nt, from 20 nt to 30 nt, or from 20 nt to 25 nt). In some cases, the specificity segment is 20 nucleotides in length. In some cases, the specificity segment is 19 nucleotides in length.

The percent complementarity between the specificity segment and the sequence of the target nucleic acid targeted by the specificity segment (e.g., a sequence of the target site, where the target site is the sequence to which the Cas9 guide RNA hybridizes) can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the specificity segment and the sequence of the target nucleic acid targeted by the specificity segment is 60% or more (e.g., 65% or more, 70% or more, 75% or more, 80% or more, 85% or more, 90% or more, 95% or more, 97% or more, 98% or more, 99% or more, or 100%) over a stretch of about 10 to 30 contiguous nucleotides (nt) (e.g. 15 to 30 contiguous nt, 15 to 25 contiguous nt, 17 to 30 contiguous t, 17 to 25 contiguous t, or 18 to 22 contiguous nt). In some cases, the percent complementarity between the specificity segment and the sequence of the target nucleic acid targeted by the specificity segment is 60% or more (e.g., 65% or more, 70% or more, 75% or more, 80% or more, 85% or more, 90% or more, 95% or more, 97% or more, 98% or more, 99% or more, or 100%) over 10 or more contiguous nucleotides (nt) (e.g. 12 or more contiguous nt, 15 or more contiguous nt, 17 or more contiguous nt, 18 or more contiguous nt, 19 or more contiguous nt, or 20 or more contiguous nt).

In some cases, the sequence targeted by the specificity segment of a PAMmer (i.e., the sequence to which the specificity segment of a PAMmer hybridizes) is 100% identical to the target site (i.e., the sequence to which the Cas9 guide RNA hybridizes). However, the sequence targeted by the specificity segment of a PAMmer need not be 100% identical to the target site. For example, in some cases, the sequence targeted by the specificity segment of a PAMmer overlaps with the sequence targeted by the Cas9 guide RNA, but the overlap is not 100%. For example, the sequence targeted by the specificity segment of a PAMmer can be a subset of the target site (e.g., a subset of the sequence to which the Cas9 guide RNA hybridizes). Thus, when a specificity segment of a PAMmer is said to hybridize with nucleotides of a target site, it does not necessarily mean that the specificity segment hybridizes with the entire target site, but encompasses cases where the specificity segment hybridizes with a subset of the nucleotides of the target site. In some cases, the sequence targeted by the specificity segment of a PAMmer (i.e., the sequence to which the specificity segment of a PAMmer hybridizes) is shorter than the sequence targeted by the Cas9 guide RNA (i.e., shorter than the sequence of the target site).

In some cases, the sequence targeted by the specificity segment of a PAMmer is longer than the sequence targeted by the targeting segment of the Cas9 guide RNA. In some cases, the sequence targeted by the specificity segment of a PAMmer is the same length as the sequence targeted by the targeting segment of the Cas9 guide RNA.

In some cases, the sequence targeted by the specificity segment of a PAMmer (i.e., the sequence to which the specificity segment of a PAMmer hybridizes) shares 2 nucleotides (nt) or more with the sequence targeted by the targeting segment of the Cas9 guide RNA (the target site) (e.g., 3 nt or more, 5 nt or more, 8 nt or more, 10 nt or more, 12 nt or more, 15 nt or more, 18 nt or more, etc.). In some cases, the sequence targeted by the specificity segment of a PAMmer (i.e., the sequence to which the specificity segment of a PAMmer hybridizes) shares 2 nucleotides (nt) to 30 nt with the sequence targeted by the targeting segment of the Cas9 guide RNA (e.g., 5 nt to 30 nt, 5 nt to 25 nt, 5 nt to 22 nt, 8 nt to 30 nt, 8 nt to 25 nt, 8 nt to 22 nt, 8 nt to 20 nt, 10 nt to 30 nt, 10 nt to 25 nt, 10 nt to 22 nt, 10 nt to 20 nt, 12 nt to 30 nt, 12 nt to 25 nt, 12 nt to 22 nt, 12 nt to 20 nt, 15 nt to 30 nt, 15 nt to 25 nt, 15 nt to 22 nt, 15 nt to 20 nt, 18 nt to 30 nt, 18 nt to 25 nt, 18 nt to 22 nt, or 18 nt to 20 nt).

In some cases, the sequence targeted by the specificity segment of a PAMmer (i.e., the sequence to which the specificity segment of a PAMmer hybridizes) shares up to 20 nucleotides (nt) with the sequence targeted by the targeting segment of the Cas9 guide RNA (e.g., up to 19 nt, up to 18 nt, up to 17 nt, up to 16 nt, up to 15 nt, up to 14 nt, up to 13 nt, up to 12 nt, up to 11 nt, up to 10 nt, up to 9 nt, up to 8 nt, up to 7 nt, up to 6 nt, up to 5 nt, or up to 4 nt with the sequence targeted by the targeting segment of the Cas9 guide RNA).

In some cases, the sequence targeted by the specificity segment of a PAMmer (i.e., the sequence to which the specificity segment of a PAMmer hybridizes) shares in a range of from 2 nucleotides (nt) to 30 nt with the sequence targeted by the targeting segment of the Cas9 guide RNA (e.g., from 5 nt to 30 nt, from 5 nt to 25 nt, from 5 nt to 22 nt, from 8 nt to 30 nt, from 8 nt to 25 nt, from 8 nt to 22 nt, from 8 nt to 20 nt, from 10 nt to 30 nt, from 10 nt to 25 nt, from 10 nt to 22 nt, from 10 nt to 20 nt, from 12 nt to 30 nt, from 12 nt to 25 nt, from 12 nt to 22 nt, from 12 nt to 20 nt, from 15 nt to 30 nt, from 15 nt to 25 nt, from 15 nt to 22 nt, from 15 nt to 20 nt, from 18 nt to 30 nt, from 18 nt to 25 nt, from 18 nt to 22 nt, from 18 nt to 20 nt, from 3 nt to 25 nt, from 3 nt to 20 nt, from 3 nt to 15 nt, from 3 nt to 12 nt, from 3 nt to 10 nt, from 3 nt to 8 nt, from 3 nt to 6 nt, from 5 nt to 25 nt, from 5 nt to 20 nt, from 5 nt to 15 nt, from 5 nt to 12 nt, from 5 nt to 10 nt, from 5 nt to 8 nt, or from 5 nt to 7 nt with the sequence targeted by the targeting segment of the Cas9 guide RNA).

Figure 8A:
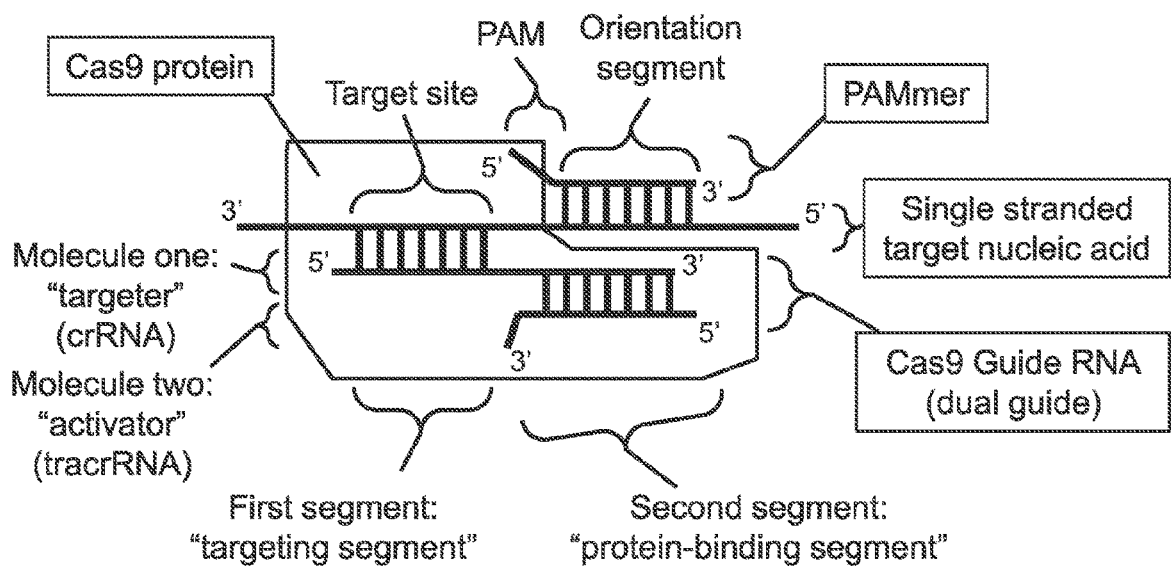
Figure 8B:
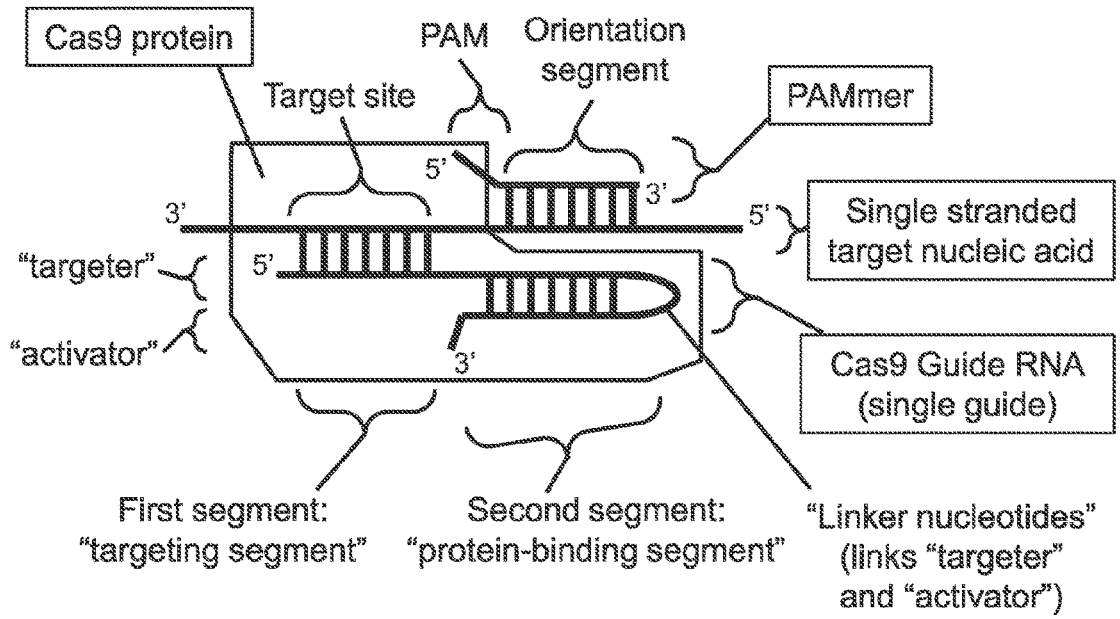
Figure 8C:
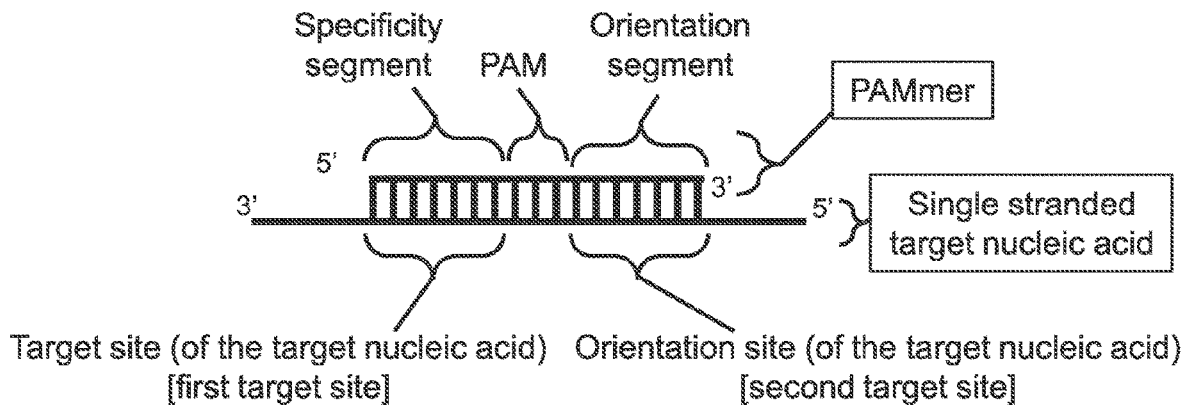
Figure 8D:
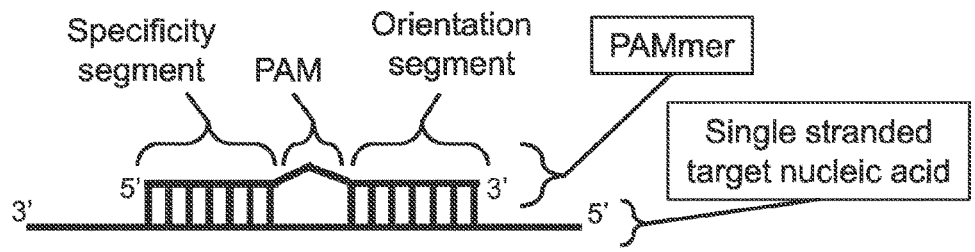
Figure 8E:
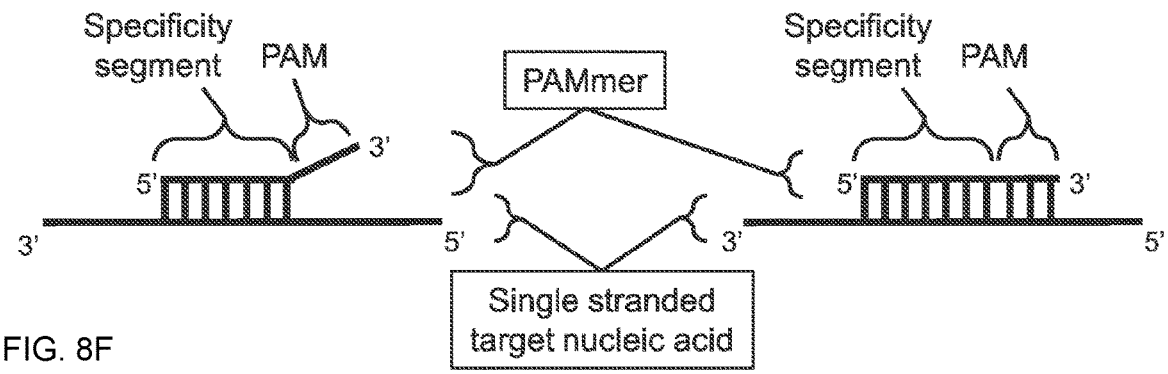

In some embodiments, a PAMmer has a specificity segment, but does not have an orientation segment (i.e., the PAMmer does not have a nucleotide sequence 3' of the PAM sequence that hybridizes with the target nucleic acid) (FIG. 8E). In some such cases, the PAM sequence can be at the 3' end of the PAMmer (i.e., the PAMmer can have 0 nucleotides 3' of the PAM sequence), or the PAMmer can have 1 or more nucleotides (nt) 3' of the PAM sequence (e.g., 2 or more nt, 3 or more nt, 4 or more nt, 5 or more nt, 10 or more nt, 15 or more nt, 20 or more nt, etc.), where the nucleotides 3' of the PAM sequence do not hybridize to the target nucleic acid. In some cases in which a PAMmer does not have an orientation segment, a PAMmer can have a nucleotide sequence, 3' of the PAM sequence, with a length in a range of from 1 nucleotide (nt) to 20 nt (e.g., from 1 nt to 18 nt, from 1 nt to 16 nt, from 1 nt to 14 nt, from 1 nt to 12 nt, from 1 nt to 10 nt, from 1 nt to 9 nt, from 1 nt to 8 nt, from 1 nt to 7 nt, from 1 nt to 6 nt, from 1 nt to 5 nt, from 1 nt to 4 nt, or from 1 nt to 3 nt), where the nucleotides 3' of the PAM sequence do not hybridize to the target nucleic acid. For example, if a PAMmer has nucleotides 3' of the PAM sequence that do hybridize to the target nucleic acid, then the nucleotides that hybridize would be considered an (or part of an) orientation segment.

In some cases, the length of the specificity segment inversely correlates with efficiency of the cleavage reaction and positively correlates with specificity (i.e., reduction of off-target effects). Thus, there can be a trade-off between the desired level of cleavage and the desired level of specificity. The presence (as well as the length) of a specificity segment can be determined based on the particular target nucleic acid, the nature/purpose of the method, and/or the desired outcome. For example, if maximum specificity is desired, but cleavage efficiency is not a concern, then a long specificity segment may be desirable. On the other hand, if maximum cleavage is desired, but specificity is not a concern (e.g., the orientation segment of the PAMmer provides for adequate specificity), then a shorter specificity segment (e.g., no specificity segment) may be desirable.

For methods of binding, the presence of a specificity segment can increase binding specificity. Not to be bound by theory, it is believed that this is because the specificity segment provides an energetic barrier to binding that can be overcome by the presence of a targeting segment in the Cas9 guide RNA that has complementarity to (i.e., can hybridize with) that target nucleic acid, thus displacing the specificity segment of the PAMmer.

Orientation Segment

An orientation segment can be present or absent in a subject PAMmer (the PAMmer has a specificity segment, an orientation segment, or both a specificity segment and an orientation segment), and when present, the orientation segment is positioned 3' of the PAM sequence. The orientation segment hybridizes to (i.e., targets) a sequence of a target nucleic (the orientation site) such that the PAM sequence is positioned near the target site (i.e., the sequence of the target nucleic acid that is targeted by the targeting segment of the Cas9 guide RNA). Thus, the PAMmer provides a PAM sequence at any desired location within a target nucleic acid (e.g., by designing the orientation segment of the PAMmer to hybridize to any desired nucleotide sequence of the target nucleic acid).

The orientation segment can have a length of from 3 nucleotides (nt) to 100 nt (e.g., from 3 nt to 80 nt, from 3 nt to 50 nt, from 3 nt to 40 nt, from 5 nt to 40 nt, from 5 nt to 35 nt, from 5 nt to 30 nt, from 5 nt to 25 nt, from 10 nt to 40 nt, from 10 nt to 35 nt, from 10 nt to 30 nt, from 10 nt to 25 nt, from 10 nt to 20 nt, from 12 nt to 40 nt, from 12 nt to 35 nt, from 12 nt to 30 nt, from 12 nt to 25 nt, from 12 nt to 20 nt, from 15 nt to 40 nt, from 15 nt to 35 nt, from 15 nt to 30 nt, from 15 nt to 25 nt, from 15 nt to 20 nt, from 17 nt to 40 nt, from 17 nt to 35 nt, from 17 nt to 30 nt, from 17 nt to 25 nt, from 17 nt to 20 nt, from 18 nt to 40 nt, from 18 nt to 35 nt, from 18 nt to 30 nt, from 18 nt to 25 nt, from 18 nt to 20 nt, from 20 nt to 40 nt, from 20 nt to 35 nt, from 20 nt to 30 nt, or from 20 nt to 25 nt). In some cases, the orientation segment is 20 nucleotides in length. In some cases, the orientation segment is 19 nucleotides in length.

The percent complementarity between the orientation segment and the sequence of the target nucleic acid targeted by the orientation segment can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the orientation segment and the sequence of the target nucleic acid targeted by the orientation segment is 60% or more (e.g., 65% or more, 70% or more, 75% or more, 80% or more, 85% or more, 90% or more, 95% or more, 97% or more, 98% or more, 99% or more, or 100%) over about 10 to 30 contiguous nucleotides (nt) (e.g. 15 to 30 contiguous nt, 15 to 25 contiguous nt, 17 to 30 contiguous nt, 17 to 25 contiguous nt, or 18 to 22 contiguous nt). In some cases, the percent complementarity between the orientation segment and the sequence of the target nucleic acid targeted by the orientation segment is 60% or more (e.g., 65% or more, 70% or more, 75% or more, 80% or more, 85% or more, 90% or more, 95% or more, 97% or more, 98% or more, 99% or more, or 100%) over 10 or more contiguous nucleotides (nt) (e.g. 12 or more contiguous nt, 15 or more contiguous nt, 17 or more contiguous nt, 18 or more contiguous nt, 19 or more contiguous nt, or 20 or more contiguous nt).

In some cases, the sequence targeted by the orientation segment of a PAMmer is immediately adjacent to the sequence targeted by the targeting segment of the Cas9 guide RNA. In some embodiments, 10 or less nt (e.g., 9 or less nt, 8 or less nt, 7 or less nt, 6 or less nt, 5 or less nt, 4 or less nt, 3 or less nt, 2 or less nt, 1 or less nt, or no nt) are present in the target nucleic acid between the sequence targeted by the targeting segment of the Cas9 guide RNA (i.e., the target site) and the sequence targeted by the orientation segment of the PAMmer (e.g., sometimes referred to as the second target site). In some cases, the sequence of the target nucleic acid that is targeted by the orientation segment of a PAMmer is within 10 or fewer nucleotides (nt) (e.g., 9 or fewer nt, 8 or fewer nt, 7 or fewer nt, 6 or fewer nt, 5 or fewer nt, 4 or fewer nt, 3 or fewer nt, 2 or fewer nt, 1 or fewer nt, or no nt) of the sequence targeted by the targeting segment of the Cas9 guide RNA. In some embodiments, the number of nucleotides (nt) present in the target nucleic acid between the sequence targeted by the targeting segment of the Cas9 guide RNA (i.e., the target site) and the sequence targeted by the orientation segment of the PAMmer is in a range of from 0 nt to 10 nt (e.g., 0 nt to 9 nt, 0 nt to 8 nt, 0 nt to 7 nt, 0 nt to 6 nt, 0 nt to 5 nt, 0 nt to 4 nt, 0 nt to 3 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 9 nt, 2 nt to 8 nt, 2 nt to 7 nt, 2 nt to 6 nt, 2 nt to 5 nt, 2 nt to 4 nt, or 2 nt to 3 nt).

Figure 8F:
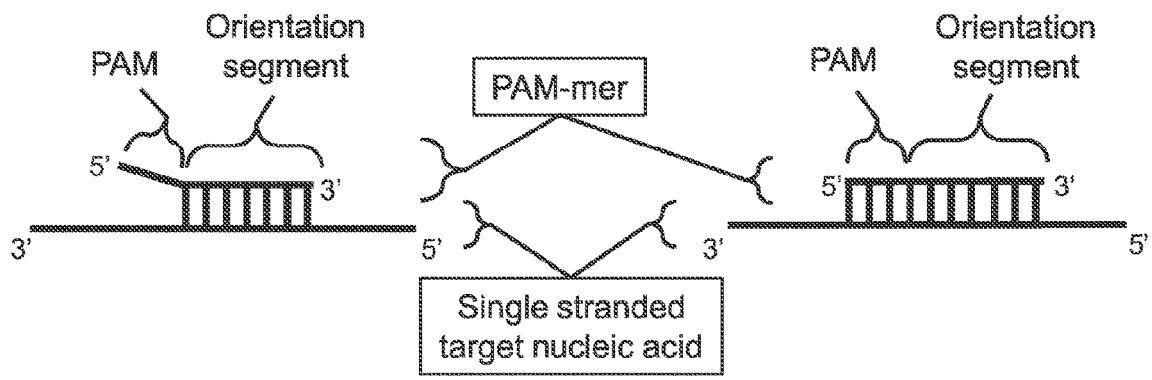

In some cases, a PAMmer has an orientation segment, but does not have a specificity segment (i.e., the PAMmer does not have a nucleotide sequence 5' of the PAM sequence that hybridizes with the target nucleic acid), but does have an orientation segment (FIG. 8F). In some such cases, the PAM sequence can be at the 5' end of the PAMmer (i.e., the PAMmer can have 0 nucleotides 5' of the PAM sequence), or the PAMmer can have 1 or more nucleotides (nt) 5' of the PAM sequence (e.g., 2 or more nt, 3 or more nt, 4 or more nt, 5 or more nt, 10 or more nt, 15 or more nt, 20 or more nt, etc.), where the nucleotides 5' of the PAM sequence do not hybridize to the target nucleic acid. In some cases in which a PAMmer does not have a specificity segment, a PAMmer can have a nucleotide sequence, 5' of the PAM sequence, with a length in a range of from 1 nucleotide (nt) to 20 nt (e.g., from 1 nt to 18 nt, from 1 nt to 16 nt, from 1 nt to 14 nt, from 1 nt to 12 nt, from 1 nt to 10 nt, from 1 nt to 9 nt, from 1 nt to 8 nt, from 1 nt to 7 nt, from 1 nt to 6 nt, from 1 nt to 5 nt, from 1 nt to 4 nt, or from 1 nt to 3 nt), where the nucleotides 5' of the PAM sequence do not hybridize to the target nucleic acid. For example, if a PAMmer has nucleotides 5' of the PAM sequence that do hybridize to the target nucleic acid, then the nucleotides that hybridize would be considered a (or part of a) specificity segment.

In some cases (e.g., those involving methods of binding, where the PAMmer does not have a specificity segment), the target site of the target nucleic acid can be determined by the orientation segment of the PAMmer and not by the targeting segment of the Cas9 guide RNA. In some cases, the targeting segment of the Cas9 guide RNA does not have complementarity to a nucleotide sequence of the target nucleic acid. In some cases, the targeting segment of the Cas9 guide RNA does not have complementarity to a nucleotide sequence of the target nucleic acid that is near (e.g., within 20 or fewer nucleotides (nt), within 30 or fewer nt, within 40 or fewer t, within 50 or fewer nt, within 60 or fewer nt, within 70 or fewer nt, within 80 or fewer nt, within 90 or fewer nt, or within 100 or fewer nt) the orientation site. However, the orientation segment of the PAMmer still positions the PAM sequence of the PAMmer such that the target nucleic acid can still be bound and/or cleaved by a Cas9 protein (e.g, see FIG. 5A-5C).

Stability Control Sequence (e.g., Transcriptional Terminator Segment)

In some embodiments, a PAMmer comprises a stability control sequence. A stability control sequence influences the stability of a nucleic acid (e.g., a Cas9 guide RNA, a targeter, an activator, a PAMmer etc.). One example of a suitable stability control sequence for use with an RNA is a transcriptional terminator segment (i.e., a transcription termination sequence). A transcriptional terminator segment of a Cas9 guide RNA can have a total length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

In some cases, the transcription termination sequence is one that is functional in a eukaryotic cell. In some cases, the transcription termination sequence is one that is functional in a prokaryotic cell.

Non-limiting examples of nucleotide sequences that can be included in a stability control sequence (e.g., transcriptional termination segment, or in any segment of the Cas9 guide RNA to provide for increased stability) include sequences set forth in SEQ ID NO:683-696 and, for example, 5'-UAAUCCCACAGCCGCCAGUUCCGCU-GGCGGCAUUUU-5' (SEQ ID NO:795) (a Rho-independent trp termination site).

Additional Sequences

In some embodiments, a PAMmer comprises an additional segment or segments (in some cases at the 5' end, in some cases the 3' end, in some cases at either the 5' or 3' end, in some cases embedded within the sequence (i.e., not at the 5' and/or 3' end), in some cases at both the 5' end and the 3' end, in some cases embedded and at the 5' end and/or the 3' end, etc). For example, a suitable additional segment can comprise a 5' cap (e.g., a 7-methylguanylate cap ($m^7G$)); a 3' polyadenylated tail (i.e., a 3' poly(A) tail); a ribozyme sequence (e.g. to allow for self-cleavage of a precursor PAMmer and release of a mature PAMmer in a regulated fashion); a riboswitch sequence (e.g., to allow for regulated stability and/or regulated accessibility by proteins and protein complexes); a sequence that forms a dsRNA duplex (i.e., a hairpin)); a sequence that targets an RNA to a subcellular location (e.g., nucleus, mitochondria, chloroplasts, and the like); a modification or sequence that provides for tracking (e.g., direct conjugation to a fluorescent molecule (i.e., fluorescent dye), conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, proteins that bind RNA (e.g., RNA aptamers), labeled proteins, fluorescently labeled proteins, protein translation components (e.g., initiation factors, elongation factors release factors, etc.), RNA editing enzymes (e.g., RNA deaminases, e.g., adenosine deaminase acting on RNA (ADAR), including A to I and/or C to U editing enzymes), RNA splicing factors (e.g., RS domains), RNA and/or DNA helicases, RNA methylases, RNA-binding proteins, and the like); a modification or sequence that provides for increased, decreased, and/or controllable stability; and combinations thereof.

Cas9 Guide RNA

A nucleic acid molecule that binds to a Cas9 protein and targets the Cas9 protein to a specific location within the target nucleic acid is referred to herein as a "guide nucleic acid" or "Cas9 guide RNA." In some cases, a guide nucleic acid is RNA, and in some cases, can be a hybrid nucleic acid that includes both deoxyribonucleotides and ribonucleotides. For the sake of simplicity, as used herein, the terms that include the phrase "guide RNA" (e.g., the terms "Cas9 guide RNA", "truncated guide RNA", "guide RNA", and such) are meant to encompass guide RNAs and guide nucleic acids that include components/regions/sections other than RNA (e.g., deoxyribonucleotide regions; modified nucleotides such as base modifications, sugar modifications, nucleotide linkage modifications, and the like; etc). Also, to distinguish a guide RNA that interacts and guides a Cas9 protein (e.g., a Cas9 variant, a Cas9 fusion protein, a Cas9 heterodimer) from other guide RNAs in the art (e.g., that interact with other proteins), the term "Cas9 guide RNA" is herein used to refer to a guide RNA (and to modified guide RNAs having deoxyribonucleotides and/or other modifications) that interacts with a Cas9 protein and targets the protein to a particular location (the target sequence) within a target nucleic acid. However, when the term "guide RNA" is used in this disclosure, it is meant to refer to a Cas9 guide RNA.

A Cas9 guide RNA and a Cas9 protein form a complex (i.e., bind via non-covalent interactions). The Cas9 guide RNA provides target specificity to the complex by comprising a nucleotide sequence that is complementary to a sequence of a target nucleic acid. The Cas9 protein of the complex provides the site-specific activity. In other words, the Cas9 protein is guided to a target nucleic acid sequence (e.g. a target sequence in a chromosomal nucleic acid; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; etc.) by virtue of its association with the Cas9 guide RNA.

A subject Cas9 guide RNA comprises: a first segment (also referred to herein as a "nucleic acid targeting segment", or simply a "targeting segment"); and a second segment (also referred to herein as a "protein-binding segment") in which two stretches of nucleotides hybridize to form a double stranded RNA duplex of a protein binding segment. The first segment (targeting segment) of a Cas9 guide RNA comprises a nucleotide sequence that is complementary to a specific sequence (a target site) within a target nucleic acid (e.g, a target ssRNA, a target ssDNA, the complementary strand of a double stranded target DNA, etc.). The protein-binding segment (or "protein-binding sequence") interacts with a Cas9 protein. Site-specific binding, modification, and/or cleavage of the target nucleic acid can occur at locations determined by base-pairing complementarity between the Cas9 guide RNA and the target nucleic acid. The protein-binding segment of a subject Cas9 guide RNA comprises two complementary stretches of nucleotides that hybridize to one another to form a double stranded RNA duplex (dsRNA duplex).

The targeting sequence (the targeting segment) of a Cas9 guide RNA can be modified so that the Cas9 guide RNA can target a Cas9 protein to any desired sequence of any desired target nucleic acid, with the exception (as is known in the art) that the PAM sequence is taken into account. Thus, for example, a Cas9 guide RNA can have a targeting segment with a sequence that can hybridize to a sequence in a eukaryotic nucleic acid (e.g., a eukaryotic chromosome, chromosomal sequence, a eukaryotic RNA, etc.).

A Cas9 guide RNA can also be described as having a targeter and an activator. In some embodiments, a subject Cas9 guide RNA comprises two separate nucleic acid molecules: an "activator" and a "targeter" and is referred to herein as a "Cas9 dual guide RNA", a "Cas9 dgRNA", a "Cas9 double-molecule guide RNA", a "Cas9 two-molecule guide RNA" a "dual guide RNA", or a "dgRNA." In some embodiments, the activator and targeter are covalently linked to one another (e.g., via intervening nucleotides) and the resulting guide RNA is referred to as a "single guide RNA", a "Cas9 single guide RNA", a "Cas9 sgRNA", a "Cas9 single-molecule guide RNA," a "Cas9 one-molecule guide RNA", or simply "sgRNA." For example, in some cases, the activator and targeter of a Cas9 single guide RNA are encoded by a DNA and are transcribed together as a single transcript (e.g., with intervening linker nucleotides). Thus, a Cas9 single guide RNA includes a targeter and an activator that are covalently linked (e.g., linked by intervening nucleotides). In some cases, the 3' end of the targeter is linked to the 5' end of the activator. In some cases, the 5' end of the targeter is linked to the 3' end of the activator. In some cases, the 5' end of the targeter is linked to the 5' end of the activator. In some cases, the 3' end of the targeter is linked to the 3' end of the activator. See FIG. 8A and FIG. 8B for schematic representations of example embodiments of Cas9 guide RNAs.

The term "activator" is used herein to mean a tracrRNA-like molecule (tracrRNA: "trans-acting CRISPR RNA") of a Cas9 dual guide RNA (and of a Cas9 single guide RNA when the "activator" and the "targeter" are linked together by, e.g., intervening nucleotides). Thus, for example, a Cas9 guide RNA (dgRNA or sgRNA) comprises an activator sequence (e.g., a tracrRNA sequence). As is known in the art a tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g, truncations, sequence variations, base modifications, backbone modifications, linkage modifications, etc.) where the activator retains at least one function of a tracrRNA (e.g., contributes to the dsRNA duplex to which Cas9 binds). In some cases the activator provides one or more stem loops that can interact with Cas9; in some cases, the activator contributes to the dsRNA duplex to which Cas9 binds (the dsRNA duplex formed from the hybridization of the targeter and the activator) and contributes stem loop 1; in some cases, contributes to the dsRNA duplex to which Cas9 binds (the dsRNA duplex formed from the hybridization of the targeter and the activator) and contributes stem loops 1 and 2; in some cases, contributes to the dsRNA duplex to which Cas9 binds (the dsRNA duplex formed from the hybridization of the targeter and the activator) and contributes stem loops 1 and 3; in some cases, contributes to the dsRNA duplex to which Cas9 binds (the dsRNA duplex formed from the hybridization of the targeter and the activator) and contributes stem loops 1, 2, and 3; etc.). Thus, an activator can be referred to as having a tracr sequence (tracrRNA sequence) and in some cases is a tracrRNA, but the term "activator" is not limited to naturally existing tracrRNAs.

The term "targeter" is used herein to refer to a crRNA-like molecule (crRNA: "CRISPR RNA") of a Cas9 dual guide RNA (and of a Cas9 single guide RNA when the "activator" and the "targeter" are linked together, e.g., by intervening nucleotides). Thus, for example, a Cas9 guide RNA (dgRNA or sgRNA) comprises a targeting segment (single stranded) (which comprises nucleotides that hybridize with a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) can include a naturally occurring sequence from a crRNA. However, the term "targeter" encompasses naturally occurring crRNAs.

The term "duplex-forming segment" is used herein to refer to the stretch of nucleotides of an activator or a targeter that contributes to the formation of the dsRNA duplex by hybridizing to a stretch of nucleotides of a corresponding activator or targeter. In other words, an activator comprises a duplex-forming segment that is complementary to the duplex-forming segment of the corresponding targeter. As such, an activator comprises a duplex-forming segment while a targeter comprises both a duplex-forming segment and the targeting segment of the Cas9 guide RNA (sgRNA or dgRNA). A subject Cas9 single guide RNA comprises an "activator" and a "targeter" where the "activator" and the "targeter" are covalently linked (e.g., by intervening nucleotides).

A Cas9 guide RNA can also be said to include 3 parts: (i) a targeting sequence (a nucleotide sequence that hybridizes with a sequence of the target nucleic acid); (ii) an activator sequence (as described above)(in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g. a dual guide RNA or a single guide RNA) can be comprised of any corresponding activator and targeter pair. Non-limiting examples of nucleotide sequences that can be included in a Cas9 guide RNA (dgRNA or sgRNA) include sequences set forth in SEQ ID NOs:431-679 and 1535-1544, or complements thereof. For example, in some cases, sequences from SEQ ID NOs: 431-562 and 1535-1544 (which are from tracrRNAs) or complements thereof, can pair with sequences from SEQ ID NOs:563-679 (which are from crRNAs), or complements thereof, to form a dsRNA duplex of a protein binding segment.

As noted above, a targeter comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the single stranded targeting segment. Thus, a targeter and an activator (as a corresponding pair) hybridize to form a Cas9 guide RNA. The exact sequence of a given naturally existing crRNA or tracrRNA molecule is characteristic of the species in which the RNA molecules are found. Examples of suitable activator and targeter sequences include, but are not limited to, those set forth in SEQ ID NOs: 431-679 and 1535-1544. A subject Cas9 guide RNA (dgRNA or sgRNA) can include any corresponding activator and targeter sequence pair. Targeting segment of a Cas9 guide RNA The first segment of a subject guide nucleic acid comprises a nucleotide sequence that is complementary to a sequence (a target site) in a target nucleic acid. In other words, the targeting segment of a subject guide nucleic acid can interact with a target nucleic acid (e.g., dsDNA, ssDNA, dsRNA, ssRNA) in a sequence-specific manner via hybridization (i.e., base pairing). As such, the sequence of the targeting segment may vary and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid).

In some cases, the targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, from 18 to 20 nt, 18 nt, 19 nt, or 20 nt).

In some cases, the nucleotide sequence (the targeting sequence) of the targeting segment that is complementary to a nucleotide sequence (target site) of the target nucleic acid can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting sequence of the targeting segment that is complementary to a target sequence of the target nucleic acid can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, from 18 to 20 nt, 18 nt, 19 nt, or 20 nt).

In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

The percent complementarity between the targeting sequence of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length.

Second Segment: Protein-Binding Segment

Figure 31:
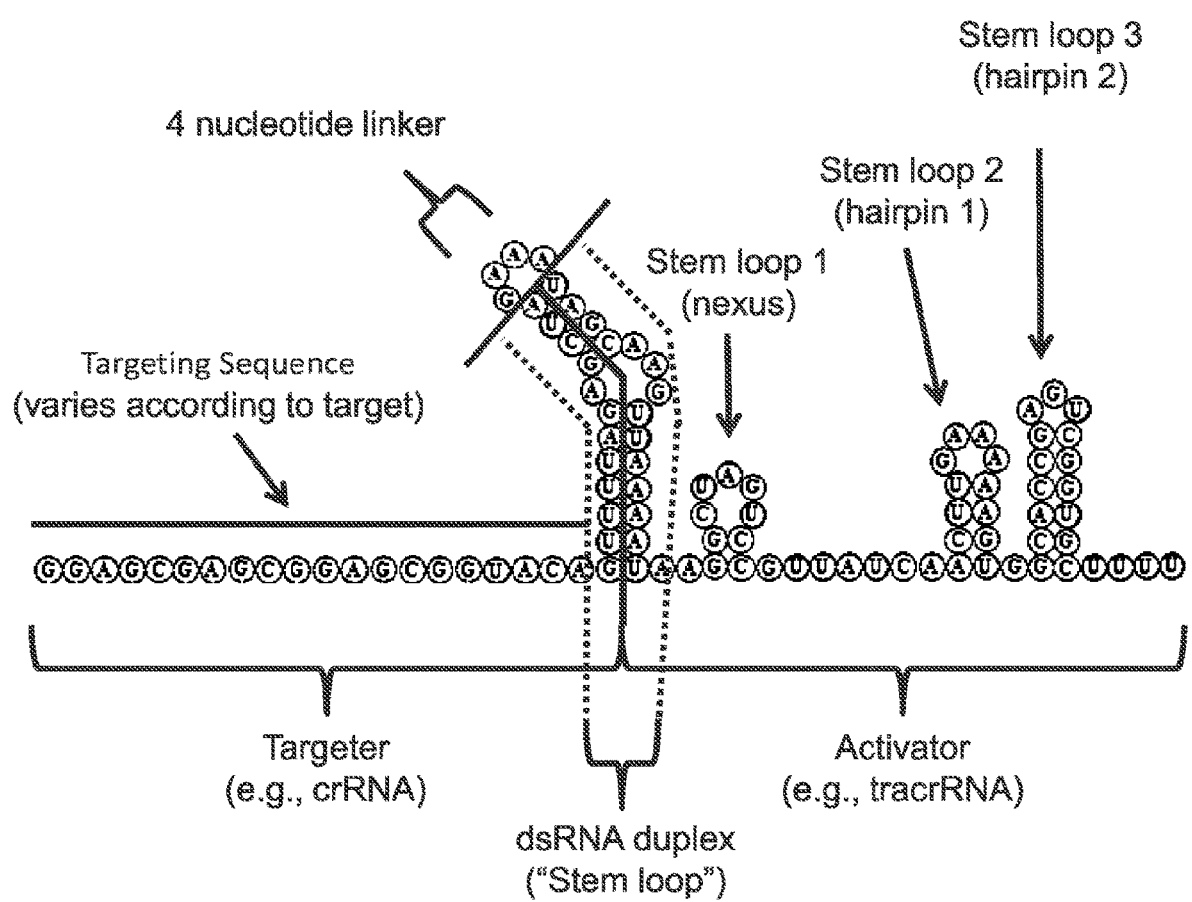
FIG. 31 presents a schematic of one possible guide RNA. The depicted guide RNA is a single guide RNA with a targeter covalently linked to an activator via 4 linker nucleotides. The nucleotides are 5' to 3' from left to right (SEQ ID NO:1643).

The protein-binding segment of a subject Cas9 guide RNA interacts with a Cas9 protein. The Cas9 guide RNA guides the bound Cas9 protein to a specific nucleotide sequence within target nucleic acid via the above mentioned targeting segment. The protein-binding segment of a Cas9 guide RNA comprises two stretches of nucleotides that are complementary to one another and hybridize to form a double stranded RNA duplex (dsRNA duplex). Thus, the protein-binding segment includes a dsRNA duplex. In some cases, the protein-binding segment also includes stem loop 1 (the "nexus") of a Cas9 guide RNA (e.g., see FIG. 31). For example, in some cases, the activator of a Cas9 guide RNA (dgRNA or sgRNA) includes (i) a duplex forming segment that contributes to the dsRNA duplex of the protein-binding segment; and (ii) nucleotides 3' of the duplex forming segment, e.g., that form stem loop 1 (the "*nexus*"). For example, in some cases, the protein-binding segment includes stem loop 1 (the "*nexus*") of a Cas9 guide RNA. In some cases, the protein-binding segment includes 5 or more nucleotides (nt) (e.g., 6 or more, 7 or more, 8 or more, 9 or more, 10 or more, 11 or more, 12 or more, 15 or more, 20 or more, 30 or more, 40 or more, 50 or more, 60 or more, 70 or more, 75 or more, or 80 or more nt) 3' of the dsRNA duplex (where 3' is relative to the duplex-forming segment of the activator sequence).

The dsRNA duplex of the guide RNA (sgRNA or dgRNA) that forms between the activator and targeter is sometimes referred to herein as the "stem loop". In addition, the activator (activator RNA, tracrRNA) of many naturally existing Cas9 guide RNAs (e.g., *S. pygogenes* guide RNAs) has 3 stem loops (3 hairpins) that are 3' of the duplex-forming segment of the activator. The closest stem loop to the duplex-forming segment of the activator (3' of the duplex forming segment) is called "stem loop 1" (and is also referred to herein as the "nexus"); the next stem loop is called "stem loop 2" (and is also referred to herein as the "hairpin 1"); and the next stem loop is called "stem loop 3" (and is also referred to herein as the "hairpin 2"). For example, see FIG. 31 for clarification of the nomenclature.

The term "truncated guide RNA", as used herein, refers to a Cas9 guide RNA (single guide or dual guide) that has the nexus ("stem loop 1"), but is missing one or both of stem loops 2 and 3. Thus, a "truncated guide RNA" is truncated from the 3' end of the activator and can have: (i) stem loop 1 only; (ii) stem loop 1 plus stem loop 2; or (iii) stem loop 1 plus stem loop 3. In some cases, a guide RNA (e.g., some naturally existing guide RNAs) have only one stem loop 3' of the nexus ("stem loop 1") and thus for purposes herein, such guide RNAs are referred to herein as having a nexus ("stem loop 1") and a "stem loop 2/3" (or "hairpin 1/2"). For more information regarding guide RNAs, see Briner et al., Mol Cell. 2014 Oct. 23; 56(2):333-9, which is hereby incorporated by reference in its entirety.

Thus, the term "truncated guide RNA", as used herein, refers to a Cas9 guide RNA (single guide or dual guide) that does not include one or both of: stem loop 2 and stem loop 3. In some cases, a Cas9 guide RNA (sgRNA or dgRNA) (a truncated Cas9 guide RNA) has stem loop 1, but does not have stem loop 2 and does not have stem loop 3. In some cases, a Cas9 guide RNA (sgRNA or dgRNA) (a truncated Cas9 guide RNA) has stem loop 1 and stem loop 2, but does not have stem loop 3. In some cases, a Cas9 guide RNA (sgRNA or dgRNA) (a truncated Cas9 guide RNA) has stem loop 1 and stem loop 3, but does not have stem loop 2. For example, in some cases, a Cas9 guide RNA (sgRNA or dgRNA) (a truncated Cas9 guide RNA) has stem loop 1, but does not have at least one of: stem loop 2 and stem loop 3. In some cases, a Cas9 guide RNA (sgRNA or dgRNA) (e.g., a full length Cas9 guide RNA) has stem loops 1, 2, and 3.

Thus, in some cases, an activator (of a Cas9 guide RNA) has stem loop 1, but does not have stem loop 2 and does not have stem loop 3. In some cases, an activator (of a Cas9 guide RNA) has stem loop 1 and stem loop 2, but does not have stem loop 3. In some cases, an activator (of a Cas9 guide RNA) has stem loop 1 and stem loop 3, but does not have stem loop 2. In some cases, an activator (of a Cas9 guide RNA) has stem loops 1, 2, and 3. For example, in some cases, an activator (of a Cas9 guide RNA) has stem loop 1, but does not have at least one of: stem loop 2 and stem loop 3.

In some cases, the activator (e.g., tracr sequence) of a Cas9 guide RNA (dgRNA or sgRNA) includes (i) a duplex forming segment that contributes to the dsRNA duplex of the protein-binding segment; and (ii) nucleotides 3' of the duplex forming segment (and therefore the Cas9 guide RNA includes (ii)). In some cases, the additional nucleotides 3' of the duplex forming segment form stem loop 1. In some cases, the activator (e.g., tracr sequence) of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment (and therefore the Cas9 guide RNA includes (ii)). In some cases, the activator of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment (and therefore the Cas9 guide RNA includes (ii)).

In some cases, the activator (e.g., tracr sequence) of a Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment (and therefore the Cas9 guide RNA includes (ii)). In some cases, the stretch of nucleotides 3' of the duplex forming segment has a length in a range of from 5 to 200 nucleotides (nt) (e.g., from 5 to 150 nt, from 5 to 130 nt, from 5 to 120 nt, from 5 to 100 nt, from 5 to 80 nt, from 10 to 200 nt, from 10 to 150 nt, from 10 to 130 nt, from 10 to 120 nt, from 10 to 100 nt, from 10 to 80 nt, from 12 to 200 nt, from 12 to 150 nt, from 12 to 130 nt, from 12 to 120 nt, from 12 to 100 nt, from 12 to 80 nt, from 15 to 200 nt, from 15 to 150 nt, from 15 to 130 nt, from 15 to 120 nt, from 15 to 100 nt, from 15 to 80 nt, from 20 to 200 nt, from 20 to 150 nt, from 20 to 130 nt, from 20 to 120 nt, from 20 to 100 nt, from 20 to 80 nt, from 30 to 200 nt, from 30 to 150 nt, from 30 to 130 nt, from 30 to 120 nt, from 30 to 100 nt, or from 30 to 80 nt).

In some embodiments, the duplex-forming segment of the activator is 60% or more identical to one of the activator (tracrRNA) molecules set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, the duplex-forming segment of the activator (or the DNA encoding the duplex-forming segment of the activator) can be 65% or more identical to one of the tracrRNA sequences set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the activator (or the DNA encoding the duplex-forming segment of the activator) can be 70% or more identical to one of the tracrRNA sequences set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the activator (or the DNA encoding the duplex-forming segment of the activator) can be 75% or more identical to one of the tracrRNA sequences set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the activator (or the DNA encoding the duplex-forming segment of the activator) can be 80% or more identical to one of the tracrRNA sequences set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the activator (or the DNA encoding the duplex-forming segment of the activator) can be 85% or more identical to one of the tracrRNA sequences set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the activator (or the DNA encoding the duplex-forming segment of the activator) can be 90% or more identical to one of the tracrRNA sequences set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

The duplex-forming segment of the activator (or the DNA encoding the duplex-forming segment of the activator) can be 95% or more identical to one of the tracrRNA sequences set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the activator (or the DNA encoding the duplex-forming segment of the activator) can be 98% or more identical to one of the tracrRNA sequences set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the activator (or the DNA encoding the duplex-forming segment of the activator) can be 99% or more identical to one of the tracrRNA sequences set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the activator (or the DNA encoding the duplex-forming segment of the activator) can be 100% identical to one of the tracrRNA sequences set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, the duplex-forming segment of the targeter is 60% or more identical to one of the targeter (crRNA) sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 contig or more contiguous nucleotides, or 20 or more contiguous nucleotides). For example, the duplex-forming segment of the targeter (or the DNA encoding the duplex-forming segment of the targeter) can be 65% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the targeter (or the DNA encoding the duplex-forming segment of the targeter) can be 70% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the targeter (or the DNA encoding the duplex-forming segment of the targeter) can be 75% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the targeter (or the DNA encoding the duplex-forming segment of the targeter) can be 80% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the targeter (or the DNA encoding the duplex-forming segment of the targeter) can be 85% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the targeter (or the DNA encoding the duplex-forming segment of the targeter) can be 90% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the targeter (or the DNA encoding the duplex-forming segment of the targeter) can be 95% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the targeter (or the DNA encoding the duplex-forming segment of the targeter) can be 98% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the targeter (or the DNA encoding the duplex-forming segment of the targeter) can be 99% or more identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). The duplex-forming segment of the targeter (or the DNA encoding the duplex-forming segment of the targeter) can be 100% identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

A dual guide RNA can be designed to allow for controlled (i.e., conditional) binding of a targeter with an activator. Because a Cas9 dual guide RNA is not functional unless both the activator and the targeter are bound in a functional complex with Cas9, a dual guide RNA can be inducible (e.g., drug inducible) by rendering the binding between the activator and the targeter to be inducible. As one non-limiting example, RNA aptamers can be used to regulate (i.e., control) the binding of the activator with the targeter. Accordingly, the activator and/or the targeter can include an RNA aptamer sequence.

Aptamers (e.g., RNA aptamers) are known in the art and are generally a synthetic version of a riboswitch. The terms "RNA aptamer" and "riboswitch" are used interchangeably herein to encompass both synthetic and natural nucleic acid sequences that provide for inducible regulation of the structure (and therefore the availability of specific sequences) of the nucleic acid molecule (e.g., RNA, DNA/RNA hybrid, etc.) of which they are part. RNA aptamers usually comprise a sequence that folds into a particular structure (e.g., a hairpin), which specifically binds a particular drug (e.g., a small molecule). Binding of the drug causes a structural change in the folding of the RNA, which changes a feature of the nucleic acid of which the aptamer is a part. As non-limiting examples: (i) an activator with an aptamer may not be able to bind to the cognate targeter unless the aptamer is bound by the appropriate drug; (ii) a targeter with an aptamer may not be able to bind to the cognate activator unless the aptamer is bound by the appropriate drug; and (iii) a targeter and an activator, each comprising a different aptamer that binds a different drug, may not be able to bind to each other unless both drugs are present. As illustrated by these examples, a Cas9 dual guide RNA can be designed to be inducible.

Examples of aptamers and riboswitches can be found, for example, in: Nakamura et al., Genes Cells. 2012 May; 17(5):344-64; Vavalle et al., Future Cardiol. 2012 May; 8(3):371-82; Citartan et al., Biosens Bioelectron. 2012 Apr. 15; 34(1):1-11; and Liberman et al., Wiley Interdiscip Rev RNA. 2012 May-June; 3(3):369-84; all of which are herein incorporated by reference in their entirety.

As noted above, a Cas9 single guide RNA comprises two stretches of nucleotides (a "targeter" and an "activator") that are complementary to one another, hybridize to form the double stranded RNA duplex (dsRNA duplex) of the protein-binding segment (thus resulting in a stem-loop structure), and are covalently linked, e.g., by a linker of intervening nucleotides ("linker nucleotides"). The linker of a Cas9 single guide RNA can have a length of from 3 nucleotides to 100 nucleotides. For example, the linker can have a length of from 3 nucleotides (nt) to 90 nt, from 3 nucleotides (nt) to 80 nt, from 3 nucleotides (nt) to 70 nt, from 3 nucleotides (nt) to 60 nt, from 3 nucleotides (nt) to 50 nt, from 3 nucleotides (nt) to 40 nt, from 3 nucleotides (nt) to 30 nt, from 3 nucleotides (nt) to 20 nt or from 3 nucleotides (nt) to 10 nt. For example, the linker can have a length of from 3 nt to 5 nt, from 5 nt to 10 nt, from 10 nt to 15 nt, from 15 nt to 20 nt, from 20 nt to 25 nt, from 25 nt to 30 nt, from 30 nt to 35 nt, from 35 nt to 40 nt, from 40 nt to 50 nt, from 50 nt to 60 nt, from 60 nt to 70 nt, from 70 nt to 80 nt, from 80 nt to 90 nt, or from 90 nt to 100 nt. In some embodiments, the linker of a Cas9 single guide RNA is 4 nt.

In some embodiments, one of the two complementary stretches of nucleotides (that hybridize to form the dsRNA duplex of the protein-binding segment) of the Cas9 single guide RNA (or the DNA encoding the stretch) is 60% or more identical to one of the activator (tracrRNA) molecules set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, one of the two complementary stretches of nucleotides of the Cas9 single guide RNA (or the DNA encoding the stretch) is 65% or more identical, 70% or more identical, 75% or more identical, 80% or more identical, 85% or more identical, 90% or more identical, 95% or more identical, 98% or more identical, 99% or more identical or 100% identical to one of the tracrRNA sequences set forth in SEQ ID NOs:431-562, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, one of the two complementary stretches of nucleotides (that hybridize to form the dsRNA duplex of the protein-binding segment) of the Cas9 single guide RNA (or the DNA encoding the stretch) is 60% or more identical to one of the targeter (crRNA) sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, one of the two complementary stretches of nucleotides of the Cas9 single guide RNA (or the DNA encoding the stretch) is 65% or more identical, 70% or more identical, 75% or more identical, 80% or more identical, 85% or more identical, 90% or more identical, 95% or more identical, 98% or more identical, 99% or more identical or 100% identical to one of the crRNA sequences set forth in SEQ ID NOs:563-679, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, one of the two complementary stretches of nucleotides (that hybridize to form the dsRNA duplex of the protein-binding segment) of the Cas9 single guide RNA (or the DNA encoding the stretch) is 60% or more identical to one of the targeter (crRNA) sequences or activator (tracrRNA) sequences set forth in SEQ ID NOs: 431-679, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). For example, one of the two complementary stretches of nucleotides of the Cas9 single guide RNA (or the DNA encoding the stretch) can be 65% or more identical to one of the sequences set forth in SEQ ID NOs: 431-679, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). One of the two complementary stretches of nucleotides of the Cas9 single guide RNA (or the DNA encoding the stretch) can be 70% or more identical to one of the sequences set forth in SEQ ID NOs: 431-679, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). One of the two complementary stretches of nucleotides of the Cas9 single guide RNA (or the DNA encoding the stretch) can be 75% or more identical to one of the sequences set forth in SEQ ID NOs: 431-679, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) One of the two complementary stretches of nucleotides of the Cas9 single guide RNA (or the DNA encoding the stretch) can be 80% or more identical to one of the sequences set forth in SEQ ID NOs: 431-679, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). One of the two complementary stretches of nucleotides of the Cas9 single guide RNA (or the DNA encoding the stretch) can be 85% or more identical to one of the sequences set forth in SEQ ID NOs: 431-679, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). One of the two complementary stretches of nucleotides of the Cas9 single guide RNA (or the DNA encoding the stretch) can be 90% or more identical to one of the sequences set forth in SEQ ID NOs: 431-679, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). One of the two complementary stretches of nucleotides of the Cas9 single guide RNA (or the DNA encoding the stretch) can be 95% or more identical to one of the sequences set forth in SEQ ID NOs: 431-679, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). One of the two complementary stretches of nucleotides of the Cas9 single guide RNA (or the DNA encoding the stretch) can be 98% or more identical to one of the sequences set forth in SEQ ID NOs: 431-679, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). One of the two complementary stretches of nucleotides of the Cas9 single guide RNA (or the DNA encoding the stretch) can be 99% or more identical to one of the sequences set forth in SEQ ID NOs: 431-679, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides). One of the two complementary stretches of nucleotides of the Cas9 single guide RNA (or the DNA encoding the stretch) can be 100% identical to one of the sequences set forth in SEQ ID NOs: 431-679, and 1535-1544, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

Appropriate cognate pairs of targeters and activators can be routinely determined for SEQ ID NOs:431-679 and 1535-1544, by taking into account the species name and base-pairing (for the dsRNA duplex of the protein-binding domain). Any activator/targeter pair can be used as part of subject Cas9 dual guide RNA or as part of a subject Cas9 single guide RNA.

In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 60% or more sequence identity (e.g., 65% or more, 70% or more, 75% or more, 80% or more, 85% or more, 90% or more, 95% or more, 98% or more, or 100% sequence identity) with a naturally existing activator (tracrRNA) molecule. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 60% or more sequence identity (e.g., 65% or more, 70% or more, 75% or more, 80% or more, 85% or more, 90% or more, 95% or more, 98% or more, or 100% sequence identity) with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 70% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 75% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 80% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 85% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 90% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 95% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 98% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 100% sequence identity with an activator (tracrRNA) molecule set forth in any one of SEQ ID NOs:431-562, and 1535-1544, or a complement thereof.

In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 60% or more sequence identity (e.g., 65% or more, 70% or more, 75% or more, 80% or more, 85% or more, 90% or more, 95% or more, 98% or more, or 100% sequence identity) with a nucleotide sequence set forth in any one of SEQ ID NOs: 431-679, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 70% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 75% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 80% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 85% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 90% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 95% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 98% or more sequence identity with an activator (tracrRNA) molecule set forth in any one of SEQ ID NOs:431-562, and 1535-1544, or a complement thereof. In some cases, an activator (e.g., a trRNA, trRNA-like molecule, etc.) of a Cas9 dual guide RNA (e.g., a dual guide RNA) or a Cas9 single guide RNA (e.g., a single guide RNA) includes a stretch of nucleotides with 100% sequence identity with an activator (tracrRNA) molecule set forth in any one of SEQ ID NOs:431-562, and 1535-1544, or a complement thereof.

In some cases, an activator (e.g., a trRNA, trRNA-like molecule, etc.) of a Cas9 dual guide RNA (e.g., a dual guide RNA) or a Cas9 single guide RNA (e.g., a single guide RNA) includes 30 or more nucleotides (nt) (e.g., 40 or more, 50 or more 60 or more, 70 or more, 75 or more nt). In some cases, an activator (e.g., a trRNA, trRNA-like molecule, etc.) of a Cas9 dual guide RNA (e.g., a dual guide RNA) or a Cas9 single guide RNA (e.g., a single guide RNA) has a length in a range of from 25 to 300 nucleotides (nt) (e.g., 30 to 300 nt, 40 to 300 nt, 50 to 300 nt, 60 to 300 nt, 65 to 300 nt, 70 to 300 nt, 75 to 300 nt, 30 to 200 nt, 40 to 200 nt, 50 to 200 nt, 60 to 200 nt, 65 to 200 nt, 70 to 200 nt, 75 to 200 nt, 30 to 150 nt, 40 to 150 nt, 50 to 150 nt, 60 to 150 nt, 65 to 150 nt, 70 to 150 nt, 75 to 150 nt, 30 to 100 nt, 40 to 100 nt, 50 to 100 nt, 60 to 100 nt, 65 to 100 nt, 70 to 100 nt, 75 to 100 nt, 30 to 75 nt, 30 to 65 nt, 30 to 50 nt, or 30 to 40 nt).

In some cases, the protein-binding segment has a length of from 10 nucleotides to 300 nucleotides. Also with regard to both a subject Cas9 single guide RNA and to a subject Cas9 dual guide RNA, the dsRNA duplex of the protein-binding segment can have a length from about 6 base pairs (bp) to about 50 bp. For example, the dsRNA duplex of the protein-binding segment can have a length from about 6 bp to about 40 bp, from about 6 bp to about 30 bp, from about 6 bp to about 25 bp, from about 6 bp to about 20 bp, from about 6 bp to about 15 bp, from about 8 bp to about 40 bp, from about 8 bp to about 30 bp, from about 8 bp to about 25 bp, from about 8 bp to about 20 bp or from about 8 bp to about 15 bp. For example, the dsRNA duplex of the protein-binding segment can have a length from about from about 8 bp to about 10 bp, from about 10 bp to about 15 bp, from about 15 bp to about 18 bp, from about 18 bp to about 20 bp, from about 20 bp to about 25 bp, from about 25 bp to about 30 bp, from about 30 bp to about 35 bp, from about 35 bp to about 40 bp, or from about 40 bp to about 50 bp. In some embodiments, the dsRNA duplex of the protein-binding segment has a length of 36 base pairs. The percent complementarity between the nucleotide sequences that hybridize to form the dsRNA duplex of the protein-binding segment can be 60% or more. For example, the percent complementarity between the nucleotide sequences that hybridize to form the dsRNA duplex of the protein-binding segment can be 65% or more, 70% or more, 75% or more, 80% or more, 85% or more, 90% or more, 95% or more, 98% or more, or 99% or more. In some cases, the dsRNA duplex of the protein binding segment includes a "bulge", e.g., a region of non-complementarity (which, e.g., can result in two (or more) sub-regions of complementarity separated by one region (or more) of non-complementarity). In some cases, the percent complementarity between the nucleotide sequences that hybridize to form the dsRNA duplex of the protein-binding segment is 100%.

In some embodiments, a suitable Cas9 guide RNA comprises two separate molecules (an activator and a targeter). In some cases, the first of the two separate molecules (the activator) comprises a nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in SEQ ID NOs:431-562, and 1535-1544, or a complement thereof. In some cases, the second of the two separate molecules (the targeter) comprises a nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in SEQ ID NOs:563-679, or a complement thereof.

In some embodiments, a suitable Cas9 guide RNA is a single RNA polynucleotide and comprises a first nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in SEQ ID NOs:431-562, and 1535-1544, and a second nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in SEQ ID NOs: 463-679.

In some embodiments, the targeter comprises the sequence 5'GUUUUAGAGCUA-3' (SEQ ID NO:679) linked at its 5' end to a stretch of nucleotides that are complementary to a target nucleic acid. In some embodiments, the activator comprises the sequence

```
                                       (SEQ ID NO: 397)
       5'-UAGCAAGUUAAAAUAAGGCUAGUCCG-3'.
```

In some embodiments, a Cas9 guide RNA comprises the sequence 5'-GUUUUAGAGCUA-linker-UAGCAAGUUAAAAUAAGGCUAGUCCG-3' (SEQ ID NO:680) linked at its 5' end to a stretch of nucleotides that are complementary to a target nucleic acid (where "linker" denotes any a linker nucleotide sequence that can comprise any nucleotide sequence). Illustrative examples of Cas9 single guide RNAs include those set forth in SEQ ID NOs: 680-682.

Hybrid Cas9 *Guide RNA*

As noted above, in some cases, a Cas9 guide RNA (sgRNA or dgRNA) is a DNA/RNA hybrid guide RNA (hybrid guide nucleic acid). In such cases, the protein-binding segment of the Cas9 guide RNA is RNA and forms an RNA duplex. Thus, the duplex-forming segments of the activator and the targeter can be RNA. However, the targeting segment of a Cas9 guide RNA can be DNA. Thus, the "targeter" can be a hybrid molecule (e.g, the targeting segment can be DNA and the duplex-forming segment can be RNA). In such cases, the duplex-forming segment of the "activator" can be RNA (e.g., in order to form an RNA-duplex with the duplex-forming segment of the targeter molecule), while nucleotides of the "activator" that are outside of the duplex-forming segment can be DNA (in which case the activator molecule is a hybrid DNA/RNA molecule) or can be RNA (in which case the activator molecule is RNA). For example, the targeting segment can be DNA, the duplex-forming segments (which make up the protein-binding segment) can be RNA, and nucleotides outside of the targeting and duplex-forming segments can be RNA or DNA. The "targeter" can also be referred to as a "targeter RNA" (even though in some cases a targeter RNA can have deoxyribonucleotides and/or other modifications) and the "activator" can be referred to as an "activator RNA" (even though in some cases a targeter RNA can have deoxyribonucleotides and/or other modifications).

A DNA/RNA hybrid guide nucleic can be useful in some cases, for example, when a target nucleic acid is an RNA. Cas9 normally associates with a Cas9 guide RNA that hybridizes with a target DNA, thus forming a DNA-RNA duplex at the target site. Therefore, when the target nucleic acid is an RNA, it is sometimes advantageous to recapitulate a DNA-RNA duplex at the target site by using a targeting segment (of the Cas9 guide RNA) that is DNA instead of RNA. In some cases, hybrid Cas9 guide RNAs can bias Cas9 binding to single stranded target nucleic acids relative to double stranded target nucleic acids.

Stability Control Sequence (e.g., Transcriptional Terminator Segment)

In some embodiments, a Cas9 guide RNA comprises a stability control sequence. A stability control sequence influences the stability of a nucleic acid (e.g., a Cas9 guide RNA, a targeter, an activator, etc.). One example of a suitable stability control sequence for use with an RNA is a transcriptional terminator segment (i.e., a transcription termination sequence). A transcriptional terminator segment of a subject Cas9 guide RNA can have a total length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

In some cases, the transcription termination sequence is one that is functional in a eukaryotic cell. In some cases, the transcription termination sequence is one that is functional in a prokaryotic cell.

Non-limiting examples of nucleotide sequences that can be included in a stability control sequence (e.g., transcriptional termination segment, or in any segment of the Cas9 guide RNA to provide for increased stability) include sequences set forth in SEQ ID NO:683-696 and, for example, 5'-UAAUCCCACAGCCGCCAGUUCCGCU-GGCGGCAUUUU-5' (SEQ ID NO: 1349) (a Rho-independent trp termination site).

Additional Sequences

In some embodiments, a Cas9 guide RNA comprises an additional segment or segments (in some cases at the 5' end, in some cases the 3' end, in some cases at either the 5' or 3' end, in some cases embedded within the sequence (i.e., not at the 5' and/or 3' end), in some cases at both the 5' end and the 3' end, in some cases embedded and at the 5' end and/or the 3' end, etc). For example, a suitable additional segment can comprise a 5' cap (e.g., a 7-methylguanylate cap ($m^7G$)); a 3' polyadenylated tail (i.e., a 3' poly(A) tail); a ribozyme sequence (e.g. to allow for self-cleavage of a Cas9 guide RNA (or component of a Cas9 guide RNA, e.g., a targeter, an activator, etc.) and release of a mature PAMmer in a regulated fashion); a riboswitch sequence (e.g., to allow for regulated stability and/or regulated accessibility by proteins and protein complexes); a sequence that forms a dsRNA duplex (i.e., a hairpin)); a sequence that targets an RNA to a subcellular location (e.g., nucleus, mitochondria, chloroplasts, and the like); a modification or sequence that provides for tracking (e.g., a direct label (e.g., direct conjugation to a fluorescent molecule (i.e., fluorescent dye)), conjugation to a moiety that facilitates fluorescent detection, a sequence that allows for fluorescent detection; a modification or sequence that provides a binding site for proteins (e.g., proteins that act on DNA, including transcriptional activators, transcriptional repressors, DNA methyltransferases, DNA demethylases, histone acetyltransferases, histone deacetylases, proteins that bind RNA (e.g., RNA aptamers), labeled proteins, fluorescently labeled proteins, and the like); a modification or sequence that provides for increased, decreased, and/or controllable stability; and combinations thereof.

Examples of various Cas9 guide RNAs can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013: 270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et. al., Genome Res. 2013 Oct. 31; Chen et. al., Nucleic Acids Res. 2013 Nov. 1; 41(20):e19; Cheng et. al., Cell Res. 2013 October; 23(10): 1163-71; Cho et. al., Genetics. 2013 November; 195(3): 1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. at., Nat Methods. 2013 October; 10(10):957-63; Nakayama et. al., Genesis. 2013 December; 51(12):835-43; Ran et. al., Nat Protoc. 2013 November; 8(11):2281-308; Ran et. al., Cell. 2013 Sep. 12; 154(6):1380-9; Upadhyay et. al., G3 (Bethesda). 2013 Dec. 9; 3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; Briner et al., Mol Cell. 2014 Oct. 23; 56(2): 333-9; and U.S. patents and patent applications: U.S. Pat. Nos. 8,906,616; 8,895,308; 8,889,418; 8,889,356; 8,871, 445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Cas9 Protein

A Cas9 guide RNA and a Cas9 protein form a complex. The guide RNA provides target specificity to the complex by having a nucleotide sequence that is complementary to a sequence (the target site) of a target nucleic acid (as noted above). The Cas9 protein of the complex provides the site-specific activity. In other words, the Cas9 protein is guided to a target site (e.g., stabilized at a target site) within a target nucleic acid sequence (e.g. a chromosomal sequence or an extrachromosomal sequence, e.g. an episomal sequence, a minicircle sequence, a mitochondrial sequence, a chloroplast sequence, etc.) by virtue of its association with the protein-binding segment of the Cas9 guide RNA.

A Cas9 protein can bind and/or modify (e.g., cleave, nick, methylate, demethylate, etc.) a target nucleic acid and/or a polypeptide associated with target nucleic acid (e.g., methylation or acetylation of a histone tail)(e.g., when the Cas9 protein includes a fusion partner with an activity). In some cases, the Cas9 protein is a naturally-occurring protein (e.g., naturally occurs in bacterial and/or archaeal cells). In other cases, the Cas9 protein is not a naturally-occurring polypeptide (e.g., the Cas9 protein is a variant Cas9 protein, a chimeric protein, and the like).

Examples of suitable Cas9 proteins include, but are not limited to, those set forth in SEQ ID NOs: 1-259, and 795-1346. Naturally occurring Cas9 proteins bind a Cas9 guide RNA, are thereby directed to a specific sequence within a target nucleic acid (a target site), and cleave the target nucleic acid (e.g., cleave dsDNA to generate a double strand break, cleave ssDNA, cleave ssRNA, etc.). A chimeric Cas9 protein (a Cas9 fusion protein) is a fusion protein that is fused to a heterologous protein. The fusion partner can provide an activity, e.g., enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases a portion of the Cas9 protein (e.g., the RuvC domain and/or the HNH domain) exhibits reduced nuclease activity relative to the corresponding portion of a wild type Cas9 protein (e.g., in some cases the Cas9 protein is a nickase). In some cases, the Cas9 protein is enzymatically inactive.

Assays to determine whether given protein interacts with a Cas9 guide RNA can be any convenient binding assay that tests for binding between a protein and a nucleic acid. Suitable binding assays (e.g., gel shift assays) will be know to one of ordinary skill in the art (e.g., assays that include adding a Cas9 guide RNA and a protein to a target nucleic acid). In some cases, a PAMmer is also added (e.g., in some cases when the target nucleic acid is a single stranded nucleic acid).

Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art and can include adding a Cas9 guide RNA and a protein to a target nucleic acid. In some cases, a PAMmer is also added (e.g., in some cases when the target nucleic acid is a single stranded nucleic acid).

In some cases, a Cas9 protein (e.g., a chimeric Cas9 protein) has enzymatic activity that modifies target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In other cases, a Cas9 protein (e.g., a chimeric Cas9 protein) has enzymatic activity that modifies a polypeptide (e.g., a histone) associated with target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Many Cas9 orthologs from a wide variety of species have been identified and the proteins share only a few identical amino acids. Identified Cas9 orthologs have similar domain architecture with a central HNH endonuclease domain and a split RuvC/RNaseH domain (e.g., RuvCI, RuvCII, and RuvCIII). Cas9 proteins share 4 key motifs with a conserved architecture. Motifs 1, 2, and 4 are RuvC like motifs while motif 3 is an HNH-motif. In some cases, a suitable Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 60% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 70% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 75% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 80% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 85% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 90% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 95% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 99% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256 and 795-1346.

In some cases, a suitable Cas9 protein comprises an amino acid sequence having 4 motifs, each of motifs 1-4 having 100% amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256 and 795-1346.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 60% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 70% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 75% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 80% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 85% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 90% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 95% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 99% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 100% amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to the Cas9 amino acid sequence set forth in SEQ ID NO: 8, or to any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 60% or more amino acid sequence identity to the Cas9 amino acid sequence set forth in SEQ ID NO: 8, or to any of the amino acid sequences set forth as SEQ ID NOs:1-256 and 795-1346. Any Cas9 protein can be used as part of a chimeric Cas9 protein for use in a subject method.

In some cases, a suitable Cas9 protein comprises an amino acid sequence having 70% or more amino acid sequence identity to the Cas9 amino acid sequence set forth in SEQ ID NO: 8, or to any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 75% or more amino acid sequence identity to the Cas9 amino acid sequence set forth in SEQ ID NO: 8, or to any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 80% or more amino acid sequence identity to the Cas9 amino acid sequence set forth in SEQ ID NO: 8, or to any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 85% or more amino acid sequence identity to the Cas9 amino acid sequence set forth in SEQ ID NO: 8, or to any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 90% or more amino acid sequence identity to the Cas9 amino acid sequence set forth in SEQ ID NO: 8, or to any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 95% or more amino acid sequence identity to the Cas9 amino acid sequence set forth in SEQ ID NO: 8, or to any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 99% or more amino acid sequence identity to the Cas9 amino acid sequence set forth in SEQ ID NO: 8, or to any of the amino acid sequences set forth as SEQ ID NOs:1-256 and 795-1346. Any Cas9 protein can be used as part of a chimeric Cas9 protein of the subject methods.

In some cases, a suitable Cas9 protein comprises an amino acid sequence having 100% amino acid sequence identity to the Cas9 amino acid sequence set forth in SEQ ID NO: 8, or to any of the amino acid sequences set forth as SEQ ID NOs:1-256 and 795-1346. Any Cas9 protein can be used as part of a chimeric Cas9 protein of the subject methods.

In some cases, a Cas9 protein comprises 4 motifs (as listed in Table 1), at least one with (or each with) amino acid sequences having 75% or more, 80% or more, 85% or more, 90% or more, 95% or more, 99% or more or 100% amino acid sequence identity to each of the 4 motifs listed in Table 1 (SEQ ID NOs:260-263), or to the corresponding portions in any of the amino acid sequences set forth as SEQ ID NOs:1-256 and 795-1346.

As used herein, the term "Cas9 protein" encompasses the term "variant Cas9 protein"; and the term "variant Cas9 protein" encompasses the term "chimeric Cas9 protein" (or "Cas9 fusion protein").

Variant Cas9 Proteins

The present disclosure provides compositions and methods that include a variant Cas9 protein. A variant Cas9 protein has an amino acid sequence that is different by one amino acid (e.g., has a deletion, insertion, substitution, fusion) (i.e., different by at least one amino acid) when compared to the amino acid sequence of a wild type Cas9 protein. In some instances, the variant Cas9 protein has an amino acid change (e.g., deletion, insertion, or substitution) that reduces the nuclease activity of the Cas9 protein. For example, in some instances, the variant Cas9 protein has 50% or less, 40% or less, 30% or less, 20% or less, 10% or less, 5% or less, or 1% or less of the nuclease activity of the corresponding wild-type Cas9 protein. In some cases, the variant Cas9 protein has no substantial nuclease activity. When a Cas9 protein is a variant Cas9 protein that has no substantial nuclease activity, it can be referred to as "dCas9."

In some cases, a variant Cas9 protein can cleave the complementary strand of a target nucleic acid but has reduced ability to cleave the non-complementary strand of a target nucleic acid (e.g., a PAMmer can be considered to be the non-complementary strand in cases where the target is a single stranded target). For example, the variant Cas9 protein can have a mutation (amino acid substitution) that reduces the function of the RuvC domain. As a non-limiting example, in some embodiments, a variant Cas9 protein has a mutation at residue D10 (e.g., D10A, aspartate to alanine) of SEQ ID NO:8 or of SEQ ID NO: 1545 (or the corresponding position of any of the proteins set forth in SEQ ID NOs:1-256 and 795-1346) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096):816-21).

In some cases, a variant Cas9 protein can cleave the non-complementary strand of a target nucleic acid (e.g., a PAMmer can be considered to be the non-complementary strand in cases where the target is a single stranded target) but has reduced ability to cleave the complementary strand of the target nucleic acid. For example, the variant Cas9 protein can have a mutation (amino acid substitution) that reduces the function of the HNH domain. Thus, the Cas9 protein can be a nickase that cleaves the non-complementary strand (e.g., a subject quenched PAMmer), but does not cleave the complementary strand (e.g., does not cleave a single stranded target nucleic acid). As a non-limiting example, in some embodiments, the variant Cas9 protein has a mutation at position H840 (e.g., an H840A mutation, histidine to alanine) of SEQ ID NO: 8 or at the corresponding position H839 (e.g., H839A) of SEQ ID NO: 1545 (or the corresponding position of any of the proteins set forth as SEQ ID NOs:1-256 and 795-1346) and can therefore cleave the non-complementary strand of the target nucleic acid (e.g., the quenched PAMmer) but has reduced ability to cleave (e.g., does not cleave) the complementary strand of the target nucleic acid. Such a Cas9 protein has a reduced ability to cleave a target nucleic acid (e.g., a single stranded target nucleic acid) but retains the ability to bind a target nucleic acid (e.g., a single stranded target nucleic acid) and can cleave a bound quenched PAMmer.

In some cases, a variant Cas9 protein has a reduced ability to cleave both the complementary and the non-complementary strands of a double stranded target nucleic acid. As a non-limiting example, in some cases, the variant Cas9 protein harbors mutations at residues D10 and H840 (e.g., D10A and H840A) of SEQ ID NO: 8 or D10 and H839 of SEQ ID NO: 1545 (or the corresponding residues of any of the proteins set forth as SEQ ID NOs:1-256 and 795-1346) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid.

As another non-limiting example, in some cases, the variant Cas9 protein harbors mutations at positions W476 and W1126 (e.g., W476A and W1126A) of SEQ ID NO: 8 (or the corresponding mutations of any of the proteins set forth as SEQ ID NOs:1-256, 795-1346, and 1545) such that the polypeptide has a reduced ability to cleave a target nucleic acid (FIG. 16A-16D). Such a Cas9 protein has a reduced ability to cleave a target nucleic acid (e.g., a single stranded target nucleic acid) but retains the ability to bind a target nucleic acid (e.g., a single stranded target nucleic acid).

As another non-limiting example, in some cases, the variant Cas9 protein harbors mutations at positions P475, W476, N477, D1125, W1126, and D1127A (e.g., P475A, W476A, N477A, D1125A, W1126A, and D1127A) of SEQ ID NO: 8 (or the corresponding mutations of any of the proteins set forth as SEQ ID NOs:1-256, 795-1346, and 1545) such that the polypeptide has a reduced ability to cleave a target nucleic acid (FIG. 16A-16D). Such a Cas9 protein has a reduced ability to cleave a target nucleic acid (e.g., a single stranded target nucleic acid) but retains the ability to bind a target nucleic acid (e.g., a single stranded target nucleic acid).

As another non-limiting example, in some cases, the variant Cas9 protein harbors mutations at positions H840, W476, and W1126 (e.g., H840A, W476A, and Wi126A) of SEQ ID NO: 8 (or the corresponding mutations of any of the proteins set forth as SEQ ID NOs:1-256, 795-1346, and 1545) such that the polypeptide has a reduced ability to cleave a target nucleic acid. Such a Cas9 protein has a reduced ability to cleave a target nucleic acid (e.g., a single stranded target nucleic acid) but retains the ability to bind a target nucleic acid (e.g., a single stranded target nucleic acid).

As another non-limiting example, in some cases, the variant Cas9 protein harbors mutations at positions H840, D10, W476, and W1126 (e.g., H840A, D10A, W476A, and W1126A) of SEQ ID NO: 8 (or the corresponding mutations of any of the proteins set forth as SEQ ID NOs:1-256, 795-1346, and 1545) such that the polypeptide has a reduced ability to cleave a target nucleic acid. Such a Cas9 protein has a reduced ability to cleave a target nucleic acid (e.g., a single stranded target nucleic acid) but retains the ability to bind a target nucleic acid (e.g., a single stranded target nucleic acid).

As another non-limiting example, in some cases, the variant Cas9 protein harbors mutations at positions H840, P475, W476, N477, D1125, W1126, and D1127 (e.g., H840A, P475A, W476A, N477A, D1125A, W1126A, and D1127A) of SEQ ID NO: 8 (or the corresponding mutations of any of the proteins set forth as SEQ ID NOs:1-256, 795-1346, and 1545) such that the polypeptide has a reduced ability to cleave a target nucleic acid. Such a Cas9 protein has a reduced ability to cleave a target nucleic acid (e.g., a single stranded target nucleic acid) but retains the ability to bind a target nucleic acid (e.g., a single stranded target nucleic acid).

As another non-limiting example, in some cases, the variant Cas9 protein harbors mutations at positions D10, H840, P475, W476, N477, D1125, W1126, and D1127 (e.g., D10A, H840A, P475A, W476A, N477A, D1125A, W1126A, and D1127A) of SEQ ID NO: 8 (or the corresponding mutations of any of the proteins set forth as SEQ ID NOs:1-256, 795-1346, and 1545) such that the polypeptide has a reduced ability to cleave a target nucleic acid. Such a Cas9 protein has a reduced ability to cleave a target nucleic acid (e.g., a single stranded target nucleic acid) but retains the ability to bind a target nucleic acid (e.g., a single stranded target nucleic acid).

In some cases, when a variant Cas9 protein harbors mutations at positions W476 and W1126 (e.g., W476A and Wi126A) of SEQ ID NO: 8 (or the corresponding mutations of any of the proteins set forth as SEQ ID NOs:1-256, 795-1346, and 1545); or when the variant Cas9 protein harbors mutations at positions P475, W476, N477, D1125, W1126, and D1127 (e.g., P475A, W476A, N477A, D1125A, W1126A, and D1127A) of SEQ ID NO: 8 (or the corresponding mutations of any of the proteins set forth as SEQ ID NOs:1-256, 795-1346, and 1545), the variant Cas9 protein does not bind efficiently to a PAM sequence. Thus, in some such cases, when such a variant Cas9 protein is used in a method of binding, the method need not include a PAMmer. In other words, in some cases, when such a variant Cas9 protein is used in a method of binding, the method can include a Cas9 guide RNA, but the method can be performed in the absence of a PAMmer (and the specificity of binding is therefore provided by the targeting segment of the Cas9 guide RNA).

Other residues can be mutated to achieve the above effects (i.e. inactivate one or the other nuclease portions). As non-limiting examples, residues D10, G12, G17, E762, H840, N854, N863, H982, H983, A984, D986, and/or A987 of SEQ ID NO: 8 (or the corresponding mutations of any of the proteins set forth as SEQ ID NOs:1-256, 795-1346, and 1545) can be altered (i.e., substituted). Also, mutations other than alanine substitutions are suitable.

In some embodiments, a variant Cas9 protein that has reduced catalytic activity (e.g., when a Cas9 protein has a D10, G12, G17, E762, H840, N854, N863, H982, H983, A984, D986, and/or a A987 mutation of SEQ ID NO: 8 or the corresponding mutations of any of the proteins set forth as SEQ ID NOs:1-256, 795-1346, and 1545, e.g., D10A, G12A, G17A, E762A, H840A, N854A, N863A, H982A, H983A, A984A, and/or D986A), the variant Cas9 protein can still bind to target nucleic acid in a site-specific manner (because it is still guided to a target nucleic acid sequence by a Cas9 guide RNA) as long as it retains the ability to interact with the Cas9 guide RNA.

TABLE 1

Table 1 lists 4 motifs that are present in Cas9 sequences from various species (see also FIG. 9 and FIG. 10). The amino acids listed in Table 1 are from the Cas9 from *S. pyogenes* (SEQ ID NO: 8).

| Motif # | Motif | Amino acids (residue #s) | Highly conserved |
|---|---|---|---|
| 1 | RuvC-like I | IGLDIGTNSVGWAVI (7-21) (SEQ ID NO: 260) | D10, G12, G17 |
| 2 | RuvC-like II | IVIEMARE (759-766) (SEQ ID NO: 261) | E762 |

TABLE 1-continued

Table 1 lists 4 motifs that are present in Cas9 sequences from various species (see also FIG. 9 and FIG. 10). The amino acids listed in Table 1 are from the Cas9 from *S. pyogenes* (SEQ ID NO: 8).

| Motif # | Motif | Amino acids (residue #s) | Highly conserved |
|---|---|---|---|
| 3 | HNH-motif | DVDHIVPQSFLKDDSIDNKVLTRSDKN (837-863) (SEQ ID NO: 262) | H840, N854, N863 |
| 4 | RuvC-like II | HHAHDAYL(982-989) (SEQ ID NO: 263) | H982, H983, A984, D986, A987 |

In addition to the above, a variant Cas9 protein can have the same parameters for sequence identity as described above for Cas9 proteins. Thus, in some cases, a suitable variant Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256, 795-1346, and 1545.

In some cases, a suitable variant Cas9 protein comprises an amino acid sequence having 4 motifs, each of motifs 1-4 having 60% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256, 795-1346, and 1545.

In some cases, a suitable variant Cas9 protein comprises an amino acid sequence having 4 motifs, each of motifs 1-4 having 70% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256, 795-1346, and 1545.

In some cases, a suitable variant Cas9 protein comprises an amino acid sequence having 4 motifs, each of motifs 1-4 having 75% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256, 795-1346, and 1545.

In some cases, a suitable variant Cas9 protein comprises an amino acid sequence having 4 motifs, each of motifs 1-4 having 80% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256, 795-1346, and 1545.

In some cases, a suitable variant Cas9 protein comprises an amino acid sequence having 4 motifs, each of motifs 1-4 having 85% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256, 795-1346, and 1545.

In some cases, a suitable variant Cas9 protein comprises an amino acid sequence having 4 motifs, each of motifs 1-4 having 90% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256, 795-1346, and 1545.

In some cases, a suitable variant Cas9 protein comprises an amino acid sequence having 4 motifs, each of motifs 1-4 having 95% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256, 795-1346, and 1545.

In some cases, a suitable variant Cas9 protein comprises an amino acid sequence having 4 motifs, each of motifs 1-4 having 99% or more amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256, 795-1346, and 1545.

In some cases, a suitable variant Cas9 protein comprises an amino acid sequence having 4 motifs, each of motifs 1-4 having 100% amino acid sequence identity to motifs 1-4 of the Cas9 amino acid sequence set forth as SEQ ID NO:8 (the motifs are in Table 1, below, and are set forth as SEQ ID NOs: 260-263, respectively), or to the corresponding portions in any of the amino acid sequences set forth in SEQ ID NOs:1-256, 795-1346, and 1545.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 60% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 70% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 75% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 80% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 85% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 90% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 95% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 99% or more amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 100% amino acid sequence identity to amino acids 7-166 or 731-1003 of the Cas9 amino acid sequence set forth in SEQ ID NO: 8, or to the corresponding portions in any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to the Cas9 amino acid sequence set forth in SEQ ID NO: 8, or to any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 60% or more amino acid sequence identity to the Cas9 amino acid sequence set forth in SEQ ID NO: 8, or to any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 70% or more amino acid sequence identity to the Cas9 amino acid sequence set forth in SEQ ID NO: 8, or to any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 75% or more amino acid sequence identity to the Cas9 amino acid sequence set forth in SEQ ID NO: 8, or to any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 80% or more amino acid sequence identity to the Cas9 amino acid sequence set forth in SEQ ID NO: 8, or to any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 85% or more amino acid sequence identity to the Cas9 amino acid sequence set forth in SEQ ID NO: 8, or to any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 90% or more amino acid sequence identity to the Cas9 amino acid sequence set forth in SEQ ID NO: 8, or to any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 95% or more amino acid sequence identity to the Cas9 amino acid sequence set forth in SEQ ID NO: 8, or to any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 99% or more amino acid sequence identity to the Cas9 amino acid sequence set forth in SEQ ID NO: 8, or to any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

In some cases, a suitable variant Cas9 protein comprises an amino acid sequence having 100% amino acid sequence identity to the Cas9 amino acid sequence set forth in SEQ ID NO: 8, or to any of the amino acid sequences set forth as SEQ ID NOs:1-256, 795-1346, and 1545. Any Cas9 protein as defined above can be used as a variant Cas9 protein or as part of a chimeric variant Cas9 protein of the subject methods.

Cas9 Heterodimers

In some cases, a variant Cas9 protein is a Cas9 heterodimer. A Cas9 heterodimer comprises two polypeptides, where the two polypeptides are not covalently linked to one another. A Cas9 heterodimer is also referred to herein as a "heterodimeric Cas9 complex" and/or or a "split Cas9 protein" and/or or a "heterodimeric Cas9 protein." A Cas9 heterodimer includes a first fusion polypeptide comprising a first polypeptide (e.g., a Cas9 nuclease lobe) covalently linked (directly or via a linker) to a first fusion partner; and a second fusion polypeptide comprising a second polypeptide (e.g., a Cas9 alpha-helical lobe) covalently linked (directly or via a linker) to a second fusion partner. In some cases, the first polypeptide (e.g., a Cas9 nuclease lobe) is circularly permuted (i.e., in some cases, the first polypeptide is a circular permutant).

A Cas9 heterodimer comprises two polypeptides that can interact to form a complex (i.e., to form the heterodimeric Cas9 protein). A Cas9 heterodimer is also referred to herein as a "split Cas9" or a "split Cas9 protein." The fusion partners present in the first fusion polypeptide and the second fusion polypeptide can be induced to dimerize (e.g, by a dimerizing agent). When the fusion partners present in the first fusion polypeptide and the second fusion polypeptide dimerize, the first fusion polypeptide and the second fusion polypeptide dimerize. In the absence of a dimerizing agent, and in the absence of a guide RNA that includes a stem loop 2 and/or a stem loop 3, the first fusion polypeptide and the second fusion polypeptide do not dimerize. When the first fusion polypeptide and the second fusion polypeptide dimerize, the Cas9 heterodimer, together with a truncated guide RNA (e.g., a guide RNA that does not include stem loop 2 and/or stem loop 3), can bind a target nucleic acid (an in some cases modify, e.g., cleave or otherwise modify the target nucleic acid). A Cas9 heterodimer and a truncated guide RNA form a "Cas9 heterodimer system," described herein. A Cas9 heterodimer system can bind to a target nucleic acid. In some cases, a Cas9 heterodimer system can bind to a target nucleic acid and cleave a PAMmer (e.g., a quenched PAMmer) that is hybridized to the target nucleic acid. In some cases, a Cas9 heterodimer system can bind to a target nucleic acid and cleave the target nucleic acid. In some cases, a Cas9 heterodimer system can bind to a target nucleic acid and modify the target nucleic acid. In some cases, a Cas9 heterodimer system can bind to a target nucleic acid and modulate transcription of/from the target nucleic acid.

A subject Cas9 heterodimer (a split Cas9 protein) includes a first polypeptide (where the first polypeptide includes a Cas9 nuclease lobe) and a second polypeptide (where the second polypeptide includes a Cas9 alpha-helical lobe). A nuclease lobe includes: (i) a RuvC domain, where a RuvC domain comprises a RuvCI polypeptide, a RuvCII polypeptide, and a RuvCIII polypeptide; (ii) an HNH domain (also referred to as an HNH polypeptide); and (iii) a PAM-interacting domain (also referred to as a "PAM-interacting polypeptide"). A Cas9 alpha-helical lobe is also referred to as an "alpha-helical recognition region."

Cas9 Heterodimers with Nuclease Lobe and Alpha-Helical Lobe

In some cases, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a first member of a dimerization pair; and B) a second fusion polypeptide comprising: a) an alpha-helical recognition region; and b) a second fusion partner, where the second fusion partner is a second member of a dimerization pair.

First Fusion Polypeptide

As noted above, in some cases, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a first member of a dimerization pair; and B) a second fusion polypeptide comprising: a) an alpha-helical recognition region; and b) a second fusion partner, where the second fusion partner is a second member of a dimerization pair.

A RuvCI polypeptide can comprise an amino acid sequence having at least 75%, at least 80%, at least 85%, at least 90%, at least 95%, at least 98%, at least 99%, or 100%, amino acid sequence identity to a contiguous stretch of from 40 amino acids to 60 amino acids of amino acids 1-60 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to 80 amino acids, e.g., from 40 amino acids to 50 amino acids, from 50 amino acids to 60 amino acids, from 60 amino acids to 70 amino acids, or from 70 amino acids to 80 amino acids. In some cases, a RuvCI polypeptide comprises an amino acid sequence having at least 75%, at least 80%, at least 85%, at least 90%, at least 95%, at least 98%, at least 99%, or 100%, amino acid sequence identity to amino acids 1-60 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 50 amino acids to 60 amino acids (e.g., 50, 51, 52, 53, 54, 55, 56, 57, 58, 59, or 60 amino acids). For example, in some cases, a RuvCI polypeptide can have at least 75%, at least 80%, at least 85%, at least 90%, at least 95%, at least 98%, at least 99%, or 100%, amino acid sequence identity to amino acids 2-56 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346.

A RuvCII polypeptide can comprise an amino acid sequence having at least 75%, at least 80%, at least 85%, at least 90%, at least 95%, at least 98%, at least 99%, or 100%, amino acid sequence identity to a contiguous stretch of from 40 to 57 amino acids of amino acids 718-774 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to about 70 amino acids, e.g., from 40 amino acids to 45 amino acids, from 45 amino acids to 50 amino acids, from 50 amino acids to 55 amino acids, from 55 amino acids to 60 amino acids, from 60 amino acids to 65 amino acids, or from 65 amino acids to 70 amino acids. In some cases, a RuvCII polypeptide comprises an amino acid sequence having at least 75%, at least 80%, at least 85%, at least 90%, at least 95%, at least 98%, at least 99%, or 100%, amino acid sequence identity to amino acids 718-774 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of 55-60 (e.g., 55, 56, 57, 58, 59, or 60) amino acids.

In some cases, a short alpha-helix (5717-L727 in the *S. pyogenes* Cas9 set forth as SEQ ID NO: 1545) can be removed, e.g., to minimize the distance between the end of RuvCI and the beginning of RuvCII. In some cases, a short alpha-helix (S717-L727 in the *S. pyogenes* Cas9 t forth as SEQ ID NO: 1545) is removed and the RuvCI polypeptide is connected to the RuvCII polypeptide with a linker (e.g., a glycine-serine-serine linker, and as described elsewhere).

A RuvCII polypeptide can comprise an amino acid sequence having at least 75%, at least 80%, at least 85%, at least 90%, at least 95%, at least 98%, at least 99%, or 100%, amino acid sequence identity to a contiguous stretch of from 40 to 46 amino acids of amino acids 729-775 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to about 60 amino acids, e.g., from 40 amino acids to 45 amino acids, from 45 amino acids to 50 amino acids, from 50 amino acids to 55 amino acids, or from 55 amino acids to 60 amino acids. In some cases, a RuvCII polypeptide comprises an amino acid sequence having at least 75%, at least 80%, at least 85%, at least 90%, at least 95%, at least 98%, at least 99%, or 100%, amino acid sequence identity to amino acids 728-774 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of 45-50 (e.g., 45, 46, 47, 48, 49, or 50) amino acids.

An HNH polypeptide can comprise an amino acid sequence having at least 75%, at least 80%, at least 85%, at least 90%, at least 95%, at least 98%, at least 99%, or 100%, amino acid sequence identity to a contiguous stretch of from 100 to 134 amino acids of amino acids 776-909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 90 amino acids to 150 amino acids, e.g., from 90 amino acids to 95 amino acids, from 95 to amino acids to 100 amino acids, from 100 amino acids to 125 amino acids, from 125 amino acids to 130 amino acids, from 130 amino acids to 135 amino acids, from 135 amino acids to 140 amino acids, from 140 amino acids to 145 amino acids, or from 145 amino acids to 150 amino acids. In some cases, an HNH polypeptide comprises an amino acid sequence having at least 75%, at least 80%, at least 85%, at least 90%, at least 95%, at least 98%, at least 99%, or 100%, amino acid sequence identity to amino acids 776-909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 130 amino acids to 140 amino acids (e.g., 130, 131, 132, 133, 134, 135, 136, 137, 138, 139, or 140 amino acids).

A RuvCIII polypeptide can comprise an amino acid sequence having at least 75%, at least 80%, at least 85%, at least 90%, at least 95%, at least 98%, at least 99%, or 100%, amino acid sequence identity to a contiguous stretch of from 150 amino acids to 190 amino acids of amino acids 910 to 1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 150 amino acids to 160 amino acids, from 160 amino acids to 170 amino acids, from 170 amino acids to 180 amino acids, from 180 amino acids to 190 amino acids, from 190 amino acids to 200 amino acids, from 200 amino acids to 210 amino acids, or from 210 amino acids to 220 amino acids. In some cases, a RuvCIII polypeptide comprises an amino acid sequence having at least 75%, at least 80%, at least 85%, at least 90%, at least 95%, at least 98%, at least 99%, or 100%, amino acid sequence identity to amino acids 910 to 1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 180 amino acids to 190 amino acids (e.g., 180, 181, 182, 183, 184, 185, 186, 187, 188, 189, or 190 amino acids).

A PAM-interacting polypeptide can comprise an amino acid sequence having at least 75%, at least 80%, at least 85%, at least 90%, at least 95%, at least 98%, at least 99%, or 100%, amino acid sequence identity to a contiguous stretch of from 200 amino acids to 268 amino acids of amino acids 1100 to 1367 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 240 amino acids to 280 amino acids, e.g., from 240 amino acids to 250 amino acids, from 250 amino acids to 260 amino acids, from 260 amino acids to 270 amino acids, or from 270 amino acids to 280 amino acids. In some cases, a PAM-interacting polypeptide comprises an amino acid sequence having at least 75%, at least 80%, at least 85%, at least 90%, at least 95%, at least 98%, at least 99%, or 100%, amino acid sequence identity to amino acids 1100 to 1367 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 260 amino acids to 270 amino acids (e.g., 260, 261, 262, 263, 264, 265, 266, 267, 268, 269, or 270 amino acids).

Heterologous Subcellular Localization Sequences

In some cases, the first fusion polypeptide comprises a heterologous sequence that provides for subcellular localization (e.g., an NLS for targeting to the nucleus; a mitochondrial localization signal for targeting to the mitochondria; a chloroplast localization signal for targeting to a chloroplast; an ER retention signal; and the like). In some cases, the first fusion polypeptide includes 2 or more, 3 or more, 4 or more, or 5 or more NLSs. In some cases, an NLS is located at or near (e.g., within 75 amino acids, 50 amino acids, or 30 amino acids) the N-terminus and/or at or near (e.g., within 75 amino acids, 50 amino acids, or 30 amino acids) the C-terminus.

In some cases, the first fusion polypeptide comprises an NLS. For example, in some cases, the first fusion polypeptide comprises, in order from N-terminus to C-terminus: a) an NLS; b) a first fusion partner; and c) a first polypeptide comprising: i) a RuvCI polypeptide; ii) a RuvCII polypeptide; iii) an HNH polypeptide; iv) a RuvCIII polypeptide; and v) a PAM-interacting polypeptide. In some cases, the first fusion polypeptide comprises an NLS. For example, in some cases, the first fusion polypeptide comprises, in order from N-terminus to C-terminus: a) an NLS; b) a first fusion partner; c) a first polypeptide comprising: i) a RuvCI polypeptide; ii) a RuvCII polypeptide; iii) an HNH polypeptide; iv) a RuvCIII polypeptide; and v) a PAM-interacting polypeptide; and d) an NLS. In some cases, the first fusion polypeptide comprises an NLS. For example, in some cases, the first fusion polypeptide comprises, in order from N-terminus to C-terminus: a) an NLS; b) a first fusion partner; c) a first polypeptide comprising: i) a RuvCI polypeptide; ii) a RuvCII polypeptide; iii) an HNH polypeptide; iv) a RuvCIII polypeptide; and v) a PAM-interacting polypeptide; and d) an NLS. In some cases, the first fusion polypeptide comprises an NLS. In some cases, the first fusion polypeptide comprises, in order from N-terminus to C-terminus: a) an NLS; b) a first polypeptide comprising: i) a RuvCI polypeptide; ii) a RuvCII polypeptide; iii) an HNH polypeptide; iv) a RuvCIII polypeptide; and v) a PAM-interacting polypeptide; and c) a first fusion partner. In some cases, the first fusion polypeptide comprises, in order from N-terminus to C-terminus: a) an NLS; b) a first polypeptide comprising: i) a RuvCI polypeptide; ii) a RuvCII polypeptide; iii) an HNH polypeptide; iv) a RuvCIII polypeptide; and v) a PAM-interacting polypeptide; c) a first fusion partner; and d) an NLS. In some cases, the NLS comprises the amino acid sequence MAPKKKRKVGIHGVPAA (SEQ ID NO: 1546). In some cases, the NLS comprises the amino acid sequence KRPAATKKAGQAKKKK (SEQ ID NO: 1547). Other suitable NLS are described elsewhere herein.

An NLS can be at or near the N-terminus and/or the C-terminus. In some cases, the first fusion polypeptide comprises two or more NLSs (e.g., 3 or more, 4 or more, or 5 or more NLSs). In some cases, the first fusion polypeptide comprises one or more NLSs (e.g., 2 or more, 3 or more, or 4 or more NLSs) at or near the N-terminus and/or one or more NLSs (e.g., 2 or more, 3 or more, or 4 or more NLSs) at or near the C-terminus. The term "at or near" is used here because, as is known in the art, the NLS need not be at the actual terminus of a protein, but can be positioned near (e.g., within 100 amino acids of) an N- and/or C-terminus (e.g., within 80, within 75, within 60, within 55, within 50, within 45, within 40, within 35, or within 30 amino acids of the an N- and/or C-terminus).

Fusion Partner at or Near N-Terminus of First Fusion Polypeptide

In some cases, the first fusion polypeptide comprises, in order from N-terminus to C-terminus: a) a first fusion partner; and b) a first polypeptide comprising: i) a RuvCI polypeptide; ii) a RuvCII polypeptide; iii) an HNH polypeptide; iv) a RuvCIII polypeptide; and v) a PAM-interacting polypeptide.

In some cases, a first fusion polypeptide comprises one or more linker polypeptides. For example, a linker polypeptide can be interposed between any of: a) an NLS and a fusion partner; b) a fusion partner and a RuvCI polypeptide; c) a RuvCI polypeptide and a RuvCII polypeptide; and d) a PAM-interacting polypeptide and an NLS.

The linker polypeptide may have any of a variety of amino acid sequences. Proteins can be joined by a spacer peptide, generally of a flexible nature, although other chemical linkages are not excluded. Suitable linkers include polypeptides of between about 6 amino acids and about 40 amino acids in length, or between about 6 amino acids and about 25 amino acids in length. These linkers are generally produced by using synthetic, linker-encoding oligonucleotides to couple the proteins. Peptide linkers with a degree of flexibility will generally be preferred. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Exemplary polypeptide linkers include glycine polymers $(G)_n$, glycine-serine polymers (including, for example, $(GS)_n$, $GSGGS_n$ (SEQ ID NO: 1548) and $GGGS_n$ (SEQ ID NO: 1549), where n is an integer of at least one), glycine-alanine polymers, alanine-serine polymers. Exemplary linkers can comprise amino acid sequences including, but not limited to, GGSG (SEQ ID NO: 1550), GGSGG (SEQ ID NO: 1551), GSGSG (SEQ ID NO: 1552), GSGGG (SEQ ID NO: 1553), GGGSG (SEQ ID NO: 1554), GSSSG (SEQ ID NO: 1555), and the like. The ordinarily skilled artisan will recognize that design of a peptide conjugated to any elements described above can include linkers that are all or partially flexible, such that the linker can include a flexible linker as well as one or more portions that confer less flexible structure.

Fusion Partner at or Near C-Terminus of First Fusion Polypeptide

In some cases, the first fusion polypeptide comprises, in order from N-terminus to C-terminus: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner.

In some cases, a first fusion polypeptide comprises one or more linker polypeptides. For example, a linker polypeptide can be interposed between any of: a) an NLS and a RuvCI polypeptide; b) a RuvCI polypeptide and a RuvCII polypeptide; c) a PAM-interacting polypeptide and an NLS; d) a PAM-interacting polypeptide and a second fusion partner; and e) a fusion partner and an NLS. Suitable linker polypeptides are as described above.

Fusion Partner Located Internally within First Fusion Polypeptide

In some cases, the fusion partner is located internally within the first polypeptide. In some cases, the first fusion partner is inserted within the HNH polypeptide. In some cases, the first fusion partner is inserted within the RuvCIII polypeptide.

Fusion Partner Inserted into HNH Polypeptide

In some cases, the first fusion partner is inserted within the HNH polypeptide. The HNH polypeptide of *S. pyogenes* Cas9 is amino acids 776-909 of the amino acid sequence set forth in SEQ ID NO: 1545. For example, in some cases, the first fusion partner is inserted in a site within Amino acids 800 to 900 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. For example, in some cases, the first fusion partner is inserted at or near amino acid 868 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 868 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 860 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 861 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 862 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 863 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 864 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 865 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 866 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 867 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 869 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 870 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 871 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 872 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 873 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 874 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 875 of amino acids 776-909 of the amino acid sequence of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346.

As one non-limiting example, the first fusion polypeptide can comprise, in order from N-terminus to C-terminus: i) a RuvCI polypeptide; ii) a RuvCII polypeptide; iii) an N-terminal portion of an HNH polypeptide; iv) a first fusion partner; v) a C-terminal portion of an HNH polypeptide; vi) a RuvCIII polypeptide; and v) a PAM-interacting polypeptide.

An N-terminal portion of an HNH polypeptide can comprise an amino acid sequence having at least 75%, at least 80%, at least 85%, at least 90%, at least 95%, at least 98%, at least 99%, or 100%, amino acid sequence identity to a contiguous stretch of from 80 amino acids to 92 amino acids of amino acids 776 to 867 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 80 amino acids to 110 amino acids, e.g., from 80 amino acids to 90 amino acids, from 90 amino acids to 100 amino acids, or from 100 amino acids to 110 amino acids. In some cases, an N-terminal portion of an HNH polypeptide comprises an amino acid sequence having at least 75%, at least 80%, at least 85%, at least 90%, at least 95%, at least 98%, at least 99%, or 100%, amino acid sequence identity to amino acids 776 to 867 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of 85 amino acids to 95 amino acids (85, 86, 87, 88, 89, 90, 91, 92, 93, 94, or 95 amino acids). An N-terminal portion of an HNH polypeptide can comprise an amino acid sequence having at least 75%, at least 80%, at least 85%, at least 90%, at least 95%, at least 98%, at least 99%, or 100%, amino acid sequence identity to a contiguous stretch of from 50 amino acids to 66 amino acids of amino acids 776-841 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 50 amino acids to 80 amino acids, e.g., from 50 amino acids to 60 amino acids, from 60 amino acids to 70 amino acids, or from 70 amino acids to 80 amino acids.

A C-terminal portion of an HNH polypeptide can comprise an amino acid sequence having at least 75%, at least 80%, at least 85%, at least 90%, at least 95%, at least 98%, at least 99%, or 100%, amino acid sequence identity to a contiguous stretch of from 35 to 42 amino acids of amino acids 868-909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 35 to 42 amino acids (e.g., 35, 36, 37, 38, 39, 40, 41, or 42 amino acids). A C-terminal portion of an HNH polypeptide can comprise an amino acid sequence having at least 75%, at least 80%, at least 85%, at least 90%, at least 95%, at least 98%, at least 99%, or 100%, amino acid sequence identity to a contiguous stretch of from 50 amino acids to 67 amino acids of amino acids 842-909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 50 amino acids to 80 amino acids, e.g., from 50 amino acids to 60 amino acids, from 60 amino acids to 70 amino acids, or from 70 amino acids to 80 amino acids.

For example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 860 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 861 to 909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 861 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 862 to 909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 862 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 863 to 909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 863 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 864 to 909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 864 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 865 to 909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 865 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 866 to 909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 866 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 867 to 909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 867 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 868 to 909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and v) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 868 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 869 to 909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 869 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 870 to 909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 870 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 871 to 909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 871 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 872 to 909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 872 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 873 to 909 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 873 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 874 to 909 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an N-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 719 to 874 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; iv) a first fusion partner; v) a C-terminal portion of an HNH polypeptide comprising an amino acid sequence having at least 75%, at least 80%, at least 85%, at least 90%, at least 95%, at least 98%, at least 99%, or 100%, amino acid sequence identity to amino acids 875 to 909 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; vi) a RuvCIII polypeptide; and vii) a PAM-interacting polypeptide.

Fusion Partner Inserted within RuvCIII Polypeptide

In some cases, the first fusion partner is inserted within the RuvCIII polypeptide. The RuvCIII polypeptide of S. pyogenes Cas9 is amino acids 910-1099 of the amino acid sequence set forth in SEQ ID NO: 1545. For example, in some cases, the first fusion partner is inserted in a site within amino acids 950 to 1060 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. For example, in some cases, the first fusion partner is inserted at or near amino acid 1016 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1016 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1010 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1011 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1012 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1013 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1014 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1015 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1017 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1018 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1019 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1020 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1021 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1022 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1023 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1024 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346. In some cases, the first fusion partner is inserted at amino acid 1025 of amino acids 910-1099 of the amino acid sequence of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346.

As one non-limiting example, the first fusion polypeptide can comprise, in order from N-terminus to C-terminus: i) a RuvCI polypeptide; ii) a RuvCII polypeptide; iii) an HNH polypeptide; iv) an N-terminal portion of a RuvCIII polypeptide; v) a first fusion partner; vi) a C-terminal portion of a RuvCIII polypeptide; and v) a PAM-interacting polypeptide.

An N-terminal portion of a RuvCIII polypeptide can comprise an amino acid sequence having at least 75%, at least 80%, at least 85%, at least 90%, at least 95%, at least 98%, at least 99%, or 100%, amino acid sequence identity to a contiguous stretch of from 80 amino acids to 106 amino acids of amino acids 910 to 1015 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 80 amino acids to 120 amino acids, from 80 amino acids to 90 amino acids, from 90 amino acids to 100 amino acids, from 100 amino acids to 110 amino acids, or from 110 amino acids to 120 amino acids. In some cases, a RuvCIII polypeptide comprises an amino acid sequence having at least 75%, at least 80%, at least 85%, at least 90%, at least 95%, at least 98%, at least 99%, or 100%, amino acid sequence identity to amino acids 910 to 1015 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 100 amino acids to 106 amino acids (e.g., 100, 101, 102, 103, 104, 105, 106, 107, 108, 109, or 110 amino acids).

A C-terminal portion of a RuvCIII polypeptide can comprise an amino acid sequence having at least 75%, at least 80%, at least 85%, at least 90%, at least 95%, at least 98%, at least 99%, or 100%, amino acid sequence identity to a contiguous stretch of from 75 amino acids to 84 amino acids of amino acids 1016 to 1099 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 70 amino acids to 100 amino acids, from 70 amino acids to 80 amino acids, from 80 amino acids to 90 amino acids, or from 90 amino acids to 100 amino acids. In some cases, a C-terminal RuvCIII polypeptide comprises an amino acid sequence having at least 75%, at least 80%, at least 85%, at least 90%, at least 95%, at least 98%, at least 99%, or 100%, amino acid sequence identity to amino acids 1016 to 1099 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 80 amino acids to 90 amino acids (e.g., 80, 81, 82, 83, 84, 85, 86, 87, 88, 89, or 90 amino acids).

For example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1010 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1011-1099 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1011 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1012-1099 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1012 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1013-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1013 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1014-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1014 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1015-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1015 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1016-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1016 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1017-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1017 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1018-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1018 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1019-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1019 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1020-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1020 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1021-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1021 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1022-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1022 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1023-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1023 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1024-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

As another example, in some cases, the first fusion polypeptide comprises, in order from N-terminus to C-terminus: i) a RuvCI polypeptide; ii) a RuvCII polypeptide; iii) an HNH polypeptide; iv) an N-terminal portion of a RuvCIII polypeptide, comprising an amino acid sequence having at least 75%, at least 80%, at least 85%, at least 90%, at least 95%, at least 98%, at least 99%, or 100%, amino acid sequence identity to amino acids 910 to 1024 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; v) a first fusion partner; vi) a C-terminal portion of a RuvCIII polypeptide comprising an amino acid sequence having at least 75%, at least 80%, at least 85%, at least 90%, at least 95%, at least 98%, at least 99%, or 100%, amino acid sequence identity to amino acids 1025-1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and vii) a PAM-interacting polypeptide.

Second Fusion Polypeptide

In some cases, the second polypeptide of a Cas9 heterodimer comprises an α-helical lobe (also referred to as "an alpha-helical recognition region") of a Cas9 polypeptide. For example, in some cases, the second polypeptide comprises an amino acid sequence having at least 75%, at least 80%, at least 85%, at least 90%, at least 95%, at least 98%, at least 99%, or 100%, amino acid sequence identity to a contiguous stretch of from 400 amino acids to 658 amino acids of amino acids 61 to 718 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 400 amino acids to 800 amino acids, e.g., from 400 amino acids to 450 amino acids, from 450 amino acids to 500 amino acids, from 500 amino acids to 550 amino acids, from 550 amino acids to 600 amino acids, from 600 amino acids to 650 amino acids, from 650 amino acids to 700 amino acids, from 700 amino acids to 750 amino acids, or from 750 amino acids to 800 amino acids. In some cases, the second polypeptide comprises an amino acid sequence having at least 75%, at least 80%, at least 85%, at least 90%, at least 95%, at least 98%, at least 99%, or 100%, amino acid sequence identity to amino acids 61-718 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 650 amino acids to 660 amino acids (e.g., 650, 651, 652, 653, 654, 655, 656, 657, 658, 659, or 660 amino acids).

In some cases, the second polypeptide comprises an amino acid sequence having at least 75%, at least 80%, at least 85%, at least 90%, at least 95%, at least 98%, at least 99%, or 100%, amino acid sequence identity to a contiguous stretch of from 400 amino acids to 624 amino acids of amino acids 95 to 718 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from about 400 amino acids to 800 amino acids, e.g., from 400 amino acids to 450 amino acids, from 450 amino acids to 500 amino acids, from 500 amino acids to 550 amino acids, from 550 amino acids to 600 amino acids, from 600 amino acids to 650 amino acids, from 650 amino acids to 700 amino acids, from 700 amino acids to 750 amino acids, or from 750 amino acids to 800 amino acids. In some cases, the second polypeptide comprises an amino acid sequence having at least 75%, at least 80%, at least 85%, at least 90%, at least 95%, at least 98%, at least 99%, or 100%, amino acid sequence identity to amino acids 95 to 718 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 620 amino acids to 630 amino acids (e.g., 620, 621, 622, 623, 624, 625, 626, 627, 628, 629, or 630 amino acids).

In some cases, G56 (of the *S. pyogenes* sequence set forth in SEQ ID NO: 1545) can be selected as the N-terminus for the alpha-helical lobe (e.g., due to its location in a poorly-conserved linker just before the arginine-rich bridge helix, which has been shown to be critical for Cas9 cleavage activity in human cells). In some cases, the second polypeptide of a Cas9 heterodimer comprises an α-helical lobe (also referred to as "an alpha-helical recognition region") of a Cas9 polypeptide. For example, in some cases, the second polypeptide comprises an amino acid sequence having at least 75%, at least 80%, at least 85%, at least 90%, at least 95%, at least 98%, at least 99%, or 100%, amino acid sequence identity to a contiguous stretch of from 400 amino acids to 658 amino acids of amino acids 56 to 714 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 400 amino acids to 800 amino acids, e.g., from 400 amino acids to 450 amino acids, from 450 amino acids to 500 amino acids, from 500 amino acids to 550 amino acids, from 550 amino acids to 600 amino acids, from 600 amino acids to 650 amino acids, from 650 amino acids to 700 amino acids, from 700 amino acids to 750 amino acids, or from 750 amino acids to 800 amino acids. In some cases, the second polypeptide comprises an amino acid sequence having at least 75%, at least 80%, at least 85%, at least 90%, at least 95%, at least 98%, at least 99%, or 100%, amino acid sequence identity to amino acids 56-714 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 650 amino acids to 660 amino acids (e.g., 650, 651, 652, 653, 654, 655, 656, 657, 658, 659, or 660 amino acids).

In some cases, the C-terminus of the alpha-helical lobe can be at the beginning, end, or within the linker between the two lobes of the WT Cas9 protein. For example, the C-terminus of the alpha-helical lobe can be at or near S714 of the WT Cas9 protein set forth in SEQ ID NO: 1545. For example, the C-terminus of the alpha-helical lobe can be S714 of the WT Cas9 protein set forth in SEQ ID NO: 1545.

In some cases, the second fusion polypeptide comprises, in order from N-terminus to C-terminus: a) a second fusion partner; and b) a second polypeptide that comprises an alpha-helical recognition region. In some cases, the second fusion polypeptide comprises, in order from N-terminus to C-terminus: a) a second polypeptide that comprises an alpha-helical recognition region; and b) a second fusion partner.

In some cases, the second fusion polypeptide comprises a heterologous sequence that provides for subcellular localization (e.g., an NLS for targeting to the nucleus; a mitochondrial localization signal for targeting to the mitochondria; a chloroplast localization signal for targeting to a chloroplast; an ER retention signal; and the like). In some cases, the second fusion polypeptide includes 2 or more, 3 or more, 4 or more, or 5 or more NLSs. In some cases, an NLS is located at or near (e.g., within 75 amino acids, 50 amino acids, or 30 amino acids) the N-terminus and/or at or near (e.g., within 75 amino acids, 50 amino acids, or 30 amino acids) the C-terminus.

In some cases, the second fusion polypeptide comprises an NLS. For example, in some cases, the second fusion polypeptide comprises, in order from N-terminus to C-terminus: a) an NLS; b) a second fusion partner; and c) a second polypeptide that comprises an alpha-helical recognition region. In some cases, the second fusion polypeptide comprises, in order from N-terminus to C-terminus: a) an NLS; b) a second fusion partner; c) a second polypeptide that comprises an alpha-helical recognition region; and d) an NLS. In some cases, the second fusion polypeptide comprises, in order from N-terminus to C-terminus: a) an NLS; b) a second polypeptide that comprises an alpha-helical recognition region; and c) a second fusion partner. In some cases, the second fusion polypeptide comprises, in order from N-terminus to C-terminus: a) an NLS; b) a second polypeptide that comprises an alpha-helical recognition region; c) a second fusion partner; and d) an NLS. In some cases, the NLS comprises the amino acid sequence MAPKKKRKVGIHGVPAA (SEQ ID NO: 1546). In some cases, the NLS comprises the amino acid sequence KRPAATKKAGQAKKKK (SEQ ID NO: 1547). Other suitable NLS are described elsewhere herein.

An NLS can be at or near the N-terminus and/or the C-terminus. In some cases, the second fusion polypeptide comprises two or more NLSs (e.g., 3 or more, 4 or more, or 5 or more NLSs). In some cases, the second fusion polypeptide comprises one or more NLSs (e.g., 2 or more, 3 or more, or 4 or more NLSs) at or near the N-terminus and/or one or more NLSs (e.g., 2 or more, 3 or more, or 4 or more NLSs) at or near the C-terminus. The term "at or near" is used here because, as is known in the art, the NLS need not be at the actual terminus of a protein, but can be positioned near (e.g., within 100 amino acids of) an N- and/or C-terminus (e.g., within 80, within 75, within 60, within 55, within 50, within 45, within 40, within 35, or within 30 amino acids of the an N- and/or C-terminus).

In some cases, the second fusion polypeptide comprises one or more linker polypeptides. For example, a linker polypeptide can be interposed between any of: a) an NLS and a fusion partner; b) a fusion partner and an alpha-helical lobe; and c) an alpha-helical lobe and an NLS. Suitable linker polypeptides are described elsewhere herein.

Cas9 Heterodimer Comprising a Circularly Permuted Polypeptide

In some embodiments, the Cas9 nuclease lobe of a Cas9 heterodimer is a circular permutant. As used herein, the term "circular permutant" refers to a variant polypeptide (e.g., of a subject Cas9 heterodimer) in which one section of the primary amino acid sequence has been moved to a different position within the primary amino acid sequence of the polypeptide, but where the local order of amino acids has not been changed, and where the three dimensional architecture of the protein is conserved. For example, a circular permutant of a wild type 500 amino acid polypeptide may have an N-terminal residue of residue number 50 (relative to the wild type protein), where residues 1-49 of the wild type protein are added the C-terminus. Such a circular permutant, relative to the wild type protein sequence would have, from N-terminus to C-terminus, amino acid numbers 50-500 followed by 1-49 (amino acid 49 would be the C-terminal residue). Thus, such an example circular permutant would have the same total number of amino acids as the wild type reference protein, and the amino acids would even be in the same order (locally), but the overall primary amino acid sequence is changed.

In some embodiments, a Cas9 heterodimer comprises: a) a first, circularly permuted, polypeptide comprising: a RuvCI polypeptide; ii) a RuvCII polypeptide; iii) an HNH polypeptide; iv) a RuvCIII polypeptide; and v) a PAM-interacting polypeptide; where the first polypeptide comprises a first member of a dimerization pair; and b) a second polypeptide comprising an alpha-helical recognition region and a second member of a dimerization pair.

For example, in some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a first member of a dimerization pair; and B) a second fusion polypeptide comprising: a) a second polypeptide that comprises an alpha-helical recognition region; and b) a second fusion partner, where the second fusion partner is a second member of the dimerization pair.

First Fusion Polypeptide

As described above, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a first member of a dimerization pair; and B) a second fusion polypeptide comprising: a) a second polypeptide that comprises an alpha-helical recognition region; and b) a second fusion partner, where the second fusion partner is a second member of the dimerization pair. In some cases, the first fusion partner (first member of the dimerization pair) is covalently linked, directly or via a linker, at or near (e.g., within 1 to 50 amino acids of) the amino terminus (N-terminus) of the first, circular permuted, polypeptide. In some cases, the first member of the dimerization pair is covalently linked, directly or via a linker, at or near (e.g., within 1 to 50 amino acids of) the carboxyl terminus (C-terminus) of the first, circular permuted, polypeptide. In some cases, the first polypeptide comprises a nuclease lobe of a Cas9 polypeptide.

In some cases, a first fusion polypeptide comprises one or more linker polypeptides. A linker polypeptide can be interposed between any of the various possible components (polypeptides) of a first fusion polypeptide. Examples of suitable positions for a linker polypeptide include, but are not limited to, interposed between: a) an NLS and a fusion partner; b) a fusion partner and a RuvCII polypeptide; c) a PAM-interacting polypeptide and a RuvCI polypeptide; d) a RuvCI polypeptide and an NLS; e) a RuvCI polypeptide and a fusion partner; and f) a RuvCI polypeptide and a RuvCII polypeptide.

The linker polypeptide may have any of a variety of amino acid sequences. Proteins can be joined by a spacer peptide, generally of a flexible nature, although other chemical linkages are not excluded. Currently, it is contemplated that the most useful linker sequences will generally be peptides of between about 6 and about 40 amino acids in length, or between about 6 and about 25 amino acids in length. These linkers are generally produced by using synthetic, linker-encoding oligonucleotides to couple the proteins. Peptide linkers with a degree of flexibility will generally be preferred. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Exemplary polypeptide linkers include glycine polymers $(G)_n$, glycine-serine polymers (including, for example, $(GS)_n$, $GSGGS_n$ (SEQ ID NO: 1548) and $GGGS_n$ (SEQ ID NO: 1549), where n is an integer of at least one), glycine-alanine polymers, alanine-serine polymers. Exemplary linkers can comprise amino acid sequences including, but not limited to, GGSG (SEQ ID NO: 1550), GGSGG (SEQ ID NO: 1551), GSGSG (SEQ ID NO: 1552), GSGGG (SEQ ID NO: 1553), GGGSG (SEQ ID NO: 1554), GSSSG (SEQ ID NO: 1555), and the like. The ordinarily skilled artisan will recognize that design of a peptide conjugated to any elements described above can include linkers that are all or partially flexible, such that the linker can include a flexible linker as well as one or more portions that confer less flexible structure.

Cas9 Nuclease Lobe Circular Permutant 1

In some cases, the first fusion polypeptide comprises, in order from N-terminus to C-terminus: a) a first fusion partner; and b) a first polypeptide comprising: i) a RuvCII polypeptide; ii) an HNH polypeptide; iii) a RuvCIII polypeptide; iv) a PAM-interacting polypeptide; and v) a RuvCI polypeptide. In some cases, the first fusion polypeptide comprises, in order from N-terminus to C-terminus: a) a first polypeptide comprising: i) a RuvCII polypeptide; ii) an HNH polypeptide; iii) a RuvCIII polypeptide; iv) a PAM-interacting polypeptide; and v) a RuvCI polypeptide; and b) a first fusion partner. In some cases, the first fusion partner is a first member of a dimerization pair. Suitable first members of a dimerization pair are described herein.

In some cases, the first fusion polypeptide comprises a heterologous sequence that provides for subcellular localization (e.g., a nuclear localization signal (NLS) for targeting to the nucleus; a mitochondrial localization signal for targeting to the mitochondria; a chloroplast localization signal for targeting to a chloroplast; an ER retention signal; and the like). In some cases, the first fusion polypeptide includes 2 or more, 3 or more, 4 or more, or 5 or more NLSs. In some cases, an NLS is located at or near (e.g., within 75 amino acids, 50 amino acids, or 30 amino acids) the N-terminus and/or at or near (e.g., within 75 amino acids, 50 amino acids, or 30 amino acids) the C-terminus. In some cases, the first fusion polypeptide comprises a nuclear localization signal (NLS). For example, in some cases, the first fusion polypeptide comprises, in order from N-terminus to C-terminus: a) an NLS; b) a first fusion partner; and c) a first polypeptide comprising: i) a RuvCII polypeptide; ii) an HNH polypeptide; iii) a RuvCIII polypeptide; iv) a PAM-interacting polypeptide; and v) a RuvCI polypeptide. In some cases, the first fusion polypeptide comprises, in order from N-terminus to C-terminus: a) an NLS; b) a first fusion partner; c) a first polypeptide comprising: i) a RuvCII polypeptide; ii) an HNH polypeptide; iii) a RuvCIII polypeptide; iv) a PAM-interacting polypeptide; and v) a RuvCI polypeptide; and d) an NLS. In some cases, the first fusion polypeptide comprises, in order from N-terminus to C-terminus: a) an NLS; b) a first polypeptide comprising: i) a RuvCII polypeptide; ii) an HNH polypeptide; iii) a RuvCIII polypeptide; iv) a PAM-interacting polypeptide; and v) a RuvCI polypeptide; and c) a first fusion partner. In some cases, the first fusion polypeptide comprises, in order from N-terminus to C-terminus: a) a first polypeptide comprising: i) a RuvCII polypeptide; ii) an HNH polypeptide; iii) a RuvCIII polypeptide; iv) a PAM-interacting polypeptide; and v) a RuvCI polypeptide; b) a first fusion partner; and c) an NLS. In some cases, the first fusion polypeptide comprises, in order from N-terminus to C-terminus: a) a first fusion partner; b a first polypeptide comprising: i) a RuvCII polypeptide; ii) an HNH polypeptide; iii) a RuvCIII polypeptide; iv) a PAM-interacting polypeptide; and v) a RuvCI polypeptide; and c) an NLS. In some cases, the first fusion partner is a first member of a dimerization pair. In some cases, the NLS comprises the amino acid sequence MAPKKKRKVGIHGVPAA (SEQ ID NO: 1546). In some cases, the NLS comprises the amino acid sequence KRPAATKKAGQAKKKK (SEQ ID NO: 1547). Other suitable NLS are described elsewhere herein.

An NLS can be at or near the N-terminus and/or the C-terminus. In some cases, the first fusion polypeptide comprises two or more NLSs (e.g., 3 or more, 4 or more, or 5 or more NLSs). In some cases, the first fusion polypeptide comprises one or more NLSs (e.g., 2 or more, 3 or more, or 4 or more NLSs) at or near the N-terminus and/or one or more NLSs (e.g., 2 or more, 3 or more, or 4 or more NLSs) at or near the C-terminus. The term "at or near" is used here because, as is known in the art, the NLS need not be at the actual terminus of a protein, but can be positioned near (e.g., within 100 amino acids of) an N- and/or C-terminus (e.g., within 80, within 75, within 60, within 55, within 50, within 45, within 40, within 35, or within 30 amino acids of the an N- and/or C-terminus).

A RuvCII polypeptide can comprise an amino acid sequence having at least 75%, at least 80%, at least 85%, at least 90%, at least 95%, at least 98%, at least 99%, or 100%, amino acid sequence identity to a contiguous stretch of from 40 to 57 amino acids of amino acids 718-774 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to about 70 amino acids, e.g., from 40 amino acids to 45 amino acids, from 45 amino acids to 50 amino acids, from 50 amino acids to 55 amino acids, from 55 amino acids to 60 amino acids, from 60 amino acids to 65 amino acids, or from 65 amino acids to 70 amino acids. In some cases, a RuvCII polypeptide comprises an amino acid sequence having at least 75%, at least 80%, at least 85%, at least 90%, at least 95%, at least 98%, at least 99%, or 100%, amino acid sequence identity to amino acids 718-774 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of 55-60 (e.g., 55, 56, 57, 58, 59, or 60) amino acids.

A RuvCII polypeptide can comprise an amino acid sequence having at least 75%, at least 80%, at least 85%, at least 90%, at least 95%, at least 98%, at least 99%, or 100%, amino acid sequence identity to a contiguous stretch of from 40 to 46 amino acids of amino acids 729-775 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to about 60 amino acids, e.g., from 40 amino acids to 45 amino acids, from 45 amino acids to 50 amino acids, from 50 amino acids to 55 amino acids, or from 55 amino acids to 60 amino acids. In some cases, a RuvCII polypeptide comprises an amino acid sequence having at least 75%, at least 80%, at least 85%, at least 90%, at least 95%, at least 98%, at least 99%, or 100%, amino acid sequence identity to amino acids 728-774 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of 45-50 (e.g., 45, 46, 47, 48, 49, or 50) amino acids.

An HNH polypeptide can comprise an amino acid sequence having at least 75%, at least 80%, at least 85%, at least 90%, at least 95%, at least 98%, at least 99%, or 100%, amino acid sequence identity to a contiguous stretch of from 100 to 134 amino acids of amino acids 776-909 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 90 amino acids to 150 amino acids, e.g., from 90 amino acids to 95 amino acids, from 95 to amino acids to 100 amino acids, from 100 amino acids to 125 amino acids, from 125 amino acids to 130 amino acids, from 130 amino acids to 135 amino acids, from 135 amino acids to 140 amino acids, from 140 amino acids to 145 amino acids, or from 145 amino acids to 150 amino acids. In some cases, an HNH polypeptide comprises an amino acid sequence having at least 75%, at least 80%, at least 85%, at least 90%, at least 95%, at least 98%, at least 99%, or 100%, amino acid sequence identity to amino acids 776-909 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 130 amino acids to 140 amino acids (e.g., 130, 131, 132, 133, 134, 135, 136, 137, 138, 139, or 140 amino acids).

A RuvCIII polypeptide can comprise an amino acid sequence having at least 75%, at least 80%, at least 85%, at least 90%, at least 95%, at least 98%, at least 99%, or 100%, amino acid sequence identity to a contiguous stretch of from 150 amino acids to 190 amino acids of amino acids 910 to 1099 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 150 amino acids to 160 amino acids, from 160 amino acids to 170 amino acids, from 170 amino acids to 180 amino acids, from 180 amino acids to 190 amino acids, from 190 amino acids to 200 amino acids, from 200 amino acids to 210 amino acids, or from 210 amino acids to 220 amino acids. In some cases, a RuvCIII polypeptide comprises an amino acid sequence having at least 75%, at least 80%, at least 85%, at least 90%, at least 95%, at least 98%, at least 99%, or 100%, amino acid sequence identity to amino acids 910 to 1099 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 180 amino acids to 190 amino acids (e.g., 180, 181, 182, 183, 184, 185, 186, 187, 188, 189, or 190 amino acids).

A PAM-interacting polypeptide can comprise an amino acid sequence having at least 75%, at least 80%, at least 85%, at least 90%, at least 95%, at least 98%, at least 99%, or 100%, amino acid sequence identity to a contiguous stretch of from 200 amino acids to 268 amino acids of amino acids 1100 to 1367 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 240 amino acids to 280 amino acids, e.g., from 240 amino acids to 250 amino acids, from 250 amino acids to 260 amino acids, from 260 amino acids to 270 amino acids, or from 270 amino acids to 280 amino acids. In some cases, a PAM-interacting polypeptide comprises an amino acid sequence having at least 75%, at least 80%, at least 85%, at least 90%, at least 95%, at least 98%, at least 99%, or 100%, amino acid sequence identity to amino acids 1100 to 1367 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 260 amino acids to 270 amino acids (e.g., 260, 261, 262, 263, 264, 265, 266, 267, 268, 269, or 270 amino acids).

A RuvCI polypeptide can comprise an amino acid sequence having at least 75%, at least 80%, at least 85%, at least 90%, at least 95%, at least 98%, at least 99%, or 100%, amino acid sequence identity to a contiguous stretch of from 40 amino acids to 60 amino acids of amino acids 1-60 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to 80 amino acids, e.g., from 40 amino acids to 50 amino acids, from 50 amino acids to 60 amino acids, from 60 amino acids to 70 amino acids, or from 70 amino acids to 80 amino acids. In some cases, a RuvCI polypeptide comprises an amino acid sequence having at least 75%, at least 80%, at least 85%, at least 90%, at least 95%, at least 98%, at least 99%, or 100%, amino acid sequence identity to amino acids 1-60 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 50 amino acids to 60 amino acids (e.g., 50, 51, 52, 53, 54, 55, 56, 57, 58, 59, or 60 amino acids).

Cas9 Nuclease Lobe Circular Permutant 2

In some cases, the first fusion polypeptide comprises, in order from N-terminus to C-terminus: a) a first fusion partner; and b) a first polypeptide comprising: i) a C-terminal portion of an HNH polypeptide; ii) a RuvCIII polypeptide; iii) a PAM-interacting polypeptide; v) a RuvCI polypeptide; vi) a RuvCII polypeptide; and vi) an N-terminal portion of an HNH polypeptide. In some cases, the first fusion polypeptide comprises, in order from N-terminus to C-terminus: a) a first polypeptide comprising: i) a C-terminal portion of an HNH polypeptide; ii) a RuvCIII polypeptide; iii) a PAM-interacting polypeptide; v) a RuvCI polypeptide; vi) a RuvCII polypeptide; and vi) an N-terminal portion of an HNH polypeptide; and b) a first fusion partner. In some cases, the first fusion partner is a first member of a dimerization pair. Suitable first members of a dimerization pair are described herein.

In some cases, the first fusion polypeptide comprises a heterologous sequence that provides for subcellular localization (e.g., a nuclear localization signal (NLS) for targeting to the nucleus; a mitochondrial localization signal for targeting to the mitochondria; a chloroplast localization signal for targeting to a chloroplast; an ER retention signal; and the like). In some cases, the first fusion polypeptide includes 2 or more, 3 or more, 4 or more, or 5 or more NLSs. In some cases, an NLS is located at or near (e.g., within 75 amino acids, 50 amino acids, or 30 amino acids) the N-terminus and/or at or near (e.g., within 75 amino acids, 50 amino acids, or 30 amino acids) the C-terminus. In some cases, the first fusion polypeptide comprises a nuclear localization signal (NLS).

In some cases, the first fusion polypeptide comprises, in order from N-terminus to C-terminus: a) an NLS; b) a first fusion partner; and c) a first polypeptide comprising: i) a C-terminal portion of an HNH polypeptide; ii) a RuvCIII polypeptide; iii) a PAM-interacting polypeptide; v) a RuvCI polypeptide; vi) a RuvCII polypeptide; and vi) an N-terminal portion of an HNH polypeptide. In some cases, the first fusion polypeptide comprises, in order from N-terminus to C-terminus: a) a first polypeptide comprising: i) a C-terminal portion of an HNH polypeptide; ii) a RuvCIII polypeptide; iii) a PAM-interacting polypeptide; v) a RuvCI polypeptide; vi) a RuvCII polypeptide; and vi) an N-terminal portion of an HNH polypeptide; b) a first fusion partner; and c) an NLS. In some cases, the first fusion polypeptide comprises, in order from N-terminus to C-terminus: a) an NLS; b) a first fusion partner; c) a first polypeptide comprising: i) a C-terminal portion of an HNH polypeptide; ii) a RuvCIII polypeptide; iii) a PAM-interacting polypeptide; v) a RuvCI polypeptide; vi) a RuvCII polypeptide; and vi) an N-terminal portion of an HNH polypeptide; and d) an NLS. In some cases, the NLS comprises the amino acid sequence MAPKKKRKVGIHGVPAA (SEQ ID NO: 1546). In some cases, the NLS comprises the amino acid sequence KRPAATKKAGQAKKKK (SEQ ID NO: 1547). Other suitable NLS are described elsewhere herein. In some cases, the first fusion partner is a first member of a dimerization pair.

An NLS can be at or near the N-terminus and/or the C-terminus. In some cases, the first fusion polypeptide comprises two or more NLSs (e.g., 3 or more, 4 or more, or 5 or more NLSs). In some cases, the first fusion polypeptide comprises one or more NLSs (e.g., 2 or more, 3 or more, or 4 or more NLSs) at or near the N-terminus and/or one or more NLSs (e.g., 2 or more, 3 or more, or 4 or more NLSs) at or near the C-terminus. The term "at or near" is used here because, as is known in the art, the NLS need not be at the actual terminus of a protein, but can be positioned near (e.g., within 100 amino acids of) an N- and/or C-terminus (e.g., within 80, within 75, within 60, within 55, within 50, within 45, within 40, within 35, or within 30 amino acids of the an N- and/or C-terminus).

In some cases, a first fusion polypeptide comprises one or more linker polypeptides. For example, a linker polypeptide can be interposed between any of: a) an NLS and a fusion partner; b) a fusion partner and a C-terminal portion of an HNH polypeptide; c) a PAM-interacting polypeptide and a RuvCI polypeptide; and d) an N-terminal portion of an HNH polypeptide and a fusion partner. Suitable linker polypeptides are as described above.

A C-terminal portion of an HNH polypeptide can comprise an amino acid sequence having at least 75%, at least 80%, at least 85%, at least 90%, at least 95%, at least 98%, at least 99%, or 100%, amino acid sequence identity to a contiguous stretch of from 35 to 42 amino acids of amino acids 868-909 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 35 to 42 amino acids (e.g., 35, 36, 37, 38, 39, 40, 41, or 42 amino acids). A C-terminal portion of an HNH polypeptide can comprise an amino acid sequence having at least 75%, at least 80%, at least 85%, at least 90%, at least 95%, at least 98%, at least 99%, or 100%, amino acid sequence identity to a contiguous stretch of from 50 amino acids to 67 amino acids of amino acids 842-909 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 50 amino acids to 80 amino acids, e.g., from 50 amino acids to 60 amino acids, from 60 amino acids to 70 amino acids, or from 70 amino acids to 80 amino acids.

An N-terminal portion of an HNH polypeptide can comprise an amino acid sequence having at least 75%, at least 80%, at least 85%, at least 90%, at least 95%, at least 98%, at least 99%, or 100%, amino acid sequence identity to a contiguous stretch of from 80 amino acids to 92 amino acids of amino acids 776 to 867 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 80 amino acids to 110 amino acids, e.g., from 80 amino acids to 90 amino acids, from 90 amino acids to 100 amino acids, or from 100 amino acids to 110 amino acids. In some cases, an N-terminal portion of an HNH polypeptide comprises an amino acid sequence having at least 75%, at least 80%, at least 85%, at least 90%, at least 95%, at least 98%, at least 99%, or 100%, amino acid sequence identity to amino acids 776 to 867 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of 85 amino acids to 95 amino acids (85, 86, 87, 88, 89, 90, 91, 92, 93, 94, or 95 amino acids). An N-terminal portion of an HNH polypeptide can comprise an amino acid sequence having at least 75%, at least 80%, at least 85%, at least 90%, at least 95%, at least 98%, at least 99%, or 100%, amino acid sequence identity to a contiguous stretch of from 50 amino acids to 66 amino acids of amino acids 776-841 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 50 amino acids to 80 amino acids, e.g., from 50 amino acids to 60 amino acids, from 60 amino acids to 70 amino acids, or from 70 amino acids to 80 amino acids.

A RuvCIII polypeptide can comprise an amino acid sequence having at least 75%, at least 80%, at least 85%, at least 90%, at least 95%, at least 98%, at least 99%, or 100%, amino acid sequence identity to a contiguous stretch of from 150 amino acids to 190 amino acids of amino acids 910 to 1099 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 150 amino acids to 160 amino acids, from 160 amino acids to 170 amino acids, from 170 amino acids to 180 amino acids, from 180 amino acids to 190 amino acids, from 190 amino acids to 200 amino acids, from 200 amino acids to 210 amino acids, or from 210 amino acids to 220 amino acids. In some cases, a RuvCIII polypeptide comprises an amino acid sequence having at least 75%, at least 80%, at least 85%, at least 90%, at least 95%, at least 98%, at least 99%, or 100%, amino acid sequence identity to amino acids 910 to 1099 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 180 amino acids to 190 amino acids (e.g., 180, 181, 182, 183, 184, 185, 186, 187, 188, 189, or 190 amino acids).

A PAM-interacting polypeptide can comprise an amino acid sequence having at least 75%, at least 80%, at least 85%, at least 90%, at least 95%, at least 98%, at least 99%, or 100%, amino acid sequence identity to a contiguous stretch of from 200 amino acids to 268 amino acids of amino acids 1100 to 1367 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 240 amino acids to 280 amino acids, e.g., from 240 amino acids to 250 amino acids, from 250 amino acids to 260 amino acids, from 260 amino acids to 270 amino acids, or from 270 amino acids to 280 amino acids. In some cases, a PAM-interacting polypeptide comprises an amino acid sequence having at least 75%, at least 80%, at least 85%, at least 90%, at least 95%, at least 98%, at least 99%, or 100%, amino acid sequence identity to amino acids 1100 to 1367 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 260 amino acids to 270 amino acids (e.g., 260, 261, 262, 263, 264, 265, 266, 267, 268, 269, or 270 amino acids).

A RuvCI polypeptide can comprise an amino acid sequence having at least 75%, at least 80%, at least 85%, at least 90%, at least 95%, at least 98%, at least 99%, or 100%, amino acid sequence identity to a contiguous stretch of from 40 amino acids to 60 amino acids of amino acids 1-60 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to 80 amino acids, e.g., from 40 amino acids to 50 amino acids, from 50 amino acids to 60 amino acids, from 60 amino acids to 70 amino acids, or from 70 amino acids to 80 amino acids. In some cases, a RuvCI polypeptide comprises an amino acid sequence having at least 75%, at least 80%, at least 85%, at least 90%, at least 95%, at least 98%, at least 99%, or 100%, amino acid sequence identity to amino acids 1-60 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 50 amino acids to 60 amino acids (e.g., 50, 51, 52, 53, 54, 55, 56, 57, 58, 59, or 60 amino acids).

A RuvCII polypeptide can comprise an amino acid sequence having at least 75%, at least 80%, at least 85%, at least 90%, at least 95%, at least 98%, at least 99%, or 100%, amino acid sequence identity to a contiguous stretch of from 40 to 46 amino acids of amino acids 729-775 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to about 60 amino acids, e.g., from 40 amino acids to 45 amino acids, from 45 amino acids to 50 amino acids, from 50 amino acids to 55 amino acids, or from 55 amino acids to 60 amino acids. In some cases, a RuvCII polypeptide comprises an amino acid sequence having at least 75%, at least 80%, at least 85%, at least 90%, at least 95%, at least 98%, at least 99%, or 100%, amino acid sequence identity to amino acids 728-774 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of 45-50 (e.g., 45, 46, 47, 48, 49, or 50) amino acids.

Cas9 Nuclease Lobe Circular Permutant 3

In some cases, the first fusion polypeptide comprises, in order from N-terminus to C-terminus: a) a first fusion partner; and b) a first polypeptide comprising: i) an HNH polypeptide; ii) a RuvCIII polypeptide; iii) a PAM-interacting polypeptide; iv) a RuvCI polypeptide; and vi) a RuvCII polypeptide. In some cases, the first fusion polypeptide comprises, in order from N-terminus to C-terminus: a) a first polypeptide comprising: i) an HNH polypeptide; ii) a RuvCIII polypeptide; iii) a PAM-interacting polypeptide; iv) a RuvCI polypeptide; and vi) a RuvCII polypeptide; and b) a first fusion partner. In some cases, the first fusion partner is a first member of a dimerization pair. Suitable first members of a dimerization pair are described herein.

In some cases, the first fusion polypeptide comprises a heterologous sequence that provides for subcellular localization (e.g., a nuclear localization signal (NLS) for targeting to the nucleus; a mitochondrial localization signal for targeting to the mitochondria; a chloroplast localization signal for targeting to a chloroplast; an ER retention signal; and the like). In some cases, the first fusion polypeptide includes 2 or more, 3 or more, 4 or more, or 5 or more NLSs. In some cases, an NLS is located at or near (e.g., within 75 amino acids, 50 amino acids, or 30 amino acids) the N-terminus and/or at or near (e.g., within 75 amino acids, 50 amino acids, or 30 amino acids) the C-terminus. In some cases, the first fusion polypeptide comprises a nuclear localization signal (NLS).

In some cases, the first fusion polypeptide comprises, in order from N-terminus to C-terminus: a) an NLS; b) a first fusion partner; and c) a first polypeptide comprising: i) an HNH polypeptide; ii) a RuvCIII polypeptide; iii) a PAM-interacting polypeptide; iv) a RuvCI polypeptide; and vi) a RuvCII polypeptide. In some cases, the first fusion polypeptide comprises, in order from N-terminus to C-terminus: a) a first polypeptide comprising: i) an HNH polypeptide; ii) a RuvCIII polypeptide; iii) a PAM-interacting polypeptide; iv) a RuvCI polypeptide; and vi) a RuvCII polypeptide; b) a first fusion partner; and c) an NLS. In some cases, the first fusion polypeptide comprises, in order from N-terminus to C-terminus: a) an NLS; b) a first fusion partner; c) a first polypeptide comprising: i) an HNH polypeptide; ii) a RuvCIII polypeptide; iii) a PAM-interacting polypeptide; iv) a RuvCI polypeptide; and vi) a RuvCII polypeptide; and d) an NLS. In some cases, the NLS comprises the amino acid sequence MAPKKKRKVGIHGVPAA (SEQ ID NO: 1546). In some cases, the NLS comprises the amino acid sequence KRPAATKKAGQAKKKK (SEQ ID NO: 1547). Other suitable NLS are described elsewhere herein. In some cases, the first fusion partner is a first member of a dimerization pair.

An NLS can be at or near the N-terminus and/or the C-terminus. In some cases, the first fusion polypeptide comprises two or more NLSs (e.g., 3 or more, 4 or more, or 5 or more NLSs). In some cases, the first fusion polypeptide comprises one or more NLSs (e.g., 2 or more, 3 or more, or 4 or more NLSs) at or near the N-terminus and/or one or more NLSs (e.g., 2 or more, 3 or more, or 4 or more NLSs) at or near the C-terminus. The term "at or near" is used here because, as is known in the art, the NLS need not be at the actual terminus of a protein, but can be positioned near (e.g., within 100 amino acids of) an N- and/or C-terminus (e.g., within 80, within 75, within 60, within 55, within 50, within 45, within 40, within 35, or within 30 amino acids of the an N- and/or C-terminus).

In some cases, a first fusion polypeptide comprises one or more linker polypeptides. For example, a linker polypeptide can be interposed between any of: a) an NLS and a fusion partner; b) a fusion partner and an HNH polypeptide; c) a PAM-interacting polypeptide and a RuvCI polypeptide; and d) a RuvCII polypeptide and a fusion partner. Suitable linker polypeptides are as described above.

A RuvCIII polypeptide can comprise an amino acid sequence having at least 75%, at least 80%, at least 85%, at least 90%, at least 95%, at least 98%, at least 99%, or 100%, amino acid sequence identity to a contiguous stretch of from 150 amino acids to 190 amino acids of amino acids 910 to 1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 150 amino acids to 160 amino acids, from 160 amino acids to 170 amino acids, from 170 amino acids to 180 amino acids, from 180 amino acids to 190 amino acids, from 190 amino acids to 200 amino acids, from 200 amino acids to 210 amino acids, or from 210 amino acids to 220 amino acids. In some cases, a RuvCIII polypeptide comprises an amino acid sequence having at least 75%, at least 80%, at least 85%, at least 90%, at least 95%, at least 98%, at least 99%, or 100%, amino acid sequence identity to amino acids 910 to 1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 180 amino acids to 190 amino acids (e.g., 180, 181, 182, 183, 184, 185, 186, 187, 188, 189, or 190 amino acids).

A PAM-interacting polypeptide can comprise an amino acid sequence having at least 75%, at least 80%, at least 85%, at least 90%, at least 95%, at least 98%, at least 99%, or 100%, amino acid sequence identity to a contiguous stretch of from 200 amino acids to 268 amino acids of amino acids 1100 to 1367 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 240 amino acids to 280 amino acids, e.g., from 240 amino acids to 250 amino acids, from 250 amino acids to 260 amino acids, from 260 amino acids to 270 amino acids, or from 270 amino acids to 280 amino acids. In some cases, a PAM-interacting polypeptide comprises an amino acid sequence having at least 75%, at least 80%, at least 85%, at least 90%, at least 95%, at least 98%, at least 99%, or 100%, amino acid sequence identity to amino acids 1100 to 1367 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 260 amino acids to 270 amino acids (e.g., 260, 261, 262, 263, 264, 265, 266, 267, 268, 269, or 270 amino acids).

A RuvCI polypeptide can comprise an amino acid sequence having at least 75%, at least 80%, at least 85%, at least 90%, at least 95%, at least 98%, at least 99%, or 100%, amino acid sequence identity to a contiguous stretch of from 40 amino acids to 60 amino acids of amino acids 1-60 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to 80 amino acids, e.g., from 40 amino acids to 50 amino acids, from 50 amino acids to 60 amino acids, from 60 amino acids to 70 amino acids, or from 70 amino acids to 80 amino acids. In some cases, a RuvCI polypeptide comprises an amino acid sequence having at least 75%, at least 80%, at least 85%, at least 90%, at least 95%, at least 98%, at least 99%, or 100%, amino acid sequence identity to amino acids 1-60 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 50 amino acids to 60 amino acids (e.g., 50, 51, 52, 53, 54, 55, 56, 57, 58, 59, or 60 amino acids).

A RuvCII polypeptide can comprise an amino acid sequence having at least 75%, at least 80%, at least 85%, at least 90%, at least 95%, at least 98%, at least 99%, or 100%, amino acid sequence identity to a contiguous stretch of from 40 to 46 amino acids of amino acids 729-775 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to about 60 amino acids, e.g., from 40 amino acids to 45 amino acids, from 45 amino acids to 50 amino acids, from 50 amino acids to 55 amino acids, or from 55 amino acids to 60 amino acids. In some cases, a RuvCII polypeptide comprises an amino acid sequence having at least 75%, at least 80%, at least 85%, at least 90%, at least 95%, at least 98%, at least 99%, or 100%, amino acid sequence identity to amino acids 728-774 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of 45-50 (e.g., 45, 46, 47, 48, 49, or 50) amino acids.

An HNH polypeptide can comprise an amino acid sequence having at least 75%, at least 80%, at least 85%, at least 90%, at least 95%, at least 98%, at least 99%, or 100%, amino acid sequence identity to a contiguous stretch of from 100 to 134 amino acids of amino acids 776-909 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 90 amino acids to 150 amino acids, e.g., from 90 amino acids to 95 amino acids, from 95 to amino acids to 100 amino acids, from 100 amino acids to 125 amino acids, from 125 amino acids to 130 amino acids, from 130 amino acids to 135 amino acids, from 135 amino acids to 140 amino acids, from 140 amino acids to 145 amino acids, or from 145 amino acids to 150 amino acids. In some cases, an HNH polypeptide comprises an amino acid sequence having at least 75%, at least 80%, at least 85%, at least 90%, at least 95%, at least 98%, at least 99%, or 100%, amino acid sequence identity to amino acids 776-909 of the S. pyogenes Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 130 amino acids to 140 amino acids (e.g., 130, 131, 132, 133, 134, 135, 136, 137, 138, 139, or 140 amino acids).

Cas9 Nuclease Lobe Circular Permutant 4

In some cases, the first fusion polypeptide comprises, in order from N-terminus to C-terminus: a) a first fusion partner; and b) a first polypeptide comprising: i) a RuvCIII polypeptide; ii) a PAM-interacting polypeptide; iii) a RuvCI polypeptide; iv) a RuvCII polypeptide; and v) an HNH polypeptide. In some cases, the first fusion polypeptide comprises, in order from N-terminus to C-terminus: a) a first polypeptide comprising: i) a RuvCIII polypeptide; ii) a PAM-interacting polypeptide; iii) a RuvCI polypeptide; iv) a RuvCII polypeptide; and v) an HNH polypeptide; and b) a first fusion partner. In some cases, the first fusion partner is a first member of a dimerization pair. Suitable first members of a dimerization pair are described herein.

In some cases, the first fusion polypeptide comprises a heterologous sequence that provides for subcellular localization (e.g., a nuclear localization signal (NLS) for targeting to the nucleus; a mitochondrial localization signal for targeting to the mitochondria; a chloroplast localization signal for targeting to a chloroplast; an ER retention signal; and the like). In some cases, the first fusion polypeptide includes 2 or more, 3 or more, 4 or more, or 5 or more NLSs. In some cases, an NLS is located at or near (e.g., within 75 amino acids, 50 amino acids, or 30 amino acids) the N-terminus and/or at or near (e.g., within 75 amino acids, 50 amino acids, or 30 amino acids) the C-terminus. In some cases, the first fusion polypeptide comprises a nuclear localization signal (NLS).

In some cases, the first fusion polypeptide comprises, in order from N-terminus to C-terminus: a) an NLS; b) a first fusion partner; and c) a first polypeptide comprising: i) a RuvCIII polypeptide; ii) a PAM-interacting polypeptide; iii) a RuvCI polypeptide; iv) a RuvCII polypeptide; and v) an HNH polypeptide. In some cases, the first fusion polypeptide comprises, in order from N-terminus to C-terminus: a)

a first polypeptide comprising: i) a RuvCIII polypeptide; ii) a PAM-interacting polypeptide; iii) a RuvCI polypeptide; iv) a RuvCII polypeptide; and v) an HNH polypeptide; b) a first fusion partner; and c) a fusion partner. In some cases, the first fusion polypeptide comprises, in order from N-terminus to C-terminus: a) an NLS; b) a first fusion partner; c) a first polypeptide comprising: i) a RuvCIII polypeptide; ii) a PAM-interacting polypeptide; iii) a RuvCI polypeptide; iv) a RuvCII polypeptide; and v) an HNH polypeptide; d) an NLS. In some cases, the first fusion partner is a first member of a dimerization pair. In some cases, the NLS comprises the amino acid sequence MAPKKKRKVGIHGVPAA (SEQ ID NO: 1546). In some cases, the NLS comprises the amino acid sequence KRPAATKKAGQAKKKK (SEQ ID NO: 1547). Other suitable NLS are described elsewhere herein. In some cases, the first fusion partner is a first member of a dimerization pair.

An NLS can be at or near the N-terminus and/or the C-terminus. In some cases, the first fusion polypeptide comprises two or more NLSs (e.g., 3 or more, 4 or more, or 5 or more NLSs). In some cases, the first fusion polypeptide comprises one or more NLSs (e.g., 2 or more, 3 or more, or 4 or more NLSs) at or near the N-terminus and/or one or more NLSs (e.g., 2 or more, 3 or more, or 4 or more NLSs) at or near the C-terminus. The term "at or near" is used here because, as is known in the art, the NLS need not be at the actual terminus of a protein, but can be positioned near (e.g., within 100 amino acids of) an N- and/or C-terminus (e.g., within 80, within 75, within 60, within 55, within 50, within 45, within 40, within 35, or within 30 amino acids of the an N- and/or C-terminus).

In some cases, a first fusion polypeptide comprises one or more linker polypeptides. For example, a linker polypeptide can be interposed between any of: a) an NLS and a fusion partner; b) a fusion partner and a RuvCIII polypeptide; c) a PAM-interacting polypeptide and a RuvCI polypeptide; and d) an HNH polypeptide and a fusion partner. Suitable linker polypeptides are as described above.

A RuvCIII polypeptide can comprise an amino acid sequence having at least 75%, at least 80%, at least 85%, at least 90%, at least 95%, at least 98%, at least 99%, or 100%, amino acid sequence identity to a contiguous stretch of from 150 amino acids to 190 amino acids of amino acids 910 to 1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 150 amino acids to 160 amino acids, from 160 amino acids to 170 amino acids, from 170 amino acids to 180 amino acids, from 180 amino acids to 190 amino acids, from 190 amino acids to 200 amino acids, from 200 amino acids to 210 amino acids, or from 210 amino acids to 220 amino acids. In some cases, a RuvCIII polypeptide comprises an amino acid sequence having at least 75%, at least 80%, at least 85%, at least 90%, at least 95%, at least 98%, at least 99%, or 100%, amino acid sequence identity to amino acids 910 to 1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 180 amino acids to 190 amino acids (e.g., 180, 181, 182, 183, 184, 185, 186, 187, 188, 189, or 190 amino acids).

A PAM-interacting polypeptide can comprise an amino acid sequence having at least 75%, at least 80%, at least 85%, at least 90%, at least 95%, at least 98%, at least 99%, or 100%, amino acid sequence identity to a contiguous stretch of from 200 amino acids to 268 amino acids of amino acids 1100 to 1367 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 240 amino acids to 280 amino acids, e.g., from 240 amino acids to 250 amino acids, from 250 amino acids to 260 amino acids, from 260 amino acids to 270 amino acids, or from 270 amino acids to 280 amino acids. In some cases, a PAM-interacting polypeptide comprises an amino acid sequence having at least 75%, at least 80%, at least 85%, at least 90%, at least 95%, at least 98%, at least 99%, or 100%, amino acid sequence identity to amino acids 1100 to 1367 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 260 amino acids to 270 amino acids (e.g., 260, 261, 262, 263, 264, 265, 266, 267, 268, 269, or 270 amino acids).

A RuvCI polypeptide can comprise an amino acid sequence having at least 75%, at least 80%, at least 85%, at least 90%, at least 95%, at least 98%, at least 99%, or 100%, amino acid sequence identity to a contiguous stretch of from 40 amino acids to 60 amino acids of amino acids 1-60 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to 80 amino acids, e.g., from 40 amino acids to 50 amino acids, from 50 amino acids to 60 amino acids, from 60 amino acids to 70 amino acids, or from 70 amino acids to 80 amino acids. In some cases, a RuvCI polypeptide comprises an amino acid sequence having at least 75%, at least 80%, at least 85%, at least 90%, at least 95%, at least 98%, at least 99%, or 100%, amino acid sequence identity to amino acids 1-60 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 50 amino acids to 60 amino acids (e.g., 50, 51, 52, 53, 54, 55, 56, 57, 58, 59, or 60 amino acids).

A RuvCII polypeptide can comprise an amino acid sequence having at least 75%, at least 80%, at least 85%, at least 90%, at least 95%, at least 98%, at least 99%, or 100%, amino acid sequence identity to a contiguous stretch of from 40 to 46 amino acids of amino acids 729-775 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to about 60 amino acids, e.g., from 40 amino acids to 45 amino acids, from 45 amino acids to 50 amino acids, from 50 amino acids to 55 amino acids, or from 55 amino acids to 60 amino acids. In some cases, a RuvCII polypeptide comprises an amino acid sequence having at least 75%, at least 80%, at least 85%, at least 90%, at least 95%, at least 98%, at least 99%, or 100%, amino acid sequence identity to amino acids 728-774 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of 45-50 (e.g., 45, 46, 47, 48, 49, or 50) amino acids.

An HNH polypeptide can comprise an amino acid sequence having at least 75%, at least 80%, at least 85%, at least 90%, at least 95%, at least 98%, at least 99%, or 100%, amino acid sequence identity to a contiguous stretch of from 100 to 134 amino acids of amino acids 776-909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 90 amino acids to 150 amino acids, e.g., from 90 amino acids to 95 amino acids, from 95 to amino acids to 100 amino acids, from 100 amino acids to 125 amino acids, from 125 amino acids to 130 amino acids, from 130 amino acids to 135 amino acids, from 135 amino acids to 140 amino acids, from 140 amino acids to 145 amino acids, or from 145 amino acids to 150 amino acids. In some cases, an HNH polypeptide comprises an amino acid sequence having at least 75%, at least 80%, at least 85%, at least 90%, at least 95%, at least 98%, at least 99%, or 100%, amino acid sequence identity to amino acids 776-909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 130 amino acids to 140 amino acids (e.g., 130, 131, 132, 133, 134, 135, 136, 137, 138, 139, or 140 amino acids).

Cas9 Nuclease Lobe Circular Permutant 5

In some cases, the first fusion polypeptide comprises, in order from N-terminus to C-terminus: a) a first fusion partner; and b) a first polypeptide comprising: i) a C-terminal portion of a RuvCIII polypeptide; ii) a PAM-interacting polypeptide; iii) a RuvCI polypeptide; iv) a RuvCII polypeptide; v) an HNH polypeptide; and vi) an N-terminal portion of a RuvCIII polypeptide. In some cases, the first fusion polypeptide comprises, in order from N-terminus to C-terminus: a) a first polypeptide comprising: i) a C-terminal portion of a RuvCIII polypeptide; ii) a PAM-interacting polypeptide; iii) a RuvCI polypeptide; iv) a RuvCII polypeptide; v) an HNH polypeptide; and vi) an N-terminal portion of a RuvCIII polypeptide; and b) a first fusion partner. In some cases, the first fusion partner is a first member of a dimerization pair. Suitable first members of a dimerization pair are described elsewhere herein.

A C-terminal portion of a RuvCIII polypeptide can comprise an amino acid sequence having at least 75%, at least 80%, at least 85%, at least 90%, at least 95%, at least 98%, at least 99%, or 100%, amino acid sequence identity to a contiguous stretch of from 75 amino acids to 84 amino acids of amino acids 1016 to 1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 70 amino acids to 100 amino acids, from 70 amino acids to 80 amino acids, from 80 amino acids to 90 amino acids, or from 90 amino acids to 100 amino acids. In some cases, a C-terminal RuvCIII polypeptide comprises an amino acid sequence having at least 75%, at least 80%, at least 85%, at least 90%, at least 95%, at least 98%, at least 99%, or 100%, amino acid sequence identity to amino acids 1016 to 1099 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 80 amino acids to 90 amino acids (e.g., 80, 81, 82, 83, 84, 85, 86, 87, 88, 89, or 90 amino acids).

An N-terminal portion of a RuvCIII polypeptide can comprise an amino acid sequence having at least 75%, at least 80%, at least 85%, at least 90%, at least 95%, at least 98%, at least 99%, or 100%, amino acid sequence identity to a contiguous stretch of from 80 amino acids to 106 amino acids of amino acids 910 to 1015 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 80 amino acids to 120 amino acids, from 80 amino acids to 90 amino acids, from 90 amino acids to 100 amino acids, from 100 amino acids to 110 amino acids, or from 110 amino acids to 120 amino acids. In some cases, a RuvCIII polypeptide comprises an amino acid sequence having at least 75%, at least 80%, at least 85%, at least 90%, at least 95%, at least 98%, at least 99%, or 100%, amino acid sequence identity to amino acids 910 to 1015 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 100 amino acids to 106 amino acids (e.g., 100, 101, 102, 103, 104, 105, 106, 107, 108, 109, or 110 amino acids).

A PAM-interacting polypeptide can comprise an amino acid sequence having at least 75%, at least 80%, at least 85%, at least 90%, at least 95%, at least 98%, at least 99%, or 100%, amino acid sequence identity to a contiguous stretch of from 200 amino acids to 268 amino acids of amino acids 1100 to 1367 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 240 amino acids to 280 amino acids, e.g., from 240 amino acids to 250 amino acids, from 250 amino acids to 260 amino acids, from 260 amino acids to 270 amino acids, or from 270 amino acids to 280 amino acids. In some cases, a PAM-interacting polypeptide comprises an amino acid sequence having at least 75%, at least 80%, at least 85%, at least 90%, at least 95%, at least 98%, at least 99%, or 100%, amino acid sequence identity to amino acids 1100 to 1367 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 260 amino acids to 270 amino acids (e.g., 260, 261, 262, 263, 264, 265, 266, 267, 268, 269, or 270 amino acids).

A RuvCI polypeptide can comprise an amino acid sequence having at least 75%, at least 80%, at least 85%, at least 90%, at least 95%, at least 98%, at least 99%, or 100%, amino acid sequence identity to a contiguous stretch of from 40 amino acids to 60 amino acids of amino acids 1-60 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to 80 amino acids, e.g., from 40 amino acids to 50 amino acids, from 50 amino acids to 60 amino acids, from 60 amino acids to 70 amino acids, or from 70 amino acids to 80 amino acids. In some cases, a RuvCI polypeptide comprises an amino acid sequence having at least 75%, at least 80%, at least 85%, at least 90%, at least 95%, at least 98%, at least 99%, or 100%, amino acid sequence identity to amino acids 1-60 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 50 amino acids to 60 amino acids (e.g., 50, 51, 52, 53, 54, 55, 56, 57, 58, 59, or 60 amino acids).

A RuvCII polypeptide can comprise an amino acid sequence having at least 75%, at least 80%, at least 85%, at least 90%, at least 95%, at least 98%, at least 99%, or 100%, amino acid sequence identity to a contiguous stretch of from 40 to 46 amino acids of amino acids 729-775 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 40 amino acids to about 60 amino acids, e.g., from 40 amino acids to 45 amino acids, from 45 amino acids to 50 amino acids, from 50 amino acids to 55 amino acids, or from 55 amino acids to 60 amino acids. In some cases, a RuvCII polypeptide comprises an amino acid sequence having at least 75%, at least 80%, at least 85%, at least 90%, at least 95%, at least 98%, at least 99%, or 100%, amino acid sequence identity to amino acids 728-774 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of 45-50 (e.g., 45, 46, 47, 48, 49, or 50) amino acids.

An HNH polypeptide can comprise an amino acid sequence having at least 75%, at least 80%, at least 85%, at least 90%, at least 95%, at least 98%, at least 99%, or 100%, amino acid sequence identity to a contiguous stretch of from 100 to 134 amino acids of amino acids 776-909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 90 amino acids to 150 amino acids, e.g., from 90 amino acids to 95 amino acids, from 95 to amino acids to 100 amino acids, from 100 amino acids to 125 amino acids, from 125 amino acids to 130 amino acids, from 130 amino acids to 135 amino acids, from 135 amino acids to 140 amino acids, from 140 amino acids to 145 amino acids, or from 145 amino acids to 150 amino acids. In some cases, an HNH polypeptide comprises an amino acid sequence having at least 75%, at least 80%, at least 85%, at least 90%, at least 95%, at least 98%, at least 99%, or 100%, amino acid sequence identity to amino acids 776-909 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 130 amino acids to 140 amino acids (e.g., 130, 131, 132, 133, 134, 135, 136, 137, 138, 139, or 140 amino acids).

Examples of First Fusion Polypeptides

In some embodiments, a first fusion polypeptide comprises an amino acid sequence having at least 75%, at least 80%, at least 85%, at least 90%, at least 95%, at least 98%, at least 99%, or 100%, amino acid sequence identity to amino acids 82-829 of the amino acid sequence depicted in the following paragraph. In some cases, the fusion partner is linked, directly or via a linker, to the N-terminus of the polypeptide. For example, in some cases, a first fusion polypeptide comprises, in order from N-terminus to C-terminus: a) a fusion partner; and b) a polypeptide comprising an amino acid sequence having at least 75%, at least 80%, at least 85%, at least 90%, at least 95%, at least 98%, at least 99%, or 100%, amino acid sequence identity to amino acids 82-829 of the amino acid sequence amino acid sequence depicted in the following paragraph. Suitable fusion partners include a first member of a dimerization pair, where suitable first members of a dimerization pair are described elsewhere herein. In some cases, a first fusion polypeptide comprises, in order from N-terminus to C-terminus: a) an NLS; b) a fusion partner; and c) a polypeptide comprising an amino acid sequence having at least 75%, at least 80%, at least 85%, at least 90%, at least 95%, at least 98%, at least 99%, or 100%, amino acid sequence identity to amino acids 82-829 of the amino acid sequence depicted in the following paragraph. In some cases, a first fusion polypeptide comprises, in order from N-terminus to C-terminus: a) an NLS; b) a fusion partner; c) a polypeptide comprising an amino acid sequence having at least 75%, at least 80%, at least 85%, at least 90%, at least 95%, at least 98%, at least 99%, or 100%, amino acid sequence identity to amino acids 82-829 of the amino acid sequence depicted in the following paragraph; and d) a fusion partner.

```
                                     (SEQ ID NO: 1595)
MDYKDHDGDYKDHDIDYKDDDDKMAPKKKRKVGIHGVPAASIAATLENDL

ARLENENARLEKDIANLERDLAKLEREEAYFGGSGGSGGSASGQGDSLHE

HIANLAGSPAIKKGILQTVKVVDELVKVMGRHKPENIVIEMARENQTTQK

GQKNSRERMKRIEEGIKELGSQILKEHPVENTQLQNEKLYLYYLQNGRDM

YVDQELDINRLSDYDVDHIVPQSFLKDDSIDNKVLTRSDKNRGKSDNVPS

EEVVKKMKNYWRQLLNAKLITQRKFDNLTKAERGGLSELDKAGFIKRQLV

ETRQITKHVAQILDSRMNTKYDENDKLIREVKVITLKSKLVSDFRKDFQF

YKVREINNYHHAHDAYLNAVVGTALIKKYPKLESEFVYGDYKVYDVRKMI

AKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIAR

KKDWDPKKYGGFDSPTVAYSVLVVAKVEKGKSKKLKSVKELLGITIMERS

SFEKNPIDFLEAKGYKEVKKDLIIKLPKYSLFELENGRKRMLASAGELQK

GNELALPSKYVNFLYLASHYEKLKGSPEDNEQKQLFVEQHKHYLDEIIEQ

ISEFSKRVILADANLDKVLSAYNKHRDKPIREQAENIIHLFTLTNLGAPA

AFKYFDTTIDRKRYTSTKEVLDATLIHQSITGLYETRIDLSQLGGDGSGG

SGGSGGSGGSGGSGGSGGSGGVDDKKYSIGLDIGTNSVGWAVITDEYKVP

SKKFKVLGNTDRHSIKKNLIGALLFDSGEKRPAATKKAGQAKKKK
```

In some embodiments, a first fusion polypeptide comprises an amino acid sequence having at least 75%, at least 80%, at least 85%, at least 90%, at least 95%, at least 98%, at least 99%, or 100%, amino acid sequence identity to amino acids 82-820 of the amino acid sequence depicted in the following paragraph. In some cases, the fusion partner is linked, directly or via a linker, to the N-terminus of the polypeptide. For example, in some cases, a first fusion polypeptide comprises, in order from N-terminus to C-terminus: a) a fusion partner; and b) a polypeptide comprising an amino acid sequence having at least 75%, at least 80%, at least 85%, at least 90%, at least 95%, at least 98%, at least 99%, or 100%, amino acid sequence identity to amino acids 82-820 of the amino acid sequence depicted in the following paragraph. Suitable fusion partners include a first member of a dimerization pair, where suitable first members of a dimerization pair are described elsewhere herein. In some cases, a first fusion polypeptide comprises, in order from N-terminus to C-terminus: a) an NLS; b) a fusion partner; and c) a polypeptide comprising an amino acid sequence having at least 75%, at least 80%, at least 85%, at least 90%, at least 95%, at least 98%, at least 99%, or 100%, amino acid sequence identity to amino acids 82-820 of the amino acid sequence depicted in the following paragraph. In some cases, a first fusion polypeptide comprises, in order from N-terminus to C-terminus: a) an NLS; b) a fusion partner; c) a polypeptide comprising an amino acid sequence having at least 75%, at least 80%, at least 85%, at least 90%, at least 95%, at least 98%, at least 99%, or 100%, amino acid sequence identity to amino acids 82-820 of the amino acid sequence depicted in the following paragraph; and d) a fusion partner.

(SEQ ID NO: 1596)
MDYKDHDGDYKDHDIDYKDDDDKMAPKKKRKVGIHGVPAASIAATLENDL

ARLENENARLEKDIANLERDLAKLEREEAYFGGSGGSGGSASGQGDNVPS

EEVVKKMKNYWRQLLNAKLITQRKFDNLTKAERGGLSELDKAGFIKRQLV

ETRQITKHVAQILDSRMNTKYDENDKLIREVKVITLKSKLVSDFRKDFQF

YKVREINNYHHAHDAYLNAVVGTALIKKYPKLESEFVYGDYKVYDVRKMI

AKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIAR

KKDWDPKKYGGFDSPTVAYSVLVVAKVEKGKSKKLKSVKELLGITIMERS

SFEKNPIDFLEAKGYKEVKKDLIIKLPKYSLFELENGRKRMLASAGELQK

GNELALPSKYVNFLYLASHYEKLKGSPEDNEQKQLFVEQHKHYLDEIIEQ

ISEFSKRVILADANLDKVLSAYNKHRDKPIREQAENIIHLFTLTNLGAPA

AFKYFDTTIDRKRYTSTKEVLDATLIHQSITGLYETRIDLSQLGGDGSGG

SGGSGGSGGSGGSGGSGGSGGVDDKKYSIGLDIGTNSVGWAVITDEYKVP

SKKFKVLGNTDRHSIKKNLIGALLFDSGGSSGSPAIKKGILQTVKVVDEL

VKVMGRHKPENIVIEMARENQTTQKGQKNSRERMKRIEEGIKELGSQILK

EHPVENTQLQNEKLYLYYLQNGRDMYVDQELDINRLSDYDVDHIVPQSFL

KDDSIDNKVLTRSDKNRGKSEKRPAATKKAGQAKKKK.

Second Fusion Polypeptide

As described above, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a first member of a dimerization pair; and B) a second fusion polypeptide comprising: a) a second polypeptide that comprises an alpha-helical recognition region (e.g., an alpha helical lobe); and b) a second fusion partner, where the second fusion partner is a second member of the dimerization pair. In some cases, the fusion partner is at or near (e.g., within the first 50 amino acids of the N-terminus) the N-terminus of the second polypeptide. In some cases, the fusion partner is at or near (e.g., within the first 50 amino acids of the C-terminus) the C-terminus of the second polypeptide. In some cases, the fusion partner is located internally within the second fusion polypeptide.

In some cases, the second polypeptide comprises an α-helical lobe (also referred to as "an alpha-helical recognition region") of a Cas9 polypeptide. For example, in some cases, the second polypeptide comprises an amino acid sequence having at least 75%, at least 80%, at least 85%, at least 90%, at least 95%, at least 98%, at least 99%, or 100%, amino acid sequence identity to a contiguous stretch of from 400 amino acids to 658 amino acids of amino acids 61 to 718 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and can have a length of from 400 amino acids to 800 amino acids, e.g., from 400 amino acids to 450 amino acids, from 450 amino acids to 500 amino acids, from 500 amino acids to 550 amino acids, from 550 amino acids to 600 amino acids, from 600 amino acids to 650 amino acids, from 650 amino acids to 700 amino acids, from 700 amino acids to 750 amino acids, or from 750 amino acids to 800 amino acids. In some cases, the second polypeptide comprises an amino acid sequence having at least 75%, at least 80%, at least 85%, at least 90%, at least 95%, at least 98%, at least 99%, or 100%, amino acid sequence identity to amino acids 61-718 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 650 amino acids to 660 amino acids (e.g., 650, 651, 652, 653, 654, 655, 656, 657, 658, 659, or 660 amino acids).

In some cases, the second polypeptide comprises an amino acid sequence having at least 75%, at least 80%, at least 85%, at least 90%, at least 95%, at least 98%, at least 99%, or 100%, amino acid sequence identity to a contiguous stretch of from 400 amino acids to 624 amino acids of amino acids 95 to 718 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from about 400 amino acids to 800 amino acids, e.g., from 400 amino acids to 450 amino acids, from 450 amino acids to 500 amino acids, from 500 amino acids to 550 amino acids, from 550 amino acids to 600 amino acids, from 600 amino acids to 650 amino acids, from 650 amino acids to 700 amino acids, from 700 amino acids to 750 amino acids, or from 750 amino acids to 800 amino acids. In some cases, the second polypeptide comprises an amino acid sequence having at least 75%, at least 80%, at least 85%, at least 90%, at least 95%, at least 98%, at least 99%, or 100%, amino acid sequence identity to amino acids 95 to 718 of the *S. pyogenes* Cas9 amino acid sequence set forth in SEQ ID NO: 1545, or a corresponding segment of a Cas9 polypeptide amino acid sequence set forth in any of SEQ ID NOs: 1-259 and 795-1346; and has a length of from 620 amino acids to 630 amino acids (e.g., 620, 621, 622, 623, 624, 625, 626, 627, 628, 629, or 630 amino acids).

In some cases, the second fusion polypeptide comprises, in order from N-terminus to C-terminus: a) a second fusion partner; and b) a second polypeptide that comprises an alpha-helical recognition region. In some cases, the second fusion polypeptide comprises, in order from N-terminus to C-terminus: a) a second polypeptide that comprises an alpha-helical recognition region; and b) a second fusion partner.

In some cases, the second fusion polypeptide comprises a heterologous sequence that provides for subcellular localization (e.g., an NLS for targeting to the nucleus; a mitochondrial localization signal for targeting to the mitochondria; a chloroplast localization signal for targeting to a chloroplast; an ER retention signal; and the like). In some cases, the second fusion polypeptide includes 2 or more, 3 or more, 4 or more, or 5 or more NLSs. In some cases, an NLS is located at or near (e.g., within 75 amino acids, 50 amino acids, or 30 amino acids) the N-terminus and/or at or near (e.g., within 75 amino acids, 50 amino acids, or 30 amino acids) the C-terminus. In some cases, the second fusion polypeptide comprises an NLS.

For example, in some cases, the second fusion polypeptide comprises, in order from N-terminus to C-terminus: a)

an NLS; b) a second fusion partner; and c) a second polypeptide that comprises an alpha-helical recognition region. In some cases, the second fusion polypeptide comprises, in order from N-terminus to C-terminus: a) an NLS; b) a second fusion partner; c) a second polypeptide that comprises an alpha-helical recognition region; and d) an NLS. In some cases, the second fusion polypeptide comprises, in order from N-terminus to C-terminus: a) an NLS; b) a second polypeptide that comprises an alpha-helical recognition region; and c) a second fusion partner. In some cases, the second fusion polypeptide comprises, in order from N-terminus to C-terminus: a) an NLS; b) a second polypeptide that comprises an alpha-helical recognition region; c) a second fusion partner; and d) an NLS. In some cases, the NLS comprises the amino acid sequence MAPKKKRKVGIHGVPAA (SEQ ID NO: 1546). In some cases, the NLS comprises the amino acid sequence KRPAATKKAGQAKKKK (SEQ ID NO: 1547). Other suitable NLS are described elsewhere herein.

An NLS can be at or near the N-terminus and/or the C-terminus. In some cases, the second fusion polypeptide comprises two or more NLSs (e.g., 3 or more, 4 or more, or 5 or more NLSs). In some cases, the second fusion polypeptide comprises one or more NLSs (e.g., 2 or more, 3 or more, or 4 or more NLSs) at or near the N-terminus and/or one or more NLSs (e.g., 2 or more, 3 or more, or 4 or more NLSs) at or near the C-terminus. The term "at or near" is used here because, as is known in the art, the NLS need not be at the actual terminus of a protein, but can be positioned near (e.g., within 100 amino acids of) an N- and/or C-terminus (e.g., within 80, within 75, within 60, within 55, within 50, within 45, within 40, within 35, or within 30 amino acids of the an N- and/or C-terminus).

In some cases, the second fusion polypeptide comprises one or more linker polypeptides. For example, a linker polypeptide can be interposed between any of: a) an NLS and a fusion partner; b) a fusion partner and an alpha-helical lobe; and c) an alpha-helical lobe and an NLS.

First and Second Fusion Partners

The first fusion partner of the first fusion polypeptide, and the second fusion partner of the second fusion polypeptide, of a Cas9 heterodimer constitute a "dimer pair." A dimer pair is a pair of polypeptides that can dimerize with one another. Each member (each polypeptide) of the dimer pair can be part of a different polypeptide, and when the members of the binding pair (the dimer pair) are brought into close proximity with one another (e.g., bind to one another), the two different polypeptides (heterologous polypeptides) to which the dimer pair members are fused are brought into proximity with one another and can be said to dimerize (i.e., as a consequence of the members of the dimer pair dimerizing).

A Cas9 heterodimer comprises two polypeptides that can interact to form a complex (i.e., to form the heterodimeric Cas9 protein). A Cas9 heterodimer is also referred to herein as a "split Cas9" or a "split Cas9 protein." The fusion partners present in the first fusion polypeptide and the second fusion polypeptide can be induced to dimerize by a dimerizing agent. When the fusion partners present in the first fusion polypeptide and the second fusion polypeptide dimerize, the first fusion polypeptide and the second fusion polypeptide dimerize. In the absence of the dimerizing agent, and in the absence of a guide RNA that includes a stem loop 2 and/or a stem loop 3, the first fusion polypeptide and the second fusion polypeptide do not dimerize. When the first fusion polypeptide and the second fusion polypeptide dimerize, the Cas9 heterodimer, together with a truncated guide RNA (e.g., a guide RNA that does not include stem loop 2 and/or stem loop 3), can bind a target nucleic acid. A Cas9 heterodimer and a truncated guide RNA form a "Cas9 heterodimer system," described hereinbelow.

As an illustrative example, a Cas9 heterodimer comprises: A) a first fusion polypeptide (comprising a Cas9 nuclease lobe) and a first fusion partner ("a first member of a dimer pair"); and B) a second fusion polypeptide (comprising a Cas9 alpha-helical lobe) and a second fusion partner ("a second member of the dimer pair"). The first and second fusion polypeptides dimerize when the first and second binding members dimerize (when the first and second binding members are brought into close proximity with one another, e.g., via a dimerizer, via binding to one another, etc.). In some cases, the dimer pair is inducible such that the members of the dimer pair do not associate (e.g., come into proximity with one another, bind to one another, etc.) in the absence of induction (e.g., chemical induction, light induction, etc.). In some cases, the dimer pair is not inducible such that the members of the dimer pair bind to one another when both members are present (e.g., synzip polypeptides).

Any convenient dimer pair can used. Example dimer pairs suitable for use in a subject heterodimeric Cas9 protein include non-inducible binding pairs. For example, in some cases, each member of the binding pair is a protein domain that binds to the other member. As an illustrative example, in some cases, each member of the binding pair is a coiled-coil domain. Examples of suitable coiled-coil domains include, but are not limited to:

```
SYNZIP14:
                                      (SEQ ID NO: 1556)
NDLDAYEREAEKLEKKNEVLRNRLAALENELATLRQEVASMKQELQS

SYNZIP17:
                                      (SEQ ID NO: 1557)
NEKEELKSKKAELRNRIEQLKQKREQLKQKIANLRKEIEAYK

SYNZIP18:
                                      (SEQ ID NO: 1558)
SIAATLENDLARLENENARLEKDIANLERDLAKLEREEAYF
```

In some cases, each of the two members of a non-inducible binding pair comprise an amino acid sequence having 75% or more amino acid sequence identity (e.g., 80% or more, 85% or more, 90% or more, 95% or more, 98% or more, or 100%, amino acid sequence identity) to a coiled coil domain. In some cases, a member of a non-inducible binding pair includes an amino acid sequence having 75% or more amino acid sequence identity (e.g., 80% or more, 85% or more, 90% or more, 95% or more, 98% or more, or 100%, amino acid sequence identity) to SYNZIP14 (the amino acid sequence set forth in SEQ ID NO: 1556). In some cases, a member of a non-inducible binding pair includes an amino acid sequence having 75% or more amino acid sequence identity (e.g., 80% or more, 85% or more, 90% or more, 95% or more, 98% or more, or 100%, amino acid sequence identity) to SYNZIP17 (the amino acid sequence set forth in SEQ ID NO: 1557). In some cases, a member of a non-inducible binding pair includes an amino acid sequence having 75% or more amino acid sequence identity (e.g., 80% or more, 85% or more, 90% or more, 95% or more, 98% or more, or 100%, amino acid sequence identity) to SYNZIP18 (the amino acid sequence set forth in SEQ ID NO: 1558).

In some cases, one member of a non-inducible binding pair includes an amino acid sequence having 75% or more amino acid sequence identity (e.g., 80% or more, 85% or more, 90% or more, 95% or more, 98% or more, or 100%, amino acid sequence identity) to SYNZIP17 (the amino acid sequence set forth in SEQ ID NO: 1557); and the other member of the non-inducible binding pair includes an amino acid sequence having 75% or more amino acid sequence identity (e.g., 80% or more, 85% or more, 90% or more, 95% or more, 98% or more, or 100%, amino acid sequence identity) to SYNZIP18 (the amino acid sequence set forth in SEQ ID NO: 1558). For example, in some cases, the two members of a non-inducible binding pair are SYNZIP17 and SYNZIP18.

In some cases, one member of a non-inducible binding pair includes an amino acid sequence having 75% or more amino acid sequence identity (e.g., 80% or more, 85% or more, 90% or more, 95% or more, 98% or more, or 100%, amino acid sequence identity) to SYNZIP14 (the amino acid sequence set forth in SEQ ID NO: 1556); and the other member of the non-inducible binding pair includes an amino acid sequence having 75% or more amino acid sequence identity (e.g., 80% or more, 85% or more, 90% or more, 95% or more, 98% or more, or 100%, amino acid sequence identity) to SYNZIP17 (the amino acid sequence set forth in SEQ ID NO: 1557). For example, in some cases, the two members of a non-inducible binding pair are SYNZIP14 and SYNZIP17.

Example dimer pairs suitable for use in a subject Cas9 heterodimer also include inducible binding pairs (binding pairs that can be induced to dimerize, e.g., with a dimerizer, as discussed in more detail below). Dimerizer-binding pairs suitable for use in a Cas9 heterodimer are in some embodiments polypeptides (e.g. protein domains) that bind to a different site of the same molecule (referred to herein as a "dimerizer"). In the presence of a dimerizer, both members of a dimerizer-binding pair bind to the dimerizer (e.g., in some cases each binding to a different site of the dimerizer) and are thus brought into proximity with one another. This can also be referred to as chemically-inducible dimerization (CID) (e.g., see DeRose et al, Pflugers Arch. 2013 March; 465(3):409-17, which is hereby incorporated by reference in its entirety). In some embodiments, binding to the dimerizer is reversible. In some embodiments, binding to the dimerizer is irreversible. In some embodiments, binding to the dimerizer is non-covalent. In some embodiments, binding to the dimerizer is covalent.

Dimer pairs suitable for use include dimerizer-binding pairs that dimerize upon binding of a first member of a dimer pair to a dimerizing agent and of a second member of the dimer pair to the same dimerizing agent. Dimer pairs suitable for use also include dimerizer-binding pairs that dimerize upon binding of a first member of a dimer pair to a dimerizing agent, where the dimerizing agent induces a conformational change in the first member of the dimer pair, and where the conformational change allows the first member of the dimer pair to bind (covalently or non-covalently) to a second member of the dimer pair. Other dimer pairs suitable for use include dimer pairs in which exposure to light (e.g., blue light) induces dimerization of the dimer pair.

Regardless of the mechanism, an inducible dimer pair will dimerize upon exposure to an agent that induces dimerization, where the agent is in some cases a small molecule, or, for example, in other cases, light. Thus, for simplicity, the discussion below referring to "dimerizer-binding pairs" includes dimer pairs that dimerize regardless of the mechanism.

Non-limiting examples of suitable dimers (e.g., dimerizer-binding pairs) include, but are not limited to:
(a) FKBP1A (FK506 binding protein) (e.g., a rapamycin binding portion) paired with FKBP1A (e.g., a rapamycin binding portion): dimerization induced by rapamycin and/or rapamycin analogs known as rapalogs;
(b) FKBP1A (e.g., a rapamycin binding portion) and FRB (Fkbp-Rapamycin Binding Domain): dimerization induced by rapamycin and/or rapamycin analogs known as rapalogs;
(c) FKBP1A (e.g., a rapamycin binding portion) and CnA (calcineurin catalytic subunit A): dimerization induced by rapamycin and/or rapamycin analogs known as rapalogs;
(d) FKBP1A (e.g., a rapamycin binding portion) and cyclophilin: dimerization induced by rapamycin and/or rapamycin analogs known as rapalogs;
(e) GyrB (Gyrase B) and GyrB: dimerization induced by coumermycin;
(f) DHFR (dihydrofolate reductase) and DHFR: dimerization induced by methotrexate);
(g) DmrB and DmrB: dimerization induced by AP20187;
(h) PYL and ABI: dimerization induced by abscisic acid;
(i) Cry2 and CIB1: dimerization induced by blue light; and
(j) GAI and GID1: dimerization induced by gibberellin.

A member (a first and/or a second member) of a binding pair (e.g., a dimerizer-binding pair) of a subject Cas9 heterodimer can have a length in a range of from 35 to 300 amino acids (e.g., from 35 to 250, from 35 to 200, from 35 to 150, from 35 to 100, from 35 to 50, from 50 to 300, from 50 to 250, from 50 to 200, from 50 to 150, from 50 to 100, from 100 to 300, from 100 to 250, from 100 to 200, from 100 to 150, from 150 to 300, from 150 to 250, from 150 to 200, from 200 to 300, from 200 to 250, or from 250 to 300 amino acids).

In some cases, a member of a dimer (e.g., a dimerizer-binding pair) of a subject Cas9 heterodimer is derived from FKBP1A (also known as FKBP12, FKBP1; PKC12; PKC12; PPIASE; FKBP-12; FKBP-1A). For example, a suitable dimerizer-binding pair member can include a rapamycin binding portion of FKBP1A. For example, a suitable dimerizer-binding pair member can comprise an amino acid sequence having 75% or more amino acid sequence identity (e.g., 80% or more, 85% or more, 90% or more, 95% or more, 98% or more, or 100% amino acid sequence identity) to the following amino acid sequence (a rapamycin binding portion of FKBP1A):

```
                                       (SEQ ID NO: 1559)
GVQVETISPGDGRTFPKRGQTCVVHYTGMLEDGKKFDSSRDRNKPFKFML
GKQEVIRGWEEGVAQMSVGQRAKLTISPDYAYGATGHPGIIPPHATLVFD
VELLKLE.
```

In some cases, a member of a dimerizer-binding pair of a Cas9 heterodimer is derived from protein phosphatase 3, catalytic subunit, alpha isozyme (PPP3CA) (also known as "Serine/threonine-protein phosphatase 2B catalytic subunit alpha isoform"; CNA; CALN; CALNA; CALNA1; CCN1; CNA1; PPP2B; "CAM-PRP catalytic subunit"; and "calmodulin-dependent calcineurin A subunit alpha isoform"). For example, a suitable dimerizer-binding pair member can include a binding portion of PPP3CA. For example, a suitable dimerizer-binding pair member can comprise an amino acid sequence having 75% or more amino acid sequence identity (e.g., 80% or more, 85% or more, 90% or more, 95% or more, 98% or more, or 100% amino acid sequence identity) to the following amino acid sequence (PP2Ac domain):

(SEQ ID NO: 1560)
LEESVALRIITEGASILRQEKNLLDIDAPVTVCGDIHGQFFDLMKLFEVG

GSPANTRYLFLGDYVDRGYFSIECVLYLWALKILYPKTLFLLRGNHECRH

LTEYFTFKQECKIKYSERVYDACMDAFDCLPLAALMNQQFLCVHGGLSPE

INTLDDIRKLDRFKEPPAYGPMCDILWSDPLEDFGNEKTQEHFTHNTVRG

CSYFYSYPAVCEFLQHNNLLSILRAHEAQDAGYRMYRKSQTTGFPSLITI

FSAPNYLDVYNNKAAVLKYENNVMNIRQFNCSPHPYWLPNFM.

In some cases, a member of a dimer (e.g., a dimerizer-binding pair) is derived from cyclophilin (also known cyclophilin A, PPIA, CYPA, CYPH, PPIase A, etc.). For example, a suitable dimerizer-binding pair member can include a binding portion of cyclophilin. For example, a suitable dimerizer-binding pair member can include an amino acid sequence having 75% or more amino acid sequence identity (e.g., 80% or more, 85% or more, 90% or more, 95% or more, 98% or more, or 100% amino acid sequence identity) to the following amino acid sequence:

(SEQ ID NO: 1561)
MVNPTVFFDIAVDGEPLGRVSFELFADKVPKTAENFRALSTGEKGFGYKG

SCFHRIIPGFMCQGGDFTRHNGTGGKSIYGEKFEDENFILKHTGPGILSM

ANAGPNTNGSQFFICTAKTEWLDGKHVVFGKVKEGMNIVEAMERFGSRNG

KTSKKITIADCGQLE.

In some cases, a member of a dimer (e.g., a dimerizer-binding pair) is derived from MTOR (also known as FKBP-rapamycin associated protein; FK506 binding protein 12-rapamycin associated protein 1; FK506 binding protein 12-rapamycin associated protein 2; FK506-binding protein 12-rapamycin complex-associated protein 1; FRAP; FRAP1; FRAP2; RAFT1; and RAPT1). For example, a suitable dimerizer-binding pair member can include the Fkbp-Rapamycin Binding Domain (also known as FRB). For example, a suitable dimerizer-binding pair member can include an amino acid sequence having 75% or more amino acid sequence identity (e.g., 80% or more, 85% or more, 90% or more, 95% or more, 98% or more, or 100% amino acid sequence identity) to the following amino acid sequence (FRB):

(SEQ ID NO: 1562)
VAILWHEMWHEGLEEASRLYFGERNVKGMFEVLEPLHAMMERGPQTLKET

SFNQAYGRDLMEAQEWCRKYMKSGNVKDLTQAWDLYYHVFRRIS.

In some cases, a member of a dimer (e.g., a dimerizer-binding pair) is derived from GyrB (also known as DNA gyrase subunit B). For example, a suitable dimerizer-binding pair member can include an amino acid sequence having 75% or more amino acid sequence identity (e.g., 80% or more, 85% or more, 90% or more, 95% or more, 98% or more, or 100% amino acid sequence identity) to a contiguous stretch of from about 100 amino acids to about 200 amino acids (aa), from about 200 aa to about 300 aa, from about 300 aa to about 400 aa, from about 400 aa to about 500 aa, from about 500 aa to about 600 aa, from about 600 aa to about 700 aa, or from about 700 aa to about 800 aa, of the following GyrB amino acid sequence from *Escherichia coli* (or to the DNA gyrase subunit B sequence from any organism): MSNSYDSSSIKVLKGLDAVRKRPGMYIGDTDD-GTGLHHMVFEVVDNAIDEALAGHCKE IIVTIHADNS-VSVQDDGRGIPTGIHPEEGVSAAEVIMTVLHAGGKF-DDNSYKVSGGLHGV GVSVVNALSQKLELVIQREG-KIHRQIYEHGVPQAPLAVTGETEKTGTMVRFWPS-LETFT NVTEFEYEILAKRLRELSFLNSGVSIRLRDK-RDGKEDHFHYEGGIKAFVEYLNKNKTPIH PNIFYF-STEKDGIGVEVALQWNDGFQENIYCFTNNIPQRDG-GTHLAGFRAAMTRTLNAY MDKEGYSKKAKVSAT-GDDAREGLIAVVSVKVPDPKFSSQTKDKLVSSEVKS-AVEQQM NELLAEYLLENPTDAKIVVGKIIDAARA-REAARRAREMTRRKGALDLAGLPGKLADCQ ERD-PALSELYLVEGDSAGGSAKQGRNRKNQAILPLKGKI-LNVEKARFDKMLSSQEVATL ITALGCGIGRDEYN-PDKLRYHSIIIMTDADVDGSHIRTLLLTFFYRQMPEIV-ERGHVYIAQ PPLYKVKKGKQEQYIKDDEAMDQYQI-SIALDGATLHTNASAPALAGEALEKLVSEYNA TQK-MINRMERRYPKAMLKELIYQPTLTEADLSDEQTVT-RWVNALVSELNDKEQHGSQ WKFDVHTNAEQNL-FEPIVRVRTHGVDTDYPLDHEFITGGEYRRICTLGE-KLRGLLEEDA FIERGERRQPVASFEQALDWLVKE-SRRGLSIQRYKGLGEMNPEQLWETTMDPESRRML RVTVKDAIAADQLFTTLMGDAVEPRRAFIEENAL-KAANIDI (SEQ ID NO:1563). In some cases, a member of a dimerizer-binding pair includes an amino acid sequence having 75% or more amino acid sequence identity (e.g., 80% or more, 85% or more, 90% or more, 95% or more, 98% or more, or 100% amino acid sequence identity) to amino acids 1-220 of the above-listed GyrB amino acid sequence from *Escherichia coli*.

In some cases, a member of a dimer (e.g., a dimerizer-binding pair) is derived from DHFR (also known as dihydrofolate reductase, DHFRP1, and DYR). For example, a suitable dimerizer-binding pair member can include an amino acid sequence having 75% or more amino acid sequence identity (e.g., 80% or more, 85% or more, 90% or more, 95% or more, 98% or more, or 100% amino acid sequence identity) to the following amino acid sequence:

(SEQ ID NO: 1564)
MVGSLNCIVAVSQNMGIGKNGDLPWPPLRNEFRYFQRMTTTSSVEGKQN

LVIMGKKTWFSIPEKNRPLKGRINLVLSRELKEPPQGAHFLSRSLDDAL

KLTEQPELANKVDMVWIVGGSSVYKEAMNHPGHLKLFVTRIMQDFESDT

FFPEIDLEKYKLLPEYPGVLSDVQEEKGIKYKFEVYEKND.

In some cases, a member of a dimer (e.g., a dimerizer-binding pair) is derived from the DmrB binding domain (i.e., DmrB homodimerization domain). For example, a suitable dimerizer-binding pair member can include an amino acid sequence having 75% or more amino acid sequence identity (e.g., 80% or more, 85% or more, 90% or more, 95% or more, 98% or more, or 100% amino acid sequence identity) to the following amino acid sequence:

(SEQ ID NO: 1565)
MASRGVQVETISPGDGRTFPKRGQTCVVHYTGMLEDGKKVDSSRDRNKPF

KFMLGKQEVIRGWEEGVAQMSVGQRAKLTISPDYAYGATGHPGIIPPHAT

LVFDVELLKLE.

In some cases, a member of a dimer (e.g., a dimerizer-binding pair) is derived from a PYL protein (also known as abscisic acid receptor and as RCAR). For example a member of a subject dimerizer-binding pair can be derived from proteins such as those of *Arabidopsis thaliana*: PYRI, RCAR1(PYL9), PYL1, PYL2, PYL3, PYL4, PYL5, PYL6, PYL7, PYL8 (RCAR3), PYL10, PYL11, PYL12, PYL13. For example, a suitable dimerizer-binding pair member can include an amino acid sequence having 75% or more amino acid sequence identity (e.g., 80% or more, 85% or more, 90% or more, 95% or more, 98% or more, or 100% amino acid sequence identity) to the following amino acid sequences:

PYL10:
(SEQ ID NO: 1566)
MNGDETKKVESEYIKKHHRHELVESQCSSTLVKHIKAPLHLVWSIVRRFD EPQKYKPFISRCVVQGKKLEVGSVREVDLKSGLPATKSTEVLEILDDNEH ILGIRIVGGDHRLKNYSSTISLHSETIDGKTGTLAIESFVVDVPEGNTKE ETCFFVEALIQCNLNSLADVTERLQAESMEKKI.

PYL11:
(SEQ ID NO: 1567)
METSQKYHTCGSTLVQTIDAPLSLVWSILRRFDNPQAYKQFVKTCNLSSG DGGEGSVREVTVVSGLPAEFSRERLDELDDESHVMMISIIGGDHRLVNYR SKTMAFVAADTEEKTVVVESYVVDVPEGNSEEETTSFADTIVGFNLKSLA KLSERVAHLKL

PYL12:
(SEQ ID NO: 1568)
MKTSQEQHVCGSTVVQTINAPLPLVWSILRRFDNPKTFKHFVKTCKLRSGD GGEGSVREVTVVSDLPASFSLERLDELDDESHVMVISIIGGDHRLVNYQSK TTVFVAAEEEKTVVVESYVVDVPEGNTEEETTLFADTIVGCNLRSLAKLSE KMMELT.

PYL13:
(SEQ ID NO: 1569)
MESSKQKRCRSSVVETIEAPLPLVWSILRSFDKPQAYQRFVKSCTMRSGGG GGKGGEGKGSVRDVTLVSGFPADFSTERLEELDDESHVMVVSIIGGNHRLV NYKSKTKVVASPEDMAKKTVVVESYVVDVPEGTSEEDTIFFVDNIIRYNLT SLAKLTKKMMK.

PYL1:
(SEQ ID NO: 1570)
MANSESSSSPVNEEENSQRISTLHHQTMPSDLTQDEFTQLSQSIAEFHTYQ LGNGRCSSLLAQRIHAPPETVWSVVRRFDRPQIYKHFIKSCNVSEDFEMRV GCTRDVNVISGLPANTSRERLDLLDDDRRVTGFSITGGEHRLRNYKSVTTV HRFEKEEEEERIWTVVLESYVVDVPEGNSEEDTRLFADTVIRLNLQKLASI TEAMNRNNNNNNSSQVR.

PYL2:
(SEQ ID NO: 1571)
MSSSPAVKGLTDEEQKTLEPVIKTYHQFEPDPTTCTSLITQRIHAPASVVW PLIRRFDNPERYKHFVKRCRLISGDGDVGSVREVTVISGLPASTSTERLEF VDDDHRVLSFRVVGGEHRLKNYKSVTSVNEFLNQDSGKVYTVVLESYTVDI PEGNTEEDTKMFVDTVVKLNLQKLGVAATSAPMHDDE.

PYL3:
(SEQ ID NO: 1572)
MNLAPIHDPSSSSTTTTSSSTPYGLTKDEFSTLDSIIRTHHTFPRSPNTCT SLIAHRVDAPAHAIWRFVRDFANPNKYKHFIKSCTIRVNGNGIKEIKVGTI REVSVVSGLPASTSVEILEVLDEEKRILSFRVLGGEHRLNNYRSVTSVNEF

VVLEKDKKKRVYSVVLESYIVDIPQGNTEEDTRMFVDTVVKSNLQNLAVIS TASPT.

PYL4:
(SEQ ID NO: 1573)
MLAVHRPSSAVSDGDSVQIPMMIASFQKRFPSLSRDSTAARFHTHEVGPN QCCSAVIQEISAPISTVWSVVRRFDNPQAYKHFLKSCSVIGGDGDNVGSL RQVHVVSGLPAASSTERLDILDDERHVISFSVVGGDHRLSNYRSVTTLHP SPISGTVVVESYVVDVPPGNTKEETCDFVDVIVRCNLQSLAKIAENTAAE SKKKMSL.

PYL5:
(SEQ ID NO: 1574)
MRSPVQLQHGSDATNGFHTLQPHDQTDGPIKRVCLTRGMHVPEHVAMHHT HDVGPDQCCSSVVQMIHAPPESVWALVRRFDNPKVYKNFIRQCRIVQGDG LHVGDLREVMVVSGLPAVSSTERLEILDEERHVISFSVVGGDHRLKNYRS VTTLHASDDEGTVVVESYIVDVPPGNTEEETLSFVDTIVRCNLQSLARST NRQ.

PYL6:
(SEQ ID NO: 1575)
MPTSIQFQRSSTAAEAANATVRNYPHHHQKQVQKVSLTRGMADVPEHVEL SHTHVVGPSQCFSVVVQDVEAPVSTVWSILSRFEHPQAYKHFVKSCHVVI GDGREVGSVREVRVVSGLPAAFSLERLEIMDDDRHVISFSVVGGDHRLMN YKSVTTVHESEEDSDGKKRTVVESYVVDVPAGNDKEETCSFADTIVRCN LQSLAKLAENTSKFS.

PYL7:
(SEQ ID NO: 1576)
MEMIGGDDTDTEMYGALVTAQSLRLRHLHHCRENQCTSVLVKYIQAPVHL VWSLVRRFDQPQKYKPFISRCTVNGDPEIGCLREVNVKSGLPATTSTERL EQLDDEEHILGINIIGGDHRLKNYSSILTVHPEMIDGRSGTMVMESFVVD VPQGNTKDDTCYFVESLIKCNLKSLACVSERLAAQDITNSIATFCNASNG YREKNHTETNL.

PYL8:
(SEQ ID NO: 1577)
MEANGIENLTNPNQEREFIRRHHKHELVDNQCSSTLVKHINAPVHIVWSL VRRFDQPQKYKPFISRCVVKGNMEIGTVREVDVKSGLPATRSTERLELLD DNEHILSIRIVGGDHRLKNYSSIISLHPETIEGRIGTLVIESFVVDVPEG NTKDETCYFVEALIKCNLKSLADISERLAVQDTTESRV.

PYL9:
(SEQ ID NO: 1578)
MMDGVEGGTAMYGGLETVQYVRTHHHQHLCRENQCTSALVKHIKAPLHLVW SLVRRFDQPQKYKPFVSRCTVIGDPEIGSLREVNVKSGLPATTSTERLEL LDDEEHILGIKIIGGDHRLKNYSSILTVHPEIIEGRAGTMVIESFVVDVP QGNTKDETCYFVEALIRCNLKSLADVSERLASQDITQ.

PYR1:
(SEQ ID NO: 1579)
MPSELTPEERSELKNSIAEFHTYQLDPGSCSSLHAQRIHAPPELVWSIVR RFDKPQTYKHFIKSCSVEQNFEMRVGCTRDVIVISGLPANTSTERLDILD DERRVTGFSIIGGEHRLTNYKSVTTVHRFEKENRIWTVVLESYVVDMPEG NSEDDTRMFADTVVKLNLQKLATVAEAMARNSGDGSGSQVT.

In some cases, a member of a dimer (e.g., a dimerizer-binding pair) is derived from an ABI protein (also known as Abscisic Acid-Insensitive). For example a member of a subject dimerizer-binding pair can be derived from proteins such as those of *Arabidopsis thaliana*: ABI1 (Also known as ABSCISIC ACID-INSENSITIVE 1, Protein phosphatase 2C 56, AtPP2C56, P2C56, and PP2C ABI1) and/or ABI2 (also known as P2C77, Protein phosphatase 2C 77, AtPP2C77, ABSCISIC ACID-INSENSITIVE 2, Protein phosphatase 2C ABI2, and PP2C ABI2). For example, a suitable dimerizer-binding pair member can include an amino acid sequence having 75% or more amino acid sequence identity (e.g., 80% or more, 85% or more, 90% or more, 95% or more, 98% or more, or 100% amino acid sequence identity) to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

ABI1:
(SEQ ID NO: 1580)
MEEVSPAIAGPFRPFSETQMDFTGIRLGKGYCNNQYSNQDSENGDLMVS

LPETSSCSVSGSHGSESRKVLISRINSPNLNMKESAAADIVVVDISAGD

EINGSDITSEKKMISRTESRSLFEFKSVPLYGFTSICGRRPEMEDAVST

IPRFLQSSSGSMLDGRFDPQSAAHFFGVYDGHGGSQVANYCRERMHLAL

AEEIAKEKPMLCDGDTWLEKWKKALFNSFLRVDSEIESVAPETVGSTSV

VAVVFPSHIFVANCGDSRAVLCRGKTALPLSVDHKPDREDEAARIEAAG

GKVIQWNGARVFGVLAMSRSIGDRYLKPSIIPDPEVTAVKRVKEDDCLI

LASDGVWDVMTDEEACEMARKRILLWHKKNAVAGDASLLADERRKEGKD

PAAMSAAEYLSKLAIQRGSKDNISVVVVDLKPRRKLKSKPLN.

ABI2:
(SEQ ID NO: 1581)
MDEVSPAVAVPFRPFTDPHAGLRGYCNGESRVTLPESSCSGDGAMKDSS

FEINTRQDSLTSSSSAMAGVDISAGDEINGSDEFDPRSMNQSEKKVLSR

TESRSLFEFKCVPLYGVTSICGRRPEMEDSVSTIPRFLQVSSSSLLDGR

VTNGFNPHLSAHFFGVYDGHGGSQVANYCRERMHLALTEEIVKEKPEFC

DGDTWQEKWKKALFNSFMRVDSEIETVAHAPETVGSTSVVAVVFPTHIF

VANCGDSRAVLCRGKTPLALSVDHKPDRDDEAARIEAAGGKVIRWNGAR

VFGVLAMSRSIGDRYLKPSVIPDPEVTSVRRVKEDDCLILASDGLWDVM

TNEEVCDLARKRILLWHKKNAMAGEALLPAEKRGEGKDPAAMSAAEYLS

KMALQKGSKDNISVVVVDLKGIRKFKSKSLN.

In some cases, a member of a dimer (e.g., a dimerizer-binding pair) is derived from a Cry2 protein (also known as cryptochrome 2). For example a member of a subject dimer (e.g., a dimerizer-binding pair) can be derived from Cry2 proteins from any organism (e.g., a plant) such as, but not limited to, those of *Arabidopsis thaliana*. For example, a suitable dimerizer-binding pair member can include an amino acid sequence having 75% or more amino acid sequence identity (e.g., 80% or more, 85% or more, 90% or more, 95% or more, 98% or more, or 100% amino acid sequence identity) to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

Cry2 (*Arabidopsis thaliana*)

(SEQ ID NO: 1582)
MKMDKKTIVWFRRDLRIEDNPALAAAAHEGSVFPVFIWCPEEEGQFYPGR

ASRWWMKQSLAHLSQSLKALGSDLTLIKTHNTISAILDCIRVTGATKVVF

NHLYDPVSLVRDHTVKEKLVERGISVQSYNGDLLYEPWEIYCEKGKPFTS

FNSYWKKCLDMSIESVMLPPPWRLMPITAAAEAIWACSIEELGLENEAEK

PSNALLTRAWSPGWSNADKLLNEFIEKQLIDYAKNSKKVVGNSTSLLSPY

LHFGEISVRHVFQCARMKQIIWARDKNSEGEESADLFLRGIGLREYSRYI

CFNPPFTHEQSLLSHLRFFPWDADVDKFKAWRQGRTGYPLVDAGMRELWA

TGWMHNRIRVIVSSFAVKFLLLPWKWGMKYFWDTLLDADLECDILGWQYI

SGSIPDGHELDRLDNPALQGAKYDPEGEYIRQWLPELARLPTEWIHHPWD

APLTVLKASGVELGTNYAKPIVDIDTARELLAKAISRTREAQIMIGAAPD

EIVADSFEALGANTIKEPGLCPSVSSNDQQVPSAVRYNGSKRVKPEEEEE

RDMKKSRGFDERELFSTAESSSSSSVFFVSQSCSLASEGKNLEGIQDSSD

QITTSLGKNGCK.

In some cases, a member of a dimer (e.g., a dimerizer-binding pair) is derived from the CIB1 *Arabidopsis thaliana* protein (also known as transcription factor bHLH63). For example, a suitable dimer (e.g., a dimerizer-binding pair) member can include an amino acid sequence having 75% or more amino acid sequence identity (e.g., 80% or more, 85% or more, 90% or more, 95% or more, 98% or more, or 100% amino acid sequence identity) to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of the following amino acid sequence:

(SEQ ID NO: 1583)
MNGAIGGDLLLNFPDMSVLERQRAHLKYLNPTFDSPLAGFFADSSMITGG

EMDSYLSTAGLNLPMMYGETTVEGDSRLSISPETTLGTGNFKKRKFDTET

KDCNEKKKKMTMNRDDLVEEGEEEKSKITEQNNGSTKSIKKMKHKAKKEE

NNFSNDSSKVTKELEKTDYIHVRARRGQATDSHSIAERVRREKISERMKF

LQDLVPGCDKITGKAGMLDEIINYVQSLQRQIEFLSMKLAIVNPRPDFDM

DDIFAKEVASTPMTVVPSPEMVLSGYSHEMVHSGYSSEMVNSGYLHVNPM

QQVNTSSDPLSCFNNGEAPSMWDSHVQNLYGNLGV.

In some cases, a member of a dimer (e.g., a dimerizer-binding pair) is derived from the GAI *Arabidopsis thaliana* protein (also known as Gibberellic Acid Insensitive, and DELLA protein GAI). For example, a suitable dimerizer-binding pair member can include an amino acid sequence having 75% or more amino acid sequence identity (e.g., 80% or more, 85% or more, 90% or more, 95% or more, 98% or more, or 100% amino acid sequence identity) to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of the following amino acid sequence:

(SEQ ID NO: 1584)
MKRDHHHHHHQDKKTMMMNEEDDGNGMDELLAVLGYKVRSSEMADVAQKL

EQLEVMMSNVQEDDLSQLATETVHYNPAELYTWLDSMLTDLNPPSSNAEY

DLKAIPGDAILNQFAIDSASSSNQGGGGDTYTTNKRLKCSNGVVETTTAT

AESTRHVVLVDSQENGVRLVHALLACAEAVQKENLTVAEALVKQIGFLAV

SQIGAMRKVATYFAEALARRIYRLSPSQSPIDHSLSDTLQMHFYETCPYL

KFAHFTANQAILEAFQGKKRVHVIDFSMSQGLQWPALMQALALRPGGPPV

FRLTGIGPPAPDNFDYLHEVGCKLAHLAEAIHVEFEYRGFVANTLADLDA

SMLELRPSEIESVAVNSVFELHKLLGRPGAIDKVLGVVNQIKPEIFTVVE

QESNHNSPIFLDRFTESLHYYSTLFDSLEGVPSGQDKVMSEVYLGKQICN

VVACDGPDRVERHETLSQWRNRFGSAGFAAAHIGSNAFKQASMLLALFNG

GEGYRVEESDGCLMLGWHTRPLIATSAWKLSTN.

In some cases, a member of a dimer (e.g., a dimerizer-binding pair) is derived from a GID1 *Arabidopsis thaliana* protein (also known as Gibberellin receptor GID1). For example, a suitable dimer member can include an amino acid sequence having 75% or more amino acid sequence identity (e.g., 80% or more, 85% or more, 90% or more, 95% or more, 98% or more, or 100% amino acid sequence identity) to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

GID1A:
(SEQ ID NO: 1585)
MAASDEVNLIESRTVVPLNTWVLISNFKVAYNILRRPDGTFNRHLAEYLD

RKVTANANPVDGVFSFDVLIDRRINLLSRVYRPAYADQEQPPSILDLEKP

VDGDIVPVILFFHGGSFAHSSANSAIYDTLCRRLVGLCKCVVVSVNYRRA

PENPYPCAYDDGWIALNWVNSRSWLKSKKDSKVHIFLAGDSSGGNIAHNV

ALRAGESGIDVLGNILLNPMFGGNERTESEKSLDGKYFVTVRDRDWYWKA

FLPEGEDREHPACNPFSPRGKSLEGVSFPKSLVVVAGLDLIRDWQLAYAE

GLKKAGQEVKLMHLEKATVGFYLLPNNNHFHNVMDEISAFVNAEC.

GID1B:
(SEQ ID NO: 1586)
MAGGNEVNLNECKRIVPLNTWVLISNFKLAYKVLRRPDGSFNRDLAEFLD

RKVPANSFPLDGVFSFDHVDSTTNLLTRIYQPASLLHQTRHGTLELTKPL

STTEIVPVLIFFHGGSFTHSSANSAIYDTFCRRLVTICGVVVVSVDYRRS

PEHRYPCAYDDGWNALNWVKSRVWLQSGKDSNVYVYLAGDSSGGNIAHNV

AVRATNEGVKVLGNILLHPMFGGQERTQSEKTLDGKYFVTIQDRDWYWRA

YLPEGEDRDHPACNPFGPRGQSLKGVNFPKSLVVVAGLDLVQDWQLAYVD

GLKKTGLEVNLLYLKQATIGFYFLPNNDHFHCLMEELNKFVHSIEDSQSK

SSPVLLTP

GID1C:
(SEQ ID NO: 1587)
MAGSEEVNLIESKTVVPLNTWVLISNFKLAYNLLRRPDGTFNRHLAEFLD

RKVPANANPVNGVFSFDVIIDRQTNLLSRVYRPADAGTSPSITDLQNPVD

GEIVPVIVFFHGGSFAHSSANSAIYDTLCRRLVGLCGAVVVSVNYRRAPE

NRYPCAYDDGWAVLKWVNSSSWLRSKKDSKVRIFLAGDSSGGNIVHNVAV

RAVESRIDVLGNILLNPMFGGTERTESEKRLDGKYFVTVRDRDWYWRAFL

PEGEDREHPACSPFGPRSKSLEGLSFPKSLVVVAGLDLIQDWQLKYAEGL

KKAGQEVKLLYLEQATIGFYLLPNNNHFHTVMDEIAAFVNAECQ.

Dimerizers

Dimerizers ("dimerizing agents") that can provide for dimerization of a first member of a dimerizer-binding pair and a second member of a dimerizer-binding pair include, e.g. (where the dimerizer is in parentheses following the dimerizer-binding pair):

a) FKBP1A and FKBP1A (rapamycin and/or a rapamycin analog, rapalog);
b) FKBP1A and FRB (rapamycin and/or a rapamycin analog, rapalog);
c) FKBP1A and PPP3CA (rapamycin and/or a rapamycin analog, rapalog);
d) FKBP1A and cyclophilin (rapamycin and/or a rapamycin analog, rapalog);
e) GyrB and GyrB (coumermycin);
f) DHFR and DHFR (methotrexate);
g) DmrB and DmrB (AP20187);
h) PYL and ABI (abscisic acid);
i) Cry2 and CIB1 (blue light); and
j) GAI and GID1 (gibberellin).

As noted above, rapamycin can serve as a dimerizer. Alternatively, a rapamycin derivative or analog can be used. See, e.g., WO96/41865; WO 99/36553; WO 01/14387; and Ye et al (1999) Science 283:88-91. For example, analogs, homologs, derivatives and other compounds related structurally to rapamycin ("rapalogs") include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. Additional information is presented in, e.g., U.S. Pat. Nos. 5,525,610; 5,310,903 5,362,718; and 5,527,907. Selective epimerization of the C-28 hydroxyl group has been described; see, e.g., WO 01/14387. Additional synthetic dimerizing agents suitable for use as an alternative to rapamycin include those described in U.S. Patent Publication No. 2012/0130076.

125

Rapamycin has the structure:

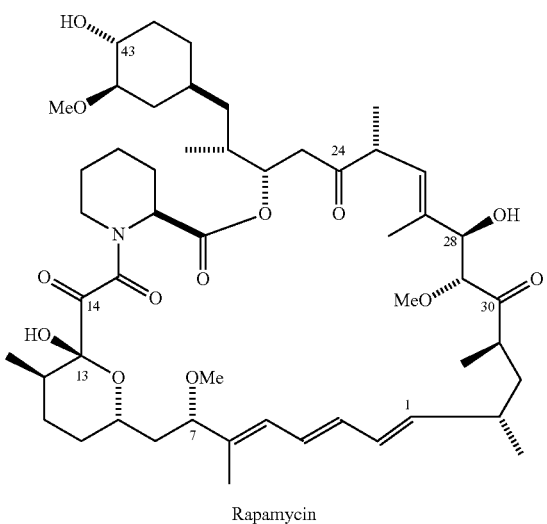

Rapamycin

Suitable rapalogs include, e.g.,

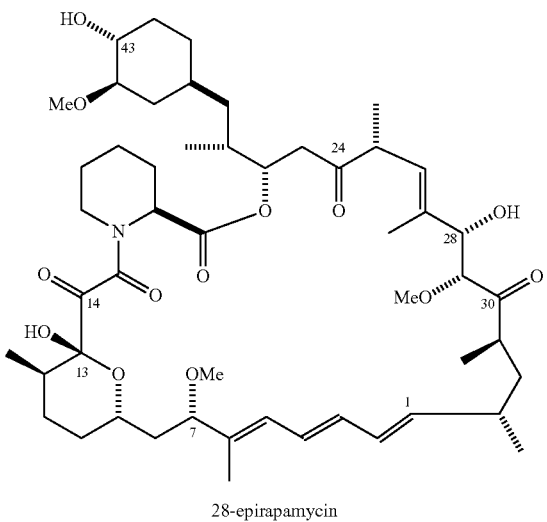

28-epirapamycin

Also suitable as a rapalog is a compound of the formula:

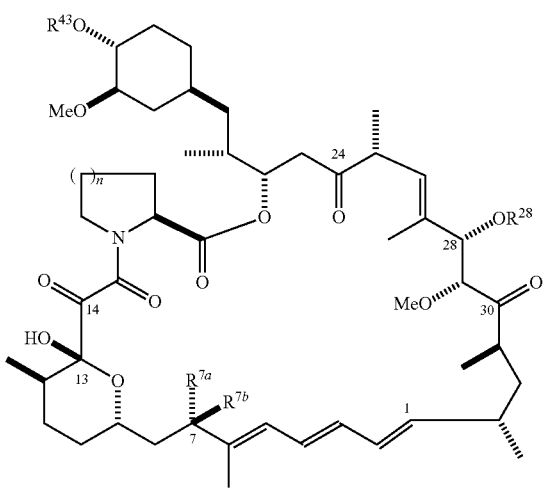

126 where n is 1 or 2; $R^{28}$ and $R^{43}$ are independently H, or a substituted or unsubstituted aliphatic or acyl moiety; one of $R^{7a}$ and $R^{7b}$ is H and the other is halo, $R^A$, $OR^A$, $SR^A$, $-OC(O)R^A$, $-OC(O)NR^AR^B$, $-NR^AR^B$, $-NR^BC(OR)R^A$, $NR^BC(O)OR^A$, $-NR^BSO_2R^A$, or $NR^BSO_2NR^AR^{B'}$; or $R^{7a}$ and $R^{7b}$, taken together, are H in the tetraene moiety:

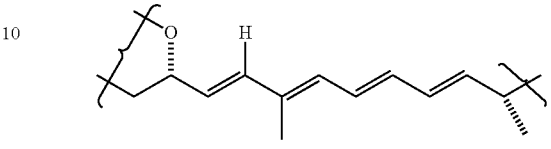

where $R^A$ is H or a substituted or unsubstituted aliphatic, heteroaliphatic, aryl, or heteroaryl moiety and where $R^B$ and $R^{B'}$ are independently H, OH, or a substituted or unsubstituted aliphatic, heteroaliphatic, aryl, or heteroaryl moiety.

As noted above, coumermycin can serve as a dimerizing agent. Alternatively, a coumermycin analog can be used. See, e.g., Farrar et al. (1996) Nature 383:178-181; and U.S. Pat. No. 6,916,846.

As noted above, in some cases, the dimerizing agent is methotrexate, e.g., a non-cytotoxic, homo-bifunctional methotrexate dimer. See, e.g., U.S. Pat. No. 8,236,925.

Examples of Cas9 Heterodimers

In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a first member of a dimerization pair; and B) a second fusion polypeptide comprising: a) an alpha-helical recognition region; and b) a second fusion partner, where the second fusion partner is a second member of a dimerization pair.

In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is an FKBP1A polypeptide; and B) a second fusion polypeptide comprising: a) an alpha-helical recognition region; and b) a second fusion partner, where the second fusion partner is an FKBP1A polypeptide.

In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is an FKBP1A polypeptide; and B) a second fusion polypeptide comprising: a) an alpha-helical recognition region; and b) a second fusion partner, where the second fusion partner is an FRB polypeptide. In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is an FRB polypeptide; and B) a second fusion polypeptide comprising: a) an alpha-helical recognition region; and b) a second fusion partner, where the second fusion partner is an FKBP1A polypeptide.

In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is an FKBP1A polypeptide; and B) a second fusion polypeptide comprising: a) an alpha-helical recognition region; and b) a second fusion partner, where the second fusion partner is a PPP3CA polypeptide. In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a PPP3CA polypeptide; and B) a second fusion polypeptide comprising: a) an alpha-helical recognition region; and b) a second fusion partner, where the second fusion partner is an FKBP1A polypeptide.

In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is an FKBP1A polypeptide; and B) a second fusion polypeptide comprising: a) an alpha-helical recognition region; and b) a second fusion partner, where the second fusion partner is a cyclophilin polypeptide. In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a cyclophilin polypeptide; and B) a second fusion polypeptide comprising: a) an alpha-helical recognition region; and b) a second fusion partner, where the second fusion partner is an FKBP1A polypeptide.

In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a GyrB polypeptide; and B) a second fusion polypeptide comprising: a) an alpha-helical recognition region; and b) a second fusion partner, where the second fusion partner is a GyrB polypeptide.

In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a DHFR polypeptide; and B) a second fusion polypeptide comprising: a) an alpha-helical recognition region; and b) a second fusion partner, where the second fusion partner is a DHFR polypeptide.

In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a DmrB polypeptide; and B) a second fusion polypeptide comprising: a) an alpha-helical recognition region; and b) a second fusion partner, where the second fusion partner is a DmrB polypeptide.

In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a PYL polypeptide; and B) a second fusion polypeptide comprising: a) an alpha-helical recognition region; and b) a second fusion partner, where the second fusion partner is an ABI polypeptide. In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is an ABI polypeptide; and B) a second fusion polypeptide comprising: a) an alpha-helical recognition region; and b) a second fusion partner, where the second fusion partner is an PYL polypeptide.

In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a Cyr2 polypeptide; and B) a second fusion polypeptide comprising: a) an alpha-helical recognition region; and b) a second fusion partner, where the second fusion partner is a CIB1 polypeptide. In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a CIB1 polypeptide; and B) a second fusion polypeptide comprising: a) an alpha-helical recognition region; and b) a second fusion partner, where the second fusion partner is an Cry2 polypeptide.

In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a GAI polypeptide; and B) a second fusion polypeptide comprising: a) an alpha-helical recognition region; and b) a second fusion partner, where the second fusion partner is a GID1 polypeptide. In some embodiments, a Cas9 heterodimer comprises: A) a first fusion polypeptide comprising: a) a first polypeptide comprising: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a GID1 polypeptide; and B) a second fusion polypeptide comprising: a) an alpha-helical recognition region; and b) a second fusion partner, where the second fusion partner is an GAI polypeptide.

In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a first member of a dimerization pair; and B) a second fusion polypeptide comprising: a) a second polypeptide that comprises an alpha-helical recognition region; and b) a second fusion partner, where the second fusion partner is a second member of the dimerization pair.

In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is an FKBP1A polypeptide; and B) a second fusion polypeptide comprising: a) a second polypeptide that comprises an alpha-helical recognition region; and b) a second fusion partner, where the second fusion partner is an FKBP1A polypeptide.

In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is an FKBP1A polypeptide; and B) a second fusion polypeptide comprising: a) a second polypeptide that comprises an alpha-helical recognition region; and b) a second fusion partner, where the second fusion partner is an FRB polypeptide. In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is an FRB polypeptide; and B) a second fusion polypeptide comprising: a) a second polypeptide that comprises an alpha-helical recognition region; and b) a second fusion partner, where the second fusion partner is an FKBP1A polypeptide.

In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is an FKBP1A polypeptide; and B) a second fusion polypeptide comprising: a) a second polypeptide that comprises an alpha-helical recognition region; and b) a second fusion partner, where the second fusion partner is a PPP3CA polypeptide. In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a PPP3CA polypeptide; and B) a second fusion polypeptide comprising: a) a second polypeptide that comprises an alpha-helical recognition region; and b) a second fusion partner, where the second fusion partner is an FKBP1A polypeptide.

In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is an FKBP1A polypeptide; and B) a second fusion polypeptide comprising: a) a second polypeptide that comprises an alpha-helical recognition region; and b) a second fusion partner, where the second fusion partner is a cyclophilin polypeptide. In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a cyclophilin polypeptide; and B) a second fusion polypeptide comprising: a) a second polypeptide that comprises an alpha-helical recognition region; and b) a second fusion partner, where the second fusion partner is an FKBP1A polypeptide.

In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a GyrB polypeptide; and B) a second fusion polypeptide comprising: a) a second polypeptide that comprises an alpha-helical recognition region; and b) a second fusion partner, where the second fusion partner is a GyrB polypeptide.

In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a DHFR polypeptide; and B) a second fusion polypeptide comprising: a) a second polypeptide that comprises an alpha-helical recognition region; and b) a second fusion partner, where the second fusion partner is a DHFR polypeptide.

In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a DmrB polypeptide; and B) a second fusion polypeptide comprising: a) a second polypeptide that comprises an alpha-helical recognition region; and b) a second fusion partner, where the second fusion partner is a DmrB polypeptide.

In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a PYL polypeptide; and B) a second fusion polypeptide comprising: a) a second polypeptide that comprises an alpha-helical recognition region; and b) a second fusion partner, where the second fusion partner is an ABI polypeptide. In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is an ABI polypeptide; and B) a second fusion polypeptide comprising: a) a second polypeptide that comprises an alpha-helical recognition region; and b) a second fusion partner, where the second fusion partner is a PYL polypeptide.

In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b)

a first fusion partner, where the first fusion partner is a Cry2 polypeptide; and B) a second fusion polypeptide comprising: a) a second polypeptide that comprises an alpha-helical recognition region; and b) a second fusion partner, where the second fusion partner is a CIB1 polypeptide. In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a CIB1 polypeptide; and B) a second fusion polypeptide comprising: a) a second polypeptide that comprises an alpha-helical recognition region; and b) a second fusion partner, where the second fusion partner is a Cry2 polypeptide.

In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a GAI polypeptide; and B) a second fusion polypeptide comprising: a) a second polypeptide that comprises an alpha-helical recognition region; and b) a second fusion partner, where the second fusion partner is a GID1 polypeptide. In some cases, a Cas9 heterodimer comprises: A) a first fusion polypeptide comprising: a) a first, circular permuted, polypeptide that comprises: i) a RuvCI polypeptide; ii) a RuvCII polypeptide; iii) an HNH polypeptide; iv) a RuvCIII polypeptide; and v) a PAM-interacting polypeptide; and b) a first fusion partner, where the first fusion partner is a GID1 polypeptide; and B) a second fusion polypeptide comprising: a) a second polypeptide that comprises an alpha-helical recognition region; and b) a second fusion partner, where the second fusion partner is a GAI polypeptide.

Chimeric Polypeptides (Fusion Polypetides)

In some embodiments, a variant Cas9 protein is a chimeric Cas9 protein (also referred to herein as a fusion protein, e.g., a "Cas9 fusion protein"). A Cas9 fusion protein can bind and/or modify a target nucleic acid (e.g., cleave, methylate, demethylate, etc.) and/or a polypeptide associated with target nucleic acid (e.g., methylation, acetylation, etc., of, for example, a histone tail).

A Cas9 fusion protein is a variant Cas9 protein, e.g., by virtue of differing in sequence from a wild type Cas9 protein. A Cas9 fusion protein is a Cas9 protein (e.g., a wild type Cas9 protein, a variant Cas9 protein, a Cas9 heterodimer, a variant Cas9 protein with reduced nuclease activity (as described above), and the like) fused to a covalently linked heterologous polypeptide (also referred to as a "fusion partner"). In some cases, a Cas9 fusion protein is a variant Cas9 protein with reduced nuclease activity (e.g., dCas9, a nickase with a functional RuvC domain but a non-functional HNH domain such that it can cleave a quenched PAMmer but does not cleave the target nucleic acid) fused to a covalently linked heterologous protein. In some cases, the heterologous protein exhibits (and therefore provides for) an activity (e.g., an enzymatic activity) that will also be exhibited by the Cas9 fusion protein (e.g., methyltransferase activity, acetyltransferase activity, kinase activity, ubiquitinating activity, etc.). In some such cases, a method of labeling, e.g., where the Cas9 protein is a variant Cas9 protein having a fusion partner (i.e., having a heterologous protein) with an activity (e.g., an enzymatic activity) that mofidies the target nucleic acid, the method can also be considered to be a method of modifying the target nucleic acid. In some cases, a method of labeling a target nucleic acid (e.g., a single stranded target nucleic acid) can result in modification of the target nucleic acid. Thus, in some cases, a method of labeling a target nucleic acid (e.g., a single stranded target nucleic acid) can be a method of modifying the target nucleic acid.

In some cases, the heterologous sequence provides for subcellular localization, i.e., the heterologous sequence is a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a variant Cas9 does not include a NLS so that the protein is not targeted to the nucleus (which can be advantageous, e.g., when the target nucleic acid is an RNA that is present in the cytosol). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6xHis tag; a hemagglutinin (HA) tag; a FLAG tag; a Myc tag; and the like). In some embodiments, the heterologous sequence can provide for increased or decreased stability (i.e., the heterologous sequence is a stability control peptide, e.g., a degron, which in some cases is controllable (e.g., a temperature sensitive or drug controllable degron sequence, see below). In some embodiments, the heterologous sequence can provide for increased or decreased transcription from the target nucleic acid (i.e., the heterologous sequence is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g., to provide the ability of a Cas9 fusion polypeptide to bind to another protein of interest, e.g., a DNA or histone modifying protein, a transcription factor or transcription repressor, a recruiting protein, an RNA modification enzyme, an RNA-binding protein, a translation initiation factor, an RNA splicing factor, etc.). A heterologous nucleic acid sequence may be linked to another nucleic acid sequence (e.g., by genetic engineering) to generate a chimeric nucleotide sequence encoding a chimeric polypeptide.

A subject Cas9 fusion polypeptide (Cas9 fusion protein) can have multiple (1 or more, 2 or more, 3 or more, 4 or more, 5 or more, 6 or more, etc.) fusion partners in any combination of the above. As an illustrative example, a Cas9 fusion protein can have a heterologous sequence that provides an activity (e.g., for transcription modulation, target modification, modification of a protein associated with a target nucleic acid, etc.) and can also have a subcellular localization sequence (e.g., 1 or more NLSs). In some cases, such a Cas9 fusion protein might also have a tag for ease of tracking and/or purification (e.g., green fluorescent protein (GFP), YFP, RFP, CFP, mCherry, tdTomato, and the like; a histidine tag, e.g., a 6xHis tag; a hemagglutinin (HA) tag; a FLAG tag; a Myc tag; and the like). As another illustrative example, a Cas9 protein can have one or more NLSs (e.g., two or more, three or more, four or more, five or more, 1, 2, 3, 4, or 5 NLSs). In some cases a fusion partner (or multiple fusion partners) (e.g., an NLS, a tag, a fusion partner providing an activity, etc.) is located at or near the C-terminus of Cas9. In some cases a fusion partner (or multiple fusion partners) (e.g., an NLS, a tag, a fusion partner providing an activity, etc.) is located at the N-terminus of Cas9. In some cases a Cas9 has a fusion partner (or multiple fusion partners)(e.g., an NLS, a tag, a fusion partner providing an activity, etc.) at both the N-terminus and C-terminus.

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled in part by the degron sequence. In some cases, a suitable degron is constitutive such that the degron exerts its influence on protein stability independent of experimental control (i.e., the degron is not drug inducible, temperature inducible, etc.) In some cases, the degron provides the variant Cas9 protein with controllable stability such that the variant Cas9 protein can be turned "on" (i.e., stable) or "off" (i.e., unstable, degraded) depending on the desired conditions. For example, if the degron is a temperature sensitive degron, the variant Cas9 protein may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non-functional (i.e., "off", degraded) above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g., Dohmen et al., Science, 1994. 263(5151): p. 1273-1276: Heat-inducible degron: a method for constructing temperature-sensitive mutants; Schoeber et al., Am J Physiol Renal Physiol. 2009 January; 296(1):F204-11: Conditional fast expression and function of multimeric TRPV5 channels using Shield-1; Chu et al., Bioorg Med Chem Lett. 2008 Nov. 15; 18(22):5941-4: Recent progress with FKBP-derived destabilizing domains; Kanemaki, Pflugers Arch. 2012 Dec. 28: Frontiers of protein expression control with conditional degrons; Yang et al., Mol Cell. 2012 Nov. 30; 48(4):487-8: Titivated for destruction: the methyl degron; Barbour et al., Biosci Rep. 2013 Jan. 18; 33(1).: Characterization of the bipartite degron that regulates ubiquitin-independent degradation of thymidylate synthase; and Greussing et al., J Vis Exp. 2012 Nov. 10; (69): Monitoring of ubiquitin-proteasome activity in living cells using a Degron (dgn)-destabilized green fluorescent protein (GFP)-based reporter protein; all of which are hereby incorporated in their entirety by reference).

Exemplary degron sequences have been well-characterized and tested in both cells and animals. Thus, fusing Cas9 (e.g., wild type Cas9; variant Cas9; variant Cas9 with reduced nuclease activity, e.g., dCas9; and the like) to a degron sequence produces a "tunable" and "inducible" Cas9 protein. Any of the fusion partners described herein can be used in any desirable combination. As one non-limiting example to illustrate this point, a Cas9 fusion protein (i.e., a chimeric Cas9 protein) can comprise a YFP sequence for detection, a degron sequence for stability, and transcription activator sequence to increase transcription of the target nucleic acid. A suitable reporter protein for use as a fusion partner for a Cas9 protein (e.g., wild type Cas9, variant Cas9, variant Cas9 with reduced nuclease function, etc.), includes, but is not limited to, the following exemplary proteins (or functional fragment thereof): his3, β-galatosidase, a fluorescent protein (e.g., GFP, RFP, YFP, cherry, tomato, etc., and various derivatives thereof), luciferase, β-glucuronidase, and alkaline phosphatase. Furthermore, the number of fusion partners that can be used in a Cas9 fusion protein is unlimited. In some cases, a Cas9 fusion protein comprises one or more (e.g. two or more, three or more, four or more, or five or more) heterologous sequences.

Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying nucleic acid directly (e.g., methylation of DNA or RNA) or at modifying a nucleic acid-associated polypeptide (e.g., a histone, a DNA binding protein, and RNA binding protein, and the like). Further suitable fusion partners include, but are not limited to boundary elements (e.g., CTCF), proteins and fragments thereof that provide periphery recruitment (e.g., Lamin A, Lamin B, etc.), and protein docking elements (e.g., FKBP/FRB, Pill/Abyl, etc.).

Examples of various additional suitable fusion partners (or fragments thereof) for a subject variant Cas9 protein include, but are not limited to those listed in FIGS. 15A-15D and are also described in the PCT patent applications: WO2010075303, WO2012068627, and WO2013155555 which are hereby incorporated by reference in their entirety.

Suitable fusion partners include, but are not limited to, a polypeptide that provides an activity that indirectly increases transcription by acting directly on the target nucleic acid or on a polypeptide (e.g., a histone, a DNA-binding protein, an RNA-binding protein, an RNA editing protein, etc.) associated with the target nucleic acid. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

Additional suitable fusion partners include, but are not limited to, a polypeptide that directly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.).

Non-limiting examples of fusion partners to accomplish increased or decreased transcription are listed in FIGS. 15B-15D and include transcription activator and transcription repressor domains (e.g., the Kruppel associated box (KRAB or SKD); the Mad mSIN3 interaction domain (SID); the ERF repressor domain (ERD), etc). In some such cases, a Cas9 fusion protein is targeted by the Cas9 guide RNA to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of fusion partners for use when targeting ssRNA target nucleic acids are listed in FIG. 15A and include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a fusion partner can include the entire protein or in some cases can include a fragment of the protein (e.g., a functional domain).

In some embodiments, the heterologous sequence can be fused to the C-terminus of the Cas9 protein. In some embodiments, the heterologous sequence can be fused to the N-terminus of the Cas9 protein. In some embodiments, the heterologous sequence can be fused to an internal portion (i.e., a portion other than the N- or C-terminus) of the Cas9 protein.

In addition to the fusion partners listed in FIG. 15A the fusion partner of a chimeric Cas9 protein can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP Si, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable fusion partner is a PUF RNA-binding domain, which is described in more detail in WO2012068627.

Some RNA splicing factors that can be used (in whole or as fragments thereof) as fusion partners for a Cas9 polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple c6>-elements that are located in either the core exon region or the exon extension region (i.e., between the two alternative 5' splice sites). For more examples, see WO2010075303.

In some embodiments, a Cas9 protein (e.g., a wild type Cas9, a variant Cas9, a variant Cas9 with reduced nuclease activity, etc.) can be linked to a fusion partner via a peptide spacer.

Nucleic Acids Encoding a PAMmer and/or a Cas9 Guide RNA, and/or a Cas9 Protein

The present disclosure provides compositions and methods that include a PAMmer and at least one of: a Cas9 guide RNA, and a Cas9 protein (e.g., a wild type Cas9 protein, a variant Cas9 protein, a chimeric Cas9 protein, and the like). In some cases, a subject PAMmer, and/or Cas9 guide RNA, and/or a Cas9 protein is provided as a nucleic acid encoding one or more of a PAMmer and/or Cas9 guide RNA, and/or a Cas9 protein. In some embodiments, a subject nucleic acid is an expression vector, e.g., a recombinant expression vector. As such, In some embodiments, a subject method involves contacting a target nucleic acid (e.g., a single stranded target nucleic acid) or introducing into a cell (or a population of cells) a PAMmer (or a nucleic acid comprising a nucleotide sequence encoding a PAMmer) and at least one of: a Cas9 guide RNA (or a nucleic acid comprising a nucleotide sequence encoding a Cas9 guide RNA), and a Cas9 protein (or a nucleic acid comprising a nucleotide sequence encoding a Cas9 protein). In some embodiments a cell comprising a target nucleic acid is in vitro and/or ex vivo. In some embodiments a cell comprising a target nucleic acid is in vivo. Suitable nucleic acids comprising nucleotide sequences encoding a PAMmer, a Cas9 guide RNA, and/or a Cas9 protein include expression vectors, where an expression vector comprising a nucleotide sequence encoding a PAMmer and/or a Cas9 guide RNA and/or a Cas9 protein is a "recombinant expression vector."

In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

In some embodiments, a nucleotide sequence encoding a PAMmer, and/or a Cas9 guide RNA and/or a Cas9 protein is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a PAMmer, and/or a Cas9 guide RNA and/or a Cas9 protein is operably linked to multiple control elements that allow expression of the nucleotide sequence encoding a PAMmer, and/or a Cas9 guide RNA and/or a Cas9 protein in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, green fluorescent protein, etc.) that are fused to the Cas9 protein, thus resulting in a chimeric polypeptide.

In some embodiments, a nucleotide sequence encoding a Cas9 guide RNA and/or a Cas9 protein is operably linked to an inducible promoter. In some embodiments, a nucleotide sequence encoding a Cas9 guide RNA and/or a Cas9 protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a Cas9 protein in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn, et al. (2010) Nat. Med. 16(10):1161-1166); a serotonin receptor promoter (see, e.g., GenBank S62283); a tyrosine hydroxylase promoter (TH) (see, e.g., Oh et al. (2009) Gene Ther 16:437; Sasaoka et al. (1992) Mol. Brain Res. 16:274; Boundy et al. (1998) J. Neurosci. 18:9989; and Kaneda et al. (1991) Neuron 6:583-594); a GnRH promoter (see, e.g., Radovick et al. (1991) Proc. Natl. Acad. Sci. USA 88:3402-3406); an L7 promoter (see, e.g., Oberdick et al. (1990) Science 248:223-226); a DNMT promoter (see, e.g., Bartge et al. (1988) Proc. Natl. Acad. Sci. USA 85:3648-3652); an enkephalin promoter (see, e.g., Comb et al. (1988) EMBO J. 17:3793-3805); a myelin basic protein (MBP) promoter; a Ca2+-calmodulin-dependent protein kinase II-alpha (CamKIIa) promoter (see, e.g., Mayford et al. (1996) Proc. Natl. Acad. Sci. USA 93:13250; and Casanova et al. (2001) Genesis 31:37); a CMV enhancer/platelet-derived growth factor-O promoter (see, e.g., Liu et al. (2004) Gene Therapy 11:52-60); and the like.

Adipocyte-specific spatially restricted promoters include, but are not limited to aP2 gene promoter/enhancer, e.g., a region from −5.4 kb to +21 bp of a human aP2 gene (see, e.g., Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (see, e.g., Knight et al. (2003) Proc. Natl. Acad. Sci. USA 100:14725); a fatty acid translocase (FAT/CD36) promoter (see, e.g., Kuriki et al. (2002) Biol. Pharm. Bull. 25:1476; and Sato et al. (2002) J. Biol. Chem. 277:15703); a stearoyl-CoA desaturase-1 (SCD1) promoter (Tabor et al. (1999) J. Biol. Chem. 274:20603); a leptin promoter (see, e.g., Mason et al. (1998) Endocrinol. 139:1013; and Chen et al. (1999) Biochem. Biophys. Res. Comm. 262:187); an adiponectin promoter (see, e.g., Kita et al. (2005) Biochem. Biophys. Res. Comm. 331:484; and Chakrabarti (2010) Endocrinol. 151:2408); an adipsin promoter (see, e.g., Platt et al. (1989) Proc. Natl. Acad. Sci. USA 86:7490); a resistin promoter (see, e.g., Seo et al. (2003) Molec. Endocrinol. 17:1522); and the like.

Cardiomyocyte-specific spatially restricted promoters include, but are not limited to control sequences derived from the following genes: myosin light chain-2, α-myosin heavy chain, AE3, cardiac troponin C, cardiac actin, and the like. Franz et al. (1997) Cardiovasc. Res. 35:560-566; Robbins et al. (1995) Ann. N.Y. Acad. Sci. 752:492-505; Linn et al. (1995) Circ. Res. 76:584-591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Smooth muscle-specific spatially restricted promoters include, but are not limited to an SM22a promoter (see, e.g., Akyurek et al. (2000) Mol. Med. 6:983; and U.S. Pat. No. 7,169,874); a smoothelin promoter (see, e.g., WO 2001/018048); an α-smooth muscle actin promoter; and the like. For example, a 0.4 kb region of the SM22a promoter, within which lie two CArG elements, has been shown to mediate vascular smooth muscle cell-specific expression (see, e.g., Kim, et al. (1997) Mol. Cell. Biol. 17, 2266-2278; Li, et al., (1996) J. Cell Biol. 132, 849-859; and Moessler, et al. (1996) Development 122, 2415-2425).

Photoreceptor-specific spatially restricted promoters include, but are not limited to, a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225); and the like.

Methods of introducing a nucleic acid into a host cell are known in the art, and any known method can be used to introduce a nucleic acid (e.g., an expression construct) into a cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

Contacting cells with a PAMmer, and/or Cas9 guide RNA, and/or Cas9 protein may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Conditions that promote the survival of cells are typically permissive of the subject cleavage and binding methods In some embodiments, a nucleotide sequence encoding a Cas9 protein can be codon optimized. In some cases, a codon optimized nucleotide sequence encoding a Cas9 protein encodes a variant Cas9 protein. In some cases, a codon optimized nucleotide sequence encoding a Cas9 protein encodes a chimeric Cas9 protein (a Cas9 fusion protein). Codon optimization is known in the art and entails the mutation of foreign-derived DNA to mimic the codon preferences of the intended host organism or host cell while encoding the same protein. Thus, the codons are changed, but the encoded protein remains unchanged. For example, if the intended target and/or host cell was a human cell, a Cas9 protein, or Cas9 variant, encoded by a human codon optimized nucleotide sequence would be a suitable Cas9 protein. As another non-limiting example, if the intended target and/or host cell was a mouse cell, a Cas9 protein, or Cas9 variant, encoded by a mouse codon optimized nucleotide sequence would be a suitable Cas9 protein. While codon optimization is not required, it is acceptable and may be preferable in certain cases.

In some embodiments, a Cas9 guide RNA and/or a Cas9 protein and/or PAMmer can be provided as RNA. In such cases, the Cas9 guide RNA and/or the RNA encoding the Cas9 protein and/or the PAMmer can be produced by direct chemical synthesis or may be transcribed in vitro from a DNA (e.g., encoding the Cas9 guide RNA, the PAMmer, and/or the Cas9 protein). Methods of synthesizing RNA from a DNA template are well known in the art. In some cases, the Cas9 guide RNA and/or the PAMmer and/or the RNA encoding the Cas9 protein will be synthesized in vitro using an RNA polymerase enzyme (e.g., T7 polymerase, T3 polymerase, SP6 polymerase, etc.). Once synthesized, the RNA may directly contact a target nucleic acid or may be introduced into a cell by any of the well-known techniques for introducing nucleic acids into cells (e.g., microinjection, electroporation, transfection, etc). In some cases, a PAMmer is a DNA oligonucleotide and can be produced using any convenient method (e.g., chemical synthesis).

Nucleotides encoding a Cas9 guide RNA (introduced either as DNA or RNA) and/or a Cas9 protein (introduced as DNA or RNA) and/or a PAMmer (introduced either as DNA or RNA) may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008) Efficient gene targeting in Drosophila by direct embryo injection with zinc-finger nucleases. PNAS 105(50): 19821-19826. Alternatively, nucleic acids encoding a Cas9 guide RNA and/or a Cas9 protein and/or a chimeric Cas9 protein and/or a PAMmer may be provided on DNA vectors. Many vectors, e.g. plasmids, cosmids, minicircles, phage, viruses, etc., useful for transferring nucleic acids into target cells are available. The vectors comprising the nucleic acid(s) may be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as MMLV, HIV-1, ALV, etc.

Vectors may be provided directly to the subject cells. In other words, the cells are contacted with vectors comprising the nucleic acid encoding Cas9 guide RNA and/or a Cas9 protein and/or a chimeric Cas9 protein and/or a PAMmer such that the vectors are taken up by the cells. Methods for contacting cells with nucleic acid vectors that are plasmids, including electroporation, calcium chloride transfection, microinjection, and lipofection are well known in the art. For viral vector delivery, the cells are contacted with viral particles comprising the nucleic acid encoding a Cas9 guide RNA and/or a Cas9 protein and/or a chimeric Cas9 protein and/or a PAMmer. Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the nucleic acid encoding the reprogramming factors into packaging cell lines and of collecting the viral particles that are generated by the packaging lines are well known in the art. Nucleic acids can also introduced by direct microinjection (e.g., injection of RNA into a zebrafish embryo).

Vectors used for providing the nucleic acids encoding Cas9 guide RNA and/or a Cas9 protein and/or a chimeric Cas9 protein and/or a PAMmer to the subject cells will typically comprise suitable promoters for driving the expression, that is, transcriptional activation, of the nucleic acid of interest. In other words, the nucleic acid of interest will be operably linked to a promoter. This may include ubiquitously acting promoters, for example, the CMV-3-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a Cas9 guide RNA and/or a Cas9 protein and/or a chimeric Cas9 protein and/or a PAMmer to the subject cells may include nucleic acid sequences that encode for selectable markers in the target cells, so as to identify cells that have taken up the Cas9 guide RNA and/or a Cas9 protein and/or a chimeric Cas9 protein and/or a PAMmer.

A Cas9 guide RNA and/or a Cas9 protein and/or a chimeric Cas9 protein may instead be used to contact DNA or introduced into cells as RNA. Methods of introducing RNA into cells are known in the art and may include, for example, direct injection, transfection, or any other method used for the introduction of DNA.

A Cas9 protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, the Cas9 protein may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence RQIKIWFQNRRMKWKK (SEQ ID NO:268). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A Cas9 protein may be produced in vitro or by eukaryotic cells or by prokaryotic cells, and it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are Cas9 guide RNAs, PAMmers (e.g., quenched PAMmers), and Cas9 proteins that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc) or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The Cas9 proteins may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The Cas9 proteins may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein.

To induce cleavage or any desired modification to a target nucleic acid, or any desired modification to a polypeptide associated with target nucleic acid, the Cas9 guide RNA and/or the Cas9 protein and/or the PAMmer, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different Cas9 guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

Nucleic Acid Modifications

In some embodiments, a subject nucleic acid (e.g., a Cas9 guide RNA, a PAMmer, etc.) has one or more modifications, e.g., a base modification, a backbone modification, etc, to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

In some cases, 2% or more of the nucleotides of a subject nucleic acid (e.g., a Cas9 guide RNA, a PAMmer, etc.) are modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject nucleic acid are modified). In some cases, 2% or more of the nucleotides of a subject PAMmer are modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject PAMmer are modified). In some cases, 2% or more of the nucleotides of a Cas9 guide RNA are modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a Cas9 guide RNA are modified).

In some cases, the number of nucleotides of a subject nucleic acid nucleic acid (e.g., a Cas9 guide RNA, a PAMmer, etc.) that are modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject PAMmer that are modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a Cas9 guide RNA that are modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a subject nucleic acid (e.g., a Cas9 guide RNA, a PAMmer, etc.) are modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject nucleic acid are modified). In some cases, one or more of the nucleotides of a subject PAMmer are modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject PAMmer are modified). In some cases, one or more of the nucleotides of a Cas9 guide RNA are modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a Cas9 guide RNA are modified).

In some cases, 99% or less of the nucleotides of a subject nucleic acid (e.g., a Cas9 guide RNA, a PAMmer, etc.) are modified (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid are modified). In some cases, 99% or less of the nucleotides of a subject PAMmer are modified (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject PAMmer are modified). In some cases, 99% or less of the nucleotides of a Cas9 guide RNA are modified (e.g., 99% or less, 95% or less, 90% or less, 85% or less, 80% or less, 75% or less, 70% or less, 65% or less, 60% or less, 55% or less, 50% or less, or 45% or less of the nucleotides of a Cas9 guide RNA are modified).

In some cases, the number of nucleotides of a subject nucleic acid nucleic acid (e.g., a Cas9 guide RNA, a PAMmer, etc.) that are modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject PAMmer that are modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a Cas9 guide RNA that are modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a subject nucleic acid (e.g., a Cas9 guide RNA, a PAMmer, etc.) are modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid are modified). In some cases, 20 or fewer of the nucleotides of a subject PAMmer are modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject PAMmer are modified). In some cases, 20 or fewer of the nucleotides of a Cas9 guide RNA are modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a Cas9 guide RNA are modified).

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stable with respect to attack by single-stranded ribonucleases and is typically 5 to 10-fold less susceptible to DNases than DNA. It is commonly used in antisense oligos as a means to increase stability and binding affinity to the target message.

In some cases, 2% or more of the nucleotides of a subject nucleic acid (e.g., a Cas9 guide RNA, a PAMmer, etc.) are 2'-O-Methyl modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject nucleic acid are 2'-O-Methyl modified). In some cases, 2% or more of the nucleotides of a subject PAMmer are 2'-O-Methyl modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject PAMmer are 2'-O-Methyl modified). In some cases, 2% or more of the nucleotides of a Cas9 guide RNA are 2'-O-Methyl modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a Cas9 guide RNA are 2'-O-Methyl modified).

In some cases, the number of nucleotides of a subject nucleic acid nucleic acid (e.g., a Cas9 guide RNA, a PAMmer, etc.) that are 2'-O-Methyl modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject PAMmer that are 2'-O-Methyl modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a Cas9 guide RNA that are 2'-O-Methyl modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a subject nucleic acid (e.g., a Cas9 guide RNA, a PAMmer, etc.) are 2'-O-Methyl modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject nucleic acid are 2'-O-Methyl modified). In some cases, one or more of the nucleotides of a subject PAMmer are 2'-O-Methyl modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject PAMmer are 2'-O-Methyl modified). In some cases, one or more of the nucleotides of a Cas9 guide RNA are 2'-O-Methyl modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a Cas9 guide RNA are 2'-O-Methyl modified).

In some cases, 99% or less of the nucleotides of a subject nucleic acid (e.g., a Cas9 guide RNA, a PAMmer, etc.) are 2'-O-Methyl modified (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid are 2'-O-Methyl modified). In some cases, 99% or less of the nucleotides of a subject PAMmer are 2'-O-Methyl modified (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject PAMmer are 2'-O-Methyl modified). In some cases, 99% or less of the nucleotides of a Cas9 guide RNA are 2'-O-Methyl modified (e.g., 99% or less, 95% or less, 90% or less, 85% or less, 80% or less, 75% or less, 70% or less, 65% or less, 60% or less, 55% or less, 50% or less, or 45% or less of the nucleotides of a Cas9 guide RNA are 2'-O-Methyl modified).

In some cases, the number of nucleotides of a subject nucleic acid nucleic acid (e.g., a Cas9 guide RNA, a PAMmer, etc.) that are 2'-O-Methyl modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject PAMmer that are 2'-O-Methyl modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a Cas9 guide RNA that are 2'-O-Methyl modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a subject nucleic acid (e.g., a Cas9 guide RNA, a PAMmer, etc.) are 2'-O-Methyl modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid are 2'-O-Methyl modified). In some cases, 20 or fewer of the nucleotides of a subject PAMmer are 2'-O-Methyl modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject PAMmer are 2'-O-Methyl modified). In some cases, 20 or fewer of the nucleotides of a Cas9 guide RNA are 2'-O-Methyl modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a Cas9 guide RNA are 2'-O-Methyl modified).

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

In some cases, 2% or more of the nucleotides of a subject nucleic acid (e.g., a Cas9 guide RNA, a PAMmer, etc.) are 2' Fluoro modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject nucleic acid are 2' Fluoro modified). In some cases, 2% or more of the nucleotides of a subject PAMmer are 2' Fluoro modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject PAMmer are 2' Fluoro modified). In some cases, 2% or more of the nucleotides of a Cas9 guide RNA are 2' Fluoro modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a Cas9 guide RNA are 2' Fluoro modified).

In some cases, the number of nucleotides of a subject nucleic acid nucleic acid (e.g., a Cas9 guide RNA, a PAMmer, etc.) that are 2' Fluoro modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject PAMmer that are 2' Fluoro modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a Cas9 guide RNA that are 2' Fluoro modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a subject nucleic acid (e.g., a Cas9 guide RNA, a PAMmer, etc.) are 2' Fluoro modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject nucleic acid are 2' Fluoro modified). In some cases, one or more of the nucleotides of a subject PAMmer are 2' Fluoro modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject PAMmer are 2' Fluoro modified). In some cases, one or more of the nucleotides of a Cas9 guide RNA are 2' Fluoro modified (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a Cas9 guide RNA are 2' Fluoro modified).

In some cases, 99% or less of the nucleotides of a subject nucleic acid (e.g., a Cas9 guide RNA, a PAMmer, etc.) are 2' Fluoro modified (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid are 2' Fluoro modified). In some cases, 99% or less of the nucleotides of a subject PAMmer are 2' Fluoro modified (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject PAMmer are 2' Fluoro modified). In some cases, 99% or less of the nucleotides of a Cas9 guide RNA are 2' Fluoro modified (e.g., 99% or less, 95% or less, 90% or less, 85% or less, 80% or less, 75% or less, 70% or less, 65% or less, 60% or less, 55% or less, 50% or less, or 45% or less of the nucleotides of a Cas9 guide RNA are 2' Fluoro modified).

In some cases, the number of nucleotides of a subject nucleic acid nucleic acid (e.g., a Cas9 guide RNA, a PAMmer, etc.) that are 2' Fluoro modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject PAMmer that are 2' Fluoro modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a Cas9 guide RNA that are 2' Fluoro modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a subject nucleic acid (e.g., a Cas9 guide RNA, a PAMmer, etc.) are 2' Fluoro modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid are 2' Fluoro modified). In some cases, 20 or fewer of the nucleotides of a subject PAMmer are 2' Fluoro modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject PAMmer are 2' Fluoro modified). In some cases, 20 or fewer of the nucleotides of a Cas9 guide RNA are 2' Fluoro modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a Cas9 guide RNA are 2' Fluoro modified).

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

In some cases, the number of nucleotides of a subject nucleic acid nucleic acid (e.g., a Cas9 guide RNA, a PAMmer, etc.) that have an LNA base is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject PAMmer that have an LNA base is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a Cas9 guide RNA that have an LNA base is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a subject nucleic acid (e.g., a Cas9 guide RNA, a PAMmer, etc.) have an LNA base (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject nucleic acid have an LNA base). In some cases, one or more of the nucleotides of a subject PAMmer have an LNA base (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject PAMmer have an LNA base). In some cases, one or more of the nucleotides of a Cas9 guide RNA have an LNA base (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a Cas9 guide RNA have an LNA base).

In some cases, 99% or less of the nucleotides of a subject nucleic acid (e.g., a Cas9 guide RNA, a PAMmer, etc.) have an LNA base (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid have an LNA base). In some cases, 99% or less of the nucleotides of a subject PAMmer have an LNA base (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject PAMmer have an LNA base). In some cases, 99% or less of the nucleotides of a Cas9 guide RNA have an LNA base (e.g., 99% or less, 95% or less, 90% or less, 85% or less, 80% or less, 75% or less, 70% or less, 65% or less, 60% or less, 55% or less, 50% or less, or 45% or less of the nucleotides of a Cas9 guide RNA have an LNA base).

In some cases, the number of nucleotides of a subject nucleic acid nucleic acid (e.g., a Cas9 guide RNA, a PAMmer, etc.) that have an LNA base is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject PAMmer that have an LNA base is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a Cas9 guide RNA that have an LNA base is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a subject nucleic acid (e.g., a Cas9 guide RNA, a PAMmer, etc.) have an LNA base (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid have an LNA base). In some cases, 20 or fewer of the nucleotides of a subject PAMmer have an LNA base (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject PAMmer have an LNA base). In some cases, 20 or fewer of the nucleotides of a Cas9 guide RNA have an LNA base (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a Cas9 guide RNA have an LNA base).

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some cases, the number of nucleotides of a subject nucleic acid nucleic acid (e.g., a Cas9 guide RNA, a PAMmer, etc.) that have a phosphorothioate linkage is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject PAMmer that have a phosphorothioate linkage is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a Cas9 guide RNA that have a phosphorothioate linkage is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a subject nucleic acid (e.g., a Cas9 guide RNA, a PAMmer, etc.) have a phosphorothioate linkage (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject nucleic acid have a phosphorothioate linkage). In some cases, one or more of the nucleotides of a subject PAMmer have a phosphorothioate linkage (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a subject PAMmer have a phosphorothioate linkage). In some cases, one or more of the nucleotides of a Cas9 guide RNA have a phosphorothioate linkage (e.g., 2 or more, 3 or more, 4 or more, 5 or more, 6 or more, 7 or more, 8 or more, 9 ore more, 10 or more, 11 or more, 12 or more, 13 or more, 14 or more, 15 or more, 16 or more, 17 or more, 18 or more, 19 ore more, 20 or more, 21 or more, 22 or more, or all of the nucleotides of a Cas9 guide RNA have a phosphorothioate linkage).

In some cases, 99% or less of the nucleotides of a subject nucleic acid (e.g., a Cas9 guide RNA, a PAMmer, etc.) have a phosphorothioate linkage (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid have a phosphorothioate linkage). In some cases, 99% or less of the nucleotides of a subject PAMmer have a phosphorothioate linkage (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject PAMmer have a phosphorothioate linkage). In some cases, 99% or less of the nucleotides of a Cas9 guide RNA have a phosphorothioate linkage (e.g., 99% or less, 95% or less, 90% or less, 85% or less, 80% or less, 75% or less, 70% or less, 65% or less, 60% or less, 55% or less, 50% or less, or 45% or less of the nucleotides of a Cas9 guide RNA have a phosphorothioate linkage).

In some cases, the number of nucleotides of a subject nucleic acid nucleic acid (e.g., a Cas9 guide RNA, a PAMmer, etc.) that have a phosphorothioate linkage is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject PAMmer that have a phosphorothioate linkage is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a Cas9 guide RNA that have a phosphorothioate linkage is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a subject nucleic acid (e.g., a Cas9 guide RNA, a PAMmer, etc.) have a phosphorothioate linkage (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid have a phosphorothioate linkage). In some cases, 20 or fewer of the nucleotides of a subject PAMmer have a phosphorothioate linkage (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject PAMmer have a phosphorothioate linkage). In some cases, 20 or fewer of the nucleotides of a Cas9 guide RNA have a phosphorothioate linkage (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a Cas9 guide RNA have a phosphorothioate linkage).

In some embodiments, a subject nucleic acid (e.g., a Cas9 guide RNA, a PAMmer, etc.) has one or more nucleotides that are 2'-O-Methyl modified nucleotides. In some embodiments, a subject nucleic acid (e.g., a Cas9 guide RNA, a PAMmer, etc.) has one or more 2' Fluoro modified nucleotides. In some embodiments, a subject nucleic acid (e.g., a Cas9 guide RNA, a PAMmer, etc.) has one or more LNA bases. In some embodiments, a subject nucleic acid (e.g., a Cas9 guide RNA, a PAMmer, etc.) has one or more nucleotides that are linked by a phosphorothioate bond (i.e., the subject nucleic acid has one or more phosphorothioate linkages). In some embodiments, a subject nucleic acid (e.g., a Cas9 guide RNA, a PAMmer, etc.) has a 5' cap (e.g., a 7-methylguanylate cap (m7G)).

In some embodiments, a subject nucleic acid (e.g., a Cas9 guide RNA, a PAMmer, etc.) has a combination of modified nucleotides. For example, a subject nucleic acid (e.g., a Cas9 guide RNA, a PAMmer, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage). See, e.g., FIGS. 17A-17B and FIGS. 21A-21H for working examples that utilize subject nucleic acids having one or more modified nucleotides. A subject nucleic acid can have any combination of modifications. For example, a subject nucleic acid can have any combination of the above described modifications.

In some embodiments, a Cas9 guide RNA has one or more nucleotides that are 2'-O-Methyl modified nucleotides. In some embodiments, a Cas9 guide RNA has one or more 2' Fluoro modified nucleotides. In some embodiments, a Cas9 guide RNA has one or more LNA bases. In some embodiments, a Cas9 guide RNA has one or more nucleotides that are linked by a phosphorothioate bond (i.e., the subject nucleic acid has one or more phosphorothioate linkages). In some embodiments, a Cas9 guide RNA has a 5' cap (e.g., a 7-methylguanylate cap (m7G)).

In some embodiments, a Cas9 guide RNA has a combination of modified nucleotides. For example, a Cas9 guide RNA can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage). A Cas9 guide RNA can have any combination of modifications. For example, a Cas9 guide RNA can have any combination of the above described modifications.

In some embodiments, a subject PAMmer has one or more nucleotides that are 2'-O-Methyl modified nucleotides. In some embodiments, a subject PAMmer has one or more 2' Fluoro modified nucleotides. In some embodiments, a subject PAMmer has one or more LNA bases. In some embodiments, a subject PAMmer has one or more nucleotides that are linked by a phosphorothioate bond (i.e., the subject nucleic acid has one or more phosphorothioate linkages). In some embodiments, a subject PAMmer has a 5' cap (e.g., a 7-methylguanylate cap (m7G)).

In some embodiments, a subject PAMmer has a combination of modified nucleotides. For example, a subject PAMmer can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage). See, e.g., FIGS. 17A-17B and FIGS. 21A-21H for working examples that utilize PAMmers having one or more modified nucleotides. A subject PAMmer can have any combination of modifications. For example, a subject PAMmer can have any combination of the above described modifications.

Modified Backbones and Modified Internucleoside Linkages

Examples of suitable nucleic acids containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3-alkylene phosphonates, 5'-alkylene phosphonates and chiral phosphonates, phosphinates, phosphoramidates including 3-amino phosphoramidate and aminoalkylphosphoramidates, phosphorodiamidates, thionophosphoramidates, thionoalkylphosphonates, thionoalkylphosphotriesters, selenophosphates and boranophosphates having normal 3-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —$CH_2$—NH—O—$CH_2$—, —$CH_2$—N($CH_3$)—O—$CH_2$-(known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (e.g., Koshkin et al., Tetrahedron, 1998, 54, 3607-3630). LNAs and preparation thereof are also described in WO 98/39352 and WO 99/14226, as well as U.S. applications 20120165514, 20100216983, 20090041809, 20060117410, 20040014959, 20020094555, and 20020086998.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_n O)_m CH_3$, $O(CH_2)_n OCH_3$, $O(CH_2)_n NH_2$, $O(CH_2)_n CH_3$, $O(CH_2)_n ONH_2$, and $O(CH_2)_n ON((CH_2)_n CH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_2 ON(CH_3)_2$ group, also known as 2'-DMAOE, as described in examples hereinbelow, and 2'-dimethylaminoethoxyethoxy (also known in the art as 2'-O-dimethylamino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—$OCH_2$ $CH_2NH_2$), allyl (—$CH_2$—CH=$CH_2$), —O-allyl (—O— $CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937.

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some cases, a PTD attached to another molecule facilitates entry of the molecule into the nucleus (e.g., in some cases, a PTD includes a nuclear localization signal). In some embodiments, a PTD is covalently linked to the amino terminus of an exogenous polypeptide (e.g., a Cas9 protein). In some embodiments, a PTD is covalently linked to the carboxyl terminus of an exogenous polypeptide (e.g., a Cas9 protein). In some embodiments, a PTD is covalently linked to the amino terminus and to the carboxyl terminus of an exogenous polypeptide (e.g., a Cas9 protein). In some embodiments, a PTD is covalently linked to a nucleic acid (e.g., a Cas9 guide RNA, a polynucleotide encoding a Cas9 guide RNA, a polynucleotide encoding a Cas9 protein, etc.). Exemplary PTDs include but are not limited to a minimal undecapeptide protein transduction domain (corresponding to residues 47-57 of HIV-1 TAT comprising YGRKKRRQRRR; SEQ ID NO:264); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:265); Transportan GWTLNSAGYLLGKINL-KALAALAKKIL (SEQ ID NO:266); KALAWEAKLAKA-LAKALAKHLAKALAKALKCEA (SEQ ID NO:267); and RQIKIWFQNRRMKWKK (SEQ ID NO:268). Exemplary PTDs include but are not limited to, YGRKKRRQRRR (SEQ ID NO:264), RKKRRQRRR (SEQ ID NO:269); an arginine homopolymer of from 3 arginine residues to 50 arginine residues; Exemplary PTD domain amino acid sequences include, but are not limited to, any of the following: YGRKKRRQRRR (SEQ ID NO:264); RKKRRQRR (SEQ ID NO:270); YARAAARQARA (SEQ ID NO:271); THRLPRRRRRR (SEQ ID NO:272); and GGR-RARRRRRR (SEQ ID NO:273). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Additional Examples

Additional targeters, activators, Cas9 proteins (including variant Cas9 proteins), Cas9 guide RNAs, and methods of using the same, can be found in the literature (see, for example, Chylinski et al., RNA Biol. 2013 May; 10(5):726-37; Jinek et al., Science. 2012 Aug. 17; 337(6096):816-21; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et. al., Genome Res. 2013 Oct. 31; Chen et. al., Nucleic Acids Res. 2013 Nov. 1; 41(20):e19; Cheng et. al., Cell Res. 2013 October; 23(10):1163-71; Cho et. al., Genetics. 2013 November; 195(3):1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. at., Nat Methods. 2013 October; 10(10):957-63; Nakayama et. al., Genesis. 2013 December; 51(12):835-43; Ran et. al., Nat Protoc. 2013 November; 8(11):2281-308; Ran et. al., Cell. 2013 Sep. 12; 154(6):1380-9; Upadhyay et. al., G3 (Bethesda). 2013 Dec. 9; 3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Methods

The present disclosure provides methods for labeling a single stranded target nucleic acid. Generally, a subject method of labeling involves contacting a single stranded target nucleic acid with (e.g., by introducing into a cell) a subject quenched PAMmer, a Cas9 guide RNA, and a Cas9 protein (e.g., a Cas9 protein that cleaves both the quenched PAMmer and the target nucleic acid, e.g., a wild type Cas9 protein; a variant Cas9 protein, a variant Cas9 protein with reduced nuclease activity; a variant Cas9 protein that cleaves the PAMmer but does not cleave the target nucleic acid; a Cas9 heterodimer, etc.). In some cases, the quenched PAMmer has a specificity segment and does not have an orientation segment. In some cases, the quenched PAMmer has an orientation segment and does not have a specificity segment. In some cases, the quenched PAMmer has a specificity segment and an orientation segment.

In performing the subject methods, one can bias the cleavage activity of the Cas9 protein to avoid cleaving the target sequence present in DNA within the sample (e.g., the target sequence present in the genome of a cell) by selecting a target sequence where the target sequence does not have an adjacent PAM sequence in the DNA (e.g., in the genome). In such a scenario, the PAM sequence would be provided by the quenched PAMmer, heavily biasing cleavage toward the single stranded target nucleic acid (e.g., a target RNA) and away from the DNA encoding the target nucleic acid. For example, if a subject method is used to label an mRNA in a living cell, and it is therefore desirable to avoid cleaving the DNA within the genome that encodes the mRNA, one can select the target sequence within the mRNA such that the corresponding sequence within the DNA does not have an adjacent PAM sequence. In such a scenario, the PAM sequence provided by the PAMmer would not hybridize with the target nucleic acid (e.g., see FIG. 8G, FIG. 8H, FIG. 8I, and FIG. 30A-30E).

In some embodiments of the subject methods, the target nucleic acid is outside of a cell. In some embodiments of the subject methods, the target nucleic acid is inside of a cell (which can be referred to as a "host cell" or a "target cell"). In some cases, the method involves contacting a cell with (e.g., introducing into a cell) a subject quenched PAMmer and/or a Cas9 guide RNA (or a nucleic acid encoding the same), and/or Cas9 protein (or a nucleic acid encoding the same). In some embodiments of the subject methods, the host cell provides one or more of the components (e.g., the cell can be genetically modified to express a Cas9 protein and/or a Cas9 guide RNA (or a component of a Cas9 dual guide RNA)). In some such cases, the methods therefore include adding those components not provided by the host cell. As an illustrative example, if the host cell is genetically modified to express a Cas9 protein, the method can include introducing into the cell a Cas9 guide RNA (or a nucleic acid encoding the guide RNA) and/or a quenched PAMmer (which would therefore constitute a method of contacting a target nucleic acid with a Cas9 protein, a Cas9 guide RNA, and a quenched PAMmer).

As discussed above, a Cas9 guide RNA and a Cas9 protein form a complex. The guide RNA provides target specificity to the complex by comprising a nucleotide sequence that is complementary to a sequence of a target nucleic acid. The Cas9 protein of the complex provides the site-specific activity. When the target nucleic acid is a single stranded target nucleic acid, a quenched PAMmer provides a PAM sequence that activates the Cas9 protein. In some embodiments, a subject complex cleaves the quenched PAMmer. In some embodiments, a subject complex cleaves the quenched PAMmer but does not cleave the target nucleic acid (e.g., when using a Cas9 protein that cleaves the non-complementary strand but does not cleave the complementary strand). In some embodiments, a subject complex cleaves the quenched PAMmer and cleaves the target nucleic acid.

In some embodiments, a subject complex cleaves the quenched PAMmer, does not cleave the target nucleic acid (e.g., when using a Cas9 protein that cleaves the non-complementary strand but does not cleave the complementary strand), but does modify the target nucleic acid (e.g., when using a Cas9 fusion protein that is fused to a heterologous protein that provides an activity for modifying a target nucleic acid). In some embodiments, a subject complex cleaves the quenched PAMmer, cleaves the target nucleic acid, and additionally modifies the target nucleic acid (e.g., when using a Cas9 fusion protein that is fused to a heterologous protein that provides an activity for modifying a target nucleic acid).

In some cases, the Cas9 protein exhibits nuclease activity that cleaves target nucleic acid at a target nucleic acid sequence (target site) defined by: (i) the region of complementarity between the guide RNA and the target nucleic acid; and/or (ii) the region of complementarity between the target nucleic acid and the orientation segment of the quenched PAMmer. A Cas9 protein is activated by the presence of a PAM sequence adjacent to the target site and a single stranded target nucleic acid does not have a PAM sequence. As defined and discussed above, a subject PAMmer facilitates the cleavage of a single stranded target nucleic acid by providing a PAM sequence (anchored into an appropriate position by the orientation segment and/or the specificity segment of the PAMmer, see FIG. 8A-8I).

In some cases where the Cas9 protein is a Cas9 heterodimer, a subject method can be performed using a truncated Cas9 guide RNA and can be performed in the presence of an appropriate dimerizing agent (as described above). Thus, in some cases where the Cas9 protein is a Cas9 heterodimer, a subject method includes contacting a target nucleic acid with a dimerizing agent and a truncated Cas9 guide RNA in addition to the other components (e.g., quenched PAMmer). In some cases where the Cas9 protein is a Cas9 heterodimer, a subject method includes contacting a target nucleic acid with a system and/or a composition the comprises a dimerizing agent and a truncated Cas9 guide RNA in addition to the other components (e.g., quenched PAMmer).

In some embodiments, a method of labeling can be used to visualize the target nucleic acid (e.g., visualize the subcellular distribution of a target nucleic acid). In addition to the quenched PAMmer, any one of the components (e.g., the Cas9 protein, the Cas9 guide RNA) can be detectably labeled (i.e., can have an indirect and/or direct label moiety, defined above). The term "detectable label" includes directly and/or indirectly detectable labels. In some cases, a Cas9 protein and/or Cas9 guide RNA can have a label moiety that can be indirectly detected (an RNA aptamer, a nucleic acid sequence that is bound by a labeled protein, biotin, etc.) and/or directly detected (e.g., a fluorescent dye).

A method for labeling a single-stranded target nucleic acid according to the present disclosure finds use in a variety of applications, which are also provided. Applications include research applications; diagnostic applications; industrial applications; and treatment applications. Applications include, e.g., determining the amount (e.g., in a target cell, in a biological sample, etc.) of a target nucleic acid (e.g., mRNA, tRNA, rRNA, microRNA, ncRNA, lncRNA, etc.)(e.g., in some cases two or more, three or more, four or more, five or more, etc. different single stranded target nucleic acids). For example, an amount of a target nucleic acid can be determined in a sample (e.g., a clinical sample, either within cells or extracellular) by contacting the target nucleic acid with a Cas9 protein, a Cas9 guide RNA, and a quenched PAMmer, and quantifying the amount of target nucleic acid by quantifying the signal from the detectable label (e.g, via flow cytometry, microscopy, etc.). For example, such a method can include (i) contacting a sample having the target nucleic acid with a quenched PAMmer, a Cas9 guide RNA, and a Cas9 protein; and (ii) detecting the presence or absence of the detectable label (e.g., measuring/detecting signal from the detectable label). Such methods can be useful for measuring the amount of the target nucleic acid (quantitative) and can also be useful for determining presence/absence of the target nucleic acid (qualitative) and/or determining whether the target nucleic acid is present above or below a threshold amount (quantitative/qualitative).

As noted above, contacting a target nucleic acid, e.g., when the nucleic acid is in a cell, can be achieved by introducing the components (Cas9 protein, Cas9 guide RNA, quenched PAMmer) into the cell and/or by introducing one or more nucleic acids encoding one or more of the components into the cell. Thus, in some cases, a subject method is a method of quantifying the amount of a target nucleic acid in a sample (e.g., in a cellular sample, in a cell, in a fixed cell, in a living cell, etc.).

Applications also include the visualization and/or subcellular localization of specific single stranded target nucleic acids (e.g., in real time in living cells, or in fixed cells) (e.g., multi-color RNA imaging inside of a cell). Such methods can be used for drug discovery and target validation (e.g, a candidate drug may alter the amount of and/or subcellular localization of a target nucleic acid). High through-put analysis can be carried out using a subject labeling method (e.g., on a genomic scale).

For all of the methods that utilize a quenched PAMmer (e.g, all of the above methods/applications disclose herein), the methods can be used for diagnostic purposes. For all of the methods that utilize a quenched PAMmer (e.g, all of the above methods/applications disclose herein), an appropriate Cas9 can be chosen for a desired purpose. For example, a Cas9 fusion protein can be used that cleaves the quenched PAMmer but modifies the target nucleic acid in another way (e.g., methylation), and the resulting modified target nucleic acid can be imaged/visualized/quantified/tracked, etc.

For all of the methods that utilize a quenched PAMmer (e.g, all of the above methods/applications disclose herein), multiple different target nucleic acids can be quantified/tracked/labeled/visualized/imaged (e.g., simultaneously), by for example, using PAMmers and Cas9 guide RNAs that target different target nucleic acids and where different PAMmers have detectable labels that are distinguishable from one another.

In some instances, one or more components (e.g., a target nucleic acid, a quenched PAMmer, a Cas9 guide RNA, and/or a Cas9 protein) is labeled with (e.g., linked to) a donor molecule, while another component is labeled with (e.g., linked to) an acceptor molecule, and detection of an association between the labeled components is by fluorescence resonance energy transfer (also referred to as "Förster resonance energy transfer" or "FRET").

In some instances, one or more components (e.g., a target nucleic acid, a PAMmer, a Cas9 guide RNA, and/or a Cas9 protein) is labeled with (e.g., linked to, fused with, bound by, etc.) a first member of a split fluorophore, while another component is labeled with (e.g., linked to, fused with, bound by, etc.) a second member of a split fluorophore, and detection of the fluorophore can occur when the first and second split fluorophores are brought into close proximity. For example, in some cases, a Cas9 protein (or a Cas9 guide RNA) can be labeled with a first member of a split fluorophore and the corresponding PAMmer can be labeled with a second member of the split fluorophore such that, when the Cas9/guide RNA complex is brought into close proximity to the corresponding PAMmer (which occurs when both are binding to (associated with) the target nucleic acid), a signal can be detected. Any convenient split fluorophore can be used. For more information related to split fluorophores (e.g., a split-GFP), refer to Cabantous et al., Sci Rep. 2013 Oct. 4; 3:2854. doi: 10.1038/srep02854, which is hereby incorporated by reference in its entirety.

A subject method can be used for detection (e.g., ultra-low background detection) and/or imaging of endogenous and/or exogenous (e.g., viral or pathogen) single stranded target nucleic acids (e.g., DNAs, RNAs). Many current technologies (e.g. fluorescent proteins tethered to RNA-binding proteins) suffer from high background and subsequent false positive signals due to the fluorescence output not being tightly controlled by target binding, and while other current technologies have provided improvements in attempt to overcome this problem (e.g. molecular beacons), they still suffer from background and false positive signals owing to the random 'opening' of these molecules when in their unbound state and when bound at off-target sites.

Methods of Treatment

In some cases, a subject method of labeling is a method of treating. For example, a Cas9 protein can be used to cleave a target nucleic acid (e.g., a viral DNA or RNA, a particular endogenous mRNA, etc. as described elsewhere) in addition to the quenched PAMmer, and the subject method would therefore label the cleaved target nucleic acid. Furthermore, a signal would only be detected upon cleavage, so one could monitor the cleavage of the target nucleic acid because detection of signal could be used as a reporter that cleavage of the target nucleic acid has occurred.

As another example, a variant Cas9 protein (e.g., Cas9 fusion protein) can be used to modify (e.g., methylate etc. as described elsewhere) a target nucleic acid (e.g., a viral DNA or RNA, a particular endogenous mRNA, etc. as described elsewhere) in addition to cleaving the quenched PAMmer (in order to label the target nucleic acid), and the subject method would therefore label the modified target nucleic acid. A signal would only be detected upon cleavage of the quenched PAMmer, so one could monitor modification of the target nucleic acid because detection of signal could be used as a reporter that cleavage of the quenched PAMmer, and simultaneously modification of the target nucleic acid, has occurred.

In some cases, where the method is a method of treatment, a pharmaceutical preparation (as described below) can be administered to an individual. Such preparations can include a quenched PAMmer, and/or guide RNA (or nucleic acid encoding the same), and/or Cas9 protein (or nucleic acid encoding the same).

Multiple Guide RNAs and/or PAMmers

In some embodiments, multiple guide RNAs and multiple PAMmers are used to simultaneously label multiple different target nucleic acids or multiple different locations on the same target nucleic. For example, in some cases, a subject labeling method involves use of: a) a first Cas9 guide RNA targeting a first target nucleic acid, and a first quenched PAMmer comprising a first detectable label; and b) a second guide RNA targeting a second target nucleic acid (or a second target sequence of the first target nucleic acid) having a nucleotide sequence that differs from the first target nucleic acid, and a second quenched PAMmer comprising a second detectable label that is distinguishable from the first detectable label. Each targeting pair (a quenched PAMmer and a Cas9 guide RNA) can have a detectable label that is distinguishable from another targeting pair, and thus, multiple different target nucleic acids can be simultaneously labeled (e.g., quantified/visualized/imaged, etc.). In some embodiments, two or more guide RNAs (and quenched PAMmers) target the same gene or transcript or locus. In some embodiments, two or more guide RNAs (and quenched PAMmers) target different unrelated target nucleic acids. In some embodiments, two or more guide RNAs (and quenched PAMmers) target different, but related target nucleic acids. In some cases, the quenched PAMmer(s) can be introduced directly (e.g, transfected into a cell).

To express multiple guide RNAs (and/or PAMmers), an artificial RNA processing system mediated by a Csy4 endoribonuclease can be used. Multiple guide RNAs can be concatenated into a tandem array on a precursor transcript (e.g., expressed from a U6 promoter), and separated by Csy4-specific RNA sequence. Co-expressed Csy4 protein cleaves the precursor transcript into multiple guide RNAs (and/or PAMmers). Advantages for using an RNA processing system include: first, there is no need to use multiple promoters; second, since all guide RNAs (and/or PAMmers) are processed from a precursor transcript, their concentrations are normalized for similar Cas9-binding.

Csy4 is a small endoribonuclease (RNase) protein derived from bacteria *Pseudomonas aeruginosa*. Csy4 specifically recognizes a minimal 17-bp RNA hairpin, and exhibits rapid (<1 min) and highly efficient (>99.9% or more) RNA cleavage. Unlike most RNases, the cleaved RNA fragment remains stable and functionally active. The Csy4-based RNA cleavage can be repurposed into an artificial RNA processing system. In this system, the 17-bp RNA hairpins are inserted between multiple RNA fragments that are transcribed as a precursor transcript from a single promoter. Co-expression of Csy4 is effective in generating individual RNA fragments.

In some embodiments (e.g., in some cases where the Cas9 protein is a chimeric Cas9 protein), a subject complex modifies a target polypeptide associated with target nucleic acid (e.g., a histone, a DNA-binding protein, an RNA-binding protein, an RNA editing protein etc.), leading to, for example, protein methylation, protein acetylation, protein ubiquitination, and the like. The target nucleic acid may be, for example, a single stranded nucleic acid outside of a cell in vitro, a single stranded nucleic acid inside of a cell in vitro, a single stranded nucleic acid inside of a cell ex vivo, or a single stranded nucleic acid inside of a cell in vivo.

In some cases, different Cas9 proteins (i.e., Cas9 proteins from various species) may be advantageous to use in the various provided methods in order to capitalize on various enzymatic characteristics of the different Cas9 proteins (e.g., for different PAM sequence preferences; for increased or decreased enzymatic activity; for an increased or decreased level of cellular toxicity; etc.). Cas9 proteins from various species (see SEQ ID NOs:1-256 and 795-1346) may require different PAM sequences. Thus, for a particular Cas9 protein of choice, the PAM sequence requirement may be different than the PAM sequences described above (e.g., 5'-NGG-3', GG, etc.).

In some cases, the Cas9 protein has enzymatic activity that modifies target nucleic acid in ways other than introducing strand cleavage. Enzymatic activity of interest that may be used to modify target nucleic acid (e.g., by fusing a heterologous polypeptide with enzymatic activity to a Cas9 protein, thereby generating a chimeric Cas9 protein) includes, but is not limited methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, the Cas9 protein has activity that modulates the production of a protein encoded by a single stranded target nucleic acid (e.g., mRNA) (e.g., by cleaving the mRNA). In some cases, the subject method is used to cleave a targeted coding-RNA (protein-encoding gene) and/ or a targeted non-coding RNA (e.g., tRNA, rRNA, snoRNA, siRNA, miRNA, long ncRNA, etc.).

In some cases, the Cas9 protein has enzymatic activity that modifies a polypeptide associated with a target nucleic acid (e.g. a histone, a DNA-binding protein, an RNA-binding protein, an RNA editing protein and the like). In some embodiments, the enzymatic activity is methyltransferase activity, demethylase activity, acetyltransferase activity, deacetylase activity, kinase activity, phosphatase activity, ubiquitin ligase activity (i.e., ubiquitination activity), deubiquitinating activity, adenylation activity, deadenylation activity, SUMOylating activity, deSUMOylating activity, ribosylation activity, deribosylation activity, myristoylation activity, demyristoylation activity glycosylation activity (e.g., from O-GlcNAc transferase) or deglycosylation activity. The enzymatic activities listed herein catalyze covalent modifications to proteins. Such modifications are known in the art to alter the stability or activity of the target protein (e.g., phosphorylation due to kinase activity can stimulate or silence protein activity depending on the target protein).

Target Cells of Interest

A target nucleic acid can be located anywhere, for example, outside of a cell in vitro (e.g., in a biological sample), inside of a cell in vitro (in a biological sample), inside of a cell in vivo, inside of a cell ex vivo (e.g., in a biological sample). Suitable target cells (which can comprise target nucleic acids) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens C. agardh*, and the like; a fungal cell (e.g., a yeast cell); an animal cell; a cell from an invertebrate animal (e.g. fruit fly, cnidarian, echinoderm, nematode, etc.); a cell from a vertebrate animal (e.g., fish, amphibian, reptile, bird, mammal); a cell from a mammal (e.g., a cell from a rodent, a cell from a human, etc.); and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a speratogonia, etc.), a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to label a target nucleic acid (e.g., for visualization, for quantification, etc.) in mitotic or post-mitotic cells in vivo and/or ex vivo and/or in vitro (e.g., for diagnostic purposes, for research purposes, etc.). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.).

Any type of cell may be of interest (e.g. a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. In some cases, the primary cell lines are maintained for fewer than 10 passages in vitro. Target cells are in many embodiments unicellular organisms, or are grown in culture.

If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% or more DMSO, 50% or more serum, and about 40% buffered medium, or some other such solution as is commonly used in the art to preserve cells at such freezing temperatures, and thawed in a manner as commonly known in the art for thawing frozen cultured cells.

Introducing Components into a Target Cell

A Cas9 guide RNA (or a nucleic acid comprising a nucleotide sequence encoding same), a PAMmer (or a nucleic acid comprising a nucleotide sequence encoding same), and/or a Cas9 protein (or a nucleic acid comprising a nucleotide sequence encoding same) can be introduced into a host cell by any of a variety of well-known methods. Similarly, where a subject method involves introducing into a host cell a nucleic acid comprising a nucleotide sequence encoding a variant Cas9 protein, such a nucleic acid can be introduced into a host cell by any of a variety of well-known methods.

Methods of introducing a nucleic acid into a host cell are known in the art, and any known method can be used to introduce a nucleic acid (e.g., an expression construct) into a stem cell or progenitor cell. Suitable methods include, include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

For methods of labeling a single stranded target nucleic acid, in some cases, the Cas9 protein is provided as a nucleic acid (e.g., an mRNA, a DNA, a plasmid, an expression vector, etc.) that encodes the Cas9 protein. In some cases, the Cas9 protein is provided directly as a protein. As one non-limiting example, fungi (e.g., yeast) can be transformed with exogenous protein and/or nucleic acid using spheroplast transformation (see Kawai et al., Bioeng Bugs. 2010 November-December; 1(6):395-403: "Transformation of *Saccharomyces cerevisiae* and other fungi: methods and possible underlying mechanism"; and Tanka et al., Nature. 2004 Mar. 18; 428(6980):323-8: "Conformational variations in an infectious protein determine prion strain differences"; both of which are herein incorporated by reference in their entirety). Thus, a Cas9 protein (e.g., Cas9) can be incorporated into a spheroplast (with or without nucleic acid encoding a Cas9 guide RNA and with or without a donor polynucleotide) and the spheroplast can be used to introduce the content into a yeast cell. A Cas9 protein can be introduced into a cell (provided to the cell) by any convenient method; such methods are known to those of ordinary skill in the art. As another non-limiting example, a Cas9 protein can be injected directly into a cell (e.g., with or without nucleic acid encoding a Cas9 guide RNA and with or without a donor polynucleotide), e.g., a cell of a zebrafish embryo, the pronucleus of a fertilized mouse oocyte, etc. As another example, a preformed complex of a Cas9 protein and a Cas9 guide RNA (an RNP) can be introduced into a cell via nucleofection.

Genetically Modified Host Cells

In some embodiments, a genetically modified host cell has been genetically modified with an exogenous nucleic acid comprising a nucleotide sequence encoding a Cas9 protein (e.g., a naturally occurring Cas9; a modified, i.e., mutated or variant, Cas9; a chimeric Cas9; etc.). Single stranded nucleic acids of the genetically modified host cell can be targeted for modification by introducing into the cell a Cas9 guide RNA (or a DNA encoding a Cas9 guide RNA, which determines the genomic location/sequence to be modified) and a PAMmer (or a nucleic acid encoding a PAMmer). In some embodiments, the nucleotide sequence encoding a Cas9 protein is operably linked to an inducible promoter (e.g., heat shock promoter, Tetracycline-regulated promoter, Steroid-regulated promoter, Metal-regulated promoter, estrogen receptor-regulated promoter, etc.). In some embodiments, the nucleotide sequence encoding a Cas9 protein is operably linked to a spatially restricted and/or temporally restricted promoter (e.g., a tissue specific promoter, a cell type specific promoter, etc.). In some embodiments, the nucleotide sequence encoding a Cas9 protein is operably linked to a constitutive promoter.

In some embodiments, a subject genetically modified host cell is in vitro. In some embodiments, a subject genetically modified host cell is in vivo. In some embodiments, a subject genetically modified host cell is a prokaryotic cell or is derived from a prokaryotic cell. In some embodiments, a subject genetically modified host cell is a bacterial cell or is derived from a bacterial cell. In some embodiments, a subject genetically modified host cell is an archaeal cell or is derived from an archaeal cell. In some embodiments, a subject genetically modified host cell is a eukaryotic cell or is derived from a eukaryotic cell. In some embodiments, a subject genetically modified host cell is a plant cell or is derived from a plant cell. In some embodiments, a subject genetically modified host cell is an animal cell or is derived from an animal cell. In some embodiments, a subject genetically modified host cell is an invertebrate cell or is derived from an invertebrate cell. In some embodiments, a subject genetically modified host cell is a vertebrate cell or is derived from a vertebrate cell. In some embodiments, a subject genetically modified host cell is a mammalian cell or is derived from a mammalian cell. In some embodiments, a subject genetically modified host cell is a rodent cell or is derived from a rodent cell. In some embodiments, a subject genetically modified host cell is a human cell or is derived from a human cell.

The present disclosure further provides progeny of a subject genetically modified cell, where the progeny can comprise the same exogenous nucleic acid or polypeptide as the subject genetically modified cell from which it was derived. The present disclosure further provides a composition comprising a subject genetically modified host cell.

Compositions

The present disclosure provides a composition comprising a quenched PAMmer and at least one of: a Cas9 guide RNA (or one or more nucleic acids encoding the same) and a Cas9 protein (or nucleic acid encoding the same). In some cases, the Cas9 protein is a variant Cas9 protein. In some cases, the Cas9 protein is a chimeric Cas9 protein (a Cas9 fusion protein). A subject composition is useful for carrying out a method of the present disclosure, e.g., a method for labeling a single stranded target nucleic acid.

Compositions and Kits Comprising a Quenched PAMmer

The present disclosure provides compositions and kits comprising a quenched PAMmer and at least one of: a Cas9 guide RNA and a Cas9 protein. The compositions and kits can comprise, in addition, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), MES sodium salt, 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a nuclease inhibitor; and the like. For example, in some cases, a subject composition or kit comprises a Cas9 guide RNA and a buffer for stabilizing nucleic acids. In some cases where the Cas9 protein is a Cas9 heterodimer, a subject composition and/or kit can include a dimerizing agent (e.g., an appropriate dimerizing agent that can facilitate dimerization).

In some embodiments, quenched PAMmer and/or a Cas9 guide RNA and/or a Cas9 protein is present in a subject composition is pure, e.g., 75% or more, 80% or more, 85% or more, 90% or more, 95% or more, 98% or more, 99% or more, or more than 99% or more pure, where "% or more purity" means that guide RNA is the recited percent free from other macromolecules, or contaminants that may be present during the production of the quenched PAMmer and/or a Cas9 guide RNA and/or a Cas9 protein.

As noted above, in some embodiments, a quenched PAMmer, and/or guide RNA, and/or Cas9 protein are employed to modify single stranded nucleic acid (ssRNA, ssDNA) in vivo, for purposes, e.g. to treat a disease or as an antiviral, antipathogenic, or anticancer therapeutic, or for biological research. In in vivo embodiments, a quenched PAMmer, and/or guide RNA (or nucleic acid encoding the same), and/or Cas9 protein (or nucleic acid encoding the same) can be administered to the individual (as protein, RNA, and/or DNA, as appropriate/convenient). A quenched PAMmer, and/or guide RNA (or nucleic acid encoding the same), and/or Cas9 protein (or nucleic acid encoding the same) may be administered by any of a number of well-known methods in the art for the administration of peptides, small molecules and nucleic acids to a subject. A quenched PAMmer, and/or guide RNA (or nucleic acid encoding the same), and/or Cas9 protein (or nucleic acid encoding the same) can be incorporated into a variety of formulations. A quenched PAMmer, and/or guide RNA (or nucleic acid encoding the same), and/or Cas9 protein (or nucleic acid encoding the same) of the present disclosure can be formulated into pharmaceutical compositions by combination with appropriate pharmaceutically acceptable carriers or diluents.

Pharmaceutical preparations are compositions that include one or more of a quenched PAMmer, and/or guide RNA (or nucleic acid encoding the same), and/or Cas9 protein (or nucleic acid encoding the same) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which an agent (e.g., one or more of a quenched PAMmer, and/or guide RNA, and/or Cas9 protein) is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the a quenched PAMmer, and/or guide RNA (or nucleic acid encoding the same), and/or Cas9 protein (or nucleic acid encoding the same) can be achieved in various ways, including oral, buccal, rectal, parenteral, intraperitoneal, intradermal, transdermal, intratracheal, intraocular, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the present disclosure when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the methods of the present disclosure, to facilitate transport across the endothelial wall of the blood vessel. Alternatively, drug delivery of therapeutics agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversably affixed (see e.g. US Application Nos. 20080081064 and 20090196903, incorporated herein by reference).

Typically, an effective amount of a quenched PAMmer, and/or guide RNA (or nucleic acid encoding the same), and/or Cas9 protein (or nucleic acid encoding the same) are provided. As discussed above with regard to ex vivo methods, an effective amount or effective dose of a quenched PAMmer, and/or guide RNA (or nucleic acid encoding the same), and/or Cas9 protein (or nucleic acid encoding the same) in vivo is the amount sufficient to induce a 2 fold (or greater) reduction in the amount of intact target nucleic acid (for methods of cleaving) and/or 2-fold change in the amount of modified target nucleic acid, relative to a negative control (e.g. a cell contacted with an empty vector and/or irrelevant polypeptide). The amount of intact target nucleic acid may be measured by any convenient method, e.g. as described above and known in the art. The calculation of the effective amount or effective dose of a quenched PAMmer, and/or guide RNA (or nucleic acid encoding the same), and/or Cas9 protein (or nucleic acid encoding the same) to be administered is within the skill of one of ordinary skill in the art. The final amount to be administered will be dependent upon the route of administration and upon the nature of the disorder or condition that is to be treated.

The effective amount given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, a quenched PAMmer, and/or guide RNA (or nucleic acid encoding the same), and/or Cas9 protein (or nucleic acid encoding the same) may be obtained from a suitable commercial source. As a general proposition, the total pharmaceutically effective amount of a quenched PAMmer, and/or guide RNA (or nucleic acid encoding the same), and/or Cas9 protein (or nucleic acid encoding the same) administered parenterally per dose will be in a range that can be measured by a dose response curve.

Therapies based on a quenched PAMmer, and/or guide RNA, and/or Cas9 protein, i.e. preparations of a quenched PAMmer, and/or guide RNA (or nucleic acid encoding the same), and/or Cas9 protein (or nucleic acid encoding the same) to be used for therapeutic administration, must be sterile. Sterility is readily accomplished by filtration through sterile filtration membranes (e.g., 0.2 µm membranes). Therapeutic compositions generally are placed into a container having a sterile access port, for example, an intravenous solution bag or vial having a stopper pierceable by a hypodermic injection needle. The therapies based on a quenched PAMmer, and/or guide RNA (or nucleic acid encoding the same), and/or Cas9 protein (or nucleic acid encoding the same) may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., National Food (NF) grade, generally analytical grade, and more typically pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under Good Manufacturing Practices (GMP) conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

A subject kit can include a quenched PAMmer and one or more of: a Cas9 protein; a nucleic acid encoding a Cas9 protein; a Cas9 guide RNA; a nucleic acid encoding a Cas9 guide RNA; an activator; a nucleic acid encoding an activator; a targeter; and a nucleic acid encoding a targeter; all of which are described in detail above.

In some embodiments of any of the above kits, the kit comprises an activator and/or a targeter. In some embodiments of any of the above kits, the kit comprises a Cas9 single guide RNA. In some embodiments of any of the above kits, the kit comprises two or more guide RNAs (e.g., dual and/or Cas9 single guide RNAs). In some embodiments of any of the above kits, the kit comprises two or more quenched PAMmers. In some embodiments of any of the above kits, quenched PAMmers and/or Cas9 guide RNAs (e.g., including two or more guide RNAs) can be provided as an array (e.g., an array of RNA molecules, an array of DNA molecules, e.g., encoding the guide RNA(s), etc.). Such kits can be useful, for example, for use in conjunction with the above described genetically modified host cells that comprise a Cas9 protein. Components of a subject kit can be in separate containers; or can be combined in a single container.

Any of the above-described kits can further include one or more additional reagents, where such additional reagents can be selected from: a dilution buffer; a reconstitution solution; a wash buffer; a control reagent; a control expression vector or RNA polynucleotide; a reagent for in vitro production of the Cas9 protein, e.g., from DNA and/or RNA, and the like.

In some cases, a subject kit includes a variant Cas9 protein that exhibits reduced nuclease activity relative to wild-type Cas9 (and/or a nucleic acid encoding the same).

A subject kit can further include one or more additional reagents, where such additional reagents can be selected from: a buffer; a wash buffer; a control reagent; a control expression vector or RNA polynucleotide; a reagent for in vitro production of a Cas9 protein, e.g., from DNA and/or RNA; and the like. In some cases, a Cas9 protein included in a subject kit is a wild type Cas9 protein. In some cases, a Cas9 protein included in a subject kit is a variant Cas9 polypeptide (e.g., a Cas9 protein with reduced nuclease activity). In some cases, a Cas9 protein included in a subject kit is a Cas9 fusion protein. Components of a subject kit can be in separate containers; or can be combined in a single container.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Libraries

The present disclosure provides a library of two or more PAMmers. The present disclosure provides a library of two or more targeting pairs, where a targeting pair is a Cas9 guide RNA and a cognate PAMmer. Thus, each targeting pair is associate with (targets) one target site of a single stranded target nucleic acid. The guide RNAs and/or PAMmers can be present in the library as nucleic acids (e.g., recombinant expression vectors) comprising nucleotides encoding guide RNAs and/or PAMmers.

A subject library can comprise from about 2 targeting pairs to about 1012 targeting pairs; e.g., a subject library can comprise from about 2 targeting pairs to about 102 targeting pairs, from about 102 targeting pairs to about 103 targeting pairs, from about 103 targeting pairs to about 105 targeting pairs, from about 105 targeting pairs to about 107 targeting pairs, from about 107 targeting pairs to about 109 targeting pairs, or from about 109 targeting pairs to about 1012 targeting pairs.

A "targeting pair" of a subject library differs from other members of the library in the nucleotide sequence of the targeting segment of the guide RNA as well as the orientation segment and/or the specificity segment of the PAMmer. Thus, e.g., each targeting pair of a subject library can comprise a Cas9 guide RNA with the same or substantially the same nucleotide sequence of the protein-binding segment as all other members of the library. In this way, the library can comprise members that bind to different target nucleic acids.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

In FIGS. 1-6 of the following working examples, a subject PAMmer is schematized above or below the appropriate experimental lanes and the PAM sequence is boxed (also refer to FIGS. 8A-8D).

Example 1: Use of Cas9 to Cleave a Single Stranded RNA (ssRNA)

The working examples demonstrate that a Cas9 protein associated with a Cas9 guide RNA can bind and cleave single stranded RNA (ssRNA) target sequences. Single stranded target nucleic binding is stabilized by including a short PAM-containing oligonucleotide ('PAMmer') that hybridizes to the single stranded target nucleic acid (e.g., RNA and/or DNA) downstream of the region that is recognized sequence-specifically through base-pairing with the guide RNA. Inclusion of the PAMmer also activates Cas9 to cleave the singled stranded target nucleic acid using the same HNH nuclease domain that cleaves double stranded target nucleic acid (dsDNA).

Figure 3:
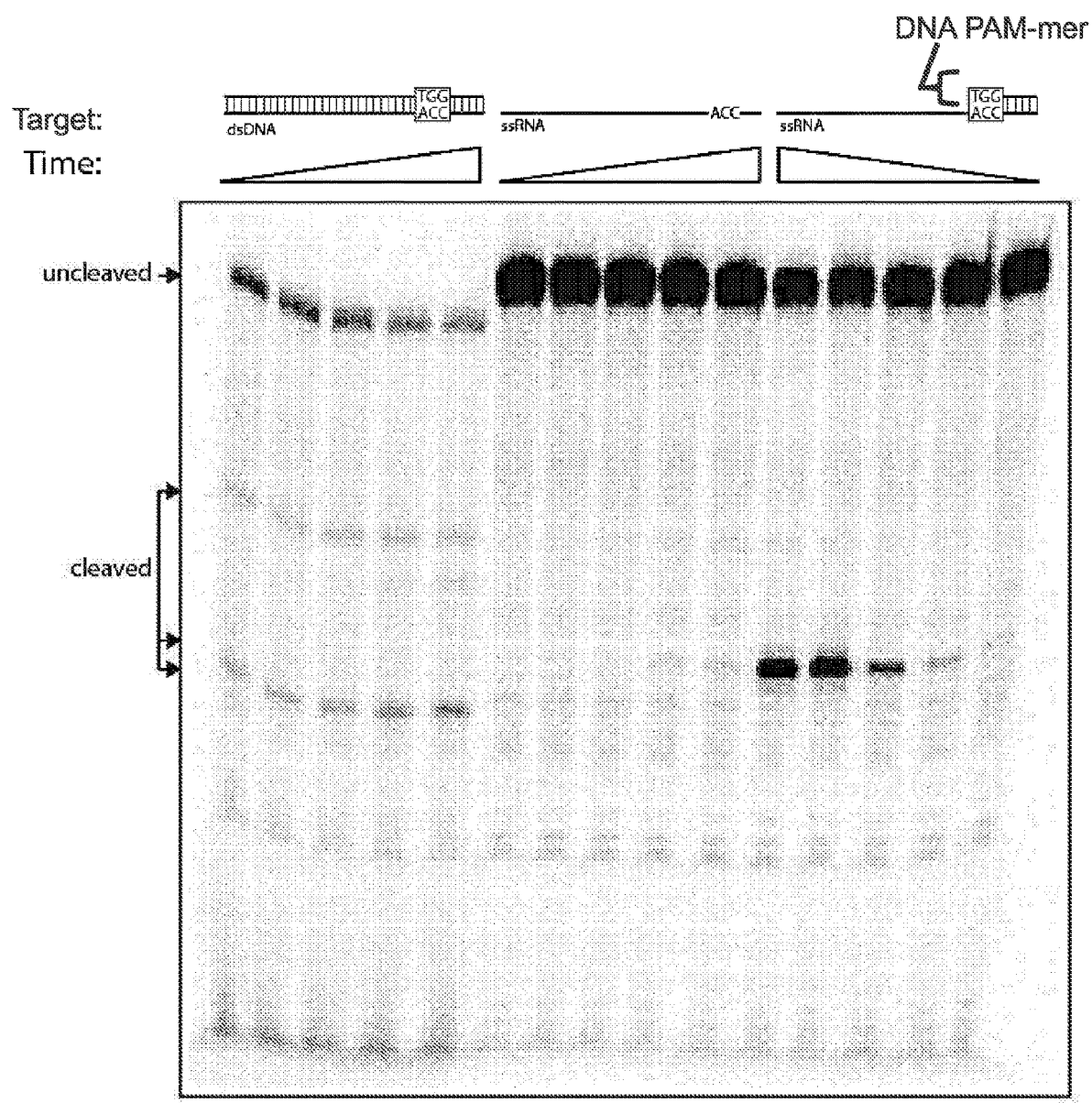
FIG. 3 presents assays for Cas9 cleavage of a single stranded RNA (ssRNA) target nucleic acid when used in combination with a PAMmer.
Figure 4B:
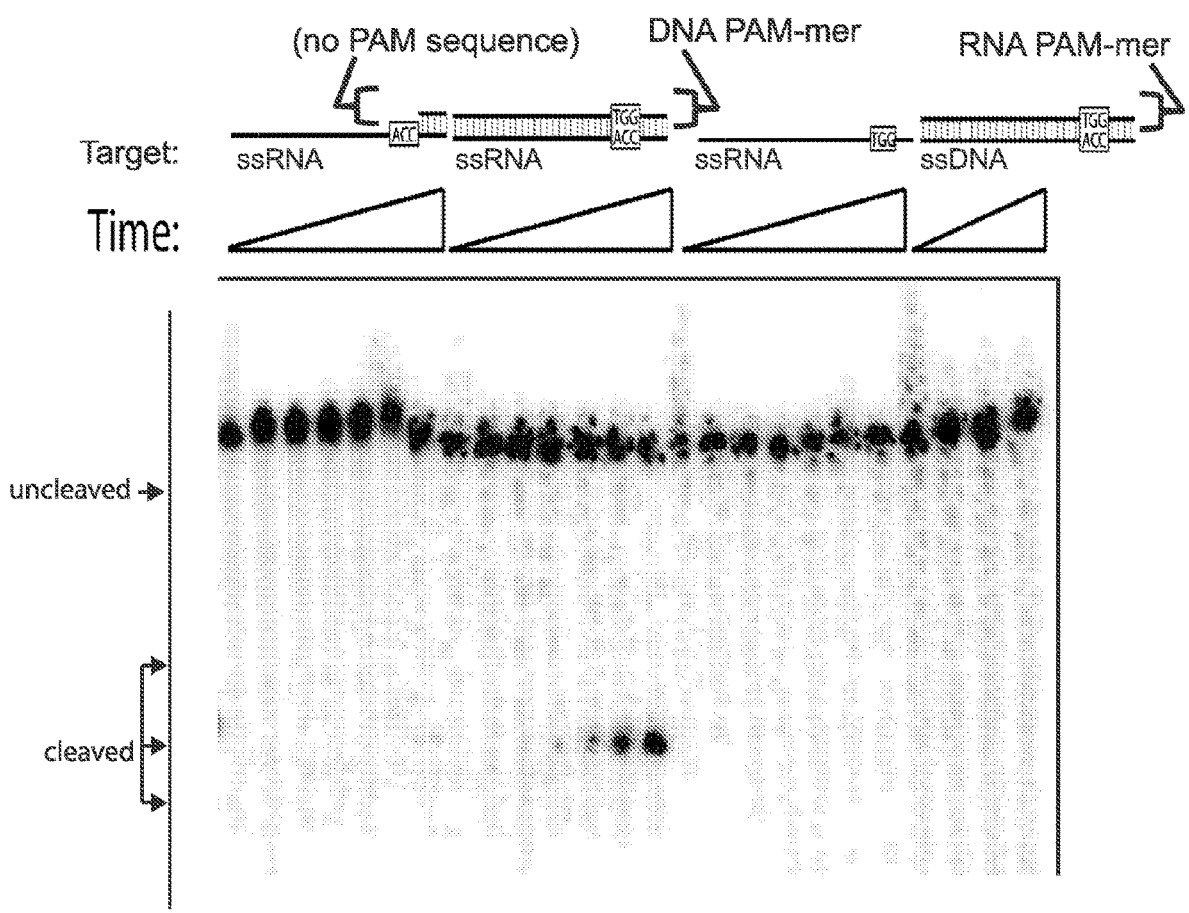

The working examples demonstrate that Cas9 complexed with guide RNA binds target RNA and that PAMmers increase the affinity of this interaction (FIG. 1); that longer PAMmers lead to higher affinity binding, and that the 5'-NGG-3' PAM itself does not need to base-pair with target nucleic acid for this effect (FIG. 2A-2B); that PAMmers activate Cas9 complexed with guide RNA to cleave target RNA (FIG. 3); that this activating effect is dependent on the PAM sequence, and is not recovered with just flanking RNA:DNA duplex (FIG. 4A-4B).

The working examples demonstrate that Cas9 can be used to target single stranded nucleic acids. This is useful for multiple applications, including (but not limited to) in vivo RNA imaging/localization, RNA-protein analysis through the affinity purification of specific RNA molecules via Cas9, and programmable cleavage/degradation of target RNAs in vitro or in vivo.

FIG. 1. Specific single-stranded RNA binding by Cas9 is the absence or presence of a PAM-containing DNA oligonucleotide ('PAMmer'). Binding assays were performed with S. pyogenes Cas9 (complexed with a Cas9 guide RNA) in the presence of ~1 nM 5'-$^{32}$P-labeled double-stranded DNA, single-stranded RNA or single-stranded RNA in the presence of a DNA oligonucleotide containing a TGG PAM, GG PAM, or no PAM at its 5' end. Cas9 was held constant at 300 nM and the guide RNA was titrated from 0.3 nM to 300 nM. Reactions were resolved on a 5% native polyacrylamide gel containing 5 mM $MgCl_2$ and visualized using a phoshorimager.

Figure 2A:
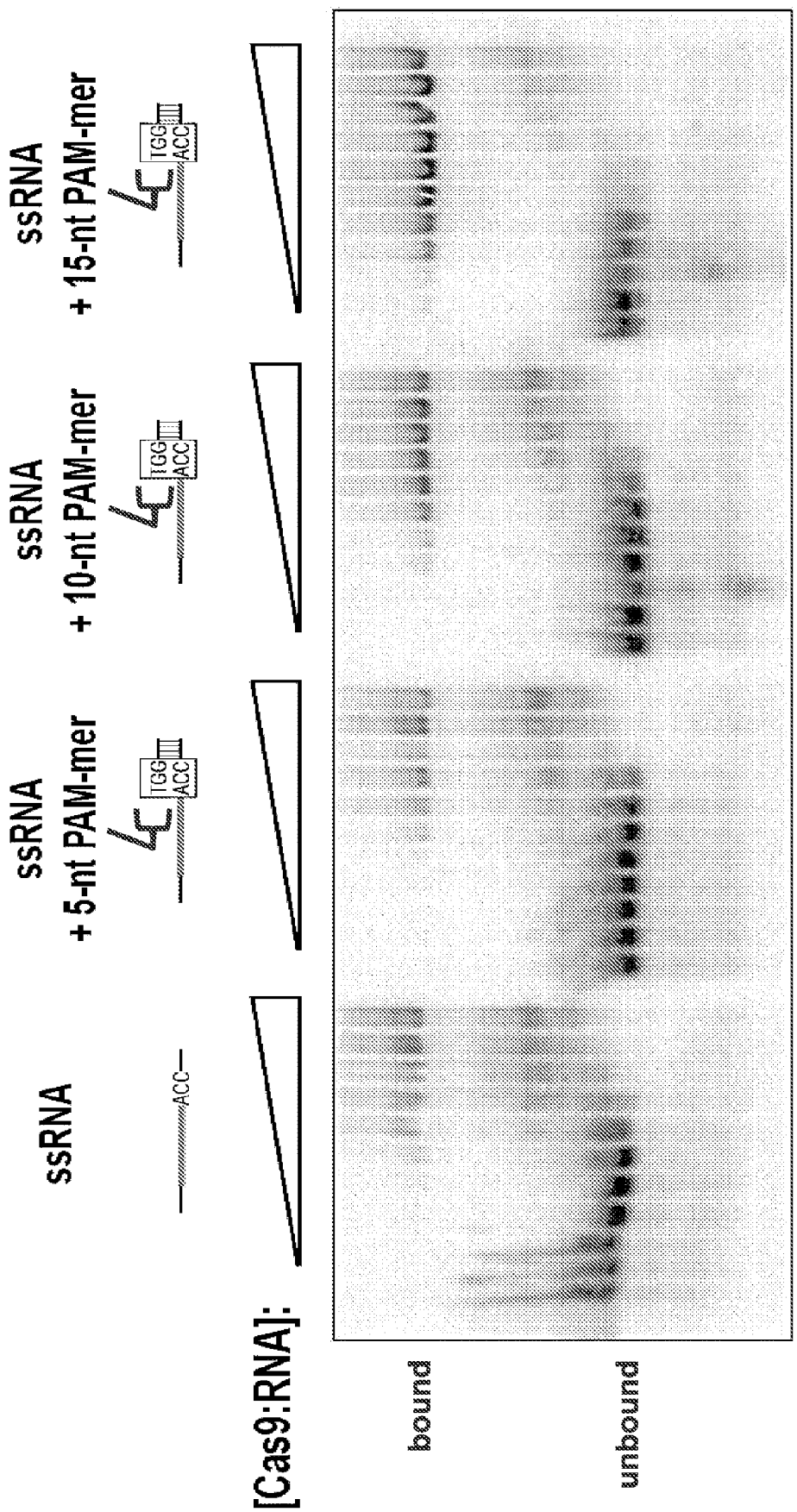
FIGS. 2A-2B present assays for binding of single stranded target nucleic acid stabilized by PAMmers of increasing length, and the effect of PAM sequence base-pairing with the single stranded target nucleic acid.
Figure 2B:
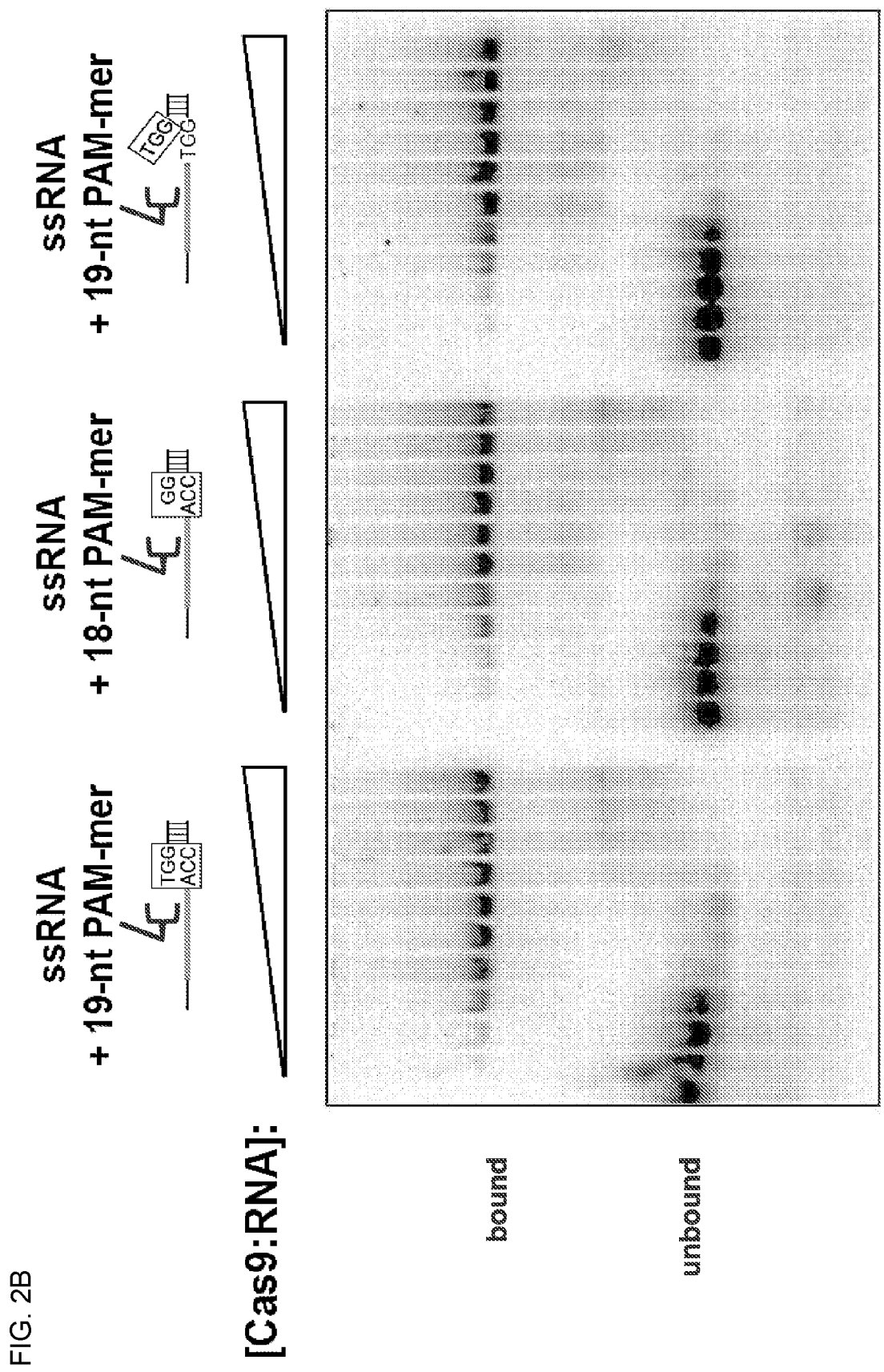

FIGS. 2A-2B. Specific single-stranded RNA binding by Cas9 is the absence or presence of PAMmers of variable length. (FIG. 2A-2B) Binding assays were performed with S. pyogenes Cas9 (complexed with a Cas9 guide RNA) in the presence of ~1 nM 5'-$^{32}$P-labeled single-stranded RNA or single-stranded RNA in the presence of PAMmers containing increasing lengths downstream of the TGG sequence. These experiments demonstrate that longer PAMmers lead to higher affinity binding, likely as a consequence of increased stability of the PAMmer:ssRNA hybrid duplex. The PAM itself does not need to base-pair with target RNA for high-affinity binding by Cas9:RNA (bottom gel, right side). Cas9 was held constant at 300 nM and the guide RNA was titrated from 0.01 nM to 300 nM. Reactions were resolved on a 5% native polyacrylamide gel containing 5 mM $MgCl_2$ and visualized using a phoshorimager. The PAM sequence itself within the PAMmer need not be base-paired to the target nucleic acid. Thus, this strategy can be used to target non PAM-containing sites within a target nucleic acid.

FIG. 3. Specific single-stranded RNA cleavage by Cas9 is activated by the addition of a PAMmer having a PAM sequence. Cleavage assays were performed with 100 nM S. pyogenes Cas9 (complexed with a Cas9 guide RNA) in the presence of ~1 nM 5'-$^{32}$P-labeled double-stranded DNA, single-stranded RNA or single-stranded RNA pre-annealed with a DNA oligonucleotide containing a TGG PAM sequence. Time points were taken at 0, 1, 5, 60 and 120 min and immediately quenched with formamide-EDTA buffer. Quenched samples were resolved on a 12% urea-polyacrylamide gel electrophoresis (PAGE) gel and visualized using a phosphorimager.

FIGS. 4A-4B. Specific single-stranded RNA cleavage by Cas9 is activated by the addition of a PAMmer having a PAM sequence, but not by a PAMmer without a PAM sequence. (A-B) Cleavage assays were performed with 100 nM S. pyogenes Cas9 (complexed with a Cas9 guide RNA) in the presence of ~1 nM 5'-$^{32}$P-labeled double-stranded DNA, single-stranded RNA or single-stranded RNA pre-annealed with various DNA oligonucleotides. Time points were taken at 0, 1, 2, 5, 10, 30 and 60 min and immediately quenched with formamide-EDTA buffer. Quenched samples were resolved on a 12% urea-PAGE gel and visualized using a phosoimager. A ssDNA target nucleic acid was not cleaved when an RNA PAMmer was used. However, ssRNA and ssDNA target nucleic acids were both cleaved when a DNA PAMmer was used (also see 6).

Figure 5A:
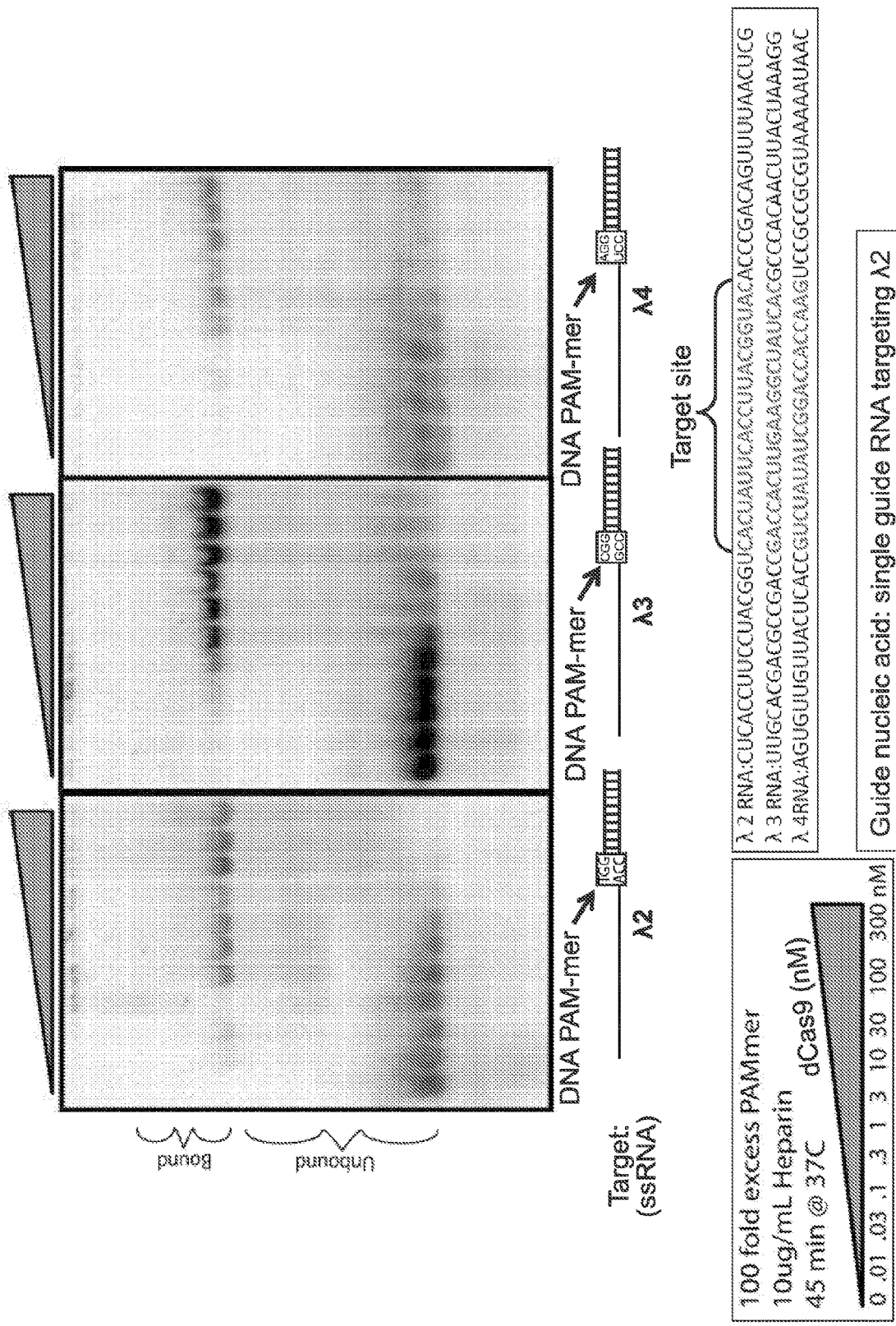
FIGS. 5A-5C present binding and cleavage assays testing off-target effects and employing various PAMmers. λ2 (SEQ ID NO:1361); λ3 (SEQ ID NO:1362); λ4 (SEQ ID NO:1363).
Figure 5B:
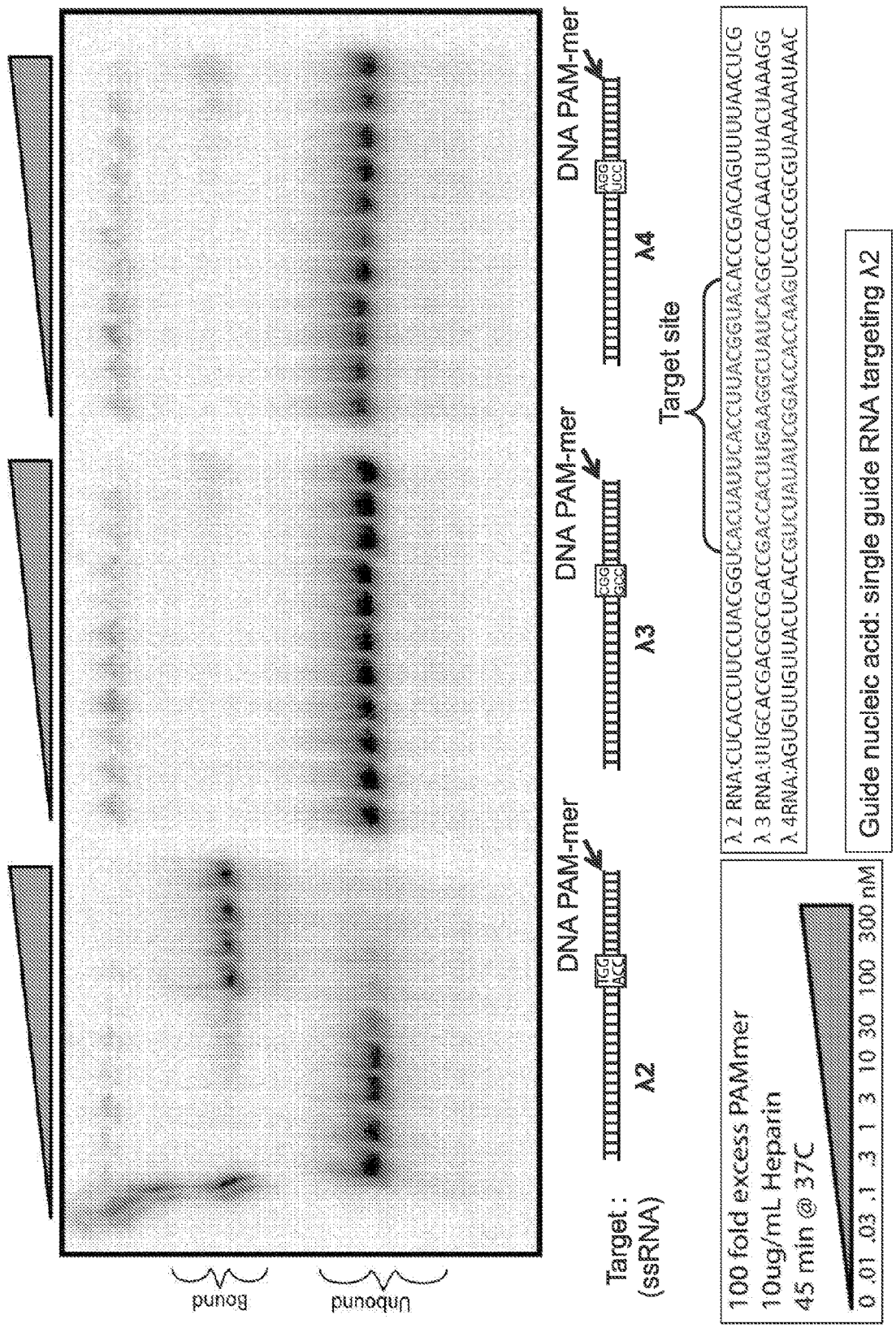
Figure 5C:
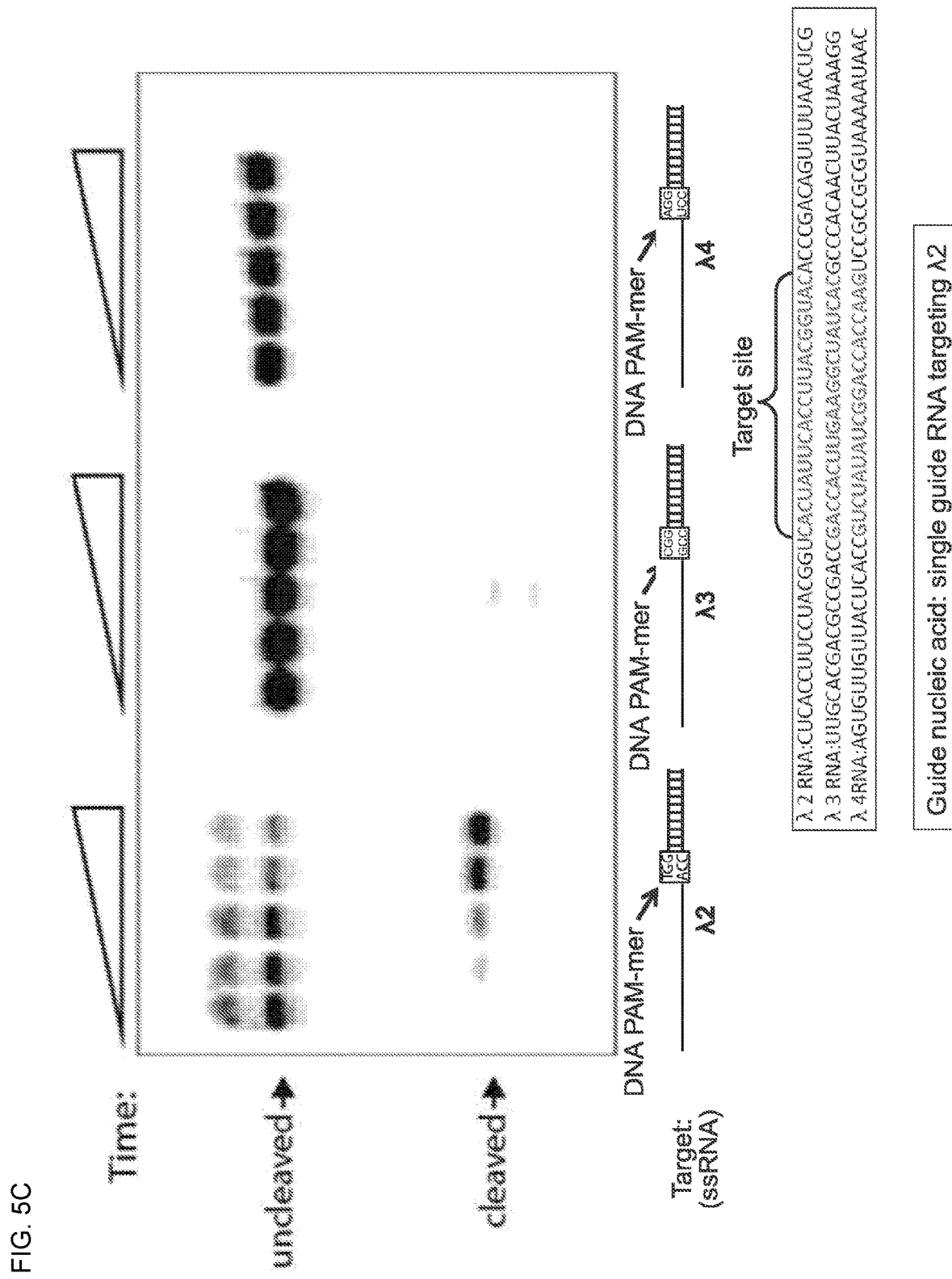

FIGS. 5A-5c. (FIG. 5A) Cas9 programmed with guide RNA was incubated with four different target ssRNA sequences; each reaction contained a 100-fold excess of complementary PAMmer (without a specificity segment) specific to each target ssRNA. Cas9 binds each of the targets with similar affinity, despite the fact that the guide RNA is complementary only to the λ2 target. These data indicate that, under these conditions, the affinity of Cas9 for these targets is dominated by presentation of the PAMmer, and not by sequence complementarity between the guide RNA and target RNA. Thus, when the PAMmer does not have a specificity segment (i.e., the PAMmer has a PAM sequence and an orientation segment), the binding of a Cas9 protein:guide RNA complex does not require complementarity between the targeting segment of the guide RNA and the target nucleic acid. (FIG. 5B) The experiment from FIG. 5A was repeated, except that the PAMmers each contained a specificity segment at the 5' end (the specificity segment was positioned 5' of the PAM sequence, as depicted). The target nucleic acids were 55 nucleotide (nt) ssRNA and the PAMmers were each 55 nt (with a 20 nt specificity segment) DNA, such that an RNA:DNA duplex was formed. When Cas9 was complexed with a λ2 guide RNA (i.e., the specificity segment of the guide RNA was complementary to the λ2 target ssRNA, but not the 3 or 4 targets). Only the λ2 target could be melted open and recognized, presumably via base pairing between guide RNA and target RNA, while the off-targets (λ3 and λ4) were unbound. These experiments demonstrate that when the PAMmer includes a specificity segment, increased specificity for the target nucleic acid can be achieved. Not to be bound by theory, this is presumably because the target duplex (PAMmer bound to the target single stranded nucleic acid) must be unwound before initiating base-pairing to the target ssRNA. Thus, in some instances when the PAMmer has a specificity segment, the binding of a Cas9 protein:guide RNA complex to a single stranded target nucleic acid requires complementarity between the targeting segment of the guide RNA and the target nucleic acid. (FIG. 5C) Cleavage assays were performed with 100 nM S. pyogenes Cas9 (complexed with a Cas9 guide RNA) in the presence of ~1 nM 5'-$^{32}$P-labeled double-stranded DNA, single-stranded RNA or single-stranded RNA pre-annealed with a PAMmer (a DNA oligonucleotide containing a TGG PAM sequence (as depicted)). Time points were taken at 0, 5, 10, 30, and 60 minutes, at 37° C. and immediately quenched with formamide-EDTA buffer. Quenched samples were resolved on a 12% urea-PAGE gel and visualized using a phosphorimager. These data show that when the PAMmer does not have a specificity segment (i.e., the PAMmer has a PAM sequence and an orientation segment), the cleavage of a single stranded target nucleic acid by a Cas9 protein does require complementarity between the targeting segment of the guide RNA and the target nucleic acid (although binding does not have this requirement, see FIG. 5A).

Figure 6:
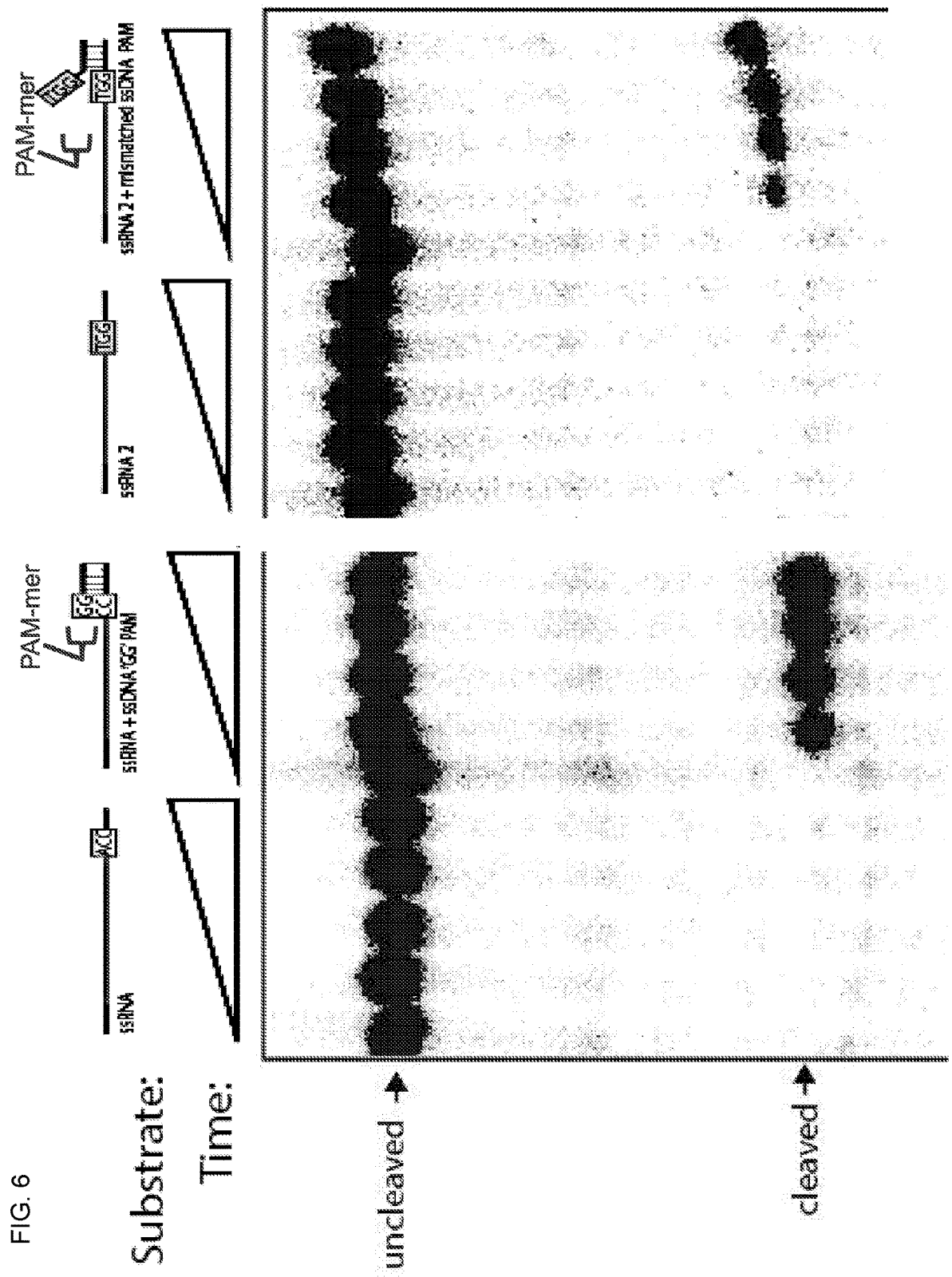
FIG. 6 presents cleavage assays employing various PAMmers.

FIG. 6. Cas9 can be activated by a PAM-containing oligonucleotide in which the TGG PAM sequence is mismatched with the target RNA. Cleavage assays were performed with 100 nM S. pyogenes Cas9 (complexed with a Cas9 guide RNA) in the presence of ~1 nM 5'-$^{32}$P-labeled single-stranded RNA, single-stranded RNA pre-annealed with various DNA oligonucleotides, or single-stranded RNA. Time points were taken at 0, 5, 10, 30 and 60 min and immediately quenched with formamide-EDTA buffer. Quenched samples were resolved on a 12% urea-PAGE gel and visualized using a phoshoimager. The results show that the PAM sequence in the PAMmer need not base-pair with the single stranded target nucleic acid (ssRNA in this case) for nuclease activation, indicating that non-PAM containing nucleic acid sequences can be targeted.

Example 2: Use of Cas9 to Cleave and/or Bind a Single Stranded DNA (ssDNA)

Materials and Methods

Wild-type Cas9 from S. pyogenes was purified. crRNAs (42 nucleotides in length) were either ordered synthetically (Integrated DNA Technologies) or transcribed in vitro with T7 polymerase using single-stranded DNA templates. tracrRNA was also transcribed in vitro and contained nucleotides 15-87 following the numbering scheme used previously. crRNA:tracrRNA duplexes were prepared by mixing equimolar concentrations of each RNA in Hybridization Buffer (20 mM Tris-HCl pH 7.5, 100 mM KCl, 5 mM $MgCl_2$), heating to 95° C. for 30 seconds, and slow-cooling. The substrates were prepared by 5'-radiolabeling only the target strand, hybridizing it to a 10× excess of the indicated unlabeled complementary strand, and gel purifying the partial/full duplex by 10% native gel electrophoresis. Cas9: RNA complexes were reconstituted prior to cleavage and binding experiments by incubating Cas9 and the crRNA: tracrRNA duplex for 10 min at 37° C. in Reaction Buffer. Cleavage assays were conducted in reaction buffer at room temperature and analyzed by 10% denaturing polyacrylamide gel electrophoresis and phosphorimaging. Aliquots were removed at each time point and quenched by the addition of gel loading buffer supplemented with 25 mM EDTA (at 1X). Reactions contained ~1 nM radiolabeled DNA substrate and 100 nM Cas9:RNA Results In the absence of a PAMmer, a ssDNA substrate was cleaved more than two orders of magnitude slower than a double-stranded DNA (dsDNA) substrate (FIG. 7A and FIG. 7B), despite the fact that dCas9:RNA (dCas9 complexed with a Cas9 guide RNA) bound both the dsDNA and ssDNA substrates with similar affinities (FIG. 7B).

Figure 7A:
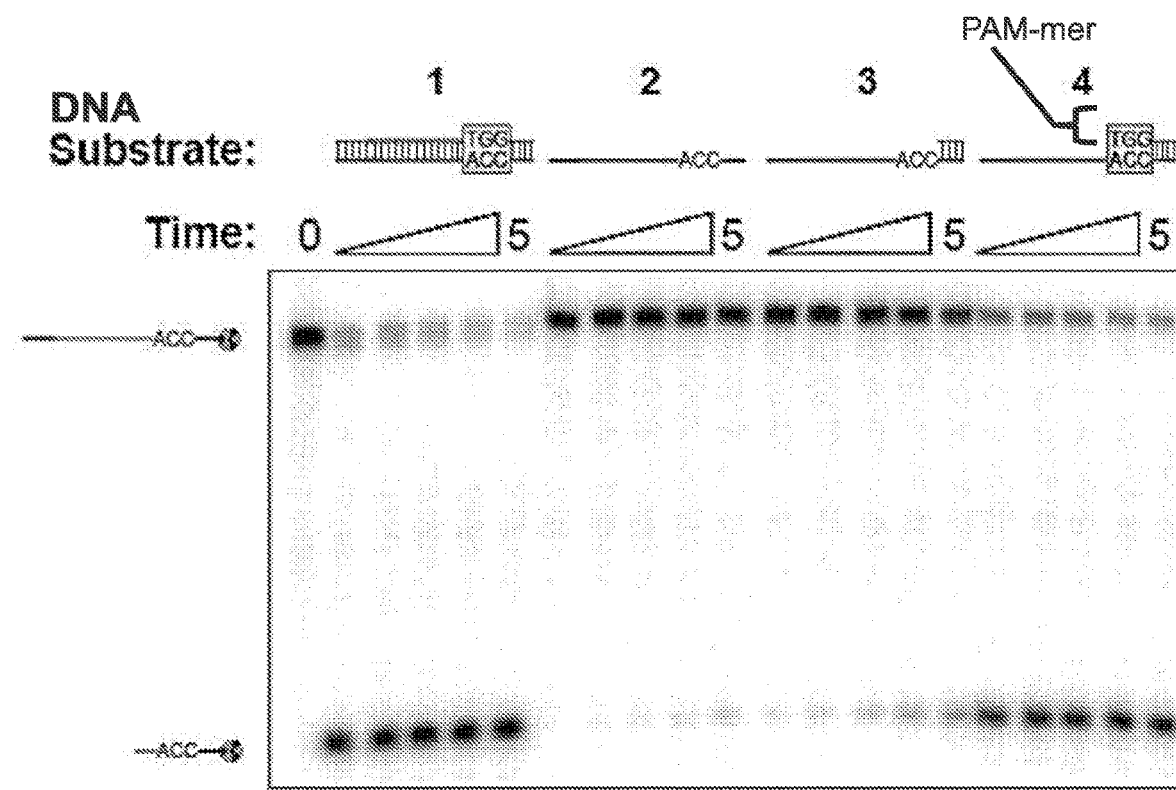
FIGS. 7A-7D present assays for cleavage and binding by Cas9 of a single stranded DNA (ssDNA) target nucleic acid when used in combination with a PAMmer.
Figure 7B:
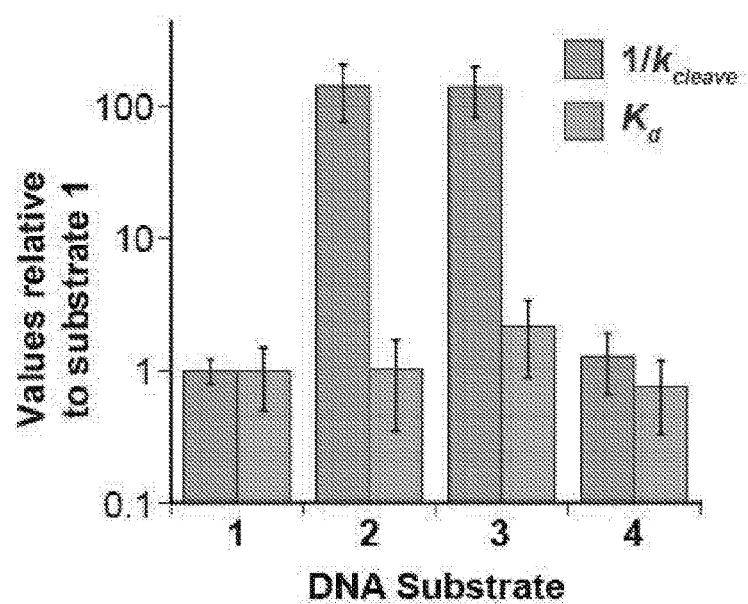
Figure 7C:
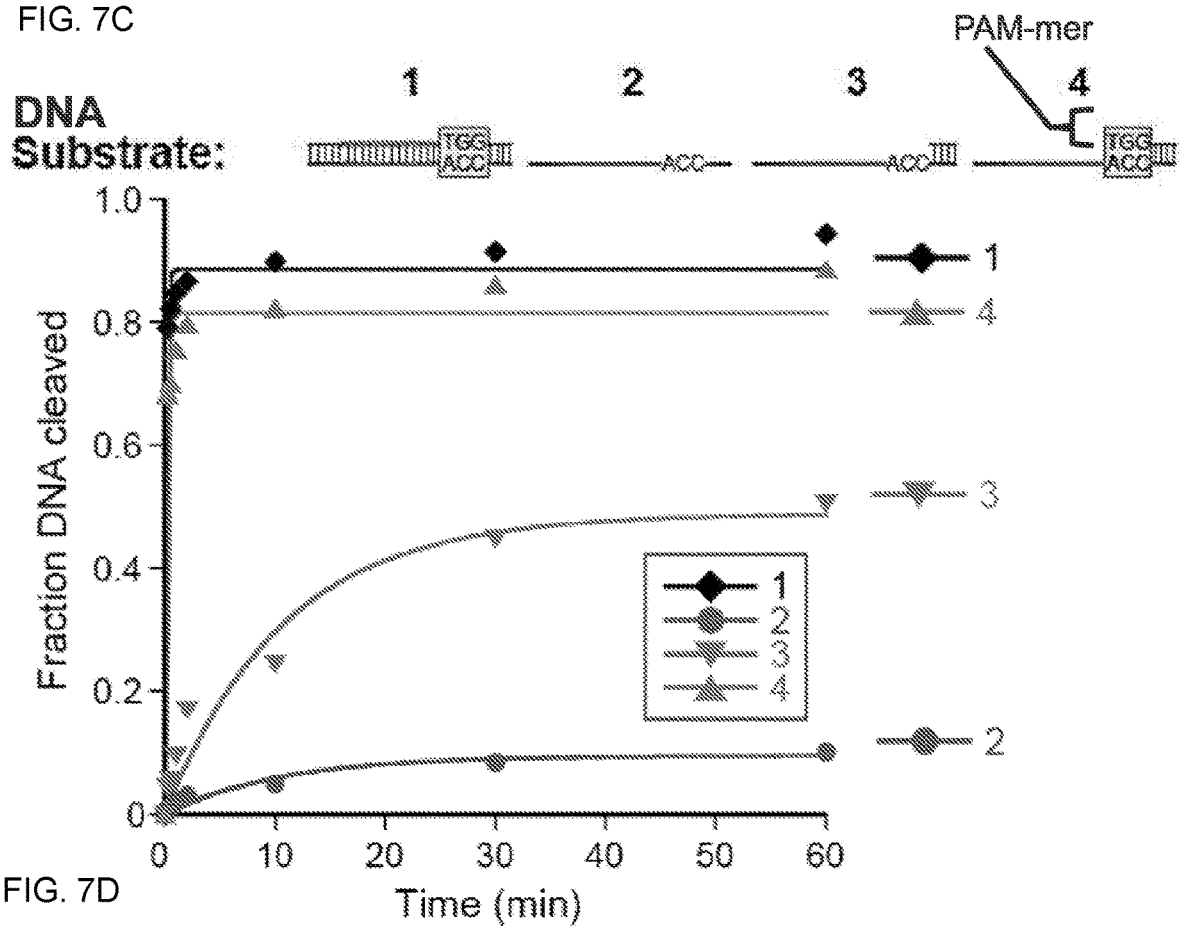
Figure 7D:
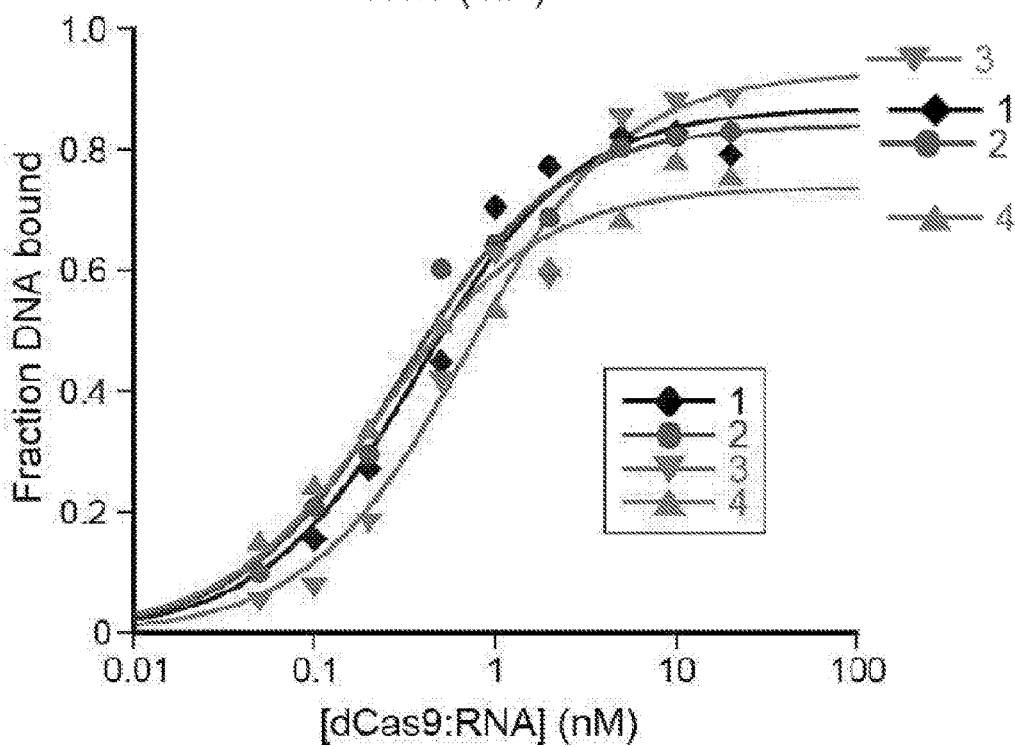

Substrates were prepared with varying lengths of dsDNA at the 3' flanking sequence (FIG. 7A). Cleavage assays revealed that the ssDNA target strand could be activated for cleavage in the presence of flanking dsDNA that extended across the PAM sequence (i.e., the presence of a PAMmer), but that this activating effect was lost when the dsDNA was truncated immediately before the PAM sequence (FIG. 7A and FIG. 7B). Binding experiments confirmed these results were not a consequence of discrimination at the level of binding (FIG. 7B). Rather, the presence of the 5'-NGG-3' PAM on the non-target strand was critical for a step of the reaction that occurred after binding. Quantification of cleavage assays can be seen in FIG. 7C. For binding experiments (quantified in FIG. 7D), substrates were gel purified after annealing the radiolabelled target strand to a 10×excess of cold complement. Binding reactions contained ~0.1 nM DNA and increasing concentrations of dCas9-RNA, and were incubated at 37° C. for 1 h before being resolved by 5% native PAGE. The quantified data were fit with standard binding isotherms (solid lines). Results from three independent experiments yielded apparent Kd values of 0.27±0.14 nM (substrate 1), 0.28±0.12 nM (substrate 2), 0.59±0.18 nM (substrate 3) and 0.21±0.06 nM (substrate 4).

Example 3: Variant Cas9 Proteins with Reduced Nuclease Activity

Materials and Methods

PAM Recognition by SpyCas9 Involves Two Tryptophan-Containing Flexible Loops

To gain insight into PAM sequence binding by S. pyogenes Cas9 ("SpyCas9"), the SpyCas9 RuvC nuclease domain structure was compared to that of the RuvC Holliday junction resolvase-substrate complex (PDB entry 4LDO). RuvC structures were then superpositioned to model the likely trajectory of the non-target DNA strand in the SpyCas9 holoenzyme. The DNA strand is located along the length of the nuclease lobe cleft in an orientation that would position the 3' end of the DNA, and hence the PAM, at the junction of the two lobes, in the vicinity of the Arg-rich segment and the Topo-homology domain.

Figure 16A:
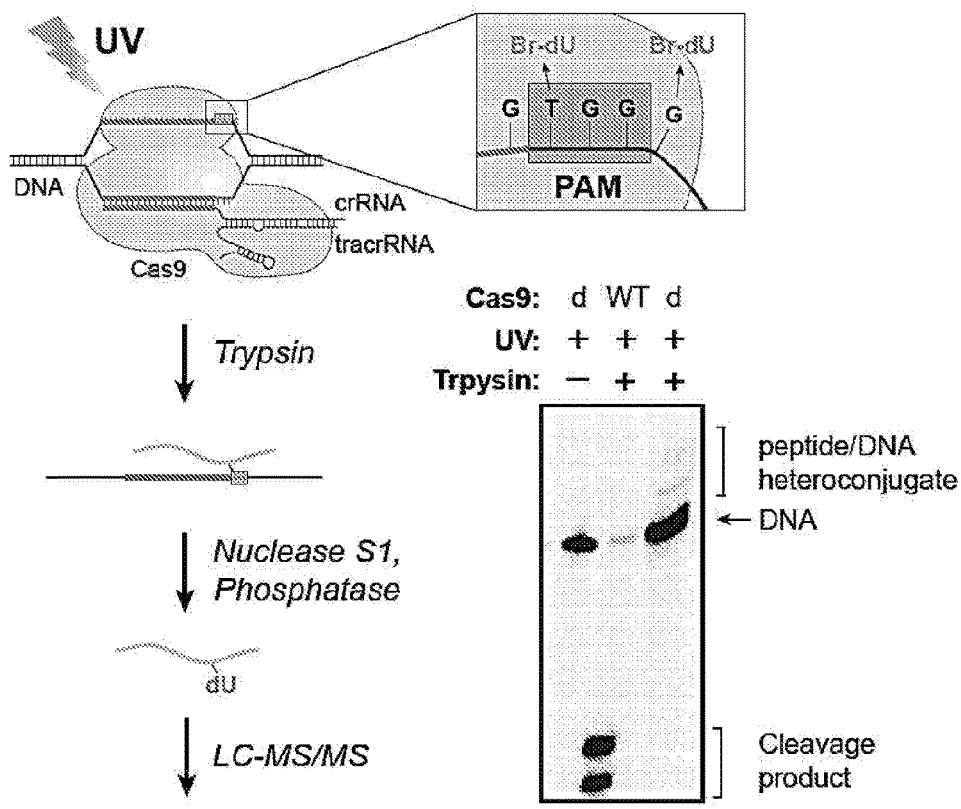
FIGS. 16A-16D depict the effect of Cas9 amino acid sequence modifications on target nucleic acid cleavage; and provide alignments of selected regions of Cas9 proteins.
Figure 16B:
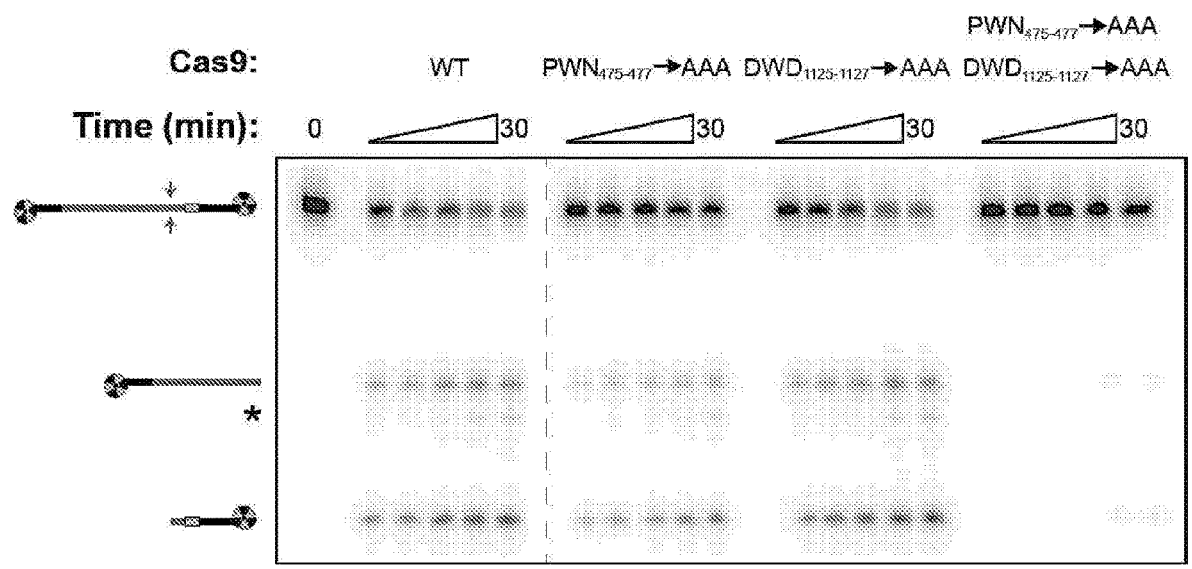
Figure 16C:
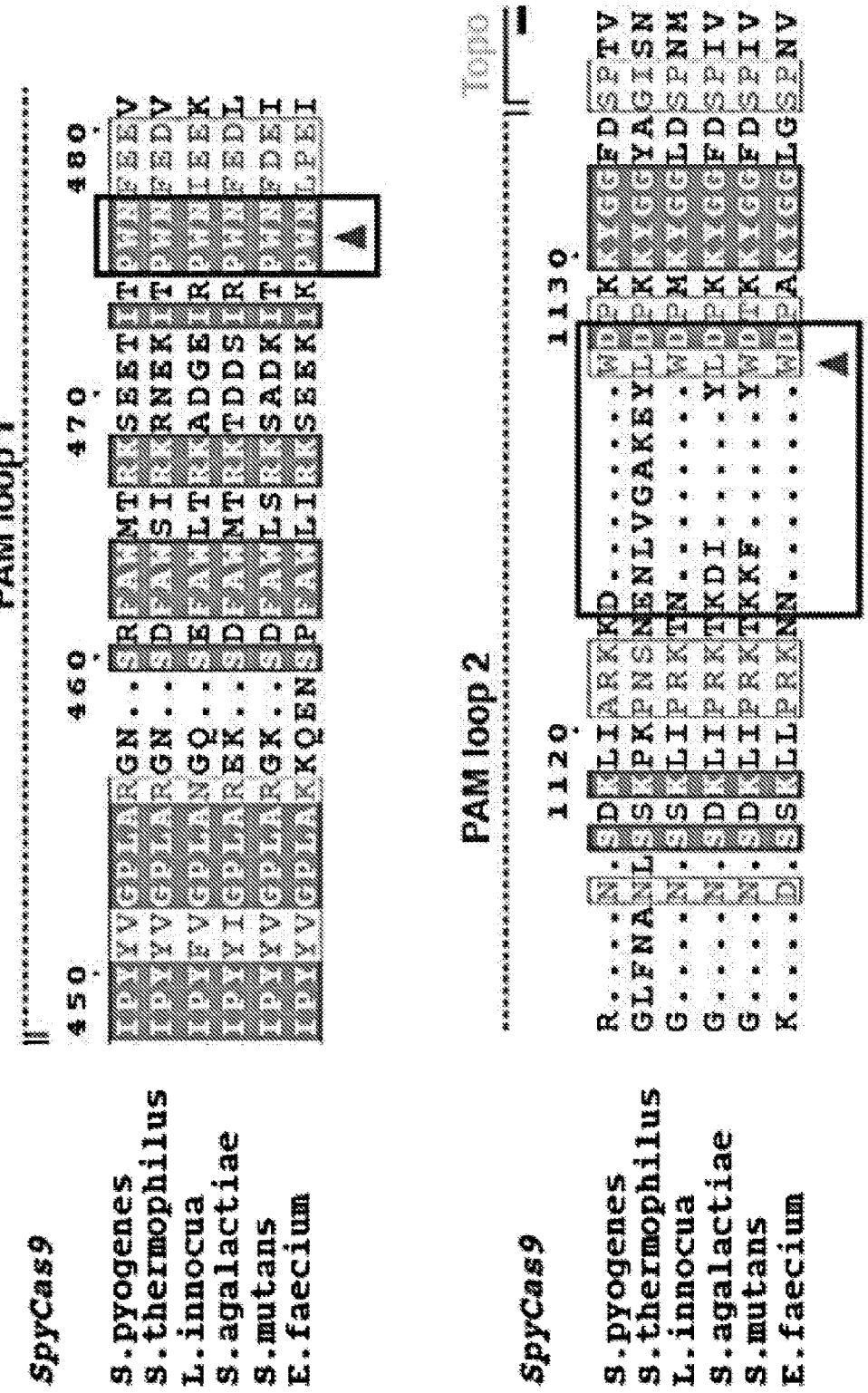
Figure 16D:
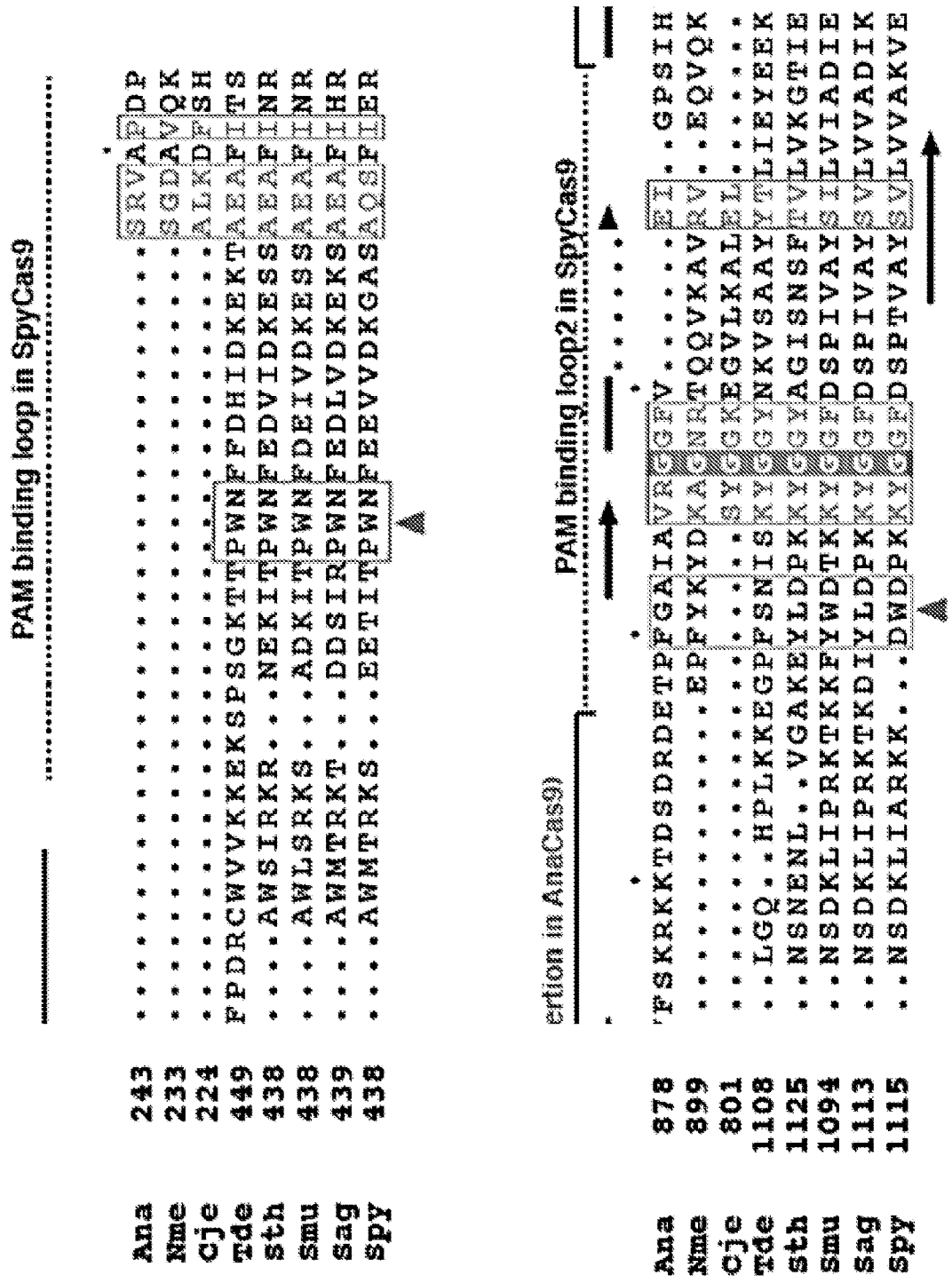

To directly identify regions of Cas9 involved in PAM binding, catalytically inactive SpyCas9 (D10A/H840A), along with a crRNA:tracrRNA guide RNA, was bound to DNA targets carrying a photoactivatable 5-bromodeoxyuridine (Br-dU) nucleotide adjacent to either end of the GG PAM motif on the non-target strand (FIG. 16A). Following UV irradiation and trypsin digestion, covalent peptide-DNA crosslinks were detected (FIG. 16A), whereas a DNA substrate containing Br-dU on the target strand opposite the PAM failed to produce a crosslink. After treatment with nuclease and phosphatase to digest cross-linked DNA, nano-HPLC MS/MS was performed to identify tryptic peptides containing an extra mass resulting from covalent dU or p-dU adducts (FIG. 16A). The nucleotide immediately 5' to the GG motif cross-linked to residue $W476^{Spy}$, whereas the residue immediately 3' to the motif cross-linked to residue $W1126^{Spy}$. Both tryptophans are located in disordered regions of the SpyCas9 structure that are ~30 Å apart. $W476^{Spy}$ resides in a 53-aa loop at the edge of the alpha helical lobe underneath the Arg-rich region, whereas $W1126^{Spy}$ is in a 33-aa loop that connects the RuvC domain and the Topo-homology domain. These tryptophan residues are conserved among Type II-A Cas9 proteins that utilize the same NGG PAM to cleave target DNA in vitro, but are absent from the Neisseria meningitidis and Streptococcus thermophilus Type II-C Cas9 proteins, which are known to recognize different PAMs (FIG. 16C, FIG. 16D).

To test the roles of both loops in DNA target recognition and cleavage, triple alanine substitutions of residues $475^{Spy}$-$477^{Spy}$ (P-W-N) and $1125^{Spy}$-$127^{Spy}$ (D-W-D) (of S. Pyogenes Cas9) were made and cleavage assays were performed with double-stranded DNA targets (FIG. 16B). SpyCas9 mutated in residues $1125^{Spy}$-$1127^{Spy}$ showed wild-type cleavage activity, whereas mutations in residues $475^{Spy}$-$477^{Spy}$ caused a subtle but reproducible decrease of activity compared to wild-type. Remarkably, mutating both loops simultaneously almost completely abolished SpyCas9 activity under the conditions tested (FIG. 16D). These data demonstrate that at least one tryptophan is necessary to promote the DNA cleavage reaction. The spatial constraints of crosslink formation and the distance of both tryptophan residues from either nuclease domain argue against a direct catalytic role of these residues, and instead suggest that they are involved in PAM binding.

FIG. 16. Crosslinking data identify a PAM binding region adjacent to the active-site cleft. (FIG. 16A) Cartoon (left) showing the design and workflow of crosslinking experiments with DNA substrates containing 5-bromodeoxyuridine (Br-dU) nucleotides for LC-MS/MS analysis. The guide/target sequence is depicted in red and the PAM is highlighted in yellow. The denaturing polyacrylamide gel (right) demonstrates the generation of covalent peptide-DNA adducts with Br-dU1 and catalytically inactive SpyCas9 (dCas9) following UV irradiation and trypsin digestion. (FIG. 16B) DNA cleavage activity assays with SpyCas9 constructs containing mutations in residues identified by crosslinking and LC-MS/MS experiments. (FIG. 16C) Multiple sequence alignments of selected portions of Cas9 proteins associated with Type II-A CRISPR loci. Primary sequences of Cas9 proteins from *Streptococcus pyogenes* (GI 15675041), *Streptococcus thermophilus* LMD-9 (GI 116628213), *Listeria innocua* Clip 11262 (GI 16801805), *Streptococcus agalactiae* A909 (GI 76788458), *Streptococcus mutans* UA159 (GI 24379809), and *Enterococcus faecium* 1,231,408 (GI 257893735) were aligned using MAFFT. The alignment was generated in ESPript using default settings. Triangles indicate the tryptophan residues involved in PAM binding based on SpyCas9 crosslinking assay. (FIG. 16D) Multiple sequence alignment of selected portions of Type II-A and II-C Cas9 orthologs. The primary sequences of Cas9 orthologs were aligned using CLUSTALW. The alignment was generated in ESPript using default settings. Triangles indicate the tryptophan residues involved in PAM binding based on SpyCas9 crosslinking assay. Accession numbers for each Cas9 ortholog are as follows: Ana (*Actinomyces naeslundii* str. Howell 279, EJN84392.1), Nme (*Neisseria meningitidis*, WP_019742773.1), Cje (*Campylobacter jejuni*, WP_002876341.1), Tde (*Treponema denticola*, WP_002676671.1), Sth (*Streptococcus thermophilus* LMD-9, YP_820832.1), Smu (*Streptococcus mutans*, WP_019803776.1), Sag (*Streptococcus agalactiae*, WP_001040088.1), and Spy (*Streptococcus pyogenes*, YP_282132.1).

Example 4: Use of PAMmers Having One or More Modified Nucleotides

Figure 17A:
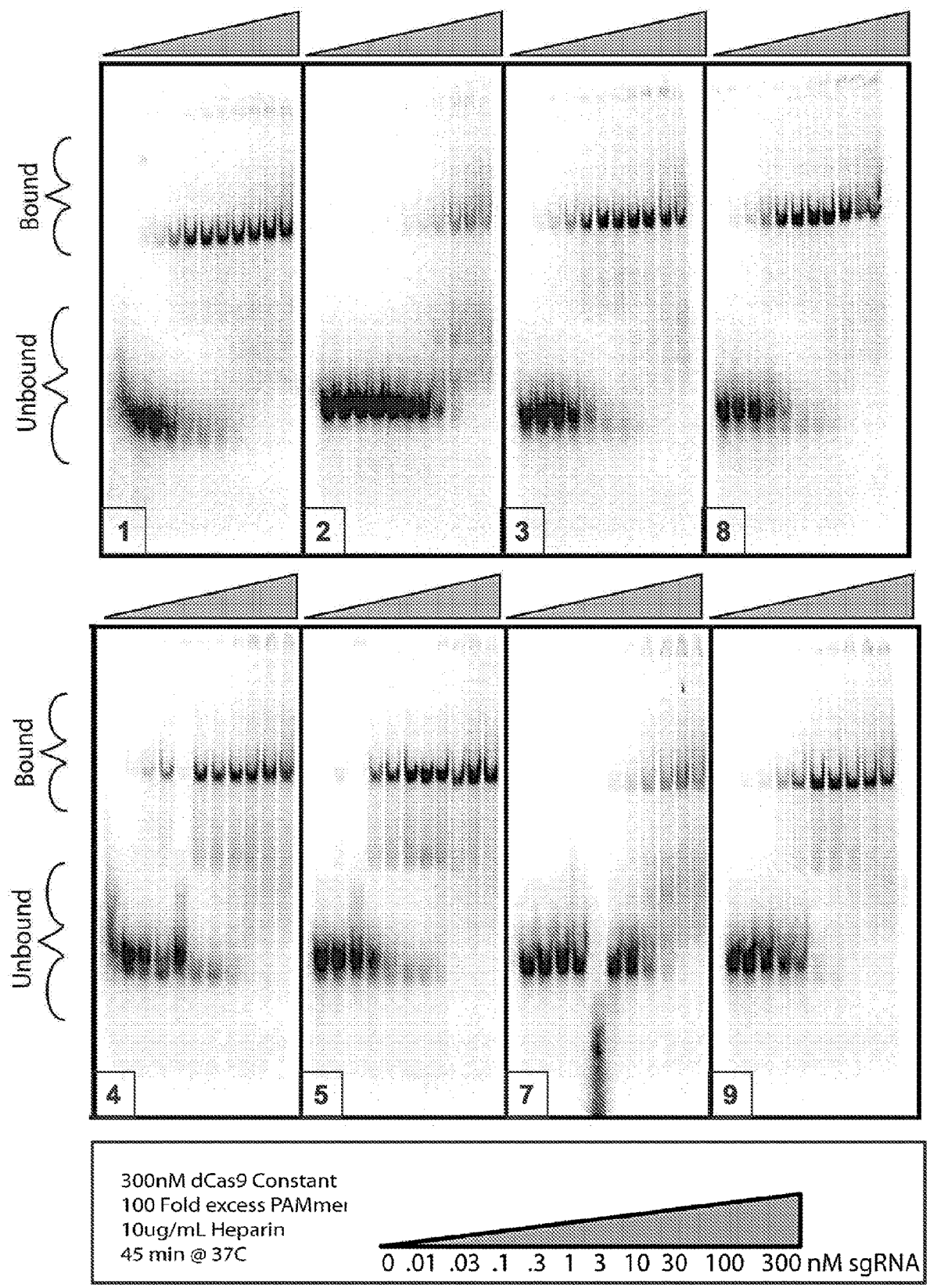
FIGS. 17A-17B depict the effect of nucleotide modifications in PAMmer on target nucleic acid binding and cleavage.
Figure 17B:
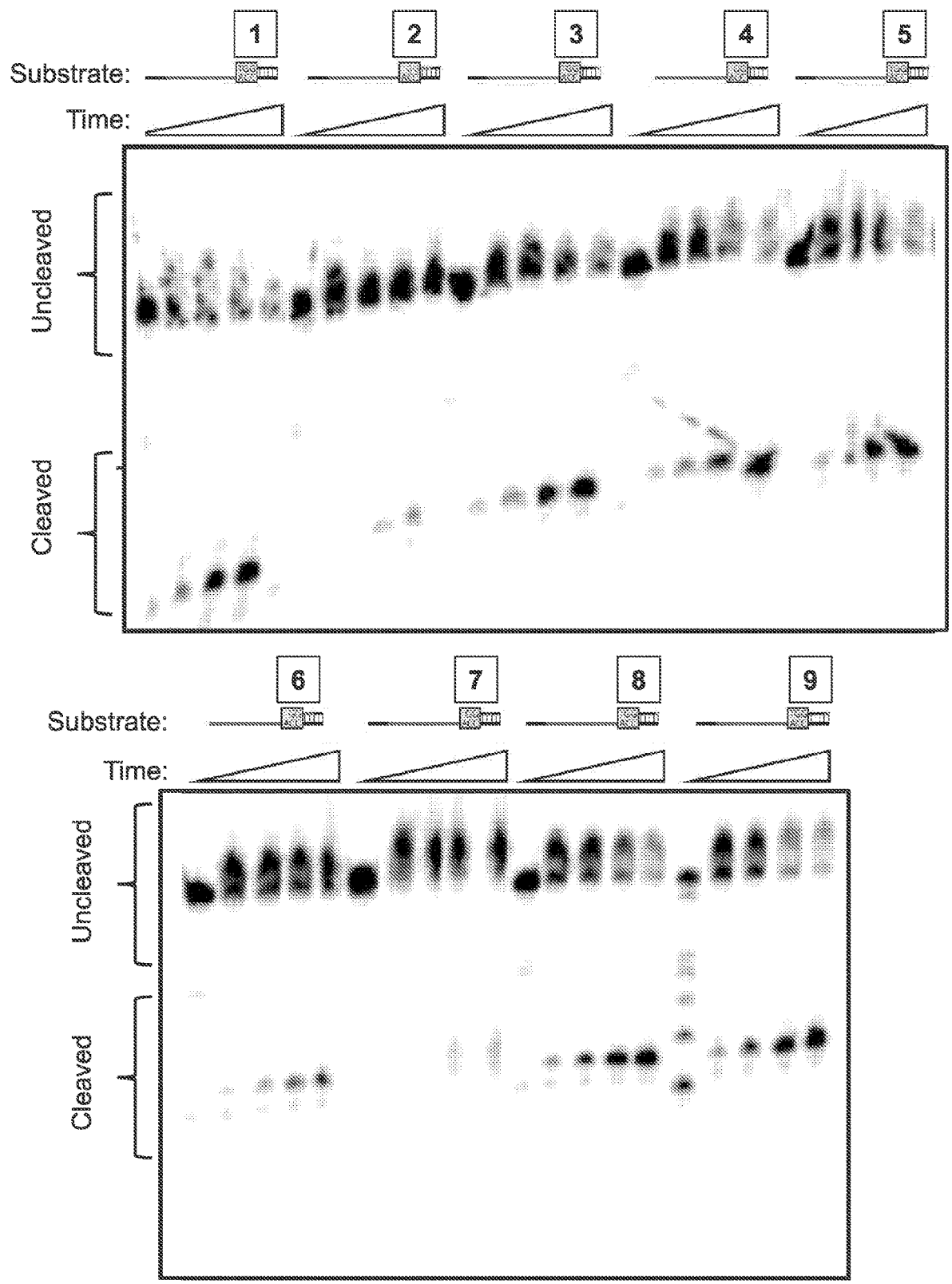

Experiments were carried out as described above for binding and cleaving, and further details are provided in FIG. 17A-17B. The data show that PAMmers having modified nucleotides can be successfully used in the subject methods, as assayed by both binding assays (FIG. 17A) and cleavage assays (FIG. 17B). The target nucleic acid is a single stranded RNA. For both FIG. 17A and FIG. 17B, the number associated with each panel (lower left in FIG. 17A; above and to the right in FIG. 17B) refers to the PAMmer that was used (see key below). Note: the gel in FIG. 17B has "smiling", but "uncleaved" and "cleaved" substrates are clearly labeled as such.

Legend for FIG. 17A and FIG. 17B (1) ssDNA PAMmer:
(SEQ ID NO: 1466)
TGGGCTGTCAAAATTGAGC;

(2) 2'OMe/ssDNA PAMmer:
(SEQ ID NO: 1588)
mGmGmGmCmUmGmUmCmAmAAATTGAGC, where mN is 2'OMe modified nucleotide N;

(3) 2'OMe/ssDNA PAMmer:
(SEQ ID NO: 1514)
mUGGGCTGTCAAAATTGAGmC, where mN is 2'OMe modified nucleotide N;

(4) phosphorothioate ssDNA PAMmer:
(SEQ ID NO: 1589)
G*G*G*C*T*G*T*C*A*AAATTGAGC,
where * is a phosphorothioate linkage;

(5) phosphorothioate ssDNA PAMmer:
(SEQ ID NO: 1590)
T*GGGCTGTCAAAATTGAG*C,
where * is a phosphorothioate linkage;

(6) 2'F/ssDNA PAMmer:
(SEQ ID NO: 1591)
fGfGfGfCfTfGfTfCfAfAAATTGAGC,
where fN is a 2'F modified nucleotide N;

(7) LNA/ssDNA PAMmer:
(SEQ ID NO: 1592)
+G + G + GCTG + T + C + AAAATTGAGC,
where +N is a LNA nucleotide N;

(8) 2'F/ssDNA PAMmer:
(SEQ ID NO: 1593)
fUGGGCTGTCAAAATTGAGfC,
where fN is a 2'F modified nucleotide N;
and (9) LNA/ssDNA PAMmer:
(SEQ ID NO: 1594)
+TGGGCTGTCAAAATTGAG + C,
where +N is a LNA nucleotide N.

Example 5: Programmable RNA Recognition and Cleavage by CRISPR/Cas9

The CRISPR-associated protein Cas9 is an RNA-guided DNA endonuclease that uses RNA-DNA complementarity to identify target sites for sequence-specific double-stranded DNA (dsDNA) cleavage. In its native context, Cas9 acts on DNA substrates exclusively because both binding and catalysis require recognition of a short DNA sequence, known as the protospacer adjacent motif (PAM), next to and on the strand opposite the twenty-nucleotide target site in dsDNA. Cas9 has proven to be a versatile tool for genome engineering and gene regulation in a large range of prokaryotic and eukaryotic cell types, and in whole organisms, but it has been thought to be incapable of targeting RNA5. The experiments herein demonstrate that Cas9 binds with high affinity to single-stranded RNA (ssRNA) targets matching the Cas9-associated guide RNA sequence when the PAM is presented in trans as a separate DNA oligonucleotide. Furthermore, PAM-presenting oligonucleotides (PAMmers) stimulate site-specific endonucleolytic cleavage of ssRNA targets, similar to PAM-mediated stimulation of Cas9-catalyzed DNA cleavage. Using PAMmers, Cas9 can be specifically directed to bind or cut RNA targets while avoiding corresponding DNA sequences. This strategy enables the isolation of a specific endogenous messenger RNA from cells. These results reveal a fundamental connection between PAM binding and substrate selection by Cas9, and highlight the utility of Cas9 for programmable transcript recognition without the need for tags.

Figure 18A:
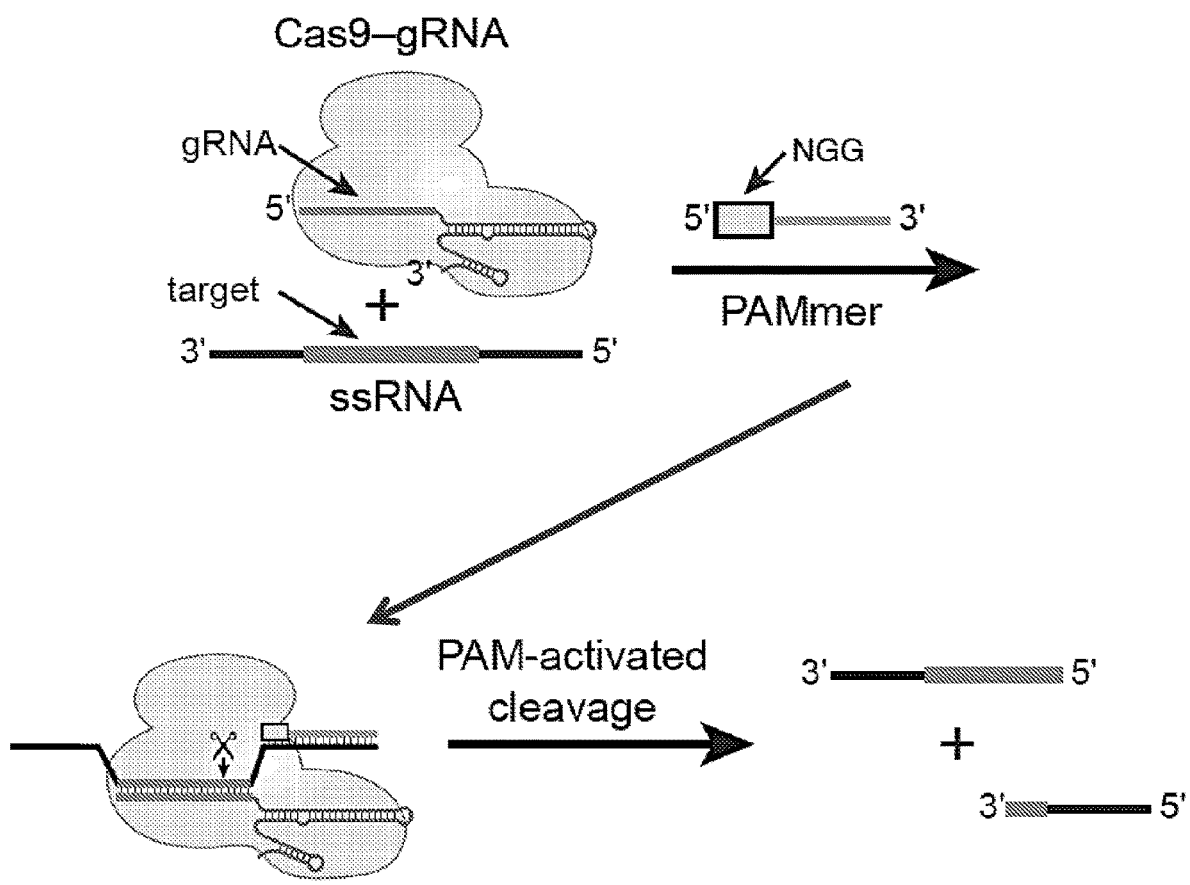
Figures 18B, 18C:
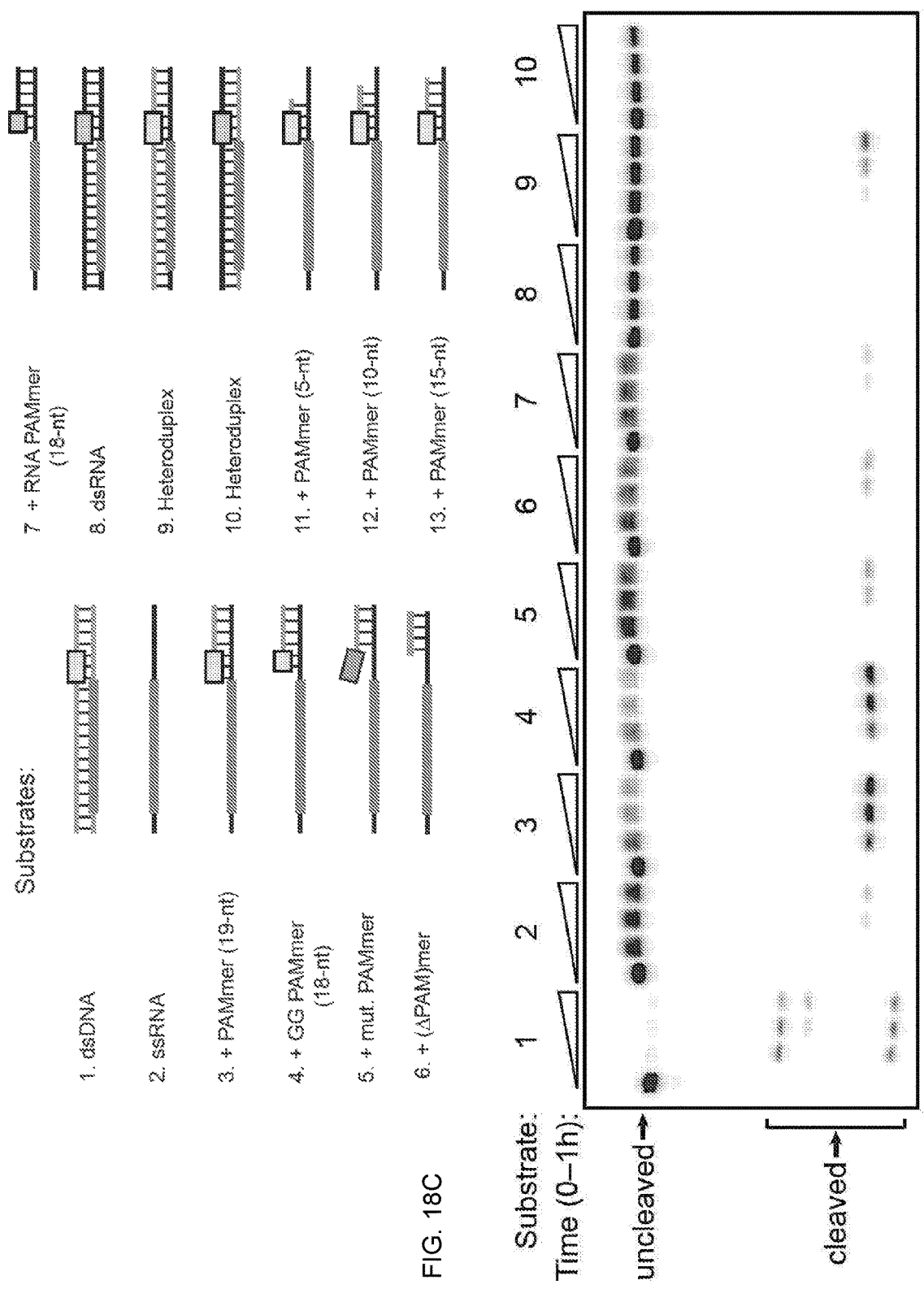

CRISPR-Cas immune systems must discriminate between self and nonself to avoid an autoimmune response. In type I and II systems, foreign DNA targets that contain adjacent PAM sequences are targeted for degradation, whereas potential targets in CRISPR loci of the host do not contain PAMs and are avoided by RNA-guided interference complexes. Single-molecule and bulk biochemical experiments showed that PAMs act both to recruit Cas9-guide-RNA (Cas9-gRNA) complexes to potential target sites and to trigger nuclease domain activation. Cas9 from *Streptococcus pyogenes* recognizes a 5'-NGG-3' PAM on the non-target (displaced) DNA strand, suggesting that PAM recognition may stimulate catalysis through allosteric regulation. Based on the observations that single-stranded DNA (ssDNA) targets can be activated for cleavage by a separate PAMmer, a similar strategy was contemplated for enabling Cas9 to cleave ssRNA targets in a programmable fashion (FIG. 18A). Using *S. pyogenes* Cas9 and dual-guide RNAs (Methods), in vitro cleavage experiments were performed using a panel of RNA and DNA targets (FIG. 18B and Table 2). Deoxyribonucleotide PAMmers specifically activated Cas9 to cleave ssRNA (FIG. 18C), an effect that required a 5'-NGG-3' or 5'-GG-3' PAM. RNA cleavage was not observed using ribonucleotide-based PAMmers, suggesting that Cas9 may recognize the local helical geometry and/or deoxyribose moieties within the PAM. Consistent with this hypothesis, dsRNA targets were not cleavable and RNA-DNA heteroduplexes could only be cleaved when the non-target strand was composed of deoxyribonucleotides. Notably, Cas9 cleaved the ssRNA target strand between positions 4 and 5 of the base-paired gRNA-target-RNA hybrid (FIG. 18D), in contrast to the cleavage between positions 3 and 4 observed for dsDNA. This is probably due to subtle differences in substrate positioning. However, a significant reduction in the pseudo-first-order cleavage rate constant of PAMmer-activated ssRNA as compared to ssDNA was not observed (FIG. 22).

FIGS. 18A-18E demonstrates RNA-guided Cas9 cleaving ssRNA targets in the presence of a short PAM presenting DNA oligonucleotide (PAMmer). FIG. 18A, Schematic depicting the approach used to target ssRNA for programmable, sequence-specific cleavage. FIG. 18B, The panel of nucleic acid substrates examined in this study. Substrate elements are coloured as follows:DNA, grey; RNA, black; guide-RNA target sequence, red; DNA PAM, yellow; mutated DNA PAM, blue; RNA PAM, orange. The 18-nucleotide 'GG PAMmer' contains only a GG dinucleotide PAM sequence. nt, nucleotide. FIG. 18C, Representative cleavage assay for 5'-radiolabelled nucleic acid substrates using Cas9-gRNA, numbered as in b. FIG. 18D, Cas9-gRNA cleavage site mapping assay for substrate 3. T1 and OH2 denote RNase T1 and hydrolysis ladders, respectively; the sequence of the target ssRNA is shown at right. Sites of G cleavage by RNase T1 are shown at left. Site of Cas9 cleavage (G24) shown at right. FIG. 18E, Representative ssRNA cleavage assay in the presence of PAMmers of increasing length, numbered as in B.

Figure 22:
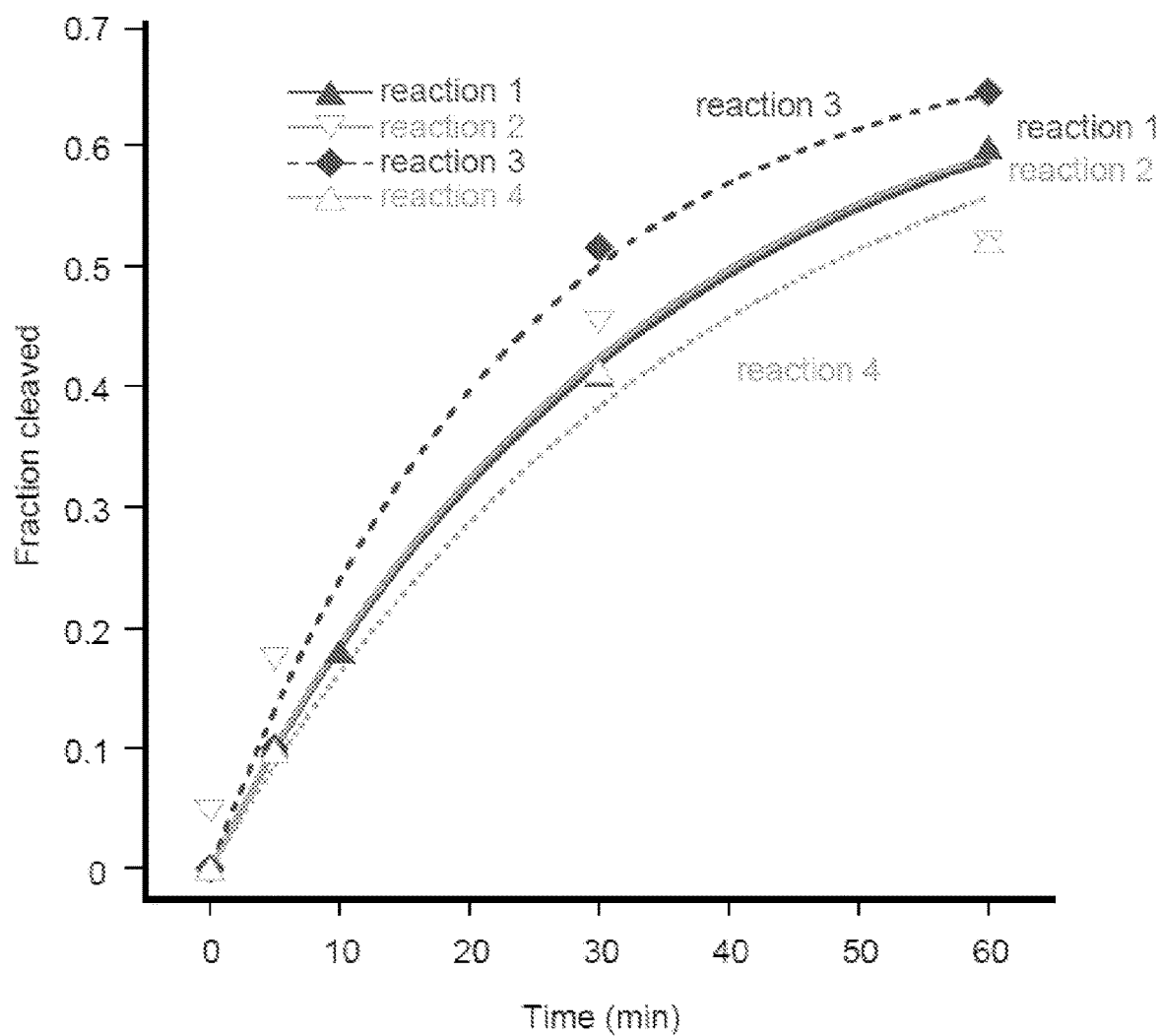
FIG. 22 depicts quantified data for cleavage of ssRNA by Cas9-gRNA in the presence of a 19-nucleotide PAMmer.

FIG. 22 depicts quantified data for cleavage of ssRNA by Cas9-gRNA in the presence of a 19-nucleotide PAMmer. Cleavage assays were conducted as described in the Methods, and the quantified data were fitted with single-exponential decays. Results from four independent experiments yielded an average apparent pseudo-first-order cleavage rate constant (mean±s.d.) of 0.032±0.007 $min^{-1}$. This is slower than the rate constant determined previously for ssDNA in the presence of the same 19-nucleotide PAMmer (7.3±3.2 $min^{-1}$).

Figure 23:
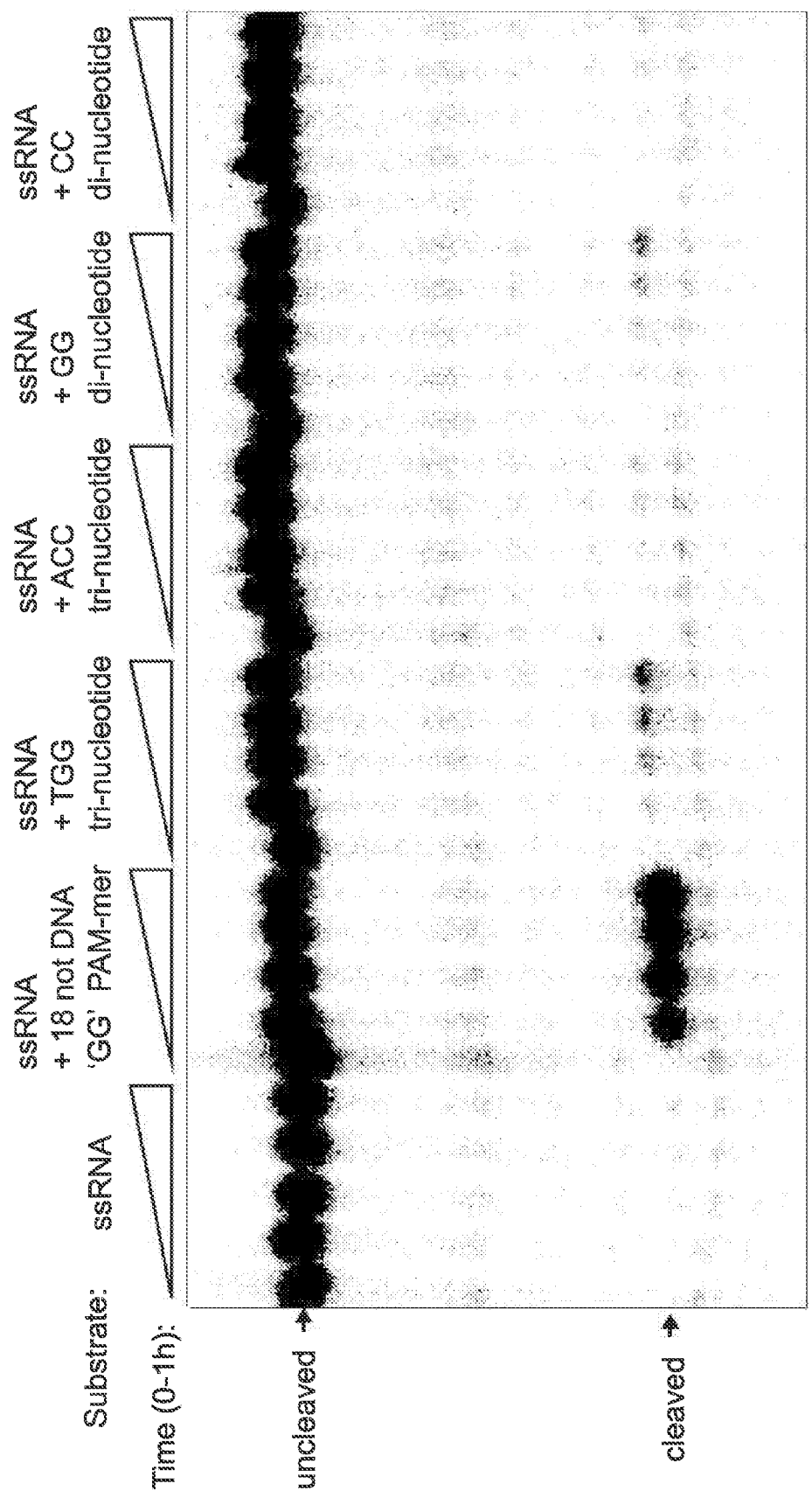
FIG. 23 depicts the effect of di- and tri-deoxyribonucleotides on RNA cleavage.

By varying PAMmer length, it was next tested whether PAMmer nuclease activation depends on the stability of the hybridized PAMmer-ssRNA duplex. ssRNA cleavage was lost when the predicted melting temperature for the duplex decreased below the temperature used in the experiments (FIG. 18E). In addition, large molar excesses of di- or tri-deoxyribonucleotides in solution were poor activators of Cas9 cleavage (FIG. 23). Collectively, these data demonstrate that hybrid substrate structures composed of ssRNA and deoxyribonucleotide-based PAMmers that anneal upstream of the RNA target sequence can be cleaved efficiently by RNA-guided Cas9.

FIG. 23 demonstrates that RNA cleavage is marginally stimulated by di- and tri-deoxyribonucleotides. Cleavage reactions contained ~1 nM 5'-radiolabelled target ssRNA and no PAMmer (left), 100 nM 18-nt PAMmer (second from left), or 1 mM of the indicated di- or tri-nucleotide (remaining lanes). Reaction products were resolved by 12% denaturing polyacrylamide gel electrophoresis (PAGE) and visualized by phosphorimaging.

Figure 19A:
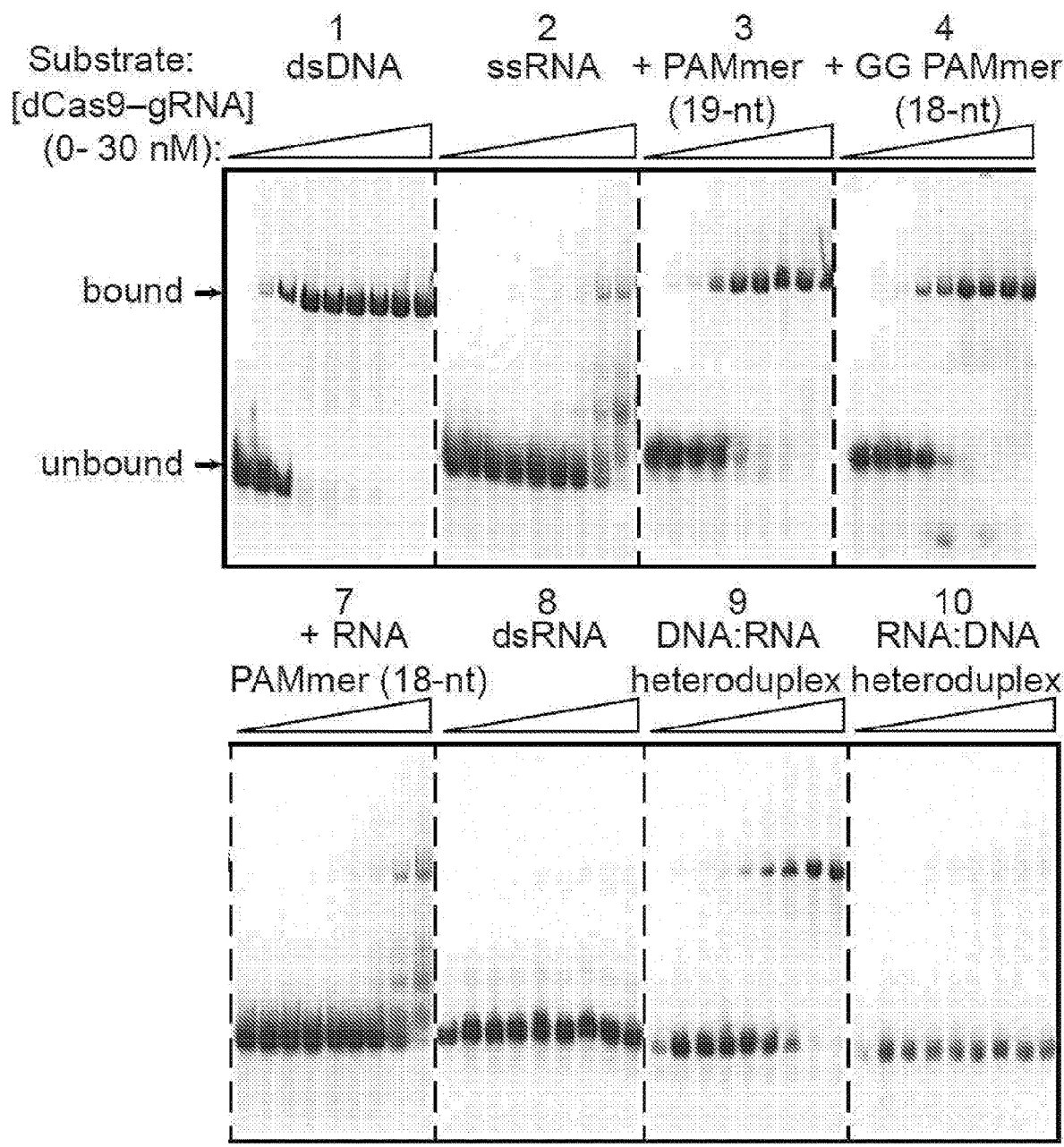
FIGS. 19A-19C depict the effect of the presence of PAMmers on dCas9-gRNA binding to ssRNA targets.
Figure 19B:
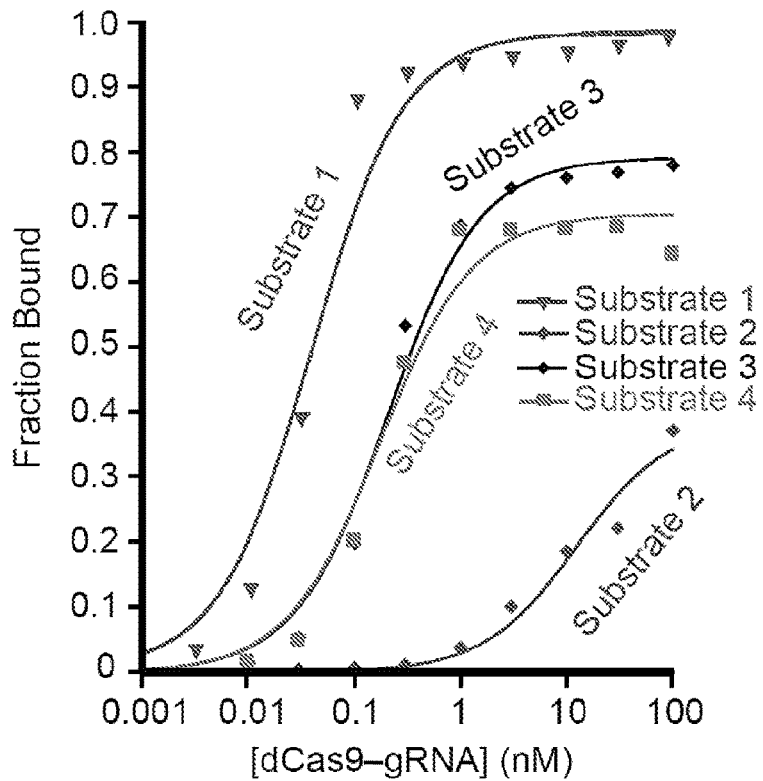

The binding affinity of catalytically inactive dCas9 (Cas9 (D10A; H840A))-gRNA for ssRNA targets with and without PAMmers was then tested using a gel mobility shift assay. Notably, whereas the previous results showed that ssDNA and PAMmer-activated ssDNA targets are bound with indistinguishable affinity, PAMmer-activated ssRNA targets were bound >500-fold tighter than ssRNA alone (FIG. 19A-19B). A recent crystal structure of Cas9 bound to a ssDNA target revealed deoxyribose-specific van der Waals interactions between the protein and the DNA backbone, suggesting that energetic penalties associated with ssRNA binding must be attenuated by favorable compensatory binding interactions with the provided PAM. The equilibrium dissociation constant measured for a PAMmer-ssRNA substrate was within five fold of that for dsDNA (FIG. 19B), and this high-affinity interaction again required a cognate deoxyribonucleotide 5'-GG-3' PAM (FIG. 19A). Tight binding also scaled with PAMmer length (FIG. 19C), consistent with the cleavage data presented above.

Figure 19C:
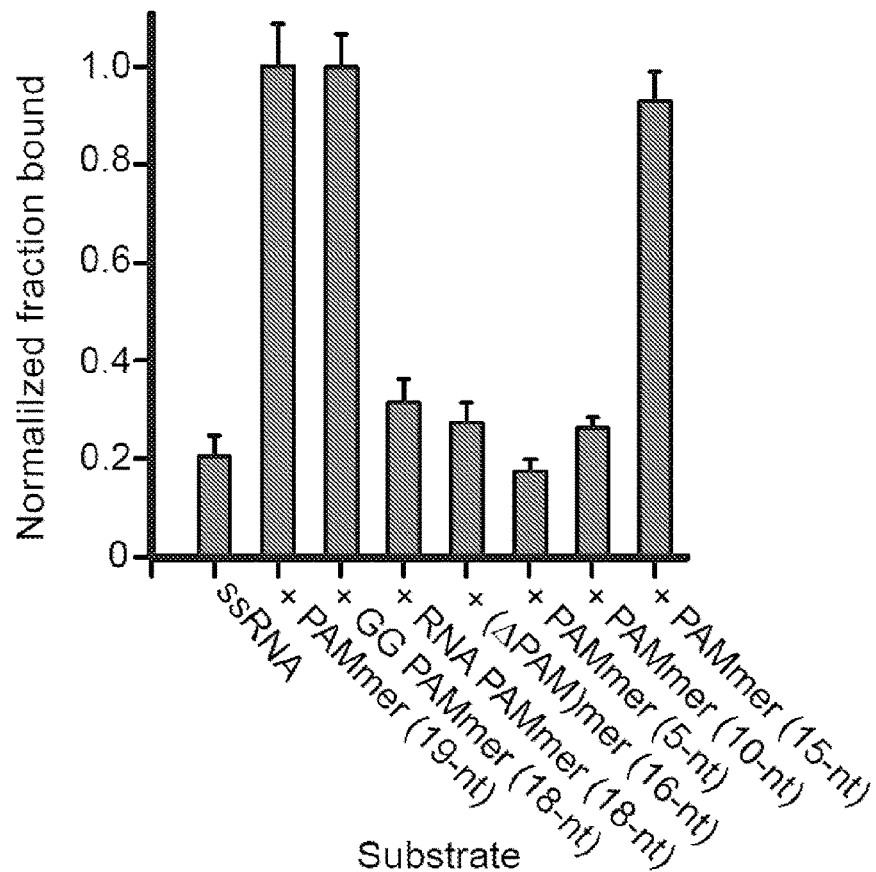

FIGS. 19A-19C demonstrates that dCas9-gRNA binds ssRNA targets with high affinity in the presence of PAMmers. FIG. 19A, Representative electrophoretic mobility shift assay for binding reactions with dCas9-gRNA and a panel of 5'-radiolabelled nucleic acid substrates, numbered as in FIG. 18B. FIG. 19B, Quantified binding data for substrates 1-4 from a fitted with standard binding isotherms. Measured dissociation constants from three independent experiments (mean±s.d.) were 0.036±0.003 nM (substrate 1), >100 nM (substrate 2), 0.20±0.09 nM (substrate 3) and 0.18±0.07 nM (substrate 4). FIG. 19C, Relative binding data for 1 nM dCas9-gRNA and 5'-radiolabelled ssRNA with a panel of different PAMmers. The data are normalized to the amount of binding observed at 1 nM dCas9-gRNA with a 19-nucleotide (nt) PAMmer; error bars represent the standard deviation from three independent experiments.

It is known that Cas9 possesses an intrinsic affinity for RNA, but sequence specificity of the interaction had not been explored. Thus, to verify the programmable nature of PAMmer-mediated ssRNA cleavage by Cas9-gRNA, three distinct guide RNAs ($\lambda 2$, $\lambda 3$, and $\lambda 4$; each targeting 20-nucleotide sequences within $\lambda 2$, $\lambda 3$, and $\lambda 4$ RNAs, respectively) were prepared and their corresponding ssRNA targets were efficiently cleaved using complementary PAMmers without any detectable cross-reactivity (FIG. 20A).

This result indicates that complementary RNA-RNA base pairing is critical in these reactions. Notably however, dCas9 programmed with the λ2 guide RNA bound all three PAMmer-ssRNA substrates with similar affinity (FIG. 20B). This observation suggests that high-affinity binding in this case may not require correct base pairing between the guide RNA and the ssRNA target, particularly given the compensatory role of the PAMmer.

Figure 20A:
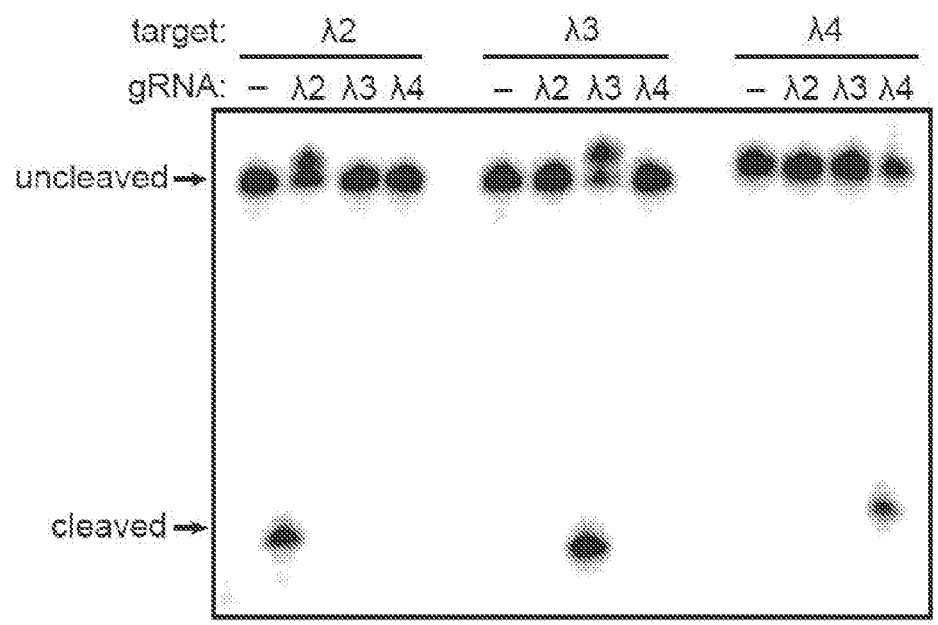
FIGS. 20A-20D depict the effect of 5'-extended PAMmers on specific target ssRNA binding.
Figure 20B:
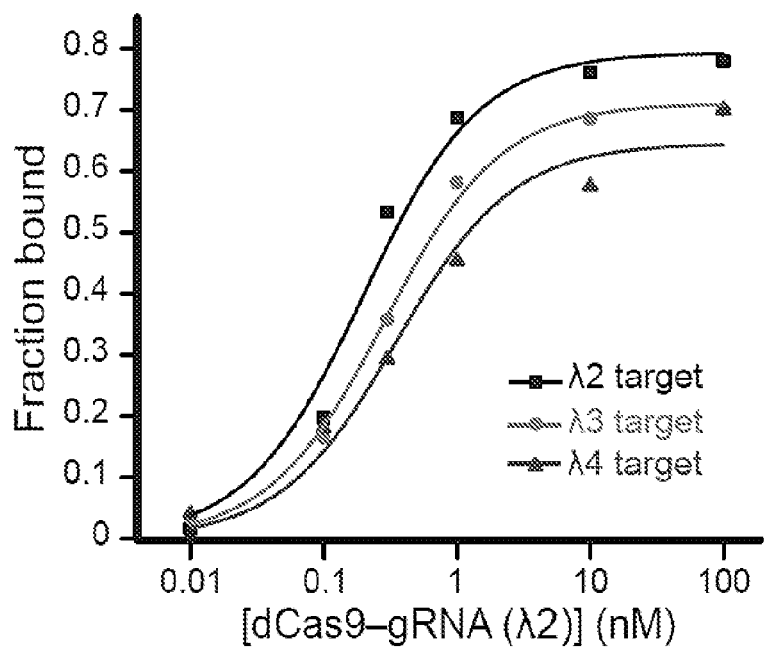
Figure 20C:
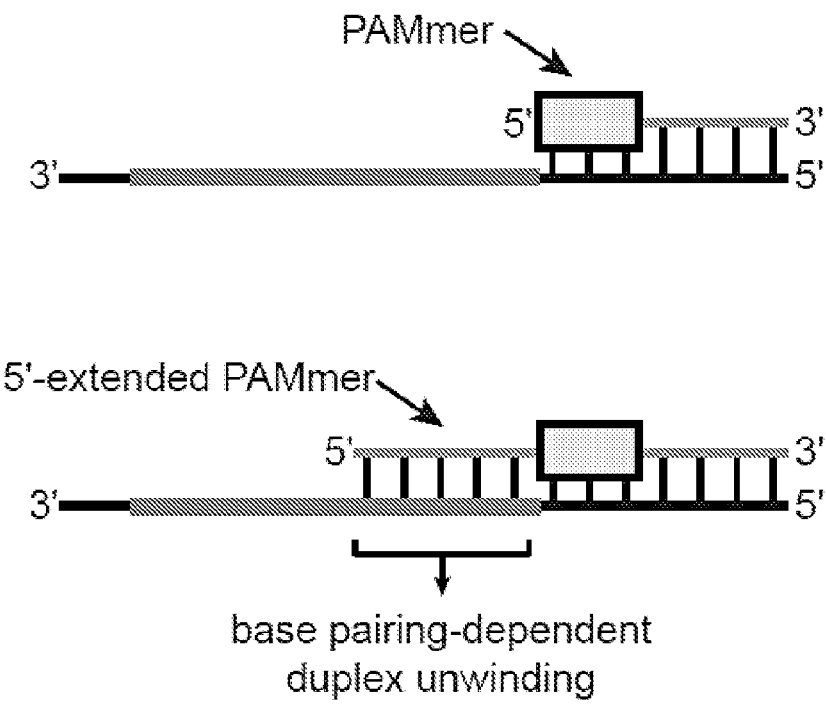
Figure 20D:
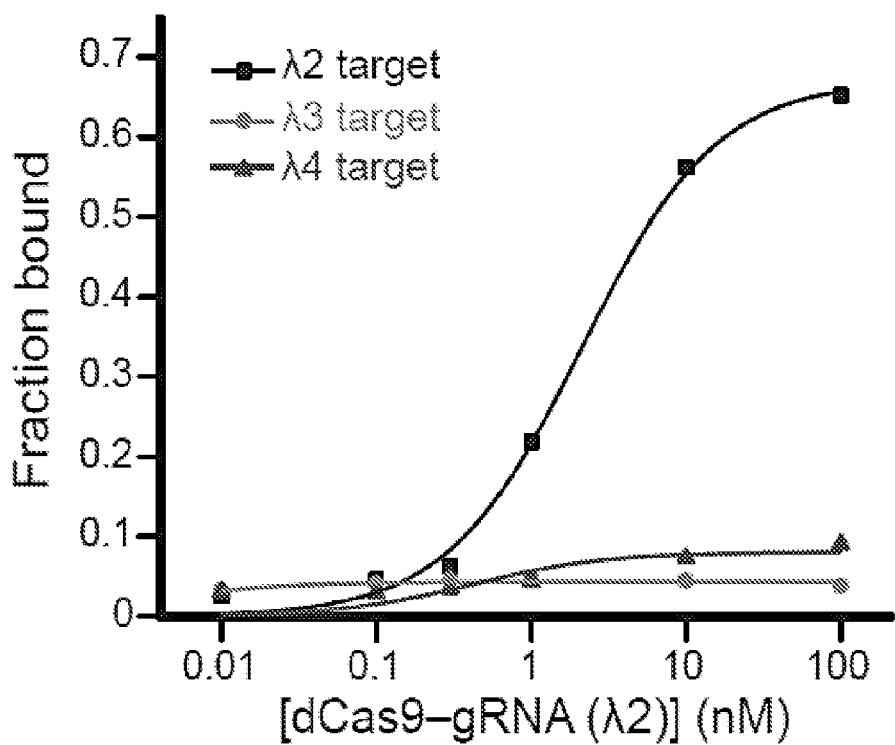

FIGS. 20A-20D shows that 5'-extended PAMmers are required for specific target ssRNA binding. FIG. 20A, Cas9 programmed with either λ2-, λ3- or λ4-targeting gRNAs exhibits sequence-specific cleavage of 5'-radiolabelled λ2, λ3, and 4 target ssRNAs, respectively, in the presence of cognate PAMmers. FIG. 20B, dCas9 programmed with a λ2-targeting gRNA exhibits similar binding affinity to λ2, λ3, and λ4 target ssRNAs in the presence of cognate PAMmers. Dissociation constants from three independent experiments (mean±s.d.) were 0.20±0.09 nM (λ2), 0.33±0.14 nM (λ3) and 0.53±0.21 nM (λ4). FIG. 20C, Schematic depicting the approach used to restore gRNA-mediated ssRNA binding specificity, which involves 5'-extensions to the PAMmer that cover part or all of the target sequence. FIG. 20D, dCas9 programmed with a λ2-targeting gRNA specifically binds the λ2 ssRNA but not 3 and 4 ssRNAs in the presence of complete 5'-extended PAMmers. Dissociation constants from three independent experiments (mean±s.d.) were 3.3±1.2 nM (λ2) and 0.100 nM (λ3 and λ4).

During dsDNA targeting by Cas9-gRNA, duplex melting proceeds directionally from the PAM and requires the formation of complementary RNA-DNA base pairs to offset the energetic costs associated with dsDNA unwinding. It was therefore tested whether binding specificity for ssRNA substrates would be recovered using PAMmers containing 5'-extensions that create a partially double-stranded target region requiring unwinding (FIG. 20C). Use of a 5'-extended PAMmer enabled dCas9 bearing the λ2 guide sequence to bind sequence selectively to the λ2 PAMmer-ssRNA target. The 3 and 4 PAMmer-ssRNA targets were not recognized (FIG. 20D and FIG. 24), although a tenfold reduction in overall ssRNA substrate binding affinity was observed. By systematically varying the length of the 5' extension, it was found that PAMmers containing 2-8 additional nucleotides upstream of the 5'-NGG-3' offer a good compromise between gains in binding specificity and concomitant losses in binding affinity and cleavage efficiency (FIG. 25A-25B).

Figure 24:
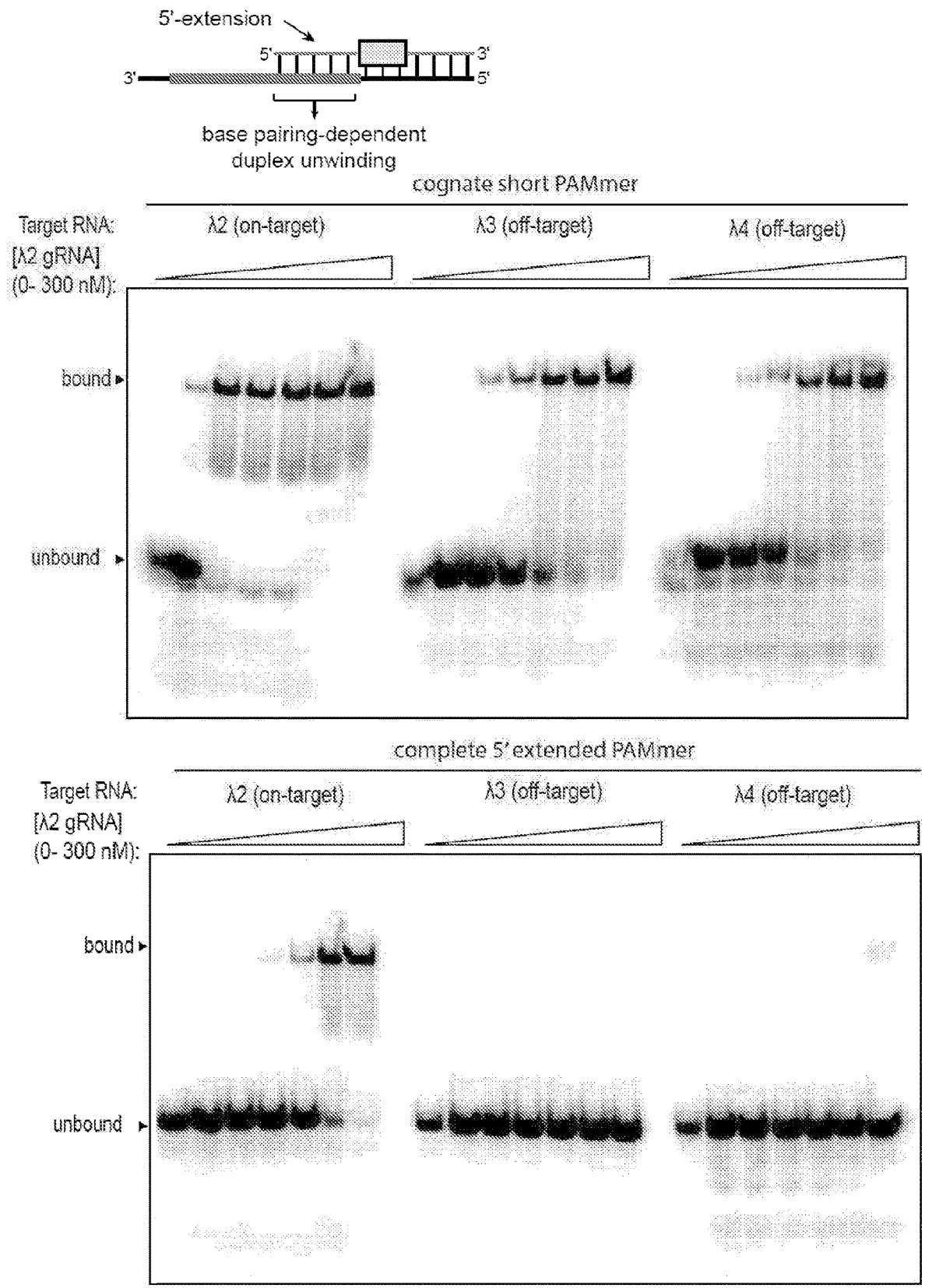
FIG. 24 provides a representative binding experiment demonstrating guide-specific ssRNA binding with 5'-extended PAMmers.

FIG. 24 depicts a representative binding experiment demonstrating guide-specific ssRNA binding with 5'-extended PAMmers. Gel shift assays were conducted as described in the Methods section below. Binding reactions contained Cas9 programmed with λ2 gRNA and either λ2 (on-target), λ3 (off-target) or λ4 (off-target) ssRNA in the presence of short cognate PAMmers or cognate PAMmers with complete 5'-extensions, as indicated. The presence of a cognate 5'-extended PAMmer abrogated off-target binding. Three independent experiments were conducted to produce the data shown in FIG. 20B, 20D.

Figure 25A:
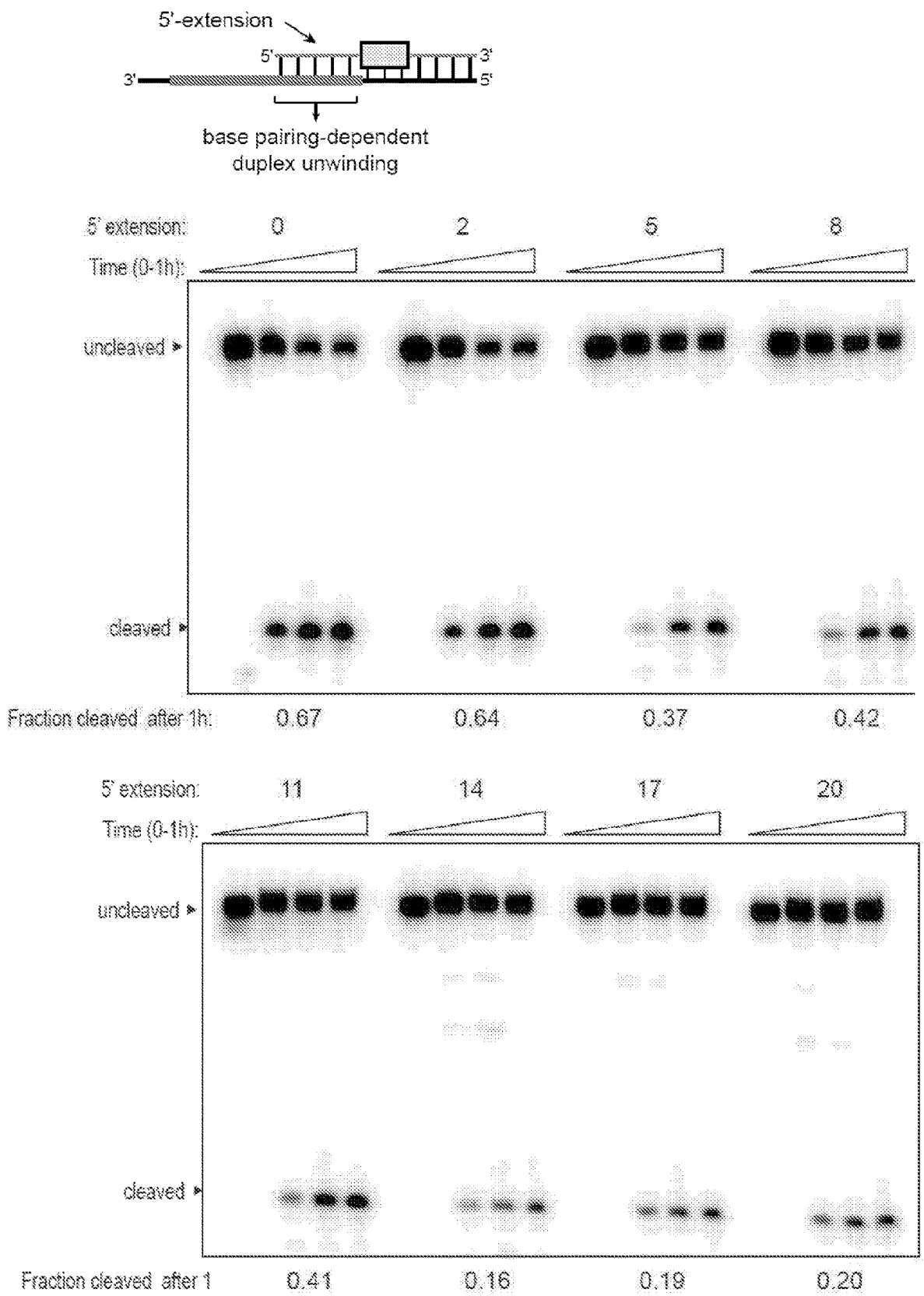
FIGS. 25A-25E depict RNA cleavage efficiencies and binding specificity using PAMmers with variable 5'-extensions.
Figure 25B:
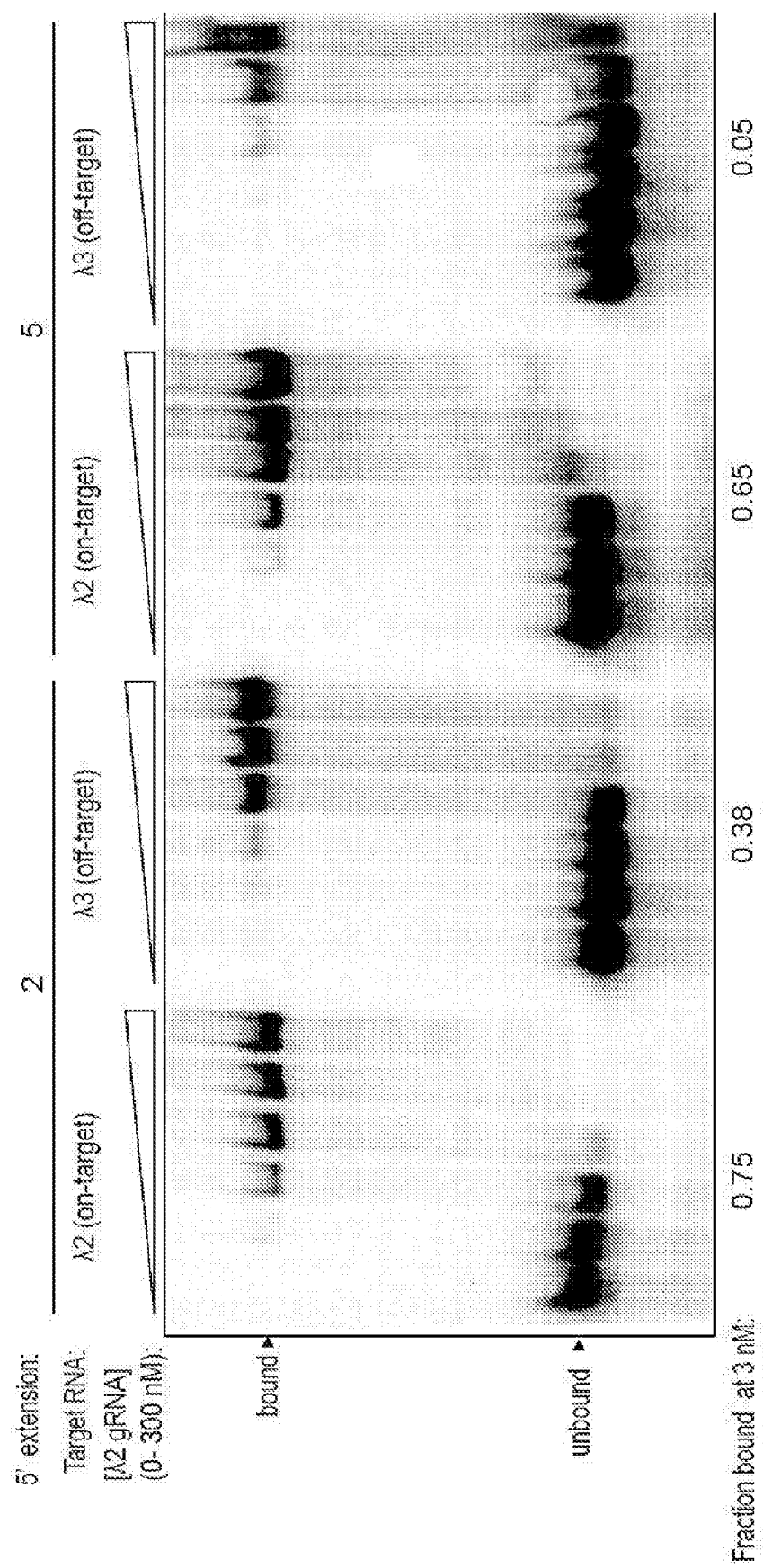

FIGS. 25A-25E depicts exploration of RNA cleavage efficiencies and binding specificity using PAMmers with variable 5'-extensions. FIG. 25A, Cleavage assays were conducted as described in the methods section below. Reactions contained Cas9 programmed with λ2 gRNA and X2 ssRNA targets in the presence of PAMmers with 5'-extensions of variable length. The ssRNA cleavage efficiency decreased as the PAMmer extended further into the target region, as indicated by the fraction of RNA cleaved after 1 h. FIG. 25B-25E, Binding assays were conducted as described in the Methods section below, using mostly the same panel of 5'-extended PAMmers as in a. Binding reactions contained Cas9 programmed with λ2 gRNA and either λ2 (on-target) or λ3 (off-target) ssRNA in the presence of cognate PAMmers with 5'-extensions of variable length. The binding specificity increased as the PAMmer extends further into the target region, as indicated by the fraction of 3 (off-target) ssRNA bound at 3 nM Cas9-gRNA. PAMmers with 5' extensions also caused a slight reduction in the relative binding affinity of λ2 (on-target) ssRNA.

Figure 21A:
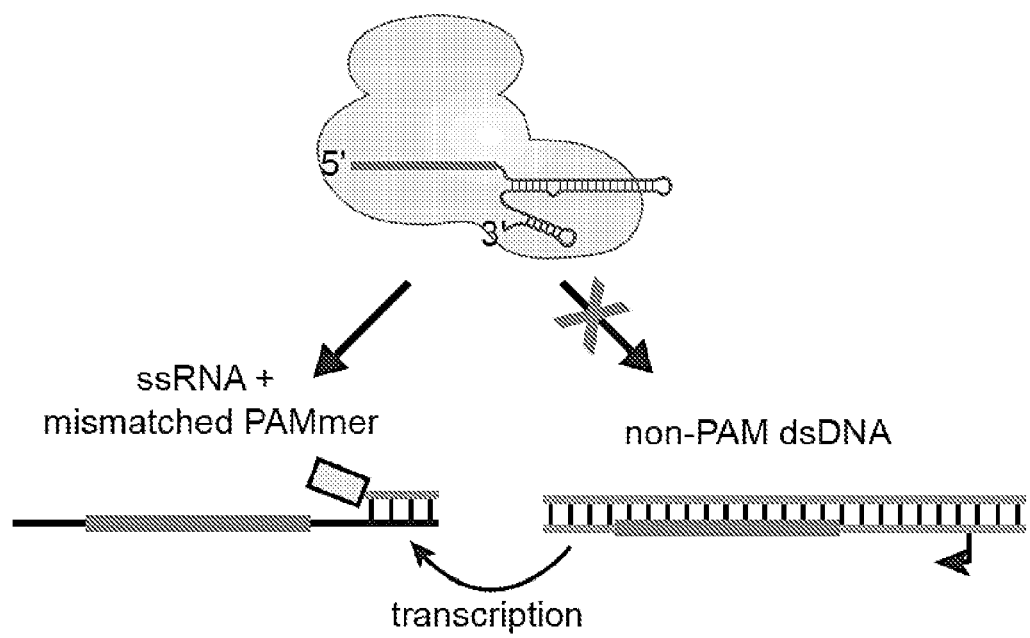
Figure 21B:
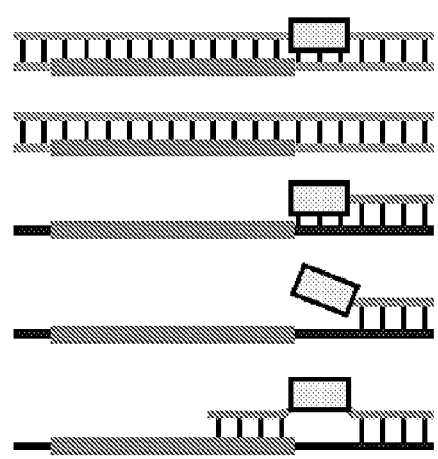
Figure 21C:
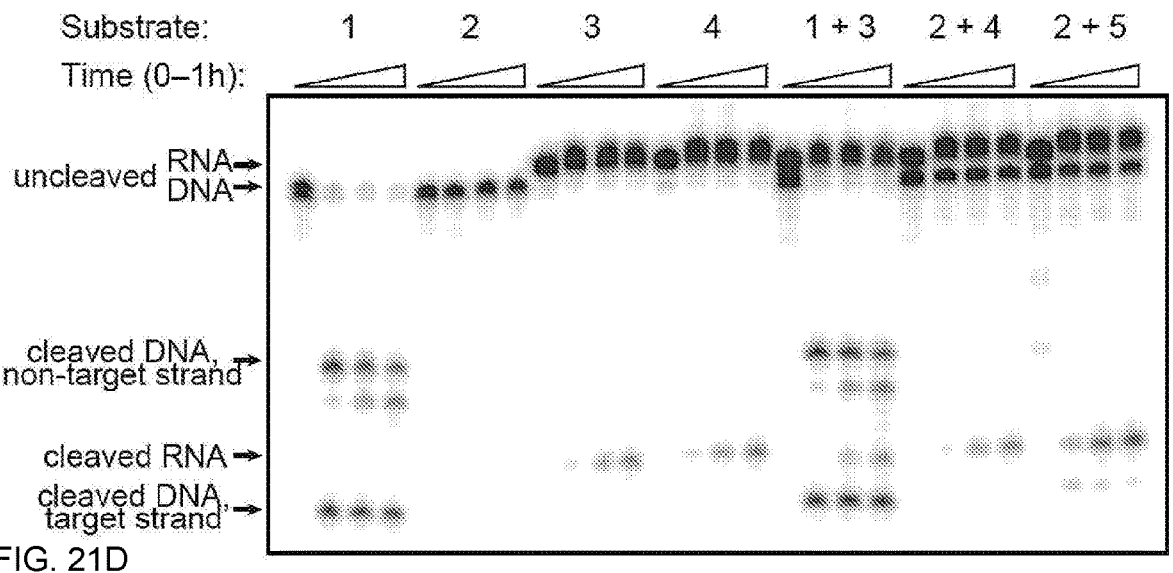

It was next investigated whether nuclease activation by PAMmers requires base pairing between the 5'-NGG-3' and corresponding nucleotides on the ssRNA. Prior studies have shown that DNA substrates containing a cognate PAM that is mismatched with the corresponding nucleotides on the target strand are cleaved as efficiently as a fully base-paired PAM. This could enable targeting of RNA while precluding binding or cleavage of corresponding genomic DNA sites lacking PAMs (FIG. 21A). To test this possibility, it was first demonstrated that Cas9-gRNA cleaves PAMmer-ssRNA substrates regardless of whether the PAM is base paired (FIG. 21B-21C). When Cas9-RNA was incubated with both a PAMmer-ssRNA substrate and the corresponding dsDNA template containing a cognate PAM, both targets were cleaved. In contrast, when a dsDNA target lacking a PAM was incubated together with a PAMmer-ssRNA substrate bearing a mismatched 5'-NGG-3' PAM, Cas9-gRNA selectively targeted the ssRNA for cleavage (FIG. 21C). The same result was obtained using a mismatched PAMmer with a 5' extension (FIG. 21C), demonstrating that this general strategy enables the specific targeting of RNA transcripts while effectively eliminating any targeting of their corresponding dsDNA template loci.

Figure 21D:
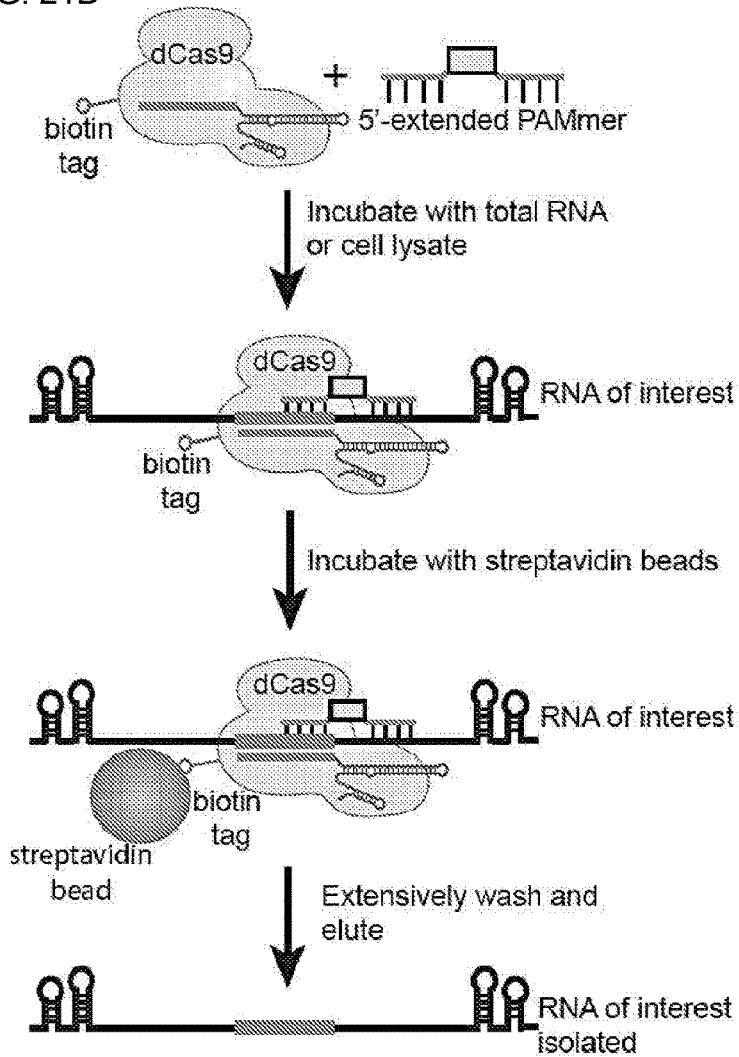

It was next tested whether Cas9-mediated RNA targeting could be applied in tagless transcript isolation from HeLa cells (FIG. 21D). The immobilization of Cas9 on a solid-phase resin is described in the Methods section below (see also FIG. 26A-26E). As a proof of concept, GAPDH mRNA was first isolated from HeLa total RNA using biotinylated dCas9, gRNAs and PAMmers (Table 2) that target four non-PAM-adjacent sequences within exons 5-7 (FIG. 21E). A substantial enrichment of GAPDH mRNA relative to control b-actin mRNA was observed by northern blot analysis, but no enrichment using a non-targeting gRNA or dCas9 alone was observed (FIG. 21F).

FIG. 21A-21H shows that RNA-guided Cas9 can target non-PAM sites on ssRNA and can be used to isolate GAPDH mRNA from HeLa cells in a tagless manner. FIG. 21A, Schematic of the approach designed to avoid cleavage of template DNA by targeting non-PAM sites in the ssRNA target. FIG. 21B, The panel of nucleic acid substrates tested in FIG. 21C. FIG. 21C, Cas9-gRNA cleaved ssRNA targets with equal efficiency when the 5'-NGG-3' of the PAMmer was mismatched with the ssRNA. This strategy enables selective cleavage of ssRNA in the presence of non-PAM target dsDNA. FIG. 21D, Schematic of the dCas9 RNA pull-down experiment. FIG. 21E, GAPDH mRNA transcript isoform 3 (GAPDH-003) shown schematically, with exons common to all GAPDH protein-coding transcripts in red and gRNA/PAMmer targets G1-G4 indicated. kb, kilobase pairs. FIG. 21F Northern blot showing that gRNAs and corresponding 5'-extended PAMmers enabled tagless isolation of GAPDH mRNA from HeLa total RNA; b-actin mRNA is shown as a control. FIG. 21G, Northern blot showing tagless isolation of GAPDH mRNA from HeLa cell lysate with varying 2'-OMe-modified PAMmers. RNase H cleavage is abrogated with v4 and v5 PAMmers; b-actin mRNA is shown as a control. u, unmodified PAMmer (G1). v1-v5, increasingly 2'-OMe-modified PAMmers (G1), see g for PAMmer sequences. FIG. 21H, Sequences of unmodified and modified GAPDH PAMmers used in g; 2'-OMe-modified nucleotides are shown in red.

Figures 26B, 26C:
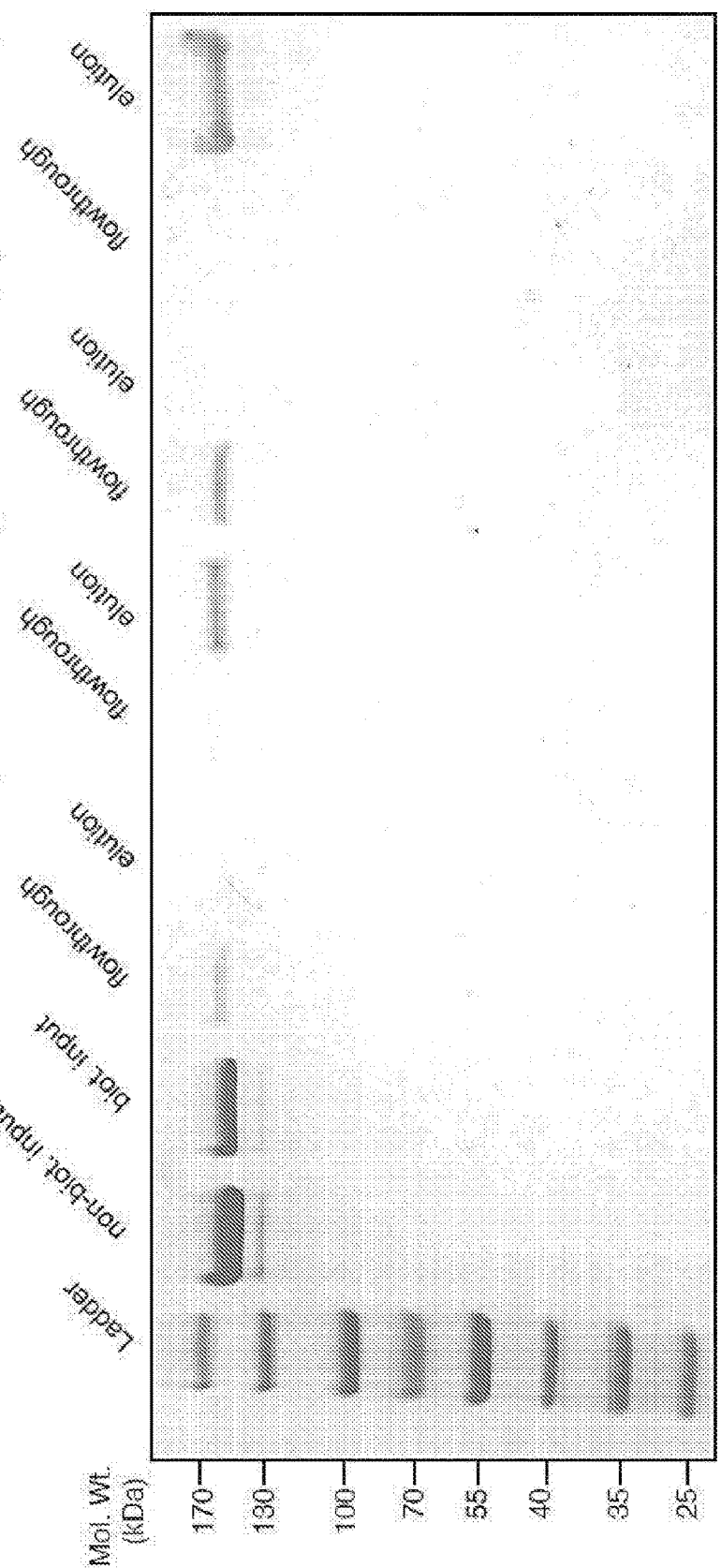
Figure 26D:
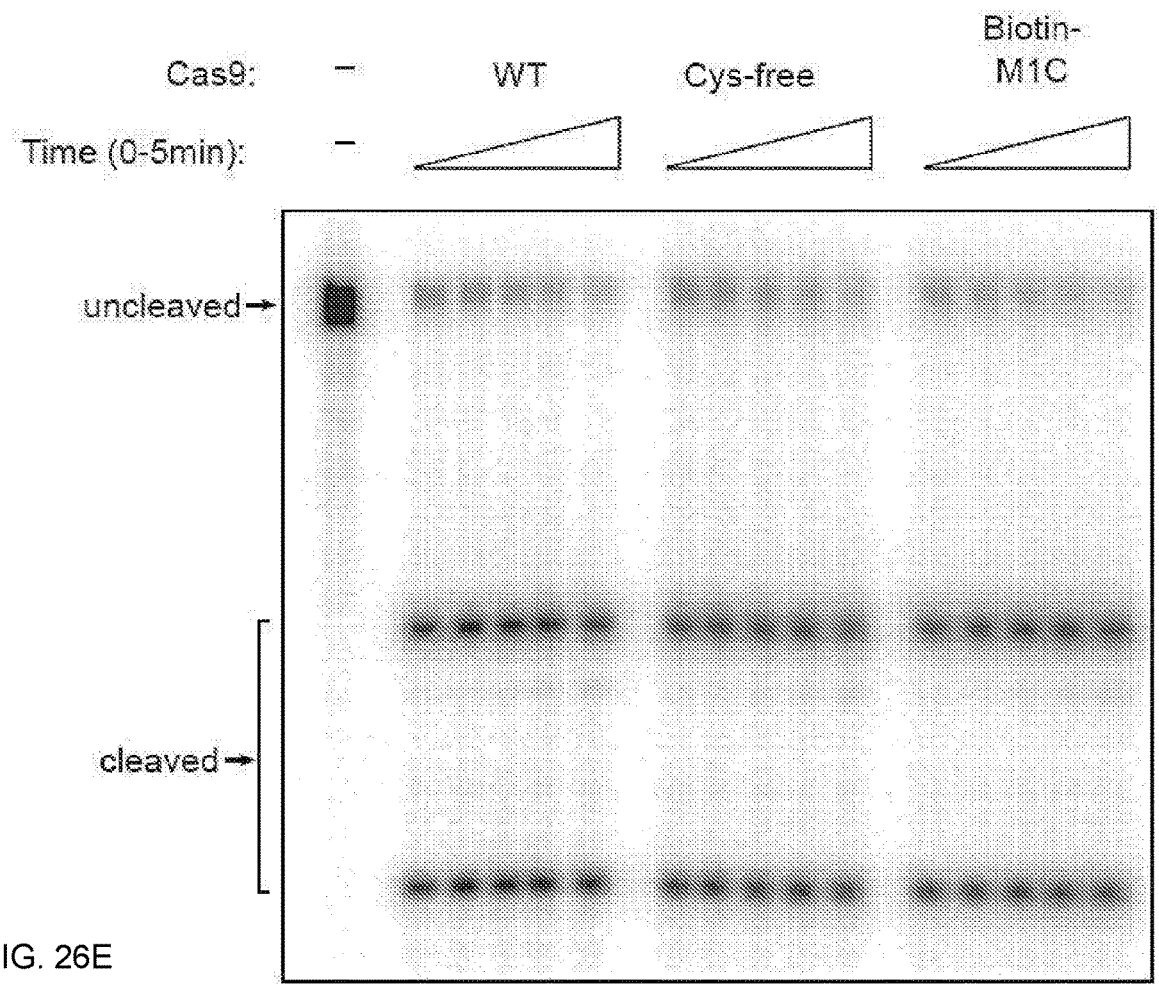
Figure 26E:
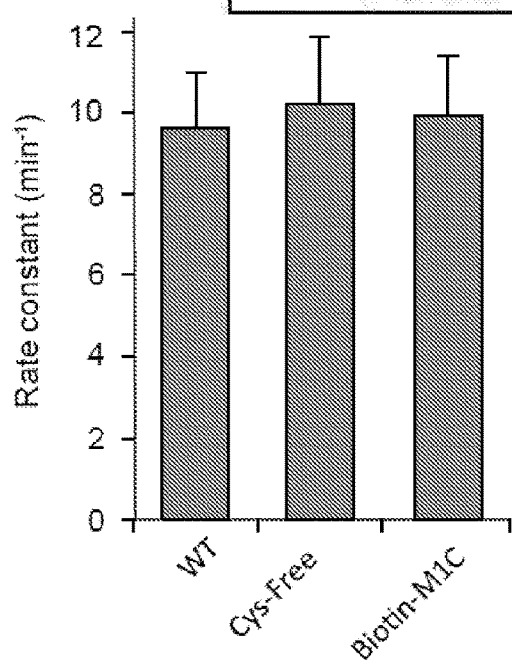

FIG. 26A-26E provides date related to site-specific biotin labeling of Cas9. FIG. 26A, In order to introduce a single biotin moiety on Cas9, the solvent accessible, non-conserved amino-terminal methionine was mutated to a cysteine (M1C; red text) and the naturally occurring cysteine residues were mutated to serine (C80S and C574S; bold text). This enabled cysteine-specific labeling with EZ-link Maleimide-PEG2-biotin through an irreversible reaction between the reduced sulphydryl group of the cysteine and the maleimide group present on the biotin label. Mutations of dCas9 are also indicated in the domain schematic. FIG. 26B, Mass spectrometry analysis of the Cas9 biotin-labeling reaction confirmed that successful biotin labeling only occurred when the M1C mutation was present in the Cys-free background (C80S; C574S). The mass of the Maleimide-PEG2-biotin reagent is 525.6 Da. FIG. 26C, Streptavidin bead binding assay with biotinylated (biot.) or non-biotinylated (non-biot.) Cas9 and streptavidin agarose or streptavidin magnetic beads. Cas9 only remained specifically bound to the beads after biotin labeling. FIG. 26D, Cleavage assays were conducted as described in the Methods and resolved by denaturing PAGE. Reactions contained 100 nM Cas9 programmed with λ2 gRNA and ~1 nM 5'-radiolabelled λ2 dsDNA target. FIG. 26E, Quantified cleavage data from triplicate experiments were fitted with single-exponential decays to calculate the apparent pseudo-first-order cleavage rate constants (average±standard deviation). Both Cys-free and biotin-labeled Cas9 (M1C) retained wild-type activity.

Figure 27:
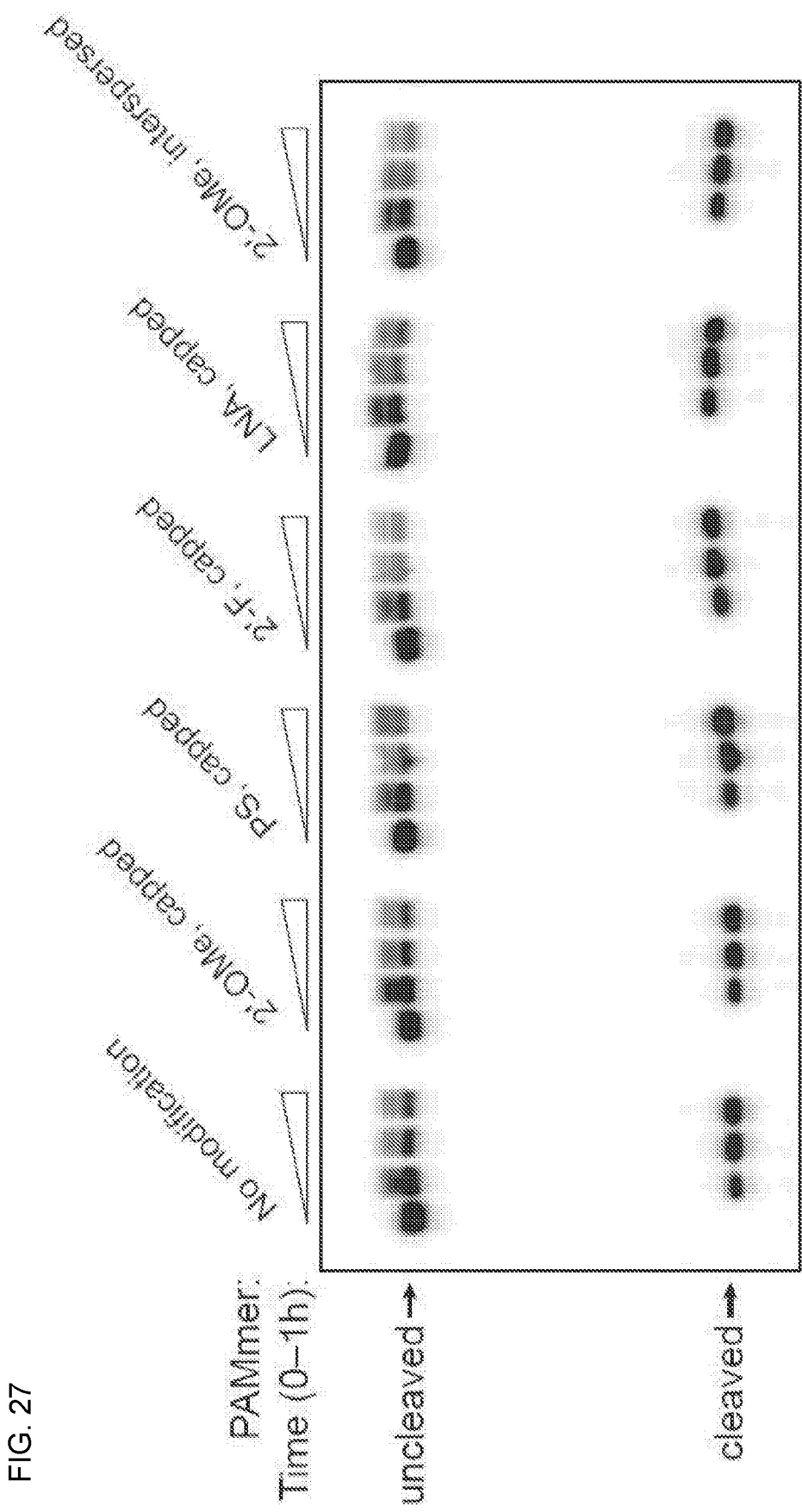
FIG. 27 depicts the effect of chemically modified PAMmers on RNA-guided Cas9 cleavage.

This approach was then used to isolate endogenous GAPDH transcripts from HeLa cell lysate under physiological conditions. In initial experiments, Cas9-gRNA captured two GAPDH-specific RNA fragments rather than the full-length mRNA (FIG. 21G). Based on the sizes of these bands, it was surmised that RNA-DNA heteroduplexes formed between the mRNA and PAMmer were cleaved by cellular RNaseH. Previous studies have shown that modified DNA oligonucleotides can abrogate RNaseH activity, and it was therefore investigated whether Cas9 would tolerate chemical modifications to the PAMmer. A wide range of modifications (locked nucleic acids, 2'-OMe and 2'-F ribose moieties) still enabled PAMmer-mediated nuclease activation (FIG. 27). Furthermore, by varying the pattern of 2'-OMe modifications in the PAMmer, RNase-H-mediated cleavage could be completely eliminated during the pull-down and intact GAPDH mRNA was successfully isolated (FIG. 21G-21H). Notably, specific isolation of GAPDH mRNA in the absence of any PAMmer occurred, albeit with lower efficiency, suggesting that Cas9-gRNA can bind to GAPDH mRNA through direct RNA-RNA hybridization (FIGS. 21F-21G and FIGS. 28A-28B). These experiments demonstrate that RNA guided Cas9 can be used to purify endogenous untagged RNA transcripts. In contrast to current oligonucleotide-mediated RNA-capture methods, this approach works well under physiological salt conditions and does not require crosslinking or large sets of biotinylated probes.

FIG. 27 depicts data showing that RNA-guided Cas9 can utilize chemically modified PAMmers. Nineteen-nucleotide PAMmer derivatives containing various chemical modifications on the 5' and 3' ends (capped) or interspersed throughout the strand still activated Cas9 for cleavage of ssRNA targets. These types of modification are often used to increase the in vivo half-life of short oligonucleotides by preventing exo- and endonuclease-mediated degradation. Cleavage assays were conducted as described in the Methods. PS, phosphorothioate bonds; LNA, locked nucleic acid.

Figure 28A:
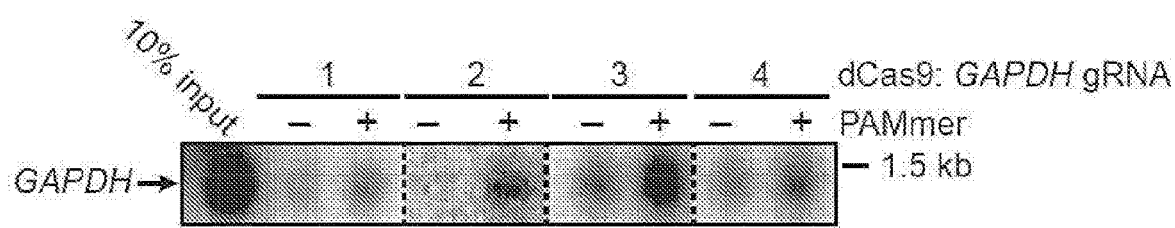
FIGS. 28A-28B depict pull down of GAPDH mRNA in the absence of PAMmers Cas9 programmed with GAPDH-specific gRNAs.
Figure 28B:
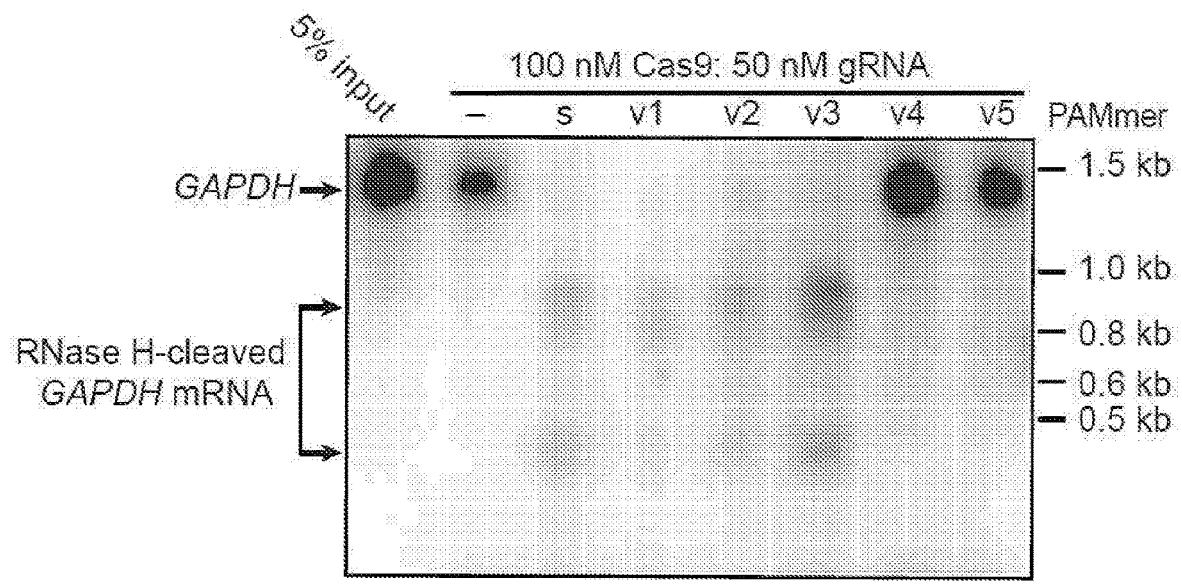

FIG. 28A-28B depicts data showing that Cas9 programmed with GAPDH-specific gRNAs can pull down GAPDH mRNA in the absence of PAMmers. FIG. 28A, Northern blot showing that, in some cases, Cas9-gRNA is able to pull down detectable amounts of GAPDH mRNA from total RNA without requiring a PAMmer. FIG. 28B, Northern blot showing that Cas9-gRNA G1 is also able to pull down quantitative amounts of GAPDH mRNA from HeLa cell lysate without requiring a PAMmer. s, standard; v1-5, increasingly 2'-OMe-modified PAMmers. See FIG. 21G for PAMmer sequences.

The data herein demonstrate the ability to re-direct the dsDNA targeting capability of CRISPR/Cas9 for RNA-guided ssRNA binding and/or cleavage (which can be referred to as RCas9, an RNA-targeting Cas9). Examples of uses for compositions and methods described herein include, but are not limited to those schematized in FIG. 29A-29B. Although certain engineered proteins such as PPR proteins and Pumilio/FBF (PUF) repeats show promise as platforms for sequence-specific RNA targeting, these strategies require re-designing the protein for every new RNA sequence of interest. In contrast to these systems, the molecular basis for RNA recognition by RCas9 is now clear and requires only the design and synthesis of a matching gRNA and complementary PAMmer. The ability to recognize endogenous RNAs within complex mixtures with high affinity and in a programmable manner allows for direct transcript detection, analysis and manipulation without the need for genetically encoded affinity tags.

FIG. 29A-29B depicts schematics of example applications of RCas9 (RNA directed Cas9) for untagged transcript analysis, detection and manipulation. FIG. 29A, Catalytically active RCas9 can be used to target and cleave RNA targets, particularly those for which RNA-interference-mediated repression/degradation is not possible. FIG. 29B, Tethering the eukaryotic initiation factor eIF4G to a catalytically inactive dRCas9 targeted to the 5' untranslated region of an mRNA can drive translation. FIG. 29C, dRCas9 tethered to beads can be used to specifically isolate RNA or native RNA-protein complexes of interest from cells for downstream analysis or assays including identification of bound-protein complexes, probing of RNA structure under native protein-bound conditions, and enrichment of rare transcripts for sequencing analysis. FIG. 29D, dRCas9 tethered to RNA deaminase or N6-mA methylase domains could direct site-specific A-to-I editing or methylation of RNA, respectively. e, dRCas9 fused to a U1 recruitment domain (arginine- and serine-rich (RS) domain) can be programmed to recognize a splicing enhancer site and thereby promote the inclusion of a targeted exon. FIG. 29F, dRCas9 tethered to a fluorescent protein such as GFP can be used to observe RNA localization and transport in living cells.

Materials and Methods

Cas9 and Nucleic Acid Preparation

Wild-typeCas9 and catalytically inactive dCas9 (Cas9 (D10A; H840A)) from S. pyogenes were purified as previously described (Jinek et al., Science. 2012 Aug. 17; 337 (6096):816-21). Forty two-nucleotide crRNAs were either ordered synthetically (Integrated DNA Technologies) or transcribed in vitro with T7 polymerase using single-stranded DNA templates. Using the previously described numbering scheme (Jinek et al., Science. 2012 Aug. 17; 337(6096):816-21), tracrRNA was transcribed in vitro and contained nucleotides 15-87. Single-guide RNAs (sgRNAs)

targeting 1-RNAs were transcribed in vitro from linearized plasmids and contain full-length crRNA and tracrRNA connected via a GAAA tetraloop insertion. GAPDH mRNA-targeting sgRNAs were transcribed in vitro from dsDNA PCR products. Target ssRNAs (55-56 nucleotides) were transcribed in vitro using single-stranded DNA templates. Sequences of all nucleic acid substrates used in this study can be found in Table 2.

All RNAs were purified using $10^{-15}$% denaturing polyacrylamide gel electrophoresis (PAGE). Duplexes of crRNA and tracrRNA were prepared by mixing equimolar concentrations of each RNA in hybridization buffer (20 mM Tris-HCl, pH7.5, 100 mM KCl, 5 mM $MgCl_2$), heating to 95° C. for 30 s and slow cooling. Fully double-stranded DNA/RNA substrates (substrates 1, 8-10 in FIG. 1 and substrates 1 and 2 in FIG. 4) were prepared by mixing equimolar concentrations of each nucleic acid strand in hybridization buffer, heating to 95° C. for 30 s, and slow cooling. RNA, DNA and chemically modified PAMmers were synthesized commercially (Intergrated DNA Technologies). DNA and RNA substrates were 5'-radiolabelled using [$\gamma$-$^{32}$P]ATP (PerkinElmer) and T4 polynucleotide kinase (New England Biolabs). Double-stranded DNA and dsRNA substrates (FIGS. 1c and 4c) were 5'-radiolabelled on both strands, whereas only the target ssRNA was 5'-radiolabelled in other experiments.

Cleavage Assays

Cas9-gRNA complexes were reconstituted before cleavage experiments by incubating Cas9 and the crRNA-tracrRNA duplex for 10 min at 37° C. in reaction buffer (20 mM Tris-HCl, pH7.5, 75 mM KCl, 5 mM $MgCl_2$, 1 mM dithiothreitol (DTT), 5% glycerol). Cleavage reactions were conducted at 37° C. and contained 1 nM 5'-radiolabelled target substrate, 100 nM Cas9-RNA, and 100 nM PAMmer, where indicated. Aliquots were removed at each time point and quenched by the addition of RNA gel-loading buffer (95% deionized formamide, 0.025% (w/v) bromophenol blue, 0.025% (w/v) xylene cyanol, 50 mM EDTA (pH 8.0), 0.025% (w/v) SDS). Samples were boiled for 10 min at 95° C. before being resolved by 12% denaturing PAGE. Reaction products were visualized by phosphorimaging and quantified with ImageQuant (GE Healthcare).

RNA Cleavage Site Mapping.

A hydrolysis ladder (OH2) was obtained by incubating, 25 nM 5'-radiolabelled λ2 target ssRNA in hydrolysis buffer (25 mM CAPS (N-cyclohexyl-3-aminopropanesulphonic acid), pH 10.0, 0.25 mM EDTA) at 95° C. for 10 min, before quenching on ice. An RNase T1 ladder was obtained by incubating, 25 nM 5'-radiolabelled λ2 target ssRNA with 1 U RNase T1 (New England Biolabs) for 5 min at 37° C. in RNase T1 buffer (20 mM sodium citrate, pH 5.0, 1 mM EDTA, 2 M urea, 0.1 mg/ml yeast transfer RNA). The reaction was quenched by phenol/chloroformextraction before adding RNA gel-loading buffer. All products were resolved by 15% denaturing PAGE.

Electrophoretic Mobility Shift Assays.

In order to avoid dissociation of the Cas9-gRNA complex at low concentrations during target ssRNA binding experiments, binding reactions contained a constant excess of dCas9 (300 nM), increasing concentrations of sgRNA, and 0.1-1 nM of target ssRNA. The reaction buffer was supplemented with 10 mg/ml heparin in order to avoid non-specific association of apo-dCas9 with target substrates. Reactions were incubated at 37° C. for 45 min before being resolved by 8% native PAGE at 4° C. (0.53 TBE buffer with 5 mM $MgCl_2$). RNA and DNA were visualized by phosphorimaging, quantified with ImageQuant (GE Healthcare), and analyzed with Kaleidagraph (Synergy Software).

Cas9 Biotin Labeling

To ensure specific labeling at a single residue on Cas9, two naturally occurring cysteine residues were mutated to serine (C80S and C574S) and a cysteine point mutant was introduced at residue Met 1. To attach the biotin moiety, 10 mM wild-type Cas9 or dCas9 was reacted with a 50-fold molar excess of EZ-LinkMaleimide-PEG2-Biotin (Thermo Scientific) at 25° C. for 2h. The reaction was quenched by the addition of 10 mM DTT, and unreacted Maleimide-PEG2-Biotin was removed using a Bio-Gel P-6 column (Bio-Rad). Labeling was verified using a streptavidin bead binding assay, where 8.5 pmol of biotinylated Cas9 or non-biotinylatedCas9 was mixed with either 25 ml streptavidin-agarose (Pierce Avidin Agarose; Thermo Scientific) or 25 ml streptavidin magnetic beads (Dynabeads MyOne StreptavidinC1; Life Technologies). Samples were incubated inCas9 reaction buffer at room temperature for 30 min, followed by three washes with Cas9 reaction buffer and elution in boiling SDS-PAGE loading buffer. Elutions were analyzed using SDS-PAGE. Cas9 M1C biotinylation was also confirmed using mass spectroscopy performed in the QB3/Chemistry Mass Spectrometry Facility at UC Berkeley. Samples of intact Cas9 proteins were analyzed using an Agilent 1200 liquid chromatograph equipped with a Viva C8 (100 mm 31.0 mm, 5 mm particles, Restek) analytical column and connected in-line with an LTQ OrbitrapXL mass spectrometer (Thermo Fisher Scientific). Mass spectra were recorded in the positive ion mode. Mass spectral deconvolution was performed using ProMass software (Novatia).

GAPDH mRNA Pull-Down

Total RNA was isolated from HeLa-S3 cells using Trizol reagent according to the manufacturer's instructions (Life Technologies). Cas9-sgRNA complexes were reconstituted before pull-down experiments by incubating a twofold molar excess of Cas9 with sgRNA for 10 min at 37° C. in reaction buffer. HeLa total RNA (40 µg) or HeLa lysate (~5×10⁶ cells) was added to reaction buffer with 40U RNasin (Promega), PAMmer (5 mM) and the biotin-dCas9 (50 nM)-sgRNA (25 nM) in a total volume of 100 ml and incubated at 37° C. for 1 h. This mixture was then added to 25 ml magnetic streptavidin beads (Dynabeads MyOne Streptavidin C1; Life Technologies) pre-equilibrated in reaction buffer and agitated at 4° C. for 2 h. Beads were then washed six times with 300 ml wash buffer (20 mMTris-HCl, pH7.5, 150 mM NaCl, 5 mM $MgCl_2$, 0.1% Triton X-100, 5% glycerol, 1 mM DTT, 10 mg/ml heparin). Immobilized RNA was eluted by heating beads at 70° C. in the presence of DEPC-treated water and a phenol/chloroform mixture. Eluates were then treated with an equal volume of glyoxal loading dye (Life Technologies) and heated at 50° C. for 1 h before separation via 1% BPTE agarose gel (30 mM Bis-Tris, 10 mM PIPES, 10 mM EDTA, pH 6.5). Following Northern blot transfers, membranes were crosslinked using UV radiation and incubated in pre-hybridization buffer (UltraHYB Ultrasensitive Hybridization Buffer; Life Technologies) for 1 h at 46° C. before hybridization. Radioactive northern probes were synthesized using random priming of GAPDH and R-actin partial cDNAs (for cDNA primers, see Table 2) in the presence of [$\alpha$-$^{32}$P]dATP (PerkinElmer), using a Prime-It II Random Primer Labeling kit (Agilent Technologies). Hybridization was carried out for 3 h in pre-hybridization buffer at 46° C. followed by two washes with 23×SSC (300 mM NaCl, 30 mM trisodiumcitrate, pH 7, 0.5% (w/v) SDS) for 15 min at 46° C. Membranes were imaged using a phosphorscreen.

TABLE 2

RNA and DNA substrates used in Example 5 (all sequence are 5' to 3' unless otherwise denoted).

Figure 25C:
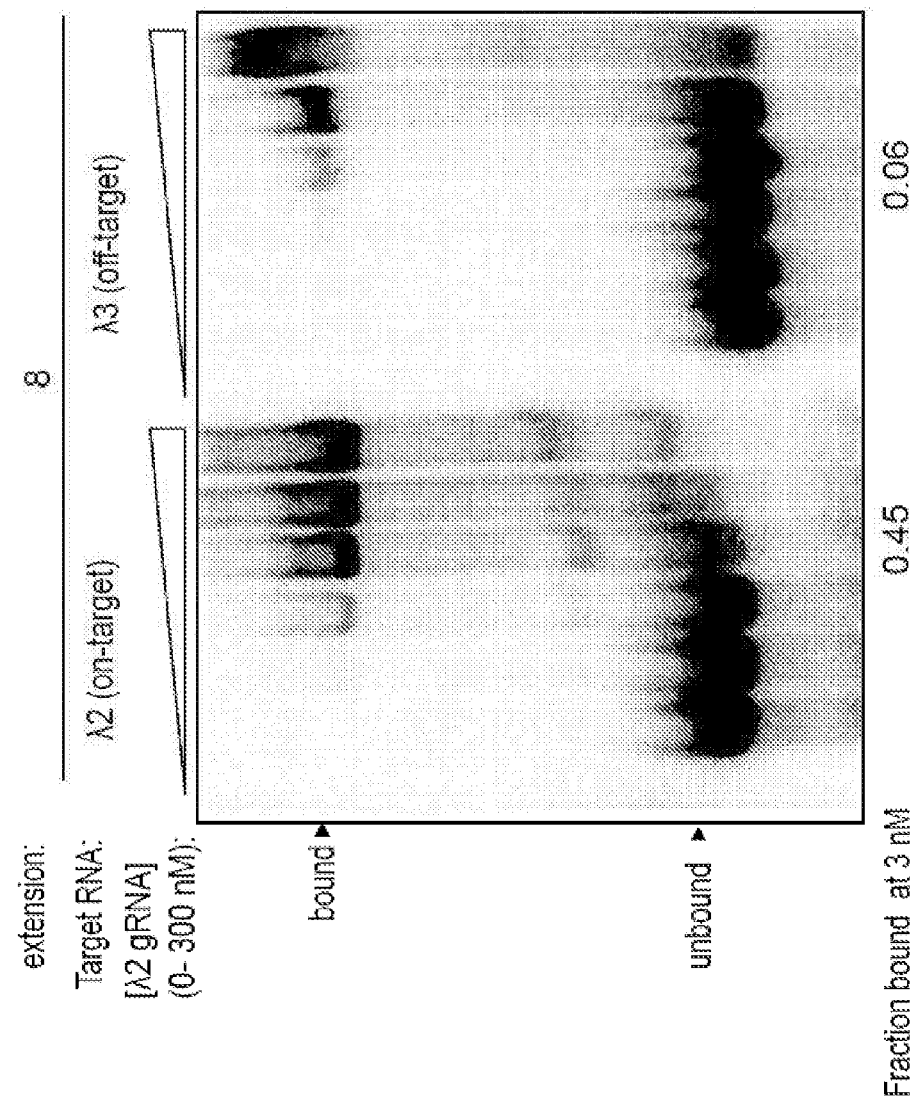
Figure 25D:
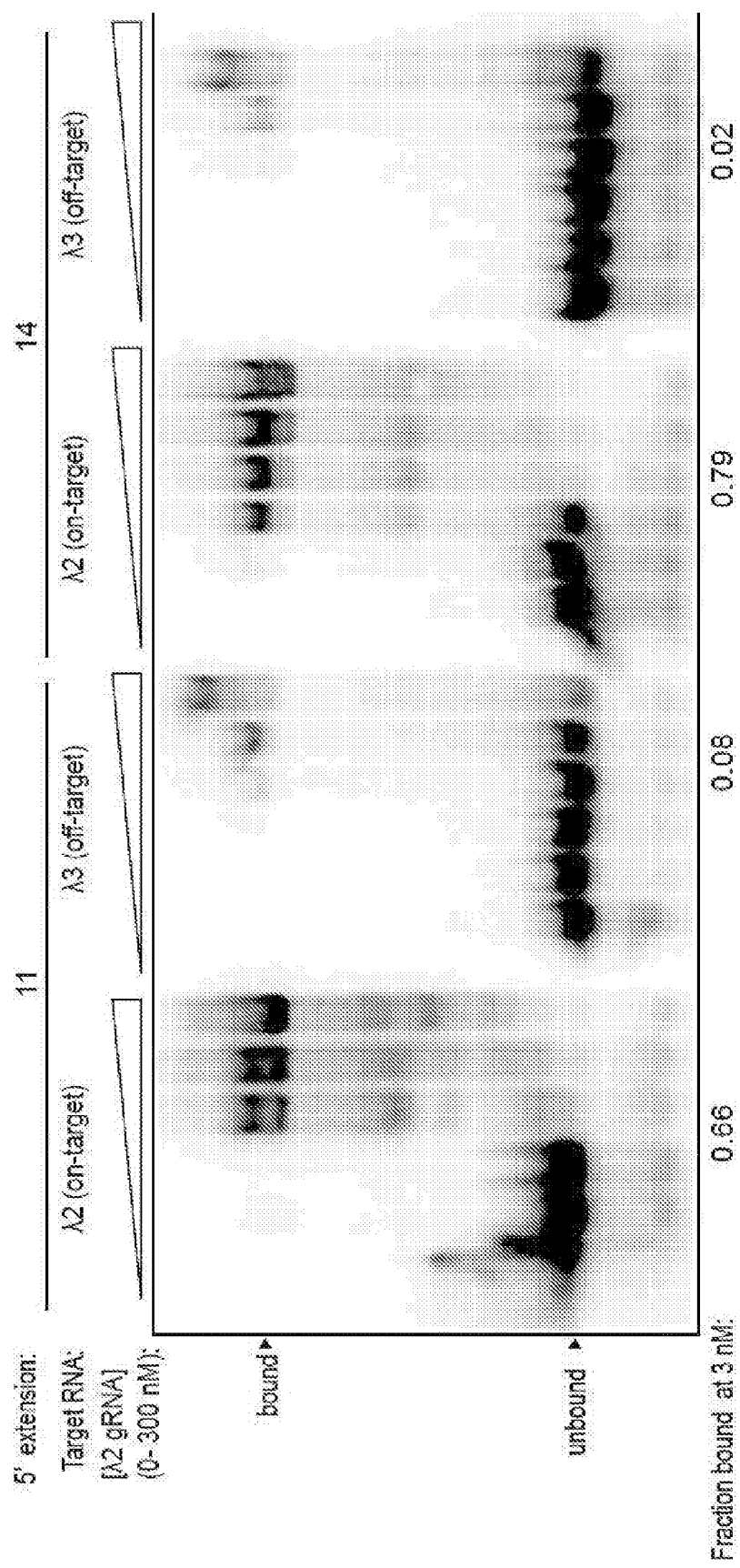
Figure 25E:
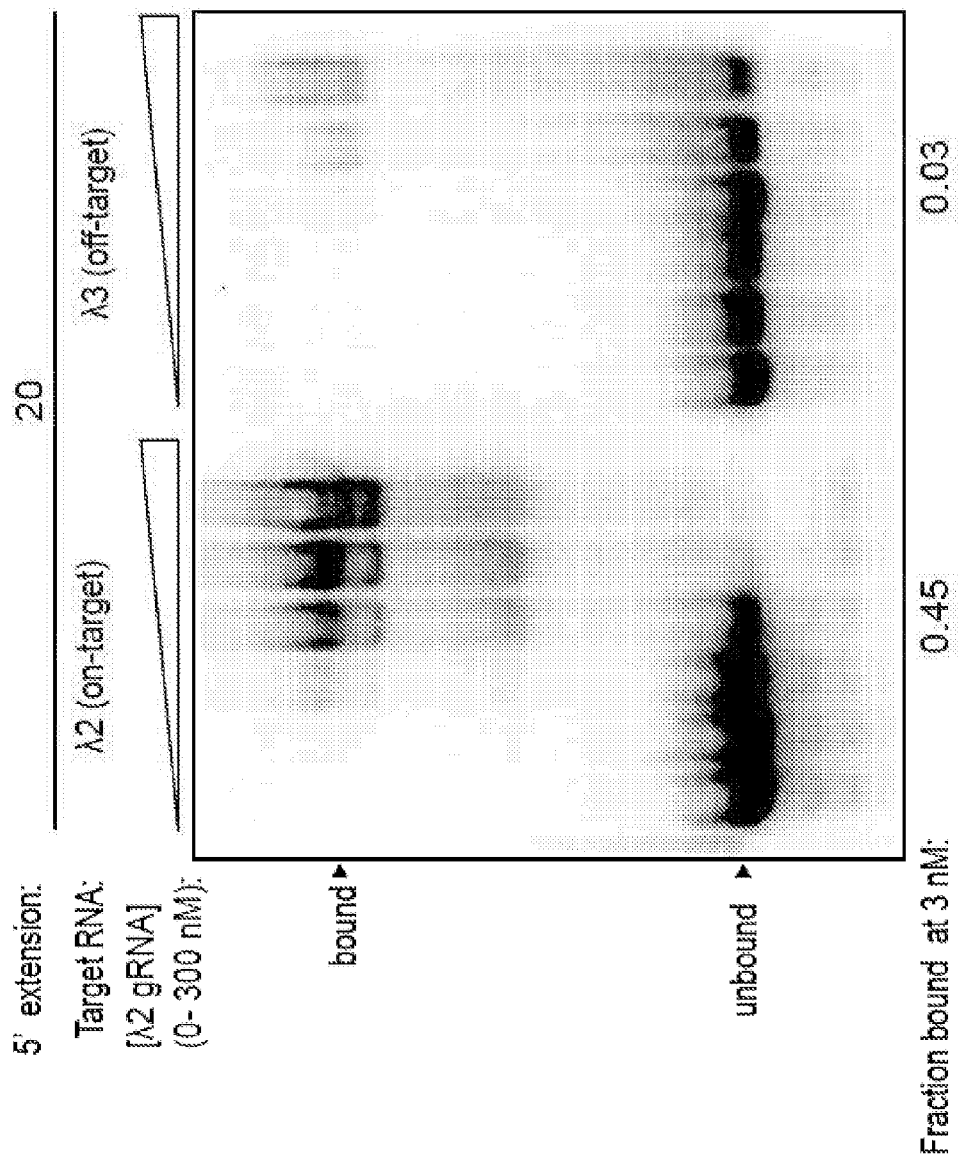

| Description | Sequence[a] | Used in: | SEQ ID NO: |
|---|---|---|---|
| Oligo for preparing dsDNA T7 promoter, in vitro transcription | TAATACGACTCACTATA | NA | 1404 |
| λ2-targeting crRNA | GUGAUAAGUGGAAUGCCAUGGUUUUAGAGCUAUGCUGUUUUG | FIG. 18C-18E, 20A, 21C-21D, 22, 23, 25A | 1407 |
| λ3-targeting crRNA | CUGGUGAACUUCCGAUAGUGGUUUUAGAGCUAUGCUGUUUUG | FIG. 20A | 1408 |
| λ4-targeting crRNA | CAGAUAUAGCCUGGUGGUUCGUUUUAGAGCUAUGCUGUUUUG | FIG. 20A | 1409 |
| ssDNA T7 template[b]: tracrRNA | AAAAAGCACCGACTCGGTGCCACTTTTTCAAGTTGATAACGGACTAGCCTTATTTTAACTTGCTATGCTGTCCTATAGTGAGTCGTATTA | NA | 1415 |
| tracrRNA (nt 15-87) | GGACAGCAUAGCAAGUUAAAAUAAGGCUAGUCCGUUAUCAACUUGAAAAAGUGGCACCGAGUCGGUGCUUUUU | FIG. 18C-18E, 20A, 21C-21D, 22, 23, 25A | 1416 |
| λ2-targeting sgRNA T7 template[c] | TAATACGACTCACTATAGGTGATAAGTGGAATGCCATGGTTTTAGAGCTATGCTGTTTTGGAAACAAAACAGCATAGCAAGTTAAAATAAGGCTAGTCCGTTATCAACTTGAAAAAGTGGCACCGAGTCGGTGCTTTTTTT | NA | 1479 |
| λ2-targeting sgRNA | GGUGAUAAGUGGAAUGCCAUGGUUUUAGAGCUAUGCUGUUUUGGAAACAAAACAGCAUAGCAAGUUAAAAUAAGGCUAGUCCGUUAUCAACUUGAAAAAGUGGCACCGAGUCGGUGCUUUUUUU | FIG. 19, 20B, 20D, 24, 25B | 1480 |
| λ2 target dsDNA duplex | 5'-GAGTGGAAGGATGCCAGTGATAAGTGGAATGCCATGTGGGCTGTCAAAATTGAGC-3'<br>3'-CTCACCTTCCTACGGTCACTATTCACCTTACGGTACACCCGACAGTTTTAACTCG-5' | FIG. 18C, 19A, 25C | 1419<br><br>1420 |
| λ2 ssDNA target strand (used to make heteroduplex DNA:RNA) | 3'-CTCACCTTCCTACGGTCACTATTCACCTTACGGTACACCCGACAGTTTTAACTCG-5' | FIG. 18C, 19A, | 1481 |
| 2λ2 ssDNA non-target strand (used to make heteroduplex DNA:RNA) | GAGTGGAAGGATGCCAGTGATAAGTGGAATGCCATGTGGGCTGTCAAAATTGAGC | FIG. 18C, 19A, 20D, 24 | 1463 |
| λ2 ssRNA target strand T7 template | GAGTGGAAGGATGCCAGTGATAAGTGGAATGCCATGTGGGCTGTCAAAATTGAGCCTATAGTGAGTCGTATTA | NA | 1482 |
| λ2 ssRNA target strand | 3'-CUCACCUUCCUACGGUCACUAUUCACCUUACGGUACACCCGACAGUUUUAACUCGG-5' | FIG. 18C-18E, 19-25 | 1483 |
| λ2 ssRNA non-target strand T7 template | GCTCAATTTTGACAGCCCACATGGCATTCCACTTATCACTGGCATCCTTCCACTCCTATAGTGAGTCGTATTA | NA | 1484 |

TABLE 2-continued

RNA and DNA substrates used in Example 5 (all sequence are 5' to 3' unless otherwise denoted).

| Description | Sequence[a] | Used in: | SEQ ID NO: |
|---|---|---|---|
| λ2 ssRNA non-target strand (used to make dsRNA) | GGAGTGGAAGGATGCCAGTGATAAGTGGA ATGCCATGTGGGCTGTCAAAATTGAGC | FIG. 18C, 19A | 1485 |
| 19 nt λ2 DNA PAMmer | TGGGCTGTCAAAATTGAGC | FIG. 18C-18E, 19, 20A-20B, 22-25 | 1466 |
| 18 nt λ2 "GG" PAMmer | GGGCTGTCAAAATTGAGC | FIG. 18C, 19 | 1486 |
| 19 nt λ2 DNA mutated PAMmer | ACCGCTGTCAAAATTGAGC | FIG. 18C, 19C | 1487 |
| 16 nt λ2 DNA "PAM-less" PAMmer | GCTGTCAAAATTGAGC | FIG. 18C, 19C | 1465 |
| 18 nt λ2 RNA PAMmer | GGGCUGUCAAAAUUGAGC | FIG. 18C, 19A | 1488 |
| 5 nt λ2 DNA PAMmer | TGGGC | FIG. 18E, 19C | |
| 10 nt λ2 DNA PAMmer | TGGGCTGTCA | FIG. 18E, 19C | 1489 |
| 15 nt λ2 DNA PAMmer | TGGGCTGTCAAAATT | FIG. 18E, 19C | 1490 |
| λ3 ssRNA target strand T7 template | AACGTGCTGCGGCTGGCTGGTGAACTTCCG ATAGTGCGGGTGTTGAATGATTTCCTATAG TGAGTCGTATTA | NA | 1491 |
| λ3 ssRNA target strand | 3'-UUGCACGACGCCGACCGACCACUUGAAG GCUAUCACGCCCACAACUUACUAAAGG-5' | FIG. 20A, 20B, 20D, 24, 25B | 1492 |
| λ4 ssRNA target strand T7 template | TCACAACAATGAGTGGCAGATATAGCCTGG TGGTTCAGGCGGCGCATTTTTATTGCCTAT AGTGAGTCGTATTA | NA | 1493 |
| λ4 ssRNA target strand | 3'-AGUGUUGUUACUCACCGUCUAUAUCGGA CCACCAAGUCCGCCGCGUAAAAAUAACG G-5' | FIG. 20A, 20B, 20D, 24 | 1494 |
| λ3 ssDNA non-target strand | AACGTGCTGCGGCTGGCTGGTGAACTTCCG ATAGTGCGGGTGTTGAATGATTTCC | FIG. 20D, 24 | 1421 |
| λ4 ssDNA non-target strand | TCACAACAATGAGTGGCAGATATAGCCTGG TGGTTCAGGCGGCGCATTTTTATTG | FIG. 20D, 24 | 1423 |
| 19 nt λ3 DNA PAMmer 25 | CGGGTGTTGAATGATTTCC | FIG. 20A-20B, 20D, 24, 25 | 1495 |
| 19 nt λ4 DNA PAMmer | AGGCGGCGCATTTTTATTG | FIG. 20A, 20B, 20D, 24 | 1496 |
| 21 nt λ2 extended DNA PAMmer | 5'-TGTGGGCTGTCAAAATTGAGC | FIG. 21C, 25A-25B | 1497 |

TABLE 2-continued

RNA and DNA substrates used in Example 5 (all sequence are 5' to 3' unless otherwise denoted).

| Description | Sequence<sup>a</sup> | Used in: | SEQ ID NO: |
|---|---|---|---|
| 21 nt λ3 extended DNA PAMmer | 5'-TGCGGGTGTTGAATGATTTCC | 25B | 1498 |
| 24 nt λ2 extended DNA PAMmer | 5'-CCATGTGGGCTGTCAAAATTGAGC | 25A-25B | 1499 |
| 24 nt λ3 extended DNA PAMmer | 5'-TAGTGCGGGTGTTGAATGATTTCC | 25B | 1500 |
| 27 nt λ2 extended DNA PAMmer | 5'-ATGCCATGTGGGCTGTCAAAATTGAGC | FIG. 21F-21G, 25A-25B | 1501 |
| 27 nt λ3 extended DNA PAMmer | 5'-CGATAGTGCGGGTGTTGAATGATTTCC | 25B | 1502 |
| 30 nt λ2 extended DNA PAMmer | 5'-GGAATGCCATGTGGGCTGTCAAAATTGAGC | 25A-25B | 1503 |
| 30 nt λ3 extended DNA PAMmer | 5'-TTCCGATAGTGCGGGTGTTGAATGATTTCC | 25B | 1504 |
| 33 nt λ2 extended DNA PAMmer | 5'-AGTGGAATGCCATGTGGGCTGTCAAAATTGAGC | 25A-25B | 1505 |
| 33 nt λ3 extended DNA PAMmer | 5'-AACTTCCGATAGTGCGGGTGTTGAATGATTTCC | 25B | 1506 |
| 36 nt λ2 extended DNA PAMmer | 5'-ATAAGTGGAATGCCATGTGGGCTGTCAAAATTGAGC | 25A | 1507 |
| 39 nt λ2 extended DNA PAMmer | 5'-GTGATAAGTGGAATGCCATGTGGGCTGTCAAAATTGAGC | 25A-25B | 1508 |
| 39 nt λ3 extended DNA PAMmer | 5'-CTGGTGAACTTCCGATAGTGCGGGTGTGAATGATTTCC | 25B | 1509 |
| non-PAM λ2 dsDNA | 5'-GAGTGGAAGGATGCCAGTGATAAGTGGAATGCCATGACCGCTGTCAAAATTGAGC-3' | FIG. 21C | 1510 |
| | 3'-CTCACCTTCCTACGGTCACTATTCACCTTACGGTACTGGCGACAGTTTTAACTCG-5' | | 1511 |
| non-PAM λ2 ssRNA target strand T7 template | GAGTGGAAGGATGCCAGTGATAAGTGGAATGCCATGACCGCTGTCAAAATTGAGCCTATAGTGAGTCGTATTA | NA | 1512 |

TABLE 2-continued

RNA and DNA substrates used in Example 5 (all sequence are 5' to 3' unless otherwise denoted).

| Description | Sequence[a] | Used in: | SEQ ID NO: |
|---|---|---|---|
| non-PAM λ2 ssRNA target strand | 3'-CUCACCUUCCUACGGUCACUAUUCACCUU ACGGUACTGGCGACAGUUUUAACUCGG-5' | FIG. 21C | 1513 |
| λ2 2' OMe capped PAMmer[d] | \*UGGGCTGTCAAAATTGAG\*C | 27 | 1514 |
| λ2 PS capped PAMmer[d] | T\*GGGCTGTCAAAATTGAG\*C | 27 | 1515 |
| λ2 2'F capped PAMmer[d] | \*UGGGCTGTCAAAATTGAG\*C | 27 | 1516 |
| λ2 LNA capped PAMmer[d] | \*TGGGCTGTCAAAATTGAG\*C | 27 | 1517 |
| λ2 19 nt 2' OMe interspersed PAMmer[d] | \*UGGGC\*UGTCA\*AAATT\*GAG\*C | 27 | 1518 |
| GAPDH-targeting sgRNA 1 T7 template[e] | TAATACGACTCACTATAGGGGCAGAGATG ATGACCCTGTTTAAGAGCTATGCTGGAAAC AGCATAGCAAGTTTAAATAAGGCTAGTCCG TTATCAACTTGAAAAAGTGGCACCGAGTCG GTGCTTTTTTT | FIG. 21F-21G, 28 | 1519 |
| GAPDH-targeting sgRNA 1 | GGGGCAGAGAUGAUGACCCUGUUUAAGA GCUAUGCUGGAAACAGCAUAGCAAGUUUA AAUAAGGCUAGUCCGUUAUCAACUUGAAA AAGUGGCACCGAGUCGGUGCUUUUUUU | FIG. 21F-21G, 28 | 1520 |
| GAPDH-targeting sgRNA 2 T7 template[e] | TAATACGACTCACTATAGGCCAAAGTTGT CATGGATGACGTTTAAGAGCTATGCTGGAA ACAGCATAGCAAGTTTAAATAAGGCTAGTC CGTTATCAACTTGAAAAAGTGGCACCGAGT CGGTGCTTTTTTT | FIG. 21F, 28 | 1521 |
| GAPDH-targeting sgRNA 2 | GGCCAAAGUUGUCAUGGAUGACGUUUAA GAGCUAUGCUGGAAACAGCAUAGCAAGUU UAAAUAAGGCUAGUCCGUUAUCAACUUGA AAAAGUGGCACCGAGUCGGUGCUUUUUUU | FIG. 21F, 28 | 1522 |
| GAPDH-targeting sgRNA 3 T7 template[e] | TAATACGACTCACTATAGGCCAAAGTTGT CATGGATGACGTTTAAGAGCTATGCTGGAA ACAGCATAGCAAGTTTAAATAAGGCTAGTC CGTTATCAACTTGAAAAAGTGGCACCGAGT CGGTGCTTTTTTT | FIG. 21F, 28 | 1521 |
| GAPDH-targeting sgRNA 3 | GGAUGUCAUCAUAUUUGGCAGGGUUUAA GAGCUAUGCUGGAAACAGCAUAGCAAGUU UAAAUAAGGCUAGUCCGUUAUCAACUUGA AAAAGUGGCACCGAGUCGGUGCUUUUUUU | FIG. 21F, 28 | 1523 |
| GAPDH-targeting sgRNA 4 T7 template[e] | TAATACGACTCACTATAGGATGTCATCAT ATTTGGCAGGGTTTAAGAGCTATGCTGGAA ACAGCATAGCAAGTTTAAATAAGGCTAGTC CGTTATCAACTTGAAAAAGTGGCACCGAGT CGGTGCTTTTTTT | FIG. 21F, 28 | 1524 |
| GAPDH-targeting sgRNA 4 | GGAUGUCAUCAUAUUUGGCAGGGUUUAAGA GCUAUGCUGGAAACAGCAUAGCAAGUUUAA AUAAGGCUAGUCCGUUAUCAACUUGAAAAA GUGGCACCGAGUCGGUGCUUUUUUU | FIG. 21F, 28 | 1525 |
| GAPDH PAMmer 1 | ATGACCCTTGGGGCTCCCCCCTGCAAA | FIG. 21F-21G, 28 | 1526 |
| GAPDH PAMmer 2 | TGGATGACCGGGGCCAGGGGTGCTAAG | FIG. 21F, 28 | 1527 |

TABLE 2-continued

RNA and DNA substrates used in Example 5 (all sequence are 5' to 3' unless otherwise denoted).

| Description | Sequence<sup>a</sup> | Used in: | SEQ ID NO: |
|---|---|---|---|
| GAPDH PAMmer 3 | TTGGCAGGTGGTTCTAGACGGCAGGTC | FIG. 21F, 28 | 1528 |
| GAPDH PAMmer 4 | CCCCAGCGTGGAAGGTGGAGGAGTGGG | FIG. 21F, 28 | 1529 |
| GAPDH PAMmer 1 2'OMe v1 | A*UGACC*CTAGG*GGCTC*CCCCC*UGCAA*A | FIG. 21G, 28 | 1474 |
| GAPDH PAMmer 1 2'OMe v2 | *ATG*ACCC*UAGG*GGCT*CCCC*CCTG*CAA*A | FIG. 21G, 28 | 1475 |
| GAPDH PAMmer 1 2'OMe v3 | *ATG*ACC*CU*AGG*GGC*UCC*CCC*CTG*CAA*A | FIG. 21G, 28 | 1476 |
| GAPDH PAMmer 1 2'OMe v4 | *AT*GA*CC*CT*AGG*GG*CT*CC*CC*CC*UG*CA*AA | FIG. 21G, 28 | 1477 |
| GAPDH PAMmer 1 2'OMe v5 | *AT*GA*CC*CT*AG*GG*GC*TC*CC*CC*CU*GC*AA*A | FIG. 21G, 28 | 1530 |
| GAPDH cDNA primer Fwd | CTCACTGTTCTCTCCCTCCGC | FIG. 21G, 21F | 1531 |
| GAPDH cDNA primer Rev | AGGGGTCTACATGGCAACTG | FIG. 21G, 21F | 1532 |
| β-actin cDNA primer Fwd | AGAAAATCTGGCACCACACC | FIG. 21G, 21F | 1533 |
| β-actin cDNA primer Rev | GGAGTACTTGCGCTCAGGAG | FIG. 21G, 21F | 1534 |

*Guide crRNA sequences and complementary DNA target strand sequences are shown in red.
PAM sites (5'-NGG-3') are highlighted in yellow on the non-target strand when adjacent to the target sequence or in the PAMmer oligonucleotides.
†The T7 promoter is indicated in bold (or reverse complement of), as well as 5' G or GG included in the ssRNA product by T7 polymerase.
NA, not applicable.
‡sgRNA template obtained from pIDT, subsequently linearised by AflII for run-off transcription.
§Positions of modifications depicted with asterisks preceding each modified nucleotide in each case (except for PS linkages which are depicted between bases)
PS: phosphorothioate bond
LNA: locked nucleic acid

Example 6: Use of Quenched PAMmers

The following demonstrates the labeling of single stranded target nucleic acids using a quenched PAMmer. This provides a low-background single-stranded nucleic acid detection system, in this example case based on a quenched PAMmer having a fluorescent detectable label and a quencher moiety. "F" is the detectable label in this example and is a fluorescent dye, which can be attached to the PAMmer in a variety of ways (e.g., through an amino-dT nucleotide and a NHS-ester containing dye or as a replacement for a nucleotide (internal Cy5)). "Q" is the quencher moiety. The quencher moiety in this example is attached 5' of the fluorescent moiety. The quenched PAMmer is sometimes referred to in this example as an "FQ PAMmer."

When uncleaved (e.g., when not yet bound to its target nucleic acid, or when bound but uncleaved), the FQ PAMmer, which contains a quenchable detectable label (e.g., a fluorophore)(e.g., 3' of the Cas9 RuvC domain cleavage site) that is quenched by a quencher moiety (e.g., present 5' of the cleavage site). Thus, when uncleaved, the FQ PAMmer produces little signal (e.g., little to no fluorescent signal). Upon concomitant hybridization of the FQ PAMmer sequence and guide RNA (e.g., guide-RNA) specific recognition and cleavage by Cas9 will the signal (e.g., fluorescent signal) is observed. Cleavage by Cas9 hydrolyses a phosphodiester bond positioned somewhere between the quenchable detectable label (e.g., the fluorophore) and the quencher moiety, allowing the quencher moiety to diffuse away from the single stranded target nucleic acid. Cas9 cleavage of the PAMmer can be predicated based on complementarity between the guide RNA (e.g., guide RNA) and the single stranded target nucleic acid.

Figure 30A:
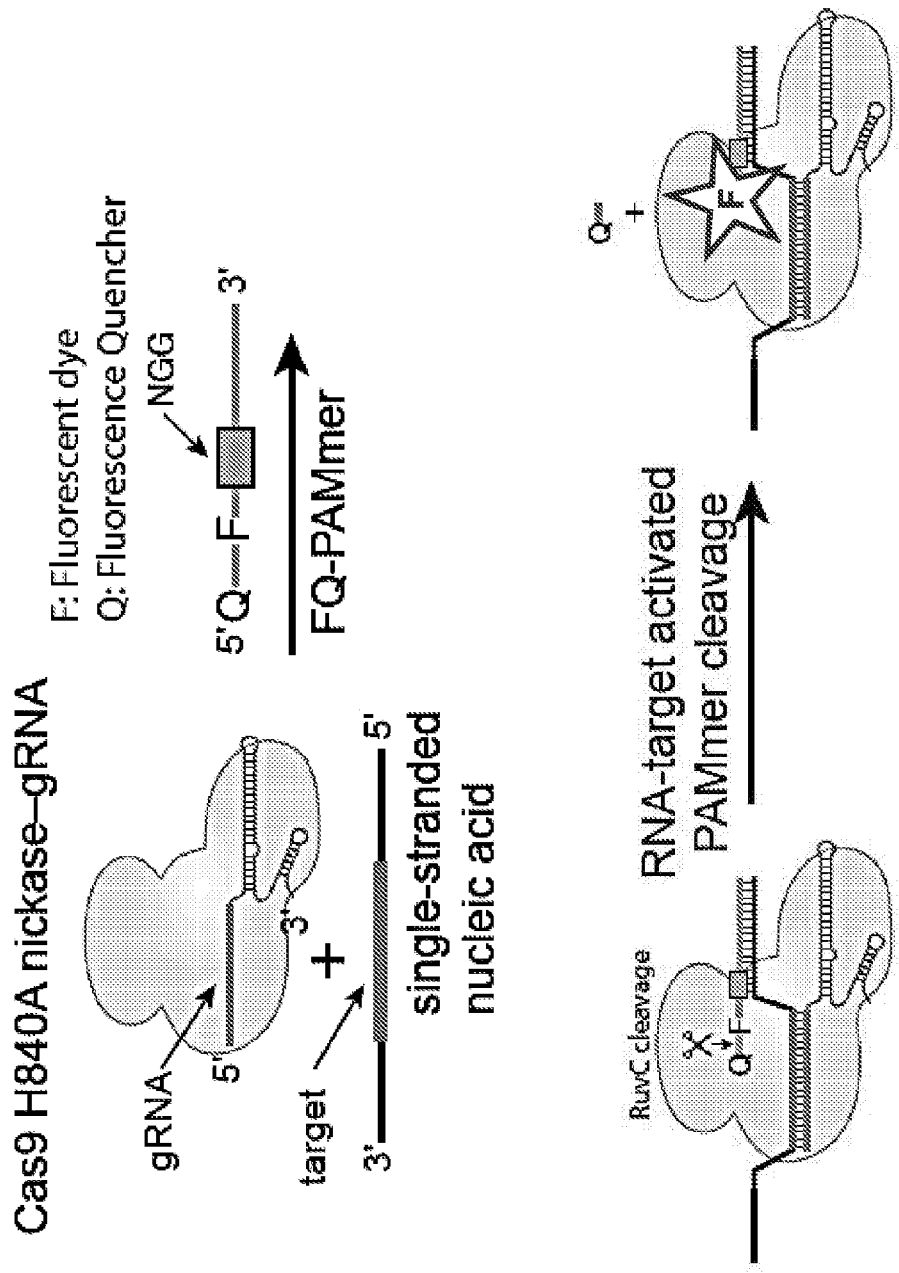
FIGS. 30A-30E provide data relating to quenched PAMmers facilitating cleavage-mediated fluorescence.
Figure 30B:
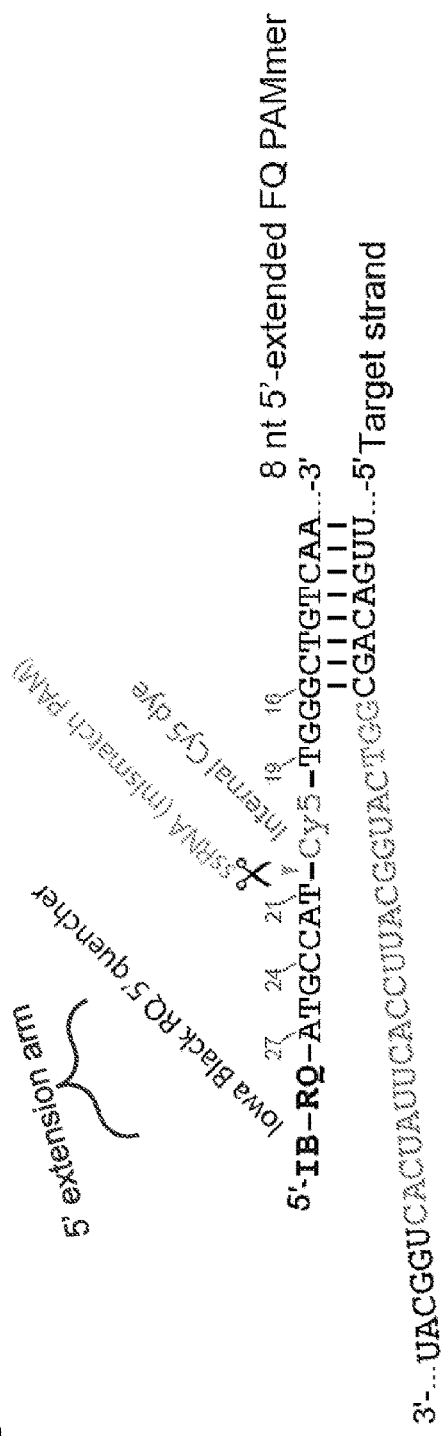
Figure 30C:
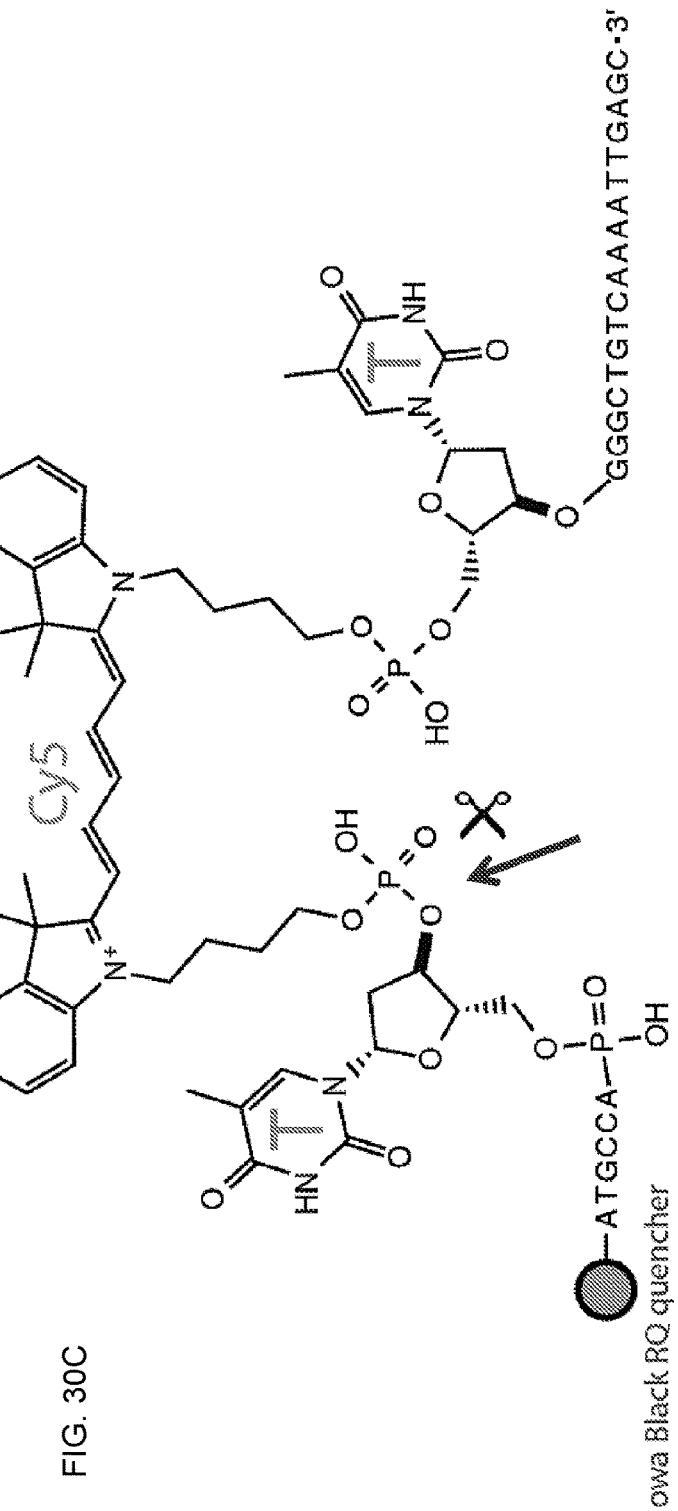

The quenched PAMmer used in this particular example is shown in FIG. 30B, with a more detailed look at the internal Cy5 attachment chemistry in FIG. 30C. Using the FQ PAMmer shown in FIG. 30B, a time-dependent increase in fluorescence was observed only when Cas9 (H840A) was in the presence of a single stranded target (an RNA target in this case) (FIG. 30D and FIG. 30E), indicating that the RuvC catalytic activity (The RuvC domain of the Cas9 protein) is responsible for the de-quenching of the quenched PAMmer. A variety of PAMmer designs (which can include different fluorescent dyes and quencher moieties, attachment chemistries, attachment positions and PAMmer nucleotide lengths and compositions) can yield even better performing quenched PAMmers.

Figure 30D:
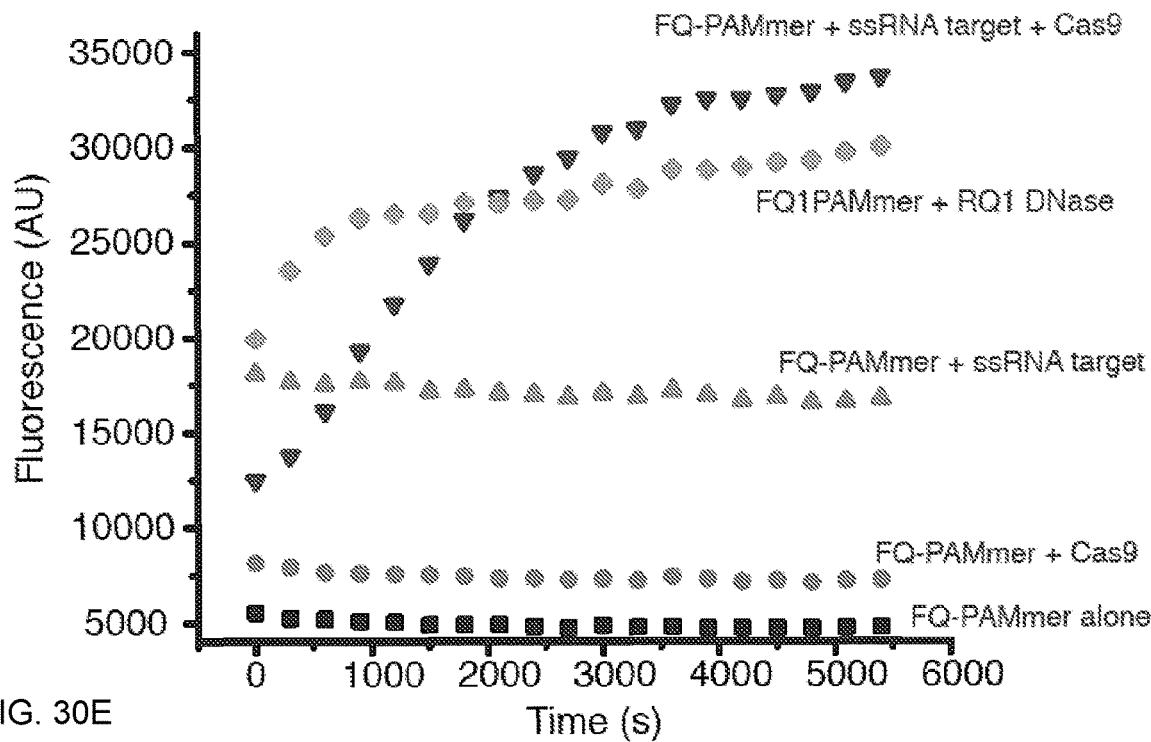
Figure 30E:
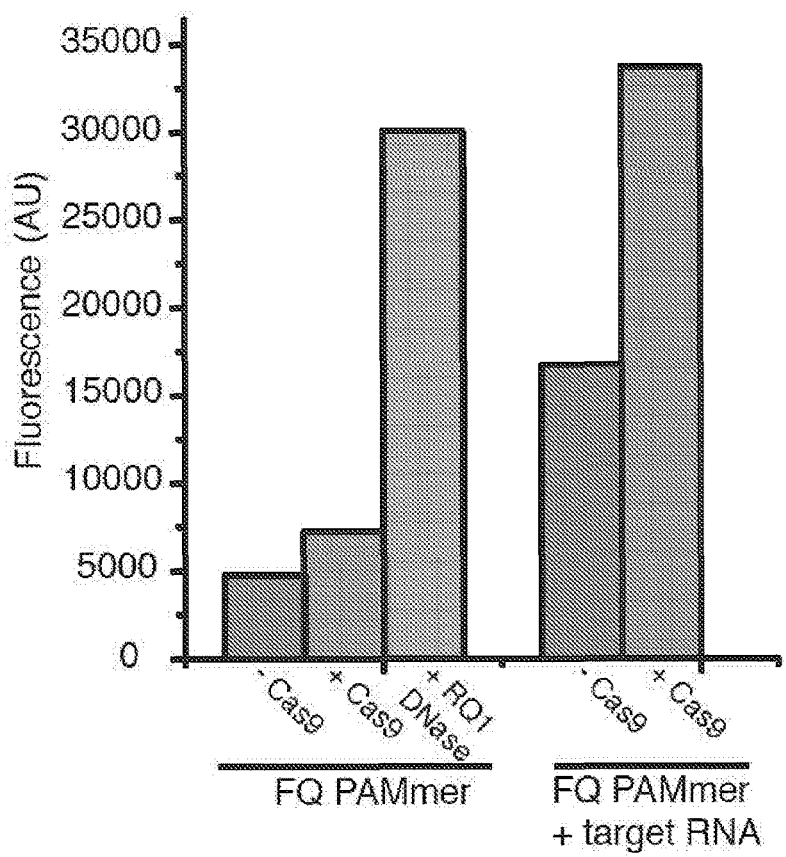

It should be noted that upon hybridization to the target single stranded RNA, the FQ PAMmer became partially de-quenched, leading to a time-independent increase in fluorescence (FIG. 30D). This is likely due to the ordering of the PAMmer through duplex formation, which effectively increases the length between the fluorophore and the quencher, leading to an increase in fluorescence signal. This effect can be reduced by reducing the number of nucleotides between the fluorophore and quencher moiety.

FIG. 29A-29B. Cas9 complexed with a Cas9 guide RNA (gRNA) is able to cleave PAMmers with 5' extensions. (FIG. 29A) Cas9 (H840A)-gRNA cleaved DNA PAMmers containing 8 nt 5' extensions when hybridized to ssDNA or ssRNA targets when the PAMmer was base-paired or mismatched to the target strand. Cleavage assays were performed with 100 nM Spy Cas9:RNA in the presence of about 1 nM 3'-$^{32}$P-labeled 27 nt PAMmers mixed with a either DNA or RNA targets. Time points were taken at 0, 5, 30, 60 minutes and immediately stopped with formamide-EDTA buffer. Samples were resolved on a 12% urea-PAGE gel and visualized using a phoshorimager. (FIG. 29B) The major PAMmer cleavage product depended on the target nucleic acid identity. Cleavage sites are indicated by colored arrows.

FIG. 30. Quenched PAMmers facilitate specific Cas9 cleavage-mediated fluorescence detection of target nucleic acids. (FIG. 30A) Schematic diagram depicting the approach to use quenched PAMmers to detect single-stranded nucleic acid targets in a Cas9 guide RNA-specific manner. (FIG. 30B) Schematic depicting one embodiment of a quenched PAMmer design for targeting single stranded target nucleic acids (e.g., single stranded target RNA). In this embodiment, an internal Cy5 dye is placed 3' of the Cas9 H840A cleavage site of the quenched PAMmer and the 5' end of the quenched PAMmer contains an Iowa Black RQ quencher moiety. (FIG. 30C) A closer look at the internal Cy5 linkage chemistry for the quenched PAMmer design in B. An arrow depicts the predicted Cas9 H840A cleavage site. The chemical structure of the Iowa Black RQ quencher (shown as a circle) is proprietary (IDT technologies). (FIG. 30D) Time course of the quenched PAMmer (see A-C) cleavage reaction by Cas9 H840A and RQ1 DNase (as a positive control). Cleavage assays were carried out using 25 nM quenched PAMmer in the presence of 100 nM Cas9 H840A and 500 nM target RNA. 1U RQ1 DNase and 25 nM quenched PAMmer was used as a positive control. Fluorescence was measured at 612 nm and 670 nm at five minute time points for 90 minutes. (FIG. 30E) End point fluorescence measurements (at 90 minutes) of the data collected in FIG. 30D.

Example 7: Use of Quenched PAMmers

The following are tables (Table 3 and Table 4) and plots of the data therein (FIG. 32 and FIG. 33, respectively) depicting accumulated data using quenched PAMmers to label RNA targets.

Figure 32:
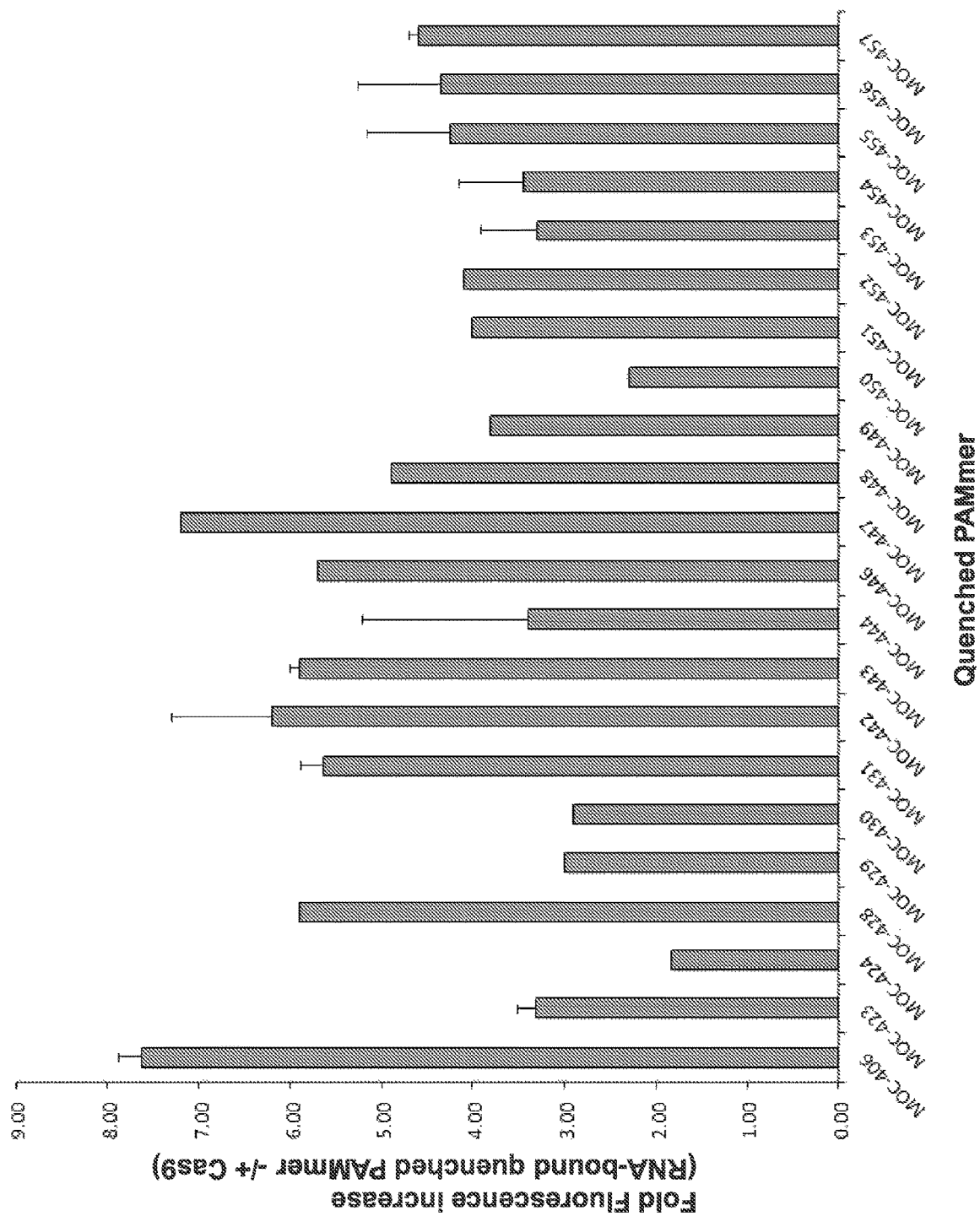
FIG. 32 presents a graphical illustration of the data presented in Table 3 (see Example 7).

FIG. 32 RCas9 (CRISPR/Cas9 directed for RNA-guided ssRNA binding and/or cleavage)-mediated fold-change in fluorescence for quenched PAMmers tested in Table 3. For quenched PAMmers tested in two independent experiments, error bars represent the range between measurements, while for quenched PAMmers tested in three or more independent experiments, error bars represent the standard deviation between measurements. See Table 3 for more details (including individual data points) for each quenched PAMmer.

Figure 33:
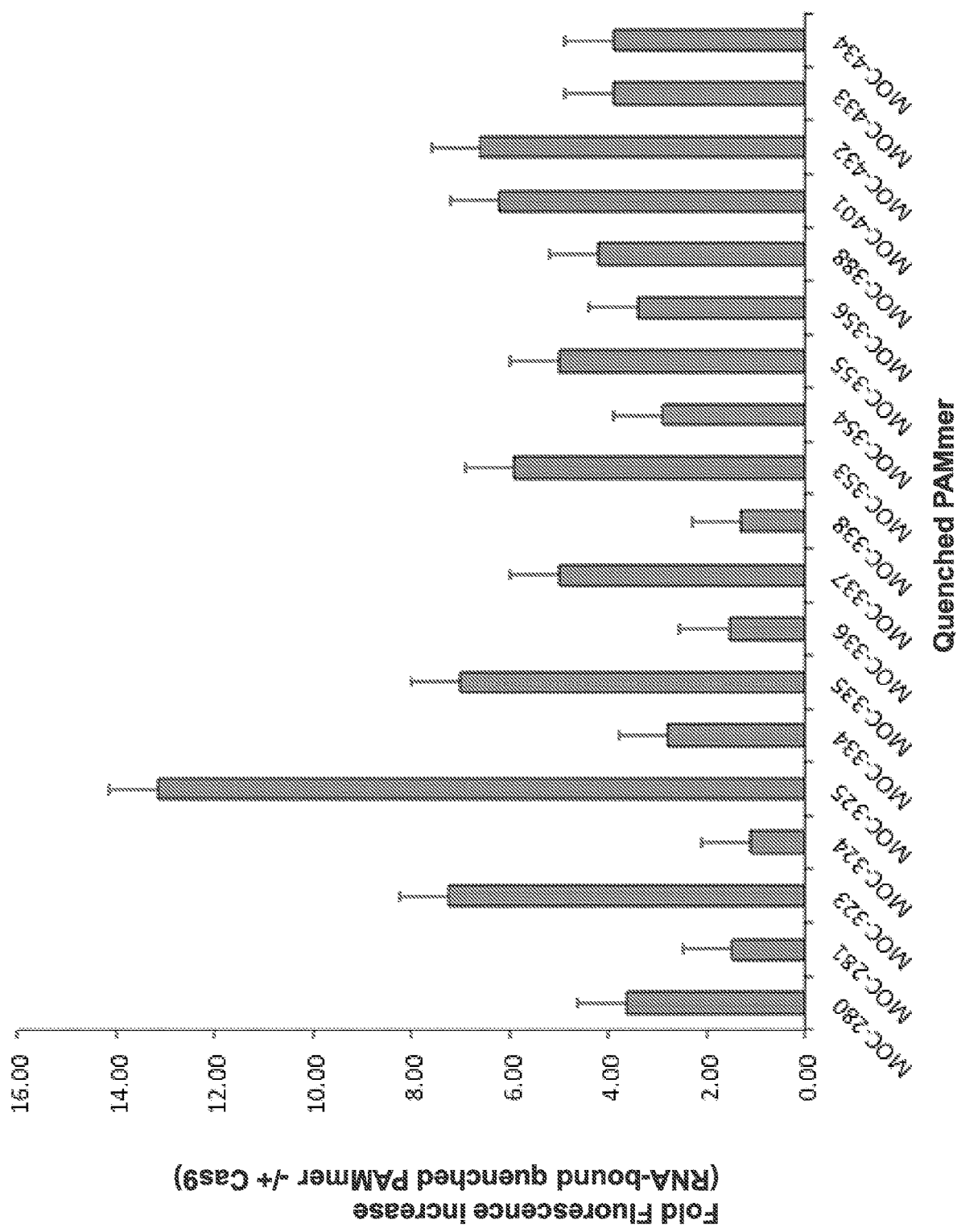
FIG. 33 presents a graphical illustration of the data presented in Table 4 (see Example 7).

FIG. 33 RCas9 (CRISPR/Cas9 directed for RNA-guided ssRNA binding and/or cleavage)-mediated fold-change in fluorescence for quenched PAMmers tested in Table 4. For quenched PAMmers tested in two independent experiments, error bars represent the range between measurements, while for quenched PAMmers tested in three or more independent experiments, error bars represent the standard deviation between measurements. See Table 4 for more details (including individual data points) for each quenched PAMmer.

TABLE 3

Quenched PAMmer 2'OH sugar and phosphodiester-linkage modification tolerance. Fluorescence fold-change values were obtained by calculating the fold-change difference between raw fluorescence values for samples containing quenched-PAMmer:RNA-target:RCas9 and samples containing quenched-PAMmer: target-RNA at the end of each time-course. Abbreviations for fluorophores, quenchers and modified nucluotides are as follows: iCy5: internal Cy5 fluorophore, replaces a complete nucleotide; Q: 5-prime quencher; mX: 2'-O-methyl(2'OMe)-modified nucleotide 'X'; fX: 2'F-modified nucleotide 'X'; * depicts a phosphorothioate linkage between neighbouring bases. 3SpC3; 3-prime C3-akyl moiety.

| SEQ ID NO | ID | Sequence | Fold-change range | Avg Fold-change | Range/SD |
|---|---|---|---|---|---|
| 1597 | MOC-406 | Q/ATGCCAT/iCy5/TGGGCTGTCAAAATTGAGC | 7.6-7.9 | 7.63 | 0.25 |
| 1598 | MOC-423 | Q/ATGCCAT/iCy5/TGGGfCTfGTfCAfAAfATfUGfAGfC | 3.4 | 3.32 | 0.20 |
| 1599 | MOC-424 | Q/ATGCCAT/iCy5/TGGGmCTmGTmCAmAAmATmUGmAGmC | 1.8 | 1.83 | 0.00 |
| 1600 | MOC-428 | Q/ATGCCAT/iCy5/TGGGCTfGTfCAfAAfATfUGfAGfC | 5.9 | 5.90 | 0.00 |

TABLE 3-continued

Quenched PAMmer 2'OH sugar and phosphodiester-linkage modification tolerance. Fluorescence fold-change values were obtained by calculating the fold-change difference between raw fluorescence values for samples containing quenched-PAMmer:RNA-target:RCas9 and samples containing quenched-PAMmer:target-RNA at the end of each time-course. Abbreviations for fluorophores, quenchers and modified nucluotides are as follows: iCy5: internal Cy5 fluorophore, replaces a complete nucleotide; Q: 5-prime quencher; mX: 2'-O-methyl(2'OMe)-modified nucleotide 'X'; fX: 2'F-modified nucleotide 'X'; * depicts a phosphorothioate linkage between neighbouring bases. 3SpC3; 3-prime C3-akyl moiety.

| SEQ ID NO | ID | Sequence | Fold-change range | Avg Fold-change | Range/SD |
|---|---|---|---|---|---|
| 1601 | MOC-429 | Q/ATGCCAT/iCy5/TGGGfCTfGTfCAfAAfATfUG*fA*G*fC | 3 | 3.00 | 0.00 |
| 1602 | MOC-430 | Q/ATGCCAT/iCy5/TGGGfCTfGTfCAfAAfATUG*fA*G*fC/3SpC3 | 2.9 | 2.90 | 0.00 |
| 1603 | MOC-431 | Q/ATGCCAT/iCy5/T*G*G*G*fC*T*fG*T*fC*A*fA*A*fA*T*fU*G*fA*G*fC | 5.4-5.9 | 5.63 | 0.25 |
| 1604 | MOC-442 | Q/ATGCCAT/iCy5/T*G*G*G*C*TmG*T*mC*A*mA*A*mA*T*mU*G*mA*G*mC | 4.6-7.6 | 6.20 | 1.09 |
| 1605 | MOC-443 | Q/ATGCCAT/iCy5/T*G*G*G*C*T*fG*T*fC*A*fA*A*fA*T*fU*G*fA*G*fC | 5.4-6.4 | 5.90 | 0.10 |
| 1606 | MOC-444 | Q/A*T*G*C*CAT/iCy5/T*G*G*G*C*T*fG*T*fC*A*fA*A*fA*T*fU*G*fA*G*fC | 2.5-4.3 | 3.40 | 1.80 |
| 1607 | MOC-446 | Q/mATGCCAT/iCy5/T*G*G*G*C*T*mG*T*mC*A*mA*A*mA*T*mU*G*mA*G*mC | 5.7 | 5.70 | 0.00 |
| 1608 | MOC-447 | Q/AmUGCCAT/iCy5/T*G*G*G*C*T*mG*T*mC*A*mA*A*mA*T*mU*G*mA*G*mC | 7.2 | 7.20 | 0.00 |
| 1609 | MOC-448 | Q/ATmGCCAT/iCy5/T*G*G*G*C*T*mG*T*mC*A*mA*A*mA*T*mU*G*mA*G*mC | 4.9 | 4.90 | 0.00 |
| 1610 | MOC-449 | Q/ATGmCCAT/iCy5/T*G*G*G*C*T*mG*T*mC*A*mA*A*mA*T*mU*G*mA*G*mC | 3.8 | 3.80 | 0.00 |
| 1611 | MOC-450 | Q/ATGCmCAT/iCy5/T*G*G*G*C*T*mG*T*mC*A*mA*A*mA*T*mU*G*mA*G*mC | 2.3 | 2.30 | 0.00 |
| 1612 | MOC-451 | Q/ATGCCmAT/iCy5/T*G*G*G*C*T*mG*T*mC*A*mA*A*mA*T*mU*G*mA*G*mC | 4 | 4.00 | 0.00 |
| 1613 | MOC-452 | Q/ATGCCAmU/iCy5/T*G*G*G*C*T*mG*T*mC*A*mA*A*mA*T*mU*G*mA*G*mC | 4.1 | 4.10 | 0.00 |
| 1614 | MOC-453 | Q/ATGCCAT/iCy5/T*G*G*G*mC*T*mG*T*mC*A*mA*A*mA*T*mU*G*mA*G*mC | 3-3.6 | 3.30 | 0.60 |
| 1615 | MOC-454 | Q/ATGCCAT/iCy5/T*G*G*mG*C*mU*G*mU*C*mA*A*mA*mU*T*mG*A*mG*C | 3.1-3.8 | 3.45 | 0.70 |
| 1616 | MOC-455 | Q/A*T*G*CCAT/iCy5/T*G*G*mG*C*mU*G*mU*C*mA*A*mA*A*mU*T*mG*A*mG*C | 3.7-4.8 | 4.25 | 0.90 |
| 1617 | MOC-456 | Q/A*T*G*CCAT/iCy5/T*G*G*G*C*T*mG*T*mC*A*mA*A*mA*T*mU*G*mA*G*mC | 3.9-4.8 | 4.35 | 0.90 |
| 1618 | MOC-457 | Q/A*T*G*CCAT/iCy5/T*G*G*G*mC*T*mG*T*mC*A*mA*A*mA*T*mU*G*mA*G*mC | 4.1-5.1 | 4.60 | 0.10 |

TABLE 4

Quenched PAMmer fluorophore-quencher spacing study. Fluorescence fold-change values were obtained by calculating the fold-change difference between raw fluorescence values for samples containing quenched-PAMmer:RNA-target:RCas9 and samples containing quenched-PAMmer:target-RNA at the end of each time-course. Abbreviations for fluorophores and quenchers : iCy5: internal Cy5 fluorophore, replaces a complete nucleotide; IATTO647NN: internal ATTO-647 fluorescent dye, which is conjugated to a T nucleotide; iCF640RN: Biotium CF 640R fluorescent dye, which is conjugated to a T nucleotide; 5IAbRQ: 5-prime Iowa-Black RQ quencher; iIB-QB: internal Iowa-Black RQ quencher; 5IAbkFQ: internal Iowa-Black FQ Quencher; ZEN: IDT ZEN quencher.

| SEQ ID NO | ID | Sequence | Fold-change range | Avg Fold-change | Range/SD |
|---|---|---|---|---|---|
| 1619 | MOC-280 | 5IAbRQ/ATGCCAT/iCy5/TGGGCTGTCAAAATTGAGC | 3.0-4.4 | 3.62 | 0.44 |
| 1620 | MOC-281 | 5IAbRQ/ATGCCA/iCy5/GTGGGCTGTCAAAATTGAGC | 1.5 | 1.50 | 0.00 |
| 1621 | MOC-323 | 5IAbRQ/CCAT/iCy5/TGGGCTGTCAAAATTGAGC | 6.0-10.5 | 7.25 | 2.46 |
| 1622 | MOC-324 | 5IAbRQ/AT/iCy5/TGGGCTGTCAAAATTGAGC | 1.1 | 1.12 | 0.04 |
| 1623 | MOC-325 | 5IAbRQ/CCAT/IATTO647NN/TGGGCTGTCAAAATTGAGC | 11.8-14.5 | 13.16 | 2.75 |
| 1624 | MOC-334 | 5IAbRQ/ATGCCAG/iCy5/TGGGCTGTCAAAATTGAGC | 2.6-3.0 | 2.79 | 0.39 |
| 1625 | MOC-335 | AATG/iIB-QB/CCAT/iCy5/TGGGCTGTCAAAATTGAGC | 6.5-7.5 | 7.02 | 1.00 |
| 1626 | MOC-336 | AATG/ZEN/CCAT/iCy5/TGGGCTGTCAAAATTGAGC | 1.5-1.6 | 1.54 | 0.10 |
| 1627 | MOC-337 | 5IAbRQ/ZEN/ATGCCAT/iCy5/TGGGCTGTCAAAATTGAGC | 4.8-5.2 | 5.00 | 0.40 |
| 1628 | MOC-338 | 5IAbRQ/ATGCCATGTGGGC/IATTO647NN/GTCAAAATTGAGC | 1.2-1.3 | 1.29 | 0.10 |
| 1629 | MOC-353 | 5IAbRQ/ZEN/CCAT/iCy5/TGGGCTGTCAAAATTGAGC | 5.9 | 5.90 | 0.00 |
| 1630 | MOC-354 | 5IAbRQ/CAT/iCy5/TGGGCTGTCAAAATTGAGC | 2.9 | 2.90 | 0.00 |
| 1631 | MOC-355 | 5IAbRQ/GCCAT/iCy5/TGGGCTGTCAAAATTGAGC | 5.0 | 5.00 | 0.00 |
| 1632 | MOC-356 | 5IAbRQ/ATG/ZEN/CCAT/iCy5/TGGGCTGTCAAAATTGAGC | 3.4 | 3.40 | 0.00 |
| 1633 | MOC-388 | 5IABkFQ/IAbRQ/CCAT/iCy5/TGGGCTGTCAAAATTGAGC | 4.2 | 4.20 | 0.00 |
| 1634 | MOC-401 | 5IAbRQ/CCAT/1CF640RN/TGGGCTGTCAAAATTGAGC | 5.3-8.7 | 6.22 | 2.17 |
| 1635 | MOC-432 | 5IAbRQ/CAT/iCF640RN/TGGGCTGTCAAAATTGAGC | 6.5-8.5 | 6.59 | 1.86 |
| 1636 | MOC-433 | 5IAbRQ/GCCAT/iCF640RN/TGGGCTGTCAAAATTGAGC | 3.8-4 | 3.90 | 0.20 |
| 1637 | MOC-434 | 5IAbRQ/TGCCAT/iCF640RN/TGGGCTGTCAAAATTGAGC | 3.3-4.5 | 3.90 | 1.20 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11180792B2). An electronic copy of the "Sequence Listing" will also be available from the USPTO upon request and payment of the fee set forth in 37 CFR 1.19(b)(3).

What is claimed is:

1. A method of labeling a single stranded target RNA, the method comprising contacting the single stranded target RNA having a first target site comprising a first sequence of nucleotides and a second target site comprising a second sequence of nucleotides, wherein the second target site is positioned on the target RNA 5' of the first target site, with:
   (a) a quenched PAMmer, wherein the quenched PAMmer is a single stranded DNA oligonucleotide comprising:
      (a.i) a protospacer adjacent motif (PAM) sequence,
      (a.ii) at least one detectable label,
      (a.iii) at least one quencher moiety that quenches the at least one detectable label,
      (a.iv) a specificity segment, positioned 5' of the PAM sequence, that is capable of hybridizing with nucleotides of the first target site, and
      (a.v) an orientation segment, positioned 3' of the PAM sequence, that hybridizes with nucleotides of the second target site;
   (b) a Cas9 protein, wherein the Cas9 protein is a nickase that cleaves the quenched PAMmer and does not cleave the target RNA; and
   (c) a Cas9 guide RNA that forms a complex with the Cas9 protein and is capable of hybridizing with the first target site,
   whereby the Cas9 protein cleaves the quenched PAMmer at a cleavage site positioned between the at least one detectable label and the at least one quencher moiety to produce: (i) a first cleavage product that is hybridized with the target RNA and comprises the at least one detectable label; and (ii) a second cleavage product that is not hybridized with the target RNA and comprises the at least one quencher moiety.

2. The method according to claim 1, wherein:
   a) the at least one detectable label is positioned 3' of the cleavage site, the at least one quencher moiety is positioned 5' of the cleavage site;
   b) the at least one detectable label is positioned 5' of the cleavage site, the at least one quencher moiety is positioned 3' of the cleavage site;
   c) the at least one detectable label and the at least one quencher moiety are both positioned 5' of the PAM sequence;
   d) the at least one detectable label is positioned 3' of the PAM sequence and the at least one quencher moiety is positioned 5' of the PAM sequence; or
   e) the at least one detectable label is positioned 5' of the PAM sequence and the at least one quencher moiety is positioned 3' of the PAM sequence.

3. The method according to claim 1, wherein the quenched PAMmer further comprises:
   a) a 5' extension arm, positioned 5' of the PAM sequence, wherein the 5' extension arm comprises: i) a nucleotide sequence that does not hybridize with the target RNA; and ii) the at least one quencher moiety; or
   b) a 3' extension arm, positioned 3' of the PAM sequence, wherein the 3' extension arm comprises: i) a nucleotide sequence that does not hybridize with the target RNA; and ii) the at least one quencher moiety.

4. The method according to claim 1, wherein the PAM sequence is GG or 5'-NGG-3', wherein N can be any nucleotide.

5. The method according to claim 1, wherein the PAM sequence does not hybridize with the target RNA when the quenched PAMmer is hybridized with the target RNA.

6. The method according to claim 1, wherein the target RNA comprises a nucleotide sequence that is 5' of and adjacent to the first target site, wherein the nucleotide sequence that is 5' of and adjacent to the first target site is not complementary to the PAM sequence.

7. The method according to claim 1, wherein 10 or fewer nucleotides are present in the target RNA between the first and second target sites.

8. The method according to claim 1, wherein the at least one detectable label is a fluorescent label.

9. The method according to claim 8, wherein the fluorescent label is selected from: a cyanine dye, fluorescein, and tetramethylrhodamine.

10. The method according to claim 1, wherein the PAMmer comprises two or more detectable labels and/or the PAMmer comprises two or more quencher moieties.

11. The method according to claim 1, wherein said contacting is:
   a) outside of a cell in vitro;
   b) in a target cell in vitro or ex vivo; or
   c) in a target cell in vivo.

12. The method according to claim 1, wherein the Cas9 guide RNA is a DNA/RNA hybrid nucleic acid comprising deoxyribonucleotides that hybridize with the target RNA.

13. The method according to claim 1, wherein the Cas9 guide RNA is a Cas9 dual guide RNA.

14. The method according to claim 1, wherein the Cas9 guide RNA is a Cas9 single guide RNA.

15. The method according to claim 1, wherein the Cas9 protein has a mutation in the HNH domain relative to a wild type Cas9 protein.

16. The method according to claim 1, wherein the single-stranded target RNA is present in a sample comprising a plurality of single stranded nucleic acids, wherein the method further comprises detecting a signal from the at least one detectable label, and wherein said detecting provides for detection of said target single stranded target RNA.

17. The method according to claim 16, wherein said detecting is quantitative.

18. The method according to claim 16, wherein the plurality of single stranded nucleic acids are not in a cell.

19. The method according to claim 16, wherein the sample comprises a cell, and wherein the target RNA is in the cell.

20. The method according to claim 1, wherein the single stranded target RNA is selected from: mRNA, rRNA, tRNA, non-coding RNA (ncRNA), long non-coding RNA (lncRNA), and microRNA (miRNA).

21. The method according to claim 1, wherein the single stranded target RNA is from a virus.

22. The method according to claim 1, wherein the at least one quencher moiety is a dark quencher.

23. The method according to claim 1, wherein the at least one quencher moiety is a dark quencher or a metal cluster.

24. The method according to claim 1, wherein the Cas9 protein comprises an amino acid substitution at a position corresponding to H840 of SEQ ID NO:8.

25. The method according to claim 1, wherein the quenched PAMmer comprises one or more modified nucleotides and/or a modified backbone.

26. The method according to claim 25, wherein the modified backbone comprises one or more phosphorothioate linkages.

27. The method according to claim 25, wherein the one or more modified nucleotides comprises a 2'-O-methyl nucleotide.

* * * * *

UNITED STATES PATENT AND TRADEMARK OFFICE
CERTIFICATE OF CORRECTION

PATENT NO. : 11,180,792 B2
APPLICATION NO. : 15/540227
DATED : November 23, 2021
INVENTOR(S) : Mitchell Ray O'Connell et al.

Page 1 of 2

It is certified that error appears in the above-identified patent and that said Letters Patent is hereby corrected as shown below:

In the Specification

Column 41, Line 30, replace "loops 1and 2" with --- loops 1 and 2 ---;

Column 41, Line 34, replace "loops 1and" with --- loops 1 and 3 ---;

Column 65, Line 26, replace "Wi126A" with --- W1126A ---;

Column 66, Line 18, replace "Wi216A" with --- W1126A ---;

Column 73, Line 21, replace "5717-L727" with --- S717-L727 ---;

Column 134, Line 31, replace "Pill/Abyl" with --- Pil1/Aby1 ---;

Column 134, Line 62, replace "Kruppel" with --- Krüppel ---;

Column 135, Line 46, replace "RNP Si" with --- RNP S1 ---;

Column 135, Line 67, replace "hnRNP A1" with --- hnRNP Al ---;

Column 136, Line 39, replace "A1" with --- Al ---;

Column 135, Line 59, replace "c6>-elements" with --- cώ-elements ---;

Column 139, Line 58, replace "KIIa" with --- KIIα ---;

Column 140, Line 27, replace "SM22a" with --- SM22α ---;

Column 140, Line 28, replace "Akyurek" with --- Akyürek ---;

Signed and Sealed this
Twenty-second Day of March, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,180,792 B2

Column 140, Line 31, replace "SM22a" with --- SM22α ---;

Column 140, Line 58, replace "50169" with --- S0169 ---;

Column 141, Line 53, replace "el1756" with --- e1174560169 ---;

Column 142, Line 45, replace "CMV-3" with --- CMB-β ---;

Column 164, Line 10, replace "IncRNA" with --- lncRNA ---;

Column 178, Line 43, replace "3 or 4" with --- λ3 or λ4 ---;

Column 180, Line 61, replace "1125$^{Spy}$-127$^{Spy}$" with --- 1125$^{Spy}$-1127$^{Spy}$ ---;

Column 185, Line 13, replace "4" with --- λ4 ---;

Column 185, Line 24, replace "3 and 4" with --- λ3 and λ4 ---;

Column 185, Line 39, replace "3 and 4" with --- λ3 or λ4 ---;

Column 185, Line 62, replace "X2" with --- λ2 ---;

Column 186, Line 8, replace the first "3" with --- λ3 ---;

Column 187, Lines 1 and 2, replace "(GI)" with --- G1 ---;

Column 189, Line 1, replace "targeting-1-RNAs" with --- targeting l-RNA ---; and Column 190, Line 58, replace "R-actin" with --- β-actin ---.